United States Patent
Alphandéry

(10) Patent No.: US 11,571,393 B2
(45) Date of Patent: Feb. 7, 2023

(54) MAGNETIC NANOPARTICLES SEQUENTIALLY IRRADIATED BY LASER RADIATION FOR MEDICAL OR CHEMICAL OR BIOLOGICAL OR COSMETIC APPLICATIONS

(71) Applicant: NANOBACTERIE, Paris (FR)

(72) Inventor: Edouard Alphandéry, Paris (FR)

(73) Assignee: NANOBACTERIE, Paris (FR)

(*) Notice: Subject to any disclaimer, the term of this patent is extended or adjusted under 35 U.S.C. 154(b) by 750 days.

(21) Appl. No.: 16/412,933

(22) Filed: May 15, 2019

(65) Prior Publication Data

US 2019/0350869 A1 Nov. 21, 2019

(30) Foreign Application Priority Data

May 16, 2018 (EP) .................... 18020211
Nov. 29, 2018 (EP) .................... 8020623

(51) Int. Cl.
| | | |
|---|---|---|
| *A61N 2/00* | (2006.01) | |
| *A61K 9/50* | (2006.01) | |
| *A61K 9/14* | (2006.01) | |
| *A61K 49/18* | (2006.01) | |
| *B82Y 5/00* | (2011.01) | |
| *B82Y 25/00* | (2011.01) | |
| *H01F 1/00* | (2006.01) | |
| *A61K 41/00* | (2020.01) | |

(52) U.S. Cl.
CPC .............. *A61K 9/5094* (2013.01); *A61K 9/14* (2013.01); *A61K 9/5089* (2013.01); *A61K 41/0052* (2013.01); *A61K 49/18* (2013.01); *A61K 49/1827* (2013.01); *A61N 2/002* (2013.01); *A61N 2/004* (2013.01); *B82Y 5/00* (2013.01); *B82Y 25/00* (2013.01); *H01F 1/0045* (2013.01)

(58) Field of Classification Search
CPC ........ A61N 2/00–12; A61N 5/10–1084; A61N 2005/1085–1098
See application file for complete search history.

(56) References Cited

U.S. PATENT DOCUMENTS

| | | | | |
|---|---|---|---|---|
| 2012/0302819 | A1* | 11/2012 | Alphandery | C12N 1/38 424/646 |
| 2013/0261368 | A1* | 10/2013 | Schwartz | A61B 18/02 607/2 |

FOREIGN PATENT DOCUMENTS

| | | |
|---|---|---|
| EP | 3 311 838 A1 | 4/2018 |
| WO | 2016/203121 A1 | 12/2016 |
| WO | 2017/068252 A1 | 4/2017 |

OTHER PUBLICATIONS

Chuanfang Chen, et al.; "Bacterial Magnetic Nanoparticles for Photothermal Therapy of Cancer Under the Guidance of MRI"; Biomaterials 104; 2016; 9 pages.

(Continued)

*Primary Examiner* — Thaddeus B Cox
(74) *Attorney, Agent, or Firm* — Maier & Maier, PLLC

(57) ABSTRACT

Magnetosomes for use in a sequential laser radiation medical treatment, wherein the magnetosomes are administered to a body part of an individual. In a first step, the magnetosomes are irradiated by a laser radiation, and in a second step, the magnetosomes are irradiated by a laser radiation of lower power than in the first step or no laser irradiation of the magnetosomes is performed. The sequence of the first step and second step is repeated at least once.

19 Claims, 6 Drawing Sheets

(56) References Cited

OTHER PUBLICATIONS

Edouard Alphandéry et al., "Chains of Magnetosomes Extracted from AMB-1 Magnetotactic Bacteria for Application in Alternative Magnetic Field Cancer Therapy", ACS Nano, vol. 5, No. 8, pp. 6279-6296, 2011.

Extended European Search Report dated Nov. 19, 2018 in corresponding European Application No. 18020211.1; 9 pages.

Anouchka Plan Sangnier et al., "Targeted thermal therapy with genetically engineered magnetite magnetosomes@RGD: Photothermia is far more efficient than magnetic hyperthermia", Journal of Controlled Release, vol. 279, Apr. 21, 2018, pp. 271-281.

Lei Qi et al., "Fur in Magnetospirillum gryphiswaldense Influences Magnetosomes Formation and Directly Regulates the Genes Involved in Iron and Oxygen Metabolism", PLoS One, vol. 7, issue 1, e29572, Jan. 2012, pp. 1-9.

Dirk Schüler et al., "A simple light scattering method to assay magnetism in Magnetospirillum gryphiswaldense", FEMS Microbiology Letters, 132, 1995, pp. 139-145.

Takeyuki Suzuki et al., "Cytoplasmic ATPase involved in ferrous ion uptake from magnetotactic bacterium Magnetospirillum magneticum AMB-1", FEBS Letters, 581, 2007, pp. 3443-3448.

Chaolong Qi et al., "Miniature Differential Mobility Analyzer for Compact Field-Portable Spectrometers", Aerosol Sci Technol., 2016 ; 50(11): 1167-1179.

Dirk Schüler, "Formation of Magnetosomes in Magnetotactic Bacteria", J. Molec. Microbiol. Biotechnol. (1999) 1(1): 79-86.

\* cited by examiner

MAGNETIC NANOPARTICLES SEQUENTIALLY IRRADIATED BY LASER RADIATION FOR MEDICAL OR CHEMICAL OR BIOLOGICAL OR COSMETIC APPLICATIONS

FIELD OF THE INVENTION

The invention relates to magnetic nanoparticles, in particular magnetosomes, being introduced to a body part of an individual and then irradiated sequentially by a laser radiation, leading to some improvement compared with a method in which magnetic nanoparticles, in particular magnetosomes, are continuously irradiated by laser radiation.

BACKGROUND

Magnetosomes have been shown to efficiently destroy tumors when they are introduced to tumors and heated under the application of an alternating magnetic field (E. Alphandéry et al, ACSNano, V. 5, P. 6279-6296, 2011). Magnetosomes were also shown to be more efficient than their chemically synthesized counterparts, due to their better crystallization, larger sizes, and/or chain arrangement. It appears however that the application of the alternating magnetic field can be difficult to achieve since it requires the use of a large and expensive induction system in order to reach a sufficiently high strength to heat magnetosomes in the body part.

SUMMARY

In this patent application, we therefore develop a method to heat the magnetic nanoparticles, in particular magnetosomes, with laser radiation, using a more compact and cheaper excitation source (a laser) than an induction system. Moreover, by sequentially irradiating magnetic nanoparticles, in particular magnetosomes, by laser radiation, we are able to increase the efficacy and/or reduce the toxicity of the treatment.

In an exemplary embodiment, magnetic nanoparticles, in particular magnetosomes, for use in a laser radiation medical or chemical or biological or cosmetic treatment, are administered to a body part of an individual and:

In a first step, the magnetic nanoparticles, in particular the magnetosomes, are irradiated by a laser radiation, and In a second step, the magnetic nanoparticles, in particular the magnetosomes, are irradiated by a laser radiation of lower power than in the first step or no laser irradiation of the magnetic nanoparticles, in particular the magnetosomes, is performed, and the sequence of the first step and the second step is repeated at least once.

In another exemplary embodiment, the invention relates to a method for sequentially irradiating magnetic nanoparticles, in particular the magnetosomes, with a laser, wherein:

In a first step, the magnetic nanoparticles, in particular the magnetosomes, are irradiated by a laser radiation, and In a second step, the magnetic nanoparticles, in particular the magnetosomes, are irradiated by a laser radiation of lower power than in the first step or no laser irradiation of the magnetic nanoparticles, in particular the magnetosomes, is performed, and the sequence of the first step and the second step is repeated at least once.

In another exemplary embodiment, irradiated magnetic nanoparticles, in particular the magnetosomes, are included in cosmetic or medical or diagnosis compositions.

In a further exemplary embodiment, a system is used for sequentially irradiating magnetic nanoparticles. The system includes a laser, magnetic nanoparticles, parameter sensor(s), and control unit that controls the application of the laser, as a function of time and the value(s) of the parameter(s) measured by the parameter sensor(s).

BRIEF DESCRIPTION OF THE FIGURES

Advantages of embodiment of the invention will be apparent from the following detailed description of the exemplary embodiments. The following detailed description should be considered in conjunction with the accompanying figures in which.

DETAILED DESCRIPTION OF THE INVENTION

Figure 1:
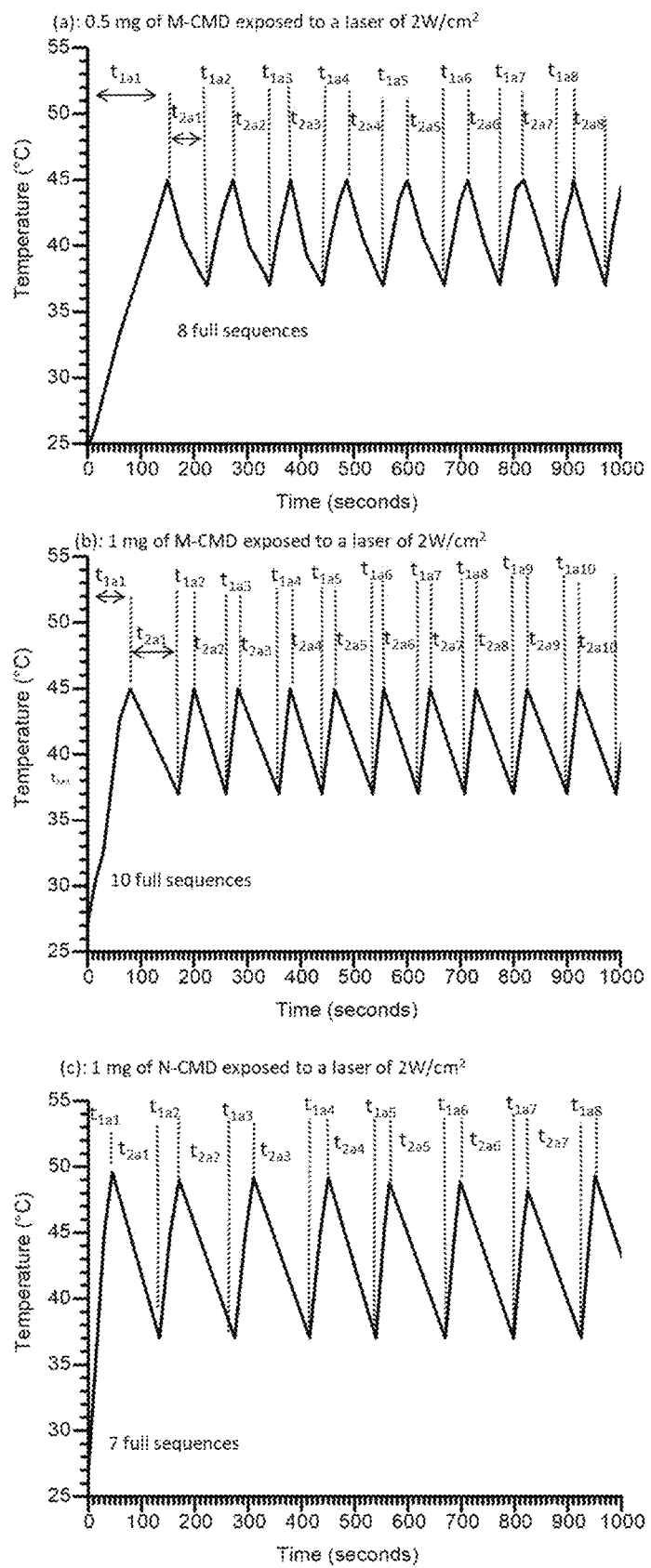
FIG. 1: Temperature variations as a function of time of suspensions comprising 0.5 mg of M-CMD, (a), 1 mg of M-CMD, (b), or 1 mg of N-CMD, (c), which are exposed to a laser power density of 2 W/cm$^2$ during heating steps of durations $t_{1ai}$ ($1<i<10$) and not exposed to the laser during cooling steps of duration $t_{2aj}$ ($1<j<10$).

As used herein, the expression "magnetic nanoparticle" is meant to include any nanoparticle which gives rise to a response when it is subjected to a magnetic field, where the response can be: i), a non-zero magnetization or coercivity, ii) a coercivity or magnetization that increases in strength with increasing magnetic field strength, iii) a nanoparticle magnetic moment that gets coupled with the magnetic field, and/or iv) a nanoparticle movement, preferentially induced when the magnetic field is non-uniform spatially. This term is meant to also include ferromagnetic, ferrimagnetic, paramagnetic, superparamagnetic and diamagnetic materials. Non-limiting suitable examples can include: i) $Fe_2O_3$, $Fe_3O_4$, $Fe_2O_4$, $Fe_xPt_y$, $Co_xPt_y$, $MnFe_xO_y$, $CoFe_xO_y$, $NiFe_xO_y$, $CuFe_xO_y$, $ZaFe_xO_y$, and $CdFe_xO_y$, wherein x and y are preferentially between 1 and 6, depending on the method of synthesis known in the art, and/or ii) nanoparticles comprising a magnetic material, preferentially predominantly, such as Fe, Pt, Au, Ag, Mg, Zn, Ni, or Si. A distinction can be made between nanoparticles that are magnetic in the absence of application of an external magnetic field or in the presence of a magnetic field of strength lower than 1 mT, such as those composed of iron or iron oxide, and nanoparticles that are magnetic in the presence of an external strength of strength preferentially higher than $10^{-5}$, $10^{-3}$, 1 or 10 mT, such as those composed of gold or silver.

As used herein, the term "nanoparticle" is meant to include any nanosized material with at least one dimension such as length, width, surface, volume, or thickness, within the size range of 0.1-1000 nm, preferentially within the size range of 1-100 nm. Sometimes assemblies of nanoparticles, such as nanoparticle aggregates, nanoparticle agglomerates, fused nanoparticles, several nanoparticles forming a geometric figure such as a chain or a circle can have a size larger than 1000 nm. Sometimes species or materials issued or originating from the nanoparticles, for example following nanoparticle dissolution, such as individual atoms or ions, can have a size smaller than 0.1 nm.

As used herein, the expression "metallic nanoparticle" is meant to include any nano sized metal with at least one dimension such as length, width, surface, volume, or thickness, within the size range of 0.1-1000 nm, preferentially within the size range of 1-100 nm. In some embodiments, the expression "metallic nanoparticle" excludes some metallic nanoparticles such as gold or silver nanoparticles. In some embodiments, the expression "metallic nanoparticle" only includes iron or iron oxide nanoparticles.

As used herein, the expression "plasmonic nanoparticle" is meant to include any nanoparticle that gives rise to plasmon, plasmon wave, surface plasmon, and/or surface plasmon wave. In some embodiments, magnetic and/or metallic nanoparticles are plasmonic, for example, when the magnetic and/or metallic property(ies) of the nanoparticles result(s) in the localization of electrons that gives rise to a Plasmon.

As used herein, the expression "mineral nanoparticle" is meant to include any nanoparticle with at least one property selected in the group consisting of: i), a metallic composition, ii) a crystalline composition, iii) a non-organic composition or non-carbonaceous composition, iv) a synthesis that is not carried out, partly or fully by a human, or that does not involve the reasoning, planning, design, process, method of a human, v) a synthesis that is due to a living organism, preferentially a living organism different from a human, and vi) a synthesis that is due to or occurs in the natural environment, where this natural environment such as the growth of microorganisms can in some embodiments be reproduced by a human.

As used herein, the term "temperature" is meant to include any temperature of the step(s), inter-step(s), sequence(s), inter-sequence(s), session(s), inter-session(s) of the method or treatment according to the invention. In particular, "temperature" may refer to a minimum, a maximum, or an average temperature as well as a temperature gradient. In some embodiments, the maximum, minimum, average, or gradient of: i) laser power, ii) percentage of dissociation, iii) radical species produced by the magnetic nanoparticles, can be defined in a similar manner as the minimum, maximum, average temperature or temperature gradient, preferentially by replacing the term temperature or the terms related to temperature by the terms: i) laser power, ii) percentage of dissociation, iii) radical species produced by the magnetic nanoparticles, or by the terms related to i) laser power, ii) percentage of dissociation, iii) radical species produced by the magnetic nanoparticles.

As used herein, the term "heating" is meant to include heating occurring during the first step.

As used herein, the term "cooling" is meant to include cooling occurring during the second step.

As used herein, the term "treatment" is meant to include treatment step, treatment sequence, treatment session, and/or whole treatment.

As used herein, the term "method" is meant to include step, sequence, session of the method, and/or whole method.

As used herein, the expression "physiological temperature" is meant to include the temperature of a healthy individual, preferentially of a body part or of the entire body of such individual.

In one embodiment of the invention, a metallic composition is a composition that comprises: i) in some cases more than 1, 10, $10^3$, $10^5$, $10^{10}$, $10^{20}$, or $10^{50}$ metallic atoms preferentially per nanoparticle, ii) in some other cases less than $10^{50}$, $10^{20}$, $10^{10}$, $10^5$, $10^3$, or 10 metallic atoms preferentially per nanoparticle, iii) in still some other cases, between 1 and $10^{100}$, 1 and $10^{50}$, 1 and $10^{20}$, 1 and $10^{10}$, 1 and $10^5$, or between 1 and $10^3$ metallic atoms preferentially per nanoparticle. In still some other cases, a metallic composition is a composition that comprises: i) in some cases more than $10^{-50}$, $10^{-10}$, $10^{-5}$, $10^{-2}$, $10^{-1}$, 0, 1, 5, 10, 25, 50, 75, 80, 90, 95, 99 or 99.9 percent in atoms or mass or volume of metallic atoms preferentially per nanoparticle, ii) in some other cases less than 100, 99.9, 99, 90, 80, 75, 50, 25, 10, 5, 0, 1, $10^{-1}$, $10^{-5}$ or $10^{-10}$ percent in atoms or mass or volume of metallic atoms preferentially per nanoparticle, iii) in still some other cases, between $10^{-50}$ and 100, between $10^{-20}$ and 100, between $10^{-10}$ and 100, between 1 and 100, between 50 and 100, between $10^{-50}$ and 99, between $10^{-20}$ and 99, or between $10^{-10}$ and 99 percent in atom or mass or volume of metallic atoms preferentially per nanoparticle.

In one embodiment of the invention, the percentage in atoms of metallic atoms is $N_{MA}/N_A$, where $N_{MA}$ is the number of metallic atoms in the nanoparticle and $N_A$ is the total number of atoms (metallic and non-metallic) in the nanoparticle.

In one embodiment of the invention, the percentage in mass of metallic atoms is $M_{MA}/M_A$, where $M_{MA}$ is the mas of the metallic atoms comprised in the nanoparticle and $M_A$ is the mass of all atoms in the nanoparticle.

In one embodiment of the invention, the percentage in volume of metallic atoms is $V_{MA}/V_A$, where $V_{MA}$ is the volume occupied by the metallic atoms in the nanoparticle and $V_A$ is the volume of the nanoparticle or of all atoms comprised in the nanoparticle.

In one embodiment of the invention, per nanoparticle means per at least one nanoparticle.

In one embodiment of the invention, a crystalline composition is a composition that comprises: i) in some embodiments more than 1, 10, $10^3$, $10^5$, $10^{10}$, $10^{20}$, or $10^{50}$ ordered atoms or ordered atomic planes or crystallographic planes or crystallographic directions preferentially per nanoparticle, ii) in some other embodiments less than $10^{50}$, $10^{20}$, $10^{10}$, $10^5$, $10^3$, or 10 ordered atoms or ordered atomic planes or crystallographic planes or crystallographic directions preferentially per nanoparticle preferentially per nanoparticle, iii) in still some other embodiments, between 1 and $10^{100}$, 1 and $10^{50}$, 1 and $10^{20}$, 1 and $10^{10}$, 1 and $10^5$, or between 1 and $10^3$ ordered atoms or ordered atomic planes or crystallographic planes or crystallographic directions preferentially per nanoparticle preferentially per nanoparticle. In still some other embodiments, a crystalline composition is a composition that comprises: i) in some embodiments more than $10^{-50}$, $10^{-10}$, $10^{-5}$, $10^{-2}$, $10^{-1}$, 0, 1, 5, 10, 25, 50, 75, 80, 90, 95, 99 or 99.9 percent of ordered atoms or ordered atomic planes or crystallographic planes or crystallographic directions preferentially per nanoparticle, ii) in some other embodiments less than 100, 99.9, 99, 90, 80, 75, 50, 25, 10, 5, 0, 1, $10^{-1}$, $10^{-5}$ or $10^{-10}$ percent of ordered atoms or ordered atomic planes or crystallographic planes or crystallographic directions preferentially per nanoparticle, iii) in still some other embodiments, between $10^{-50}$ and 100, between $10^{-20}$ and 100, between $10^{-10}$ and 100, between 1 and 100, between 50 and 100, between $10^{-50}$ and 99, between $10^{-20}$ and 99, or between $10^{-10}$ and 99 percent of ordered atoms or ordered atomic planes or crystallographic planes or crystallographic directions preferentially per nanoparticle.

In some embodiments, the percentage of ordered atoms or ordered atomic planes or crystallographic planes or crystallographic directions preferentially per nanoparticle can be $\alpha/\beta$, where $\alpha$ is the number of atoms that are ordered, the number of crystallographic planes, the number of crystallographic directions, preferentially per nanoparticle, and $\beta$ is the total number of atoms, the total number of planes, the total number of direction such as elongation direction or orientation, preferentially per nanoparticle.

In some embodiments, a non-organic or non-carbonaceous composition is a composition that comprises a low amount or low quantity or low concentration of carbon or organic material or carbonaceous material. A non-organic or non-carbonaceous composition can comprise: i) in some embodiments more than 1, 10, $10^3$, $10^5$, $10^{10}$, $10^{20}$, or $10^{50}$ carbon atoms or organic material or carbonaceous material preferentially per nanoparticle, ii) in some other embodiments less than $10^{50}$, $10^{20}$, $10^{10}$, $10^5$, $10^3$, or 10 carbon atoms or organic material or carbonaceous material preferentially per nanoparticle, iii) in still some other embodiments, between 1 and $10^{100}$, 1 and $10^{50}$, 1 and $10^{20}$, 1 and $10^{10}$, 1 and $10^5$, or between 1 and $10^3$ carbon atoms or organic material or carbonaceous material preferentially per nanoparticle. In still some other embodiments, a non-organic or non-carbonaceous composition is a composition that comprises: i) in some embodiments more than $10^{-50}$, $10^{-10}$, $10^{-5}$, $10^{-2}$, $10^{-1}$, 0, 1, 5, 10, 25, 50, 75, 80, 90, 95, 99 or 99.9 percent in atoms or mass or volume of carbon atoms or organic material or carbonaceous material preferentially per nanoparticle, ii) in some other embodiments less than 100, 99.9, 99, 90, 80, 75, 50, 25, 10, 5, 0, 1, $10^{-1}$, $10^{-5}$ or $10^{-10}$ percent in atoms or mass or volume of carbon atoms or organic material or carbonaceous material preferentially per nanoparticle, iii) in still some other embodiments, between $10^{-50}$ and 100, between $10^{-20}$ and 100, between $10^{-10}$ and 100, between 1 and 100, between 50 and 100, between $10^{-50}$ and 99, between $10^{-20}$ and 99, or between $10^{-10}$ and 99 percent in atom or mass or volume of carbon atoms or organic material or carbonaceous material preferentially per nanoparticle.

In some embodiments, the percentage in atoms of carbon atoms is $N_{CA}/N_A$, where $N_{CA}$ is the number of carbon atoms in the nanoparticle and $N_A$ is the total number of atoms (metallic and non-metallic) in the nanoparticle.

In some embodiments, the percentage in mass of carbon atoms or organic material or carbonaceous material is $M_{MC}/$ $M_A$, where $M_{MC}$ is the mas of carbon atoms or organic material or carbonaceous material comprised in the nanoparticle and $M_A$ is the mass of all atoms in the nanoparticle.

In some embodiments, the percentage in volume of carbon atoms or organic material or carbonaceous material can be $V_{MC}/V_A$, where $V_{MC}$ is the volume occupied by the carbon atoms or organic material or carbonaceous material in the nanoparticle and $V_A$ is the volume of the nanoparticle or of all atoms comprised in the nanoparticle.

In some embodiments, a crystalline composition is a composition that comprises: i) in some embodiments more than 1, 10, $10^3$, $10^5$, $10^{10}$, $10^{20}$, or $10^{50}$ ordered atoms or ordered atomic planes or crystallographic planes or crystallographic directions preferentially per nanoparticle, ii) in some other embodiments less than $10^{50}$, $10^{20}$, $10^{10}$, $10^5$, $10^3$, or 10 ordered atoms or ordered atomic planes or crystallographic planes or crystallographic directions preferentially per nanoparticle, iii) in still some other embodiments, between 1 and $10^{100}$, 1 and $10^{50}$, 1 and $10^{20}$, 1 and $10^{10}$, 1 and $10^5$, or between 1 and $10^3$ ordered atoms or ordered atomic planes or crystallographic planes or crystallographic directions preferentially per nanoparticle. In still some other embodiments, a crystalline composition is a composition that comprises: i) in some cases more than $10^{-50}$, $10^{-10}$, $10^{-5}$, $10^{-2}$, $10^{-1}$, 0, 1, 5, 10, 25, 50, 75, 80, 90, 95, 99 or 99.9 percent of ordered atoms or ordered atomic planes or crystallographic planes or crystallographic directions preferentially per nanoparticle, ii) in some other embodiments less than 100, 99.9, 99, 90, 80, 75, 50, 25, 10, 5, 0, 1, $10^{-1}$, $10^{-5}$ or $10^{-10}$ percent of ordered atoms or ordered atomic planes or crystallographic planes or crystallographic directions preferentially per nanoparticle, iii) in still some other embodiments, between $10^{-50}$ and 100, between $10^{-20}$ and 100, between $10^{-10}$ and 100, between 1 and 100, between 50 and 100, between $10^{-50}$ and 99, between $10^{-20}$ and 99, or between $10^{-10}$ and 99 percent of ordered atoms or ordered atomic planes or crystallographic planes or crystallographic directions preferentially per nanoparticle.

In some embodiments, a "mineral nanoparticle" is characterized by a mineral part, preferentially predominantly a mineral part, preferentially a mineral part that is the center or the heart or the central part of the nanoparticle. The mineral nanoparticle can be covered or mixed with or include non-mineral material, where the non-mineral material is the coating of the nanoparticle or is a material that serves to stabilize or disperse or preserve or conserve or administer or mix or homogenize the mineral.

In some embodiments, the predominant mineral part is or represents: i) more than $10^{-50}$, $10^{-5}$, 1, 5, 10, 20, 50, 75, 80, 90, 95, 99 or 99.9 percent in mass or volume of the mineral part comprised in the nanoparticle, ii) in some other embodiments less than 100, 99, 90, 80, 75, 50, 20, 10, 5 or 1 percent in mass or volume of the of the mineral part comprised in the nanoparticle, iii) in still some other embodiments, between $10^{-50}$ and 100, $10^{-10}$ and 100, 1 and 100, 25 and 100, 50 and 100, or between 75 and 100 percent in mass or volume of the of the mineral part comprised in the nanoparticle.

In some embodiments, the percent in mass or volume of the mineral part comprised in the nanoparticle is $M_M/M_N$ or $V_M/V_N$, where $M_M$ and $M_N$ are the masses of the mineral and nanoparticle, respectively, $V_M$ and $V_N$ are the volumes of the mineral and nanoparticle, respectively.

As used herein, the term "magnetosome" is meant to include magnetic nanoparticles which comprise a mineral central part surrounded fully or partly by a membrane which surrounds the central part and preferentially stabilizes the central part or prevents the aggregation or agglomeration of the central part. The membrane can be a synthetic membrane, i.e. preferentially a membrane that is not synthesized by the organism that produces the central part, or a membrane synthesized by a living organism such as a magnetotactic microorganism comprising lipids, lipopolysaccharide, endotoxins, and/or proteins or membrane-associated polypeptides produced by said microorganism. The central part and/or membrane is/are preferentially of well-defined composition such as predominantly an iron oxide or iron sulfide for the central part and an organic or carbonaceous composition for the membrane. Preferably, the magnetic nanoparticles, preferentially magnetosomes, preferentially the central part of the magnetic nanoparticles, are iron oxide nanoparticles made of magnetite ($Fe_3O_4$), iron sulfide (greigite or $Fe_3S_4$) or mixtures thereof. The magnetite found in the magnetic nanoparticles, preferentially magnetosomes, can become oxidized to maghemite after extraction from the bacteria. Therefore, the magnetic nanoparticles, preferentially magnetosomes, may contain mixtures of magnetite and maghemite.

Magnetosomes can offer a series of advantages compared with other types of nanoparticles such as: i) better heating properties, ii) chain arrangement that can yield less aggregation and enable the attachment of more therapeutic compounds at their surface, iii) less toxicity, iv) a mode of fabrication that can involve the use of a lower number of toxic compounds.

The expression "the magnetic nanoparticles", preferentially magnetosomes, can refer to: i) chains of the magnetic nanoparticles, preferentially magnetosomes, since the magnetic nanoparticles, preferentially magnetosomes, can be arranged in chains within magnetotactic bacteria or after their extraction or isolation from these bacteria, by contrast to other types of nanoparticles that will usually not spontaneously arrange in chains without the application of an external magnetic field much stronger than the earth magnetic field, or ii) individual magnetic nanoparticles, preferentially magnetosomes, i.e. magnetosomes that are not arranged in chains. In some embodiments, the magnetic nanoparticles, preferentially magnetosomes, comprise the central part without the membrane or without the full membrane, for example when the membrane is removed partly or fully. In some other embodiments, the magnetic nanoparticles, preferentially magnetosomes, comprise the membrane without the central part, for example when the central part is removed partly or fully.

The expression "synthetizing living organism" is meant to include any organism that is capable of synthetizing metal-rich nanoparticle. Such organism is preferentially chosen among: a cell, preferentially a eukaryotic or prokaryotic cell, a *bacterium*, an assembly of cells, a fish, a bird, a mammal, a plant, a tree, a fungus, an archa, a shellfish, or a part of a living organism, such as an enzyme, a protein, DNA, RNA, or biological material. Such organism is preferentially not a human. In some embodiments, the synthetizing living organism synthesizes nanoparticles intra-cellularly or extra-cellularly, for example through enzymatic reactions, or through interactions between biological material and metals that preferentially yield the formation of the nanoparticle.

The expression "magnetotactic microorganism" equivalently designated as "magnetotactic *bacterium*/bacteria", as used herein, is meant to include any microorganism which is capable of synthesizing iron-rich particles, preferentially intra-cellularly, preferentially which may be arranged in chains of 2 to 100 particles apiece. The presence of these particles preferentially provides the microorganism with a permanent dipole moment or ferromagnetic or ferromagnetic properties, which can enable these microorganisms to orientate in a preferred direction, preferentially parallel to the geomagnetic field. Suitable magnetotactic microorganisms that can be used in the present invention include, without limitation, *Nitrospira, Nitrospira moscoviensis, Magnetobacterium bavaricum, Desulfovibrio magneticus* RS-1, *Desulfovibrio desulfuricans, Geobacter metallireducens*, δ-Protobacteria, MMP5, MMP2, where MM designates magnetotactic many-celled prokaryote, magnetic *cossus*, MC-1, CS103, NKMC5, α-Protobacteria, *Rhodospirillum rubrum, Agrobacterium vitis, Magnetospirillum magnetotacticum* MS-1, *Magnetospirillum magneticum* AMB-1, *Magnetospirillum magneticum* MGT-1, *Magnetospirillum gryphiswaldense* MSR-1, marine magnetic vibrio MV-1, *Magnetospirillum gryphiswaldense* MSR-1, *Magnetospirillum magneticum* AMB-1, *Magnetospirillum magnetotacticum* MS-1, *Magnetospirillum magneticum* strain MGT-1, magnetotactic *coccus* strain MC-1, *Desulfovibrio magneticus* RS-1 and anaerobic vibrio strains MV-1, MV-2 and MV-4. Suitable methods for determining whether a microorganism is magnetotactic include, without limitation: i) determination of the total content of iron, preferentially crystallized iron, inside these microorganisms, for example by atom absorption spectrophotometry as described by Suzuki T. et al (FEBS Lett., 2007, 581: 3443-3448) or Inductive coupled plasma mass spectrometry or iron dosage, ii) determination of the value of the $C_{mag}$ parameter using light scattering technique (Schuler D. et al FEMS Microbiology Lett., 1995, 132: 139-145), iii) imaging these microorganisms by transmission electron microscopy as described by Qi et al. (PLoSOne. 2012; 7(1): e29572).

As used herein, the expression "method of sequential laser application" is meant to include any method in which a laser is applied, preferentially on nanoparticles, in a sequential manner, where the sequences of laser application preferentially comprise a first step during which the laser power is switched on and a second step that follows the first step during which the laser power is switched off or is of lower power than during the first step. The first and second steps consist in a sequence. A sequence is repeated at least once, and the combination of several sequences is a session. While the duration between two sessions is usually long, preferentially longer than 30 minutes, for example to enable the patient to rest, the duration of steps or sequences or the duration between steps and sequences is usually short, preferentially shorter than 30 minutes, preferentially to enable the repetition of a sufficiently large number of steps or sequences until the treatment or method is efficient. Importantly, the "method of sequential laser application" is preferentially different from the "method of continuous laser application", where the method of continuous laser application does not comprise steps or sequences and consists in the continuous laser application, i.e. without switching off or reducing laser power, during a session. Several advantages can occur by using the method of sequential laser application instead of using the method of continuous laser application, such as: i) the average temperature reached during treatment is lower using the sequential method compared with the continuous method, ii) with the sequential method, there is no need to stabilize the temperature of the treatment to a fixed temperature over a large percentage of the duration of the heating cycle (corresponding to heating step or heating session), which can be a difficult task in humans since it necessitates to accurately and continuously measure the heating temperature in the body part and take corrective actions such as adjusting the laser power to maintain the temperature at a given value, iii) with the sequential method, temperature gradients are achieved during the first and second steps that can be more efficient, preferentially in destroying pathological or tumor cells, and can also generate less side effect, than maintaining a fixed temperature over the majority of the heating cycle in the continuous method, and/or iv) the laser power or current or intensity necessary to carry out the sequential method may be lower than that necessary to carry out the continuous method.

In one embodiment of the invention, the nanoparticles possess at least one property selected in the group consisting of: i) they are magnetic, ii) they are mineral, iii) they are synthesized by a living organism, partly or fully, which is preferentially different from a human, iv) they are metallic, v) they are plasmonic, and iv) they are magnetosomes.

In one aspect of the invention, the invention relates to magnetic nanoparticles, in particular magnetosomes, for use in a sequential laser radiation medical or biological or chemical or cosmetic treatment, wherein the magnetic nanoparticles, in particular the magnetosomes, are administered to a body part of an individual and:

In a first step, the magnetic nanoparticles, in particular the magnetosomes, are irradiated by a laser radiation at a first power, and In a second step, the magnetic nanoparticles, in particular the magnetosomes, are irradiated by a laser radiation of lower power than in the first step or no laser irradiation of the magnetic nanoparticles, in particular the magnetosomes, is performed, and the sequence of the first step and the second step is repeated at least once.

In one embodiment of the invention, the laser radiation at a first power is the laser power or laser power of or during the first step.

In another embodiment of the invention, the laser radiation at a second power is the laser power or laser power of or during the second step.

In one aspect of the invention, the invention relates to magnetic nanoparticles, in particular magnetosomes, for use in a sequential laser radiation medical or chemical or biological or cosmetic treatment, wherein the magnetic nanoparticles, in particular magnetosomes, are administered to a body part of an individual and:

In a first step, the magnetic nanoparticles, in particular the magnetosomes, are irradiated by a laser radiation, and In a second step, the magnetic nanoparticles, in particular the magnetosomes, are irradiated by a laser radiation of lower power than in the first step or no laser irradiation of the magnetic nanoparticles is performed, and the sequence comprising the first step and the second step is repeated at least once.

In one aspect of the invention, the invention relates to a method of medically, chemically, biologically or cosmetically treating a body part of an individual by sequential laser radiation, comprising:

administering an effective amount of magnetic nanoparticles, in particular magnetosomes, to the body part of an individual in need thereof; and subjecting the magnetic nanoparticles, in particular magnetosomes, to sequential laser radiation comprising:

i) performing a first step comprising irradiating the magnetic nanoparticles, in particular magnetosomes, by laser radiation at a first power;

ii) optionally performing a second step comprising not irradiating the irradiated magnetic nanoparticles, in particular magnetosomes, obtained from the first step or irradiating the irradiated magnetic nanoparticles, in particular magnetosomes, obtained from the first step by laser radiation at a second power lower than the first power; and iii) repeating the step or steps as at least once sequence.

In some embodiments, the first power of laser radiation is designated as $P_1$ and the second power of laser radiation is designated as $P_2$.

In one embodiment, $P_1$ and/or $P_2$ is/are larger than $10^{-50}$, $10^{-10}$, $10^{-5}$, $10^{-2}$, $10^{-1}$, 1, 5, 10, $10^3$ Watt, Watt per cm$^3$ of body part or Watt per gram of magnetic nanoparticle.

In some other embodiments, $P_1$ and/or $P_2$ is/are lower than $10^{50}$, $10^{10}$, $10^5$, $10^2$, 10, 5, 2, 1, $10^{-1}$, $10^{-3}$ or $10^{-5}$ Watt, Watt per cm$^3$ of body part or Watt per gram of magnetic nanoparticle.

In some other embodiments, $P_1$ and/or $P_2$ is/are between $10^{-50}$ and $10^{50}$, $10^{-20}$ and $10^{20}$, $10^{-10}$ and $10^{10}$, $10^{-5}$ and $10^5$, $10^{-3}$ and $10^3$, or between $10^{-1}$ and $10^3$ Watt, Watt per cm$^3$ preferentially of body part or Watt per gram of magnetic nanoparticle.

In some other embodiments, $P_1$ is different from 0 Watt or is a value that results in heating the magnetic nanoparticle.

In some embodiments, $P_2$ is equal to 0 Watt or close to 0 Watt or is a value that does not result in heating the magnetic nanoparticle.

In some other embodiments, $P_1$ and/or $P_2$ is/are sufficiently small, preferentially smaller than $10^5$, $10^3$, $10^2$, 10, 5, 2, 1 or $10^{-1}$ Watt, or Watt per cm$^3$ preferentially of body part, that it/they do/does not result in heating the body part not comprising the magnetic nanoparticle.

In some other embodiments, $P_1$ is stable over the first step. In this case, $P_1$ preferentially varies by less than 100, 75, 50, 30, 20, 10, 5, 2 or 1%, where this percentage is preferentially equal to $(P_{1max}-P_{1min})/P_{1max}$, where $P_{1max}$ and $P_{1min}$ are the maximum and minimum values of the laser power of the first step.

In some other embodiments, $P_2$ is stable over the second step. In this case, $P_2$ preferentially varies by less than 100, 75, 50, 30, 20, 10, 5, 2 or 1%, where this percentage is preferentially equal to $(P_{2max}-P_{2min})/P_{2max}$, where $P_{2max}$ and $P_{2min}$ are the maximum and minimum values of the laser power of the second step.

In some other embodiments, $P_1$ is unstable over the first step. In this case, $P_1$ preferentially varies by more than $10^{-10}$, $10^{-5}$, $10^{-3}$, $10^{-1}$, 1, 5, 10, 50, 75, 80, 90 or 95%, where this percentage is preferentially equal to $(P_{1max}-P_{1min})/P_{1max}$, where $P_{1max}$ and $P_{1min}$ are the maximum and minimum values of the laser power of the first step.

In some other embodiments, $P_2$ is unstable over the second step. In this case, $P_2$ preferentially varies by more than $10^{-10}$, $10^{-5}$, $10^{-3}$, $10^{-1}$, 1, 5, 10, 50, 75, 80, 90 or 95%, where this percentage is preferentially equal to $(P_{2max}-P_{2min})/P_{2max}$, where $P_{2max}$ and $P_{2min}$ are the maximum and minimum values of the laser power of the second step.

In some embodiments, the laser power is the maximum or minimum laser power of the first step or second step.

In one embodiment of the invention, medically, chemically, biologically or cosmetically treating a body part of an individual by sequential laser radiation means treating the body part of an individual by: i) subjecting the body part of the individual to sequential laser radiation, where the body part comprises magnetic nanoparticles, ii) subjecting the magnetic nanoparticle to sequential laser radiation, iii) applying the sequential radiation to the body part or magnetic nanoparticle.

In one embodiment of the invention, the laser radiation is the same as the laser irradiation and preferentially designated the laser radiation of the magnetic nanoparticle or body part or the application of the laser radiation on the magnetic nanoparticle or body part.

In one embodiment of the invention, the sequential laser radiation is the same as the application of sequences as defined in the invention.

In one embodiment of the invention, the effective amount of magnetic nanoparticles is the amount of nanoparticles that can produce heat, a cosmetic, therapeutic, or diagnosis effect or that can be effective in the method of the invention. Preferentially, when the amount of magnetic nanoparticle is different from the effective amount, the treatment according to the invention is not efficient. For example, an amount of magnetic nanoparticles lower than the effective amount can be insufficient to produce heat under laser radiation. For example, an amount of magnetic nanoparticles larger than the effective amount can be toxic.

In one embodiment of the invention, the magnetic nanoparticle is non-irradiated, preferentially before or without laser irradiation.

In another embodiment, the magnetic nanoparticle is irradiated, preferentially, during, after, or with laser irradiation.

In one embodiment of the invention, the treatment is selected in the group consisting of: i), a(the) medical, chemical, biological or cosmetic treatment, ii) a(the) laser treatment, iii) a(the) treatment of a disease, iv) a(the) treatment step, v) a(the) treatment sequence, vi) a(the) treatment session, a(the) whole treatment comprising steps, sequences and sessions, vii) a(the) method, and viii) a(the) method of treatment.

In one embodiment of the invention, a biological or chemical treatment can be a treatment that involves biological or chemical material, without necessarily being a medical treatment, for example when the nanoparticle is mixed with biological or chemical material and treated by the method, for example to soften the biological or chemical material, to detect the substance, to color the biological or chemical material, to change the composition or the structure of the biological or chemical material.

In one embodiment of the invention, a cosmetic treatment can be a treatment that leads to the improvement of the appearance of an individual, without necessarily being a medical treatment, for example when it does not involve the destruction or detection of at least one cell, but can for example result in the change of color of the skin of the individual.

In one embodiment of the invention, a medical treatment can be a treatment that leads to the detection or destruction of at least one cell, preferentially a pathological cell.

In another aspect of the invention, the invention relates to a method for sequentially irradiating magnetosomes with a laser, wherein:

In a first step, the magnetosomes are irradiated by a laser radiation, and

In a second step, the magnetosomes the magnetosomes are irradiated by a laser radiation of lower power than in the first step or no laser irradiation of the magnetosomes is performed, and the sequence of the first step and the second step is repeated at least once.

In another aspect of the invention, the invention relates to a method for treating an individual by sequential laser radiation, comprising administering an effective amount of magnetosomes to a body part of the individual and:

In a first step, irradiating the magnetic nanoparticles, in particular the magnetosomes, with a laser radiation, and In a second step, irradiating the magnetic nanoparticles, in particular the magnetosomes, by a laser radiation of lower power that in the first step, or performing no laser irradiation of the magnetosomes, wherein the sequence of the first step and the second step is repeated at least once.

In one embodiment of the invention, the magnetic nanoparticle has at least one property in common with a magnetosome.

In the present invention, said "first step" and "second step" corresponds a "sequence" which is repeated at least once, several "sequences" correspond to a "treatment session" and successive "treatment sessions" corresponds to the whole treatment.

In one aspect of the invention, the invention relates to magnetic nanoparticles for use according to the invention, wherein the magnetic nanoparticles are mineral nanoparticles, preferably magnetosomes, and/or wherein the magnetic nanoparticles are synthetized by a synthetizing living organism, preferably magnetotactic microorganisms.

In one aspect of the invention, the invention relates to magnetic nanoparticles for use according to the invention, wherein the magnetic nanoparticle is a magnetic nanoparticle synthesized by a living organism, preferentially a magnetosome.

In one aspect of the invention, the invention relates to magnetosomes for use according to the invention, wherein the magnetosomes are synthesized by a living organism, preferentially a magnetotactic *bacterium*.

In one aspect of the invention, the invention relates to the method according to the invention, wherein the magnetic nanoparticle is a magnetic nanoparticle synthesized by a living organism, preferably a magnetosome.

In one embodiment of the invention, the living organism that synthetizes the magnetic nanoparticle is the synthetizing living organism. It is preferentially not a human. It is preferentially a microorganism such as a magnetotactic microorganism.

Preferentially, magnetotactic microorganisms can be magnetotactic bacteria.

In one embodiment, the magnetic nanoparticles of the present invention are mineral nanoparticles, preferably magnetosomes.

In one embodiment, the magnetic nanoparticles of the present invention are synthetized by a synthetizing living organism, preferably magnetotactic microorganisms.

In another embodiment of the invention, the magnetic nanoparticle has at least one property different from that of a magnetosome In one embodiment of the invention, magnetic nanoparticle(s), in particular magnetosome(s), or the magnetic nanoparticle(s), in particular the magnetosome(s), can be characterized by an assembly comprising more than 1, 10, $10^2$, $10^3$, $10^5$, $10^{10}$, $10^{20}$, or $10^{50}$ magnetic nanoparticle(s), in particular magnetosome(s).

In still another embodiment of the invention, magnetic nanoparticle(s), in particular magnetosome(s), or the magnetic nanoparticles, in particular the magnetosome(s), can be characterized by an assembly comprising less than 1, 10, $10^2$, $10^3$, $10^5$, $10^{10}$, $10^{20}$, or $10^{50}$ magnetic nanoparticle(s), in particular magnetosome(s).

In still another embodiment of the invention, magnetic nanoparticle(s), in particular magnetosome(s), or the magnetic nanoparticle(s), in particular the magnetosome(s), can be characterized by an assembly comprising more than $10^{-50}$, $10^{-40}$, $10^{-30}$, $10^{-20}$, $10^{-10}$, $10^{-5}$, $10^{-3}$, 1, or $10^2$ mg of: i), magnetic nanoparticle(s), in particular magnetosome(s), or, ii), mg of iron comprised in magnetic nanoparticle(s), in particular magnetosome(s), or, iii), mg of magnetic nanoparticle(s), in particular magnetosome(s), per $cm^3$ or, iv), mg of magnetic nanoparticle(s), in particular magnetosome(s), per $cm^3$ of body part or, v), mg of iron comprised in magnetic nanoparticle(s), in particular magnetosome(s), per $cm^3$ or, vi), mg of iron comprised in magnetic nanoparticle(s), in particular magnetosome(s), per $cm^3$ of body part.

In still another embodiment of the invention, magnetic nanoparticle(s), in particular magnetosome(s), or the magnetic nanoparticle(s), in particular the magnetosome(s), can be characterized by an assembly comprising less than $10^{-50}$, $10^{-40}$, $10^{-30}$, $10^{-20}$, $10^{-10}$, $10^{-5}$, $10^{-3}$, 1, $10^2$, $10^5$, $10^{10}$ or $10^{20}$ mg of: i), magnetic nanoparticle(s), in particular magnetosome(s), or, ii), mg of iron comprised in magnetic nanoparticle(s), in particular magnetosome(s), or, iii), mg of magnetic nanoparticle(s), in particular magnetosome(s), per $cm^3$ or, iv), mg of magnetic nanoparticle(s), in particular magnetosome(s), per $cm^3$ of body part, or, v), mg of iron comprised in magnetic nanoparticle(s), in particular magnetosome(s), per $cm^3$ or, vi), mg of iron comprised in magnetic nanoparticle(s), in particular magnetosome(s), per $cm^3$ of body part.

In one embodiment of the invention, magnetic nanoparticle(s), in particular magnetosome(s), can be bound to, linked to, or associated with the compound as defined in this invention.

In one embodiment of the invention, the magnetic nanoparticles, in particular magnetosomes, are nanoparticles characterized by at least one of the following properties: i), the presence of a core, preferentially magnetic, preferentially mineral, preferentially composed of iron oxide, most preferentially composed of maghemite or magnetite, or an intermediate composition between maghemite and magnetite, ii), the presence of a coating that surrounds the core of the magnetic nanoparticle, in particular magnetosome, and preferably prevents aggregation of the magnetic nanoparticle, in particular magnetosome, preferentially enabling the administration in an organism or in the body part of the magnetic nanoparticle, in particular the magnetosome, or stabilizing the core of the magnetic nanoparticle, in particular the magnetosome, where coating thickness may preferably lie between 0.1 nm and 10 μm, between 0.1 nm and 1 μm, between 0.1 nm and 100 nm, between 0.1 nm and 10 nm, or between 1 nm and 5 nm, iii), magnetic properties leading to diamagnetic, paramagnetic, superparamagnetic, ferromagnetic, or ferrimagnetic behavior or properties, iv), a coercivity higher than 0.01, 0.1, 1, 10, 100, $10^3$, $10^4$, $10^5$, $10^9$, or $10^{20}$ Oe, v), a ratio between remanent and saturating magnetization higher than 0.01, 0.1, 0.2, 0.3, 0.4, 0.5, 0.75, 0.9, or 0.99, vi), a saturating magnetization higher than 0.1, 1, 5, 10, or 50 emu/g, vii), magnetic properties such as coercivity, remanent and saturating magnetization, preferentially measured or observed at a temperature higher than 0.1 K, 1 K, 10 K, 20 K, 50 K, 100 K, 200 K, 300 K, 350 K, or 3000 K, viii), a crystallinity, i.e. magnetic nanoparticles, in particular magnetosomes, preferentially possessing at least 1, 2, 5, 10, or 100 crystalline plane(s), preferentially observable or measured by electron microscopy, ix), the presence of a single domain, x), a size that is higher than 0.1, 0.5, 1.5, 10, 15, 20, 25, 30, 50, 60, 70, 80, 100, 120, 150, or 200 nm, xi), a size lying between 0.1 nm and 10 μm, between 0.1 nm and 1 μm, between 0.1 nm and 100 nm, between 1 nm and 100 nm, or between 5 nm and 80 nm, xii), a non-pyrogenicity or apyrogenicity, which preferentially means that magnetic nanoparticles, in particular magnetosomes, possess an endotoxin concentration lower than 10000, 1000, 100, 50, 10, 5, 2, or 1 EU (endotoxin unit) per mg of magnetic nanoparticle, in particular magnetosome, or per mg of iron comprised in magnetic nanoparticle, in particular magnetosome, or which means that magnetic nanoparticles, in particular magnetosomes, do not trigger fever or do not trigger an increase in whole body temperature of an organism individual of more than 100, 50, 10, 6, 5, 3, 2, or 1° C., preferentially following administration of magnetic nanoparticles, in particular magnetosomes, to a living organism or body part, xiii), a synthesis by a synthetizing living organism, preferentially by magnetotactic bacteria, leading to the production of magnetic nanoparticles, in particular magnetosomes, preferentially extracted from magnetotactic bacteria, preferentially only or mostly or in majority comprising the mineral magnetic core of the magnetic nanoparticles, in particular the magnetosomes, xiv), the presence of less than 50, 25, 15, 10, 5, 2, or 1% of organic or carbon material originating from the synthetizing living organism, xv), a cubic, spherical, cubo-octahedral, cigar-shaped, or elongated geometry, xvi), a ratio between length(s) and width(s), between the longest and largest edge(s) of the magnetic nanoparticles, in particular magnetosomes, or between two different edge(s), dimension(s), preferentially crossing dimension(s), or diameter(s) of the magnetic nanoparticles, in particular magnetosomes, that is/are comprised between $10^{-3}$ and $10^3$, $10^{-2}$ and $10^2$, $10^{-1}$ and 10, 0.5 and 5, 0.2 and 2, or between 0.1 and 1.1, or xvii), the presence of more than 99, 95, 80, 70, 60, 50, or 25% of mineral material originating from the synthetizing living organism, or xvi), a specific absorption rate (SAR) that is higher than 1, 10, 1000, or $10^4$ Watt per gram of magnetic nanoparticle, in particular magnetosome, where the SAR is preferentially measured under the irradiation by the laser radiation.

In one embodiment of the invention, the heating rate of the magnetic nanoparticle is the ratio $\Delta T_{HS}/D_{HS}$ between the temperature increase of the heating step, $\Delta T_{HS}$, and the duration of the heating step, $D_{HS}$, where the temperature increase of the heating step is preferentially the difference between the maximum and minimum temperatures of the heating step.

In another embodiment of the invention, the heating rate of the magnetic nanoparticle is the ratio $\delta T_{HS}/d_{HS}$ between the temperature increase at the beginning of the heating step, $\delta T_{HS}$, and the duration of the beginning of the heating step, $d_{HS}$, where the beginning of the heating step preferentially represents the few first seconds or few first percent of the duration of the heating steps.

In one embodiment of the invention, the magnetic nanoparticle, in particular magnetosome, is characterized by a heating rate, which is higher than $10^{-20}$, $10^{-10}$, $10^{-5}$, $10^{-3}$, $10^{-1}$, 1, 5, 10, $10^3$ or $10^5$° C. per second, as preferentially measured per mg of nanoparticle, preferably higher than $10^{-10}$° C. per second, as preferentially measured per mg of nanoparticle, most preferably higher than $10^{-5}$° C. per second, as preferentially measured per mg of nanoparticle.

In one embodiment of the invention, the magnetic nanoparticle, in particular magnetosome, can be characterized by a heating rate, which is lower than $10^{20}$, $10^{10}$, $10^5$, $10^3$, 10, 1, $10^{-1}$, $10^{-3}$ or $10^{-5}$° C. per second, as preferentially measured per mg of nanoparticle, preferably lower than $10^{10}$° C. per second, as preferentially measured per mg of nanoparticle, most preferably lower than $10^5$° C. per second, as preferentially measured per mg of nanoparticle.

In one embodiment, the heating rate exists under conditions where the nanoparticle is exposed to a laser of: i) power lower than $10^5$, $10^3$, 100, 50, 10, 5, 1 or $10^{-1}$ Watt or Watt per cm$^3$ or cm$^2$ or cm or gram of body part of nanoparticle, or ii) power sufficiently low that when the body part not comprising the nanoparticle is exposed to the laser it results in no temperature increase of the body part or in a temperature increase of the body part lower than $10^5$, $10^3$, 100, 50, 20, 10, 5, 2, 1 or 0.1° C. preferentially per cm$^3$, cm$^2$, cm or gram of body part.

In some other embodiments of the invention, the heating rate exists under conditions where the nanoparticle is exposed to a laser of sufficiently large power to induce a temperature increase of the nanoparticle, preferentially of laser power higher than $10^{-10}$, $10^{-5}$, $10^{-1}$, 1, 5, 10 Watt or Watt per cm$^3$ or cm$^2$ or cm or gram of body part of nanoparticle.

In one embodiment of the invention, the cooling rate of the magnetic nanoparticle is the ratio $\Delta T_{CS}/D_{CS}$ between the temperature decrease of the cooling step, $\Delta T_{CS}$, and the duration of the cooling step, $D_{CS}$, where the temperature decrease of the cooling step is preferentially the difference between the maximum and minimum temperatures of the cooling step.

In another embodiment of the invention, the cooling rate of the magnetic nanoparticle is the ratio $\delta T_{CS}/d_{CS}$ between the temperature decrease at the beginning of the cooling step, $\delta T_{CS}$, and the duration of the beginning of the cooling step, $d_{CS}$, where the beginning of the cooling step preferentially represents the few first seconds or few first percent of the duration of the cooling steps.

In one embodiment, the magnetic nanoparticle, in particular magnetosome, is characterized by a cooling rate, which is higher than $10^{-20}$, $10^{-10}$, $10^{-5}$, $10^{-3}$, $10^{-1}$, 1, 5, 10, $10^3$ or $10^5$° C. per second, as preferentially measured per mg of nanoparticle, preferably higher than $10^{-5}$° C. per second, as preferentially measured per mg of nanoparticle, most preferably higher than $10^{-3}$° C. per second, as preferentially measured per mg of nanoparticle.

In one embodiment, the magnetic nanoparticle, in particular magnetosome, has a cooling rate, which is lower than $10^{20}$, $10^{10}$, $10^5$, $10^3$, 10, 1, $10^{-1}$, $10^{-3}$ or $10^{-5}$° C. per second, as preferentially measured per mg of nanoparticle, preferably lower than 10° C. per second, as preferentially measured per mg of nanoparticle, most preferably lower than $10^5$° C. per second, as preferentially measured per mg of nanoparticle.

In one embodiment, the cooling rate exists under conditions where the nanoparticle is not exposed to a laser or is exposed to a laser of power lower by a factor of at least 0, 1, 1.1, 1.5, 2, 5, 10, $10^3$, $10^5$ or $10^{10}$ than the laser power of the heating step.

As shown in the experimental examples, typical values of heating rates are 0.2-0.4° C./sec per mg of nanoparticle while a typical value of cooling rate is 0.1° C./sec per mg of nanoparticle. In some cases, a different value of the heating or cooling rate can be reached, preferentially by a factor higher than 0, 1, 1.1, 1.5, 2, 5, 10, $10^3$ or $10^5$, by: i) varying nanoparticle concentration, ii) varying the laser power, or iii) adjusting the nanoparticle size, size distribution, coating, surface to volume ratio or nanoparticle crystallinity. In one embodiment of the invention, the duration of the cooling step is lower than the duration of the heating step, preferentially by a factor of at least 0, 1, 1.1, 1.5, 2, 5, 10, $10^3$ or $10^5$ preferably by a factor of at least 2, more preferably by a factor of at least 5. This may preferentially be the case, when the production of heat occurs at the surface of the nanoparticle, hence easing heat transfer between nanoparticle surface and the environment or surrounding of the nanoparticle.

In one embodiment of the invention, preferentially within a heating step, the difference between the maximum temperature reached by applying the laser on the nanoparticle and the temperature reached at the end of the heating step is smaller than $10^{50}$, $10^{20}$, $10^{10}$, $10^5$, $10^3$, $10^2$, 10, 5, 2, 1, $10^{-1}$ or $10^{-3}$° C., preferably lower than 5° C., most preferably lower than 1° C. Such difference can occur when the nanoparticles continue to heat after the laser has been switched of (or reduced in power) at the end of the heating step.

In one embodiment of the invention, the difference between the duration of application of the laser at a given power and the lapse of time during which the body part heats during this laser application is lower than $10^5$, $10^3$, 10, 5, 2, 1 or $10^{-3}$ second(s), preferably lower than $10^3$ seconds, most preferably lower than 10 seconds. This can be the case when the nanoparticles stop or reduce heating after the laser has been switched off or reduced in power. Such difference can occur when the nanoparticles continue to heat after the laser has been switched of (or reduced in power) at the end of the heating step.

In some other embodiments of the invention, preferentially within a heating step, the difference between the maximum temperature reached by applying the laser on the nanoparticle and the temperature reached at the end of the heating step is higher than $10^{-50}$, $10^{-20}$, $10^{-10}$, $10^{-5}$, $10^{-3}$, $10^{-2}$, 1, 5, 10 or $10^3$° C., preferably higher than $10^{-20}$° C., most preferably higher than $10^{-2}$° C.

In one embodiment of the invention, the difference between the duration of application of the laser at a given power and the lapse of time during which the body part heats during this laser application is higher than $10^5$, $10^3$, 10, 5, 2, 1 $10^{-3}$, $10^{-5}$, $10^{-10}$ or $10^{-20}$ second(s), preferably higher than $10^{-5}$ seconds, most preferably higher than $10^{-3}$ seconds. This can be the case when the nanoparticles do not stop or do not reduce heating after the laser has been switched off or reduced in power.

In one embodiment, the number of sequences of the first step and the second step increases, preferentially by a factor of at least 0, 1, 5, 10, $10^3$ or $10^5$, when the nanoparticle concentration increases, preferentially by a factor of at least 0, 1, 5, 10, $10^3$ or $10^5$.

In one embodiment, the heating rate increases, preferentially by a factor of at least 0, 1, 5, 10, $10^3$ or $10^5$, when the nanoparticle concentration increases, preferentially by a factor of at least 0, 1, 5, 10, $10^3$ or $10^5$.

In one embodiment, the cooling rate decreases, preferentially by a factor of at least 0, 1, 5, 10, $10^3$ or $10^5$, when the nanoparticle concentration increases, preferentially by a factor of at least 0, 1, 5, 10, $10^3$ or $10^5$.

In one embodiment, the number of sequences of the first step and the second step can be higher than 1, 5, 10, $10^3$, $10^5$ or $10^{10}$ sequence(s) per second, minute, hour, day, month or year, preferentially per mg of nanoparticle.

In some other embodiments, the number of sequences of the first step and the second step can be lower than $10^{10}$, $10^5$, $10^3$, 10, 5 or 1 sequence(s) per second, minute, hour, day, month or year, preferentially per mg of nanoparticle.

In another embodiment of the invention, the magnetic nanoparticles, in particular magnetosomes, are nanoparticles characterized by at least one of the following properties: i), a coercivity lower than 0.01, 0.1, 1, 10, 100, $10^3$, $10^4$, $10^5$, $10^9$, or $10^{20}$ Oe, ii), a ratio between remanent and saturating magnetization lower than 0.01, 0.1, 0.2, 0.3, 0.4, 0.5, 0.75, 0.9, or 0.99, iii), a saturating magnetization lower than 0.1, 1, 5, 10, 50, 200, 1000, or 5000 emu/g, iv), magnetic properties preferentially measured or observed at a temperature lower than 0.1 K, 1 K, 10 K, 20 K, 50 K, 100 K, 200 K, 300 K, 350 K, or 3000 K, viii), a size that is lower than 0.1, 0.5, 1.5, 10, 15, 20, 25, 30, 50, 60, 70, 80, 100, 120, 150, or 200 nm, ix), the presence of more than 50, 25, 15, 10, 5, 2, or 1% of organic or carbon material originating from the synthetizing living organism, x), the presence of less than 99, 95, 80, 70, 60, 50, or 25% of mineral material originating from the synthetizing living organism, or xi), a specific absorption rate (SAR) that is lower than 1, 10, 1000, or $10^4$ Watt per gram of magnetic nanoparticle, in particular magnetosome, preferentially measured under the irradiation by the laser radiation.

In one embodiment of the invention, the nanoparticles are metallic. Preferably, metallic nanoparticles comprise at least 1, 10, $10^3$, $10^5$ or $10^9$ metallic atom(s) or comprise at least 1, 10, 50, 75 or 90% of metallic atoms, where this percentage can be the ratio between the number or mass of metallic atoms in the nanoparticles divided by the total number or mass of all atoms in the nanoparticles. In one embodiment, the nanoparticles, preferentially metal oxide nanoparticles, can also comprise at least 1, 10, $10^3$, $10^5$ or $10^9$ oxygen atom(s), or comprise at least 1, 10, 50, 75 or 90% of oxygen atoms, where this percentage can be the ratio between the number or mass of oxygen atoms in the nanoparticles divided by the total number or mass of all atoms in the nanoparticles.

In one embodiment, an atom can be a chemical element or an element.

In another embodiment of the invention, the metal or metal atom is selected in the list consisting of: Lithium, Beryllium, Sodium, Magnesium, Aluminum, Potassium, Calcium, Scandium, Titanium, Vanadium, Chromium, Manganese, Iron, Cobalt, Nickel, Copper, Zinc, Gallium, Rubidium, Strontium, Yttrium, Zirconium, Niobium, Molybdenum, Technetium, Ruthenium, Rhodium, Palladium, Silver, Cadmium, Indium, Tin, Cesium, Barium, Lanthanum, Cerium, Praseodymium, Neodymium, Promethium, Samarium, Europium, Gadolinium, Terbium, Dysprosium, Holmium, Erbium, Thulium, Ytterbium, Lutetium, Hafnium, Tantalum, Tungsten, Rhenium, Osmium, Iridium, Platinum, Gold, Mercury, Thallium, Lead, Bismuth, Polonium, Francium, Radium, Actinium, Thorium, Protactinium, Uranium, Neptunium, Plutonium, Americium, Curium, Berkelium, Californium, Einsteinium, Fermium, Mendelevium, Nobelium, Lawrencium, Rutherfordium, Dubnium, Seaborgium, Bohrium, Hassium, Meitnerium, Darmstadtium, Roentgenium, Copernicium, Nihonium, Flerovium, Moscovium, and Livermorium or Livermorium atom.

In another embodiment of the invention, the nanoparticles comprise less than 1, 10, $10^3$, $10^5$ or $10^9$ metallic atom(s) or comprises less than 1, 10, 50, 75 or 90% of metallic atoms, where this percentage can be the ratio between the number or mass of metallic atoms in the nanoparticles divided by the total number or mass of all atoms in the nanoparticles. It can also comprise less than 1, 10, $10^3$, $10^5$ or $10^9$ oxygen atom(s), or comprise less than 1, 10, 50, 75 or 90% of oxygen atoms, where this percentage can be the ratio between the number or mass of oxygen atoms in the nanoparticles divided by the total number or mass of all atoms in the nanoparticles.

In one embodiment, the nanoparticles comprise a metal oxide or metallic and oxygen atoms.

In one embodiment of the invention, the nanoparticle is magnetic when it has a magnetic behavior or property, where the magnetic behavior or property is preferentially selected from the group consisting of a diamagnetic, superparamagnetic, paramagnetic, ferromagnetic, and ferrimagnetic behavior or property.

In one embodiment, the magnetic behavior or property exists at a temperature, which is lower than: i) $10^5$, $10^3$, 500, 350, 200, 100, 50, 20, 10, 1, 0.5 or 1 K (Kelvin), ii) the Curie temperature, iii) the melting or fusion temperature, or iv) the blocking temperature.

In some other embodiments, the magnetic behavior or property exists at a temperature, which is higher than: i) 0.5, 1, 10, 20, 50, 100, 200, 350, 500, $10^3$ or $10^5$ K, ii) the Curie temperature, iii) the melting temperature, or iv) the blocking temperature.

In still some other embodiments, the magnetic behavior or property exists at a temperature, which is between $10^{-20}$ and $10^{20}$ K, or between 0.1 and 1000 K.

In one embodiment, it can be necessary to image the body part, preferentially to follow the evolution or growth of the body part following the treatment, using an imaging technique such as magnetic resonance imaging (MRI), computing tomography (CT), scanner, positron emission tomography (PET), radiography, or echography.

In one embodiment of the invention, the composition of the magnetic nanoparticle, in particular magnetosome, prevents efficient imaging of the body part.

In some other embodiments of the invention, the concentration of the magnetic nanoparticle, in particular magnetosome, is too large to enable efficient imaging of the body part.

In still some other embodiments of the invention, the magnetic nanoparticle, in particular magnetosome, acts like a screen or hide the body part and can prevent efficient imaging of the body part.

In one embodiment of the invention, the composition of the magnetic nanoparticle, in particular the magnetosome, is adjusted or changed to enable imaging of the body part. In one embodiment, the iron oxide composition is replaced by a composition comprising another substance selected among the families of lithium, beryllium, scandium, titanium, vanadium, chromium, manganese, iron, nickel, copper, zinc, boron, carbon, nitrogen, oxygen, fluorine, or helium, or among alkali metals, alkaline earth metals, coinage metals, triels, tetrels, pentels, pnictogens, chalcogens, halogens, or noble gases.

In another embodiment of the invention, the concentration of the magnetic nanoparticle, in particular magnetosome, is decreased, preferentially below $10^{-20}$, $10^{-9}$, $10^{-6}$, $10^{-3}$, $10^{-1}$, 1, 10, $10^3$, $10^6$, $10^9$, or $10^{20}$ mg per $cm^3$ or mg per $cm^3$ of body part, to enable efficient imaging of the body part.

In still another embodiment of the invention, the concentration of the magnetic nanoparticle, in particular magnetosome, is comprised between a minimum value and a maximum value.

In one embodiment of the invention, the minimum value is sufficiently large to enable the production of heat by the magnetic nanoparticle, in particular magnetosome, or the dissociation of the compound from the magnetic nanoparticle, in particular magnetosome, preferentially under the irradiation by the laser radiation. In one embodiment of the invention, the minimum value is higher than $10^{-20}$, $10^{-9}$, $10^{-6}$, $10^{-3}$, $10^{-1}$, 1, 10, $10^3$, $10^6$, $10^9$, or $10^{20}$ mg per $cm^3$ or mg per $cm^3$ of body part.

In some other embodiments of the invention, the maximum value is sufficiently low to enable imaging of the body part.

In one embodiment of the invention, the maximum value is higher than $10^{-20}$, $10^{-9}$, $10^{-6}$, $10^{-3}$, $10^{-1}$, 1, 10, $10^3$, $10^6$, $10^9$, or $10^{20}$ mg per $cm^3$ or mg per $cm^3$ of body part.

In one embodiment of the invention, the SAR of the magnetic nanoparticle, in particular magnetosome, can be designated as $SAR_M$ or $SAR_{real}$, as defined later in this invention.

In one embodiment of the invention, the magnetic nanoparticles, in particular magnetosomes, are arranged in chains comprising more than 1, 2, 3, 4, 5, 6, 7, 8, 9, 10, 15, 20, 25, 30, 35, or 40 magnetic nanoparticle(s), in particular magnetosome(s). Magnetic nanoparticle(s), in particular magnetosome(s), can be arranged in chains inside magnetotactic bacteria or outside magnetotactic bacteria, preferentially after their extraction or isolation from magnetotactic bacteria.

In one embodiment of the invention, magnetic nanoparticles, in particular magnetosomes, are not arranged in chains.

In one embodiment of the invention, magnetic nanoparticles, in particular magnetosomes, are purified to remove more than 10, 50, or 90% of endotoxins and/or other biological or carbonaceous material such as proteins and lipids originating from magnetotactic bacteria. Such purification can use a detergent such as NaOH or KOH. Purified magnetic nanoparticles, in particular magnetosomes, can be recoated with a synthetic coating such as a substance comprising a function selected in the group comprising carboxylic acids, phosphoric acids, sulfonic acids, esters, amides, ketones, alcohols, phenols, thiols, amines, ether, sulfides, acid anhydrides, acyl halides, amidines, amides, nitriles, hydroperoxides, imines, aldehydes, or peroxides. The coating can be made of carboxy-methyl-dextran, citric acid, phosphatidylcholine (DOPC), or oleic acid.

In one embodiment of the invention, the coating enables the dispersion of the magnetic nanoparticles, in particular magnetosomes, in a matrix or solvent such as water. Purified magnetic nanoparticles, in particular magnetosomes, (recoated or not) are preferentially non-pyrogenic. They preferentially comprise less than $10^8$, $10^5$, $10^3$, or 10 EU (endotoxin unit) per: i), $mm^3$ or, ii), mL of magnetic nanoparticles, in particular magnetosomes, iii), mL of magnetic nanoparticle, in particular magnetosome, suspension, or iv), mL or $cm^3$ of body part. Purified magnetic nanoparticles, in particular magnetosomes, (recoated or not) can be re-suspended in a liquid or re-dispersed in a matrix to result in a homogenous dispersion or in a high stability.

In one embodiment of the invention, a suspension of magnetic nanoparticles, in particular magnetosomes, is stable, which preferentially means that it is stable at a concentration higher than 1, 5, 10, 50, 100, 200, 500, or 1000 mg of magnetic nanoparticles, in particular magnetosomes, per mL of solvent, i.e. the optical density of this suspension, preferentially measured at 480 nm or another fixed wavelength, does not decrease by more than 1, 5, 10, 50, 75, or 90%, preferentially within more than 1, 5, 10, $10^3$, $10^7$, or $10^{20}$ second(s) following homogenization or mixing of this suspension.

In another embodiment of the invention, an assembly of magnetic nanoparticles, in particular magnetosomes, is homogenously distributed. This preferentially means that magnetic nanoparticles, in particular magnetosomes, occupy more than $10^{-6}$, $10^{-3}$, $10^{-1}$, 1, 5, 10, 50, or 75% of the volume in which magnetic nanoparticles, in particular magnetosomes, are administered, mixed, inserted, or introduced. This percentage preferentially represents the ratio between the volume of the body part, in which magnetic nanoparticles, in particular magnetosomes, are administered, mixed, inserted, or introduced, measured before magnetic nanoparticle, in particular magnetosome, administration, mixing, insertion, or introduction, to/in the body part divided by the volume of the body part occupied by the magnetic nanoparticles, in particular magnetosomes, measured after magnetic nanoparticle, in particular magnetosome, administration, mixing, insertion, or introduction, to/in the body part, preferentially measured less than $10^{50}$, $10^{20}$, $10^{10}$, $10^5$, $10^2$, 10, or 1 minute(s) following magnetic nanoparticle, in particular magnetosome, administration, mixing, insertion, or introduction to/in the body part.

In one embodiment of the invention, magnetic nanoparticles, in particular magnetosomes, are synthesized by a living organism, designated as synthetizing living organism, which consists or comprises at least 1, 2, 5, 10, $10^3$, $10^6$, or $10^9$ eukaryotic or prokaryotic cell(s).

In one embodiment of the invention, magnetic nanoparticles, in particular magnetosomes, are synthesized intracellularly, i.e. inside a eukaryotic or prokaryotic cell.

In another embodiment of the invention, magnetic nanoparticles, in particular magnetosomes, are synthesized extra-cellularly, i.e. outside a eukaryotic or prokaryotic cell.

In still another embodiment of the invention, magnetic nanoparticles, in particular magnetosomes, are synthesized or produced or crystallized or assembled or transformed into a nanoparticle by a living organism, a cell, compartment, organelle, or other biological material, such as protein, lipid, enzyme, DNA, or RNA, which is preferentially produced by or originates from an eukaryotic or prokaryotic cell.

In some other embodiments of the invention, a chemical synthesis is used to produce a chemical substance or compound that mimics, copies, or reproduces the compartment, organelle, or other biological material, wherein this chemical synthesis or chemical substance can be used or can result in the production of the magnetic nanoparticle, in particular the magnetosome.

In one embodiment of the invention, the compartment, organelle, or other biological material, is a lysosome, an endosome, a vesicle, preferentially biological material that has the capacity or the function either to dissolve or transform crystallized iron into free iron or to transform free iron into crystalized iron.

In one embodiment of the invention, this transformation is partial and preferentially results in the destruction or formation of partly crystallized assembly of iron atoms or ions, or preferentially results in a mixture of crystallized iron and non-crystallized iron.

In one embodiment of the invention, crystallized iron is defined as an assembly of iron atoms or ions that leads to the presence of crystallographic planes, preferentially observable using a technique such as transmission or scanning electron microscopy as a characterization method, and free iron can preferentially be defined as one of several iron atoms or ions that do not lead to the presence of crystallographic planes, preferentially highlighted by the absence of diffraction patterns, using for example transmission or scanning electron microscopy as a characterization method.

In one embodiment of the invention, magnetic nanoparticles, in particular magnetosomes, are synthesized by a living organism when at least 1, 2, 5, 10 or 100 step(s) of their production, such as crystallization of iron oxide, stabilization of the iron oxide mineral, organization of the minerals of the magnetic nanoparticles, in particular magnetosome, for example in chains or aggregates, involves or is due to a living organism, a cell, compartment, organelle, or other biological material, such as protein, lipid, enzyme, DNA, or RNA, which is preferentially produced by or originates from an eukaryotic or prokaryotic cell. In this case, this can mean that magnetic nanoparticles, in particular magnetosomes, are not synthesized chemically or are different from chemical nanoparticles.

In another embodiment of the invention, magnetic nanoparticles are not synthesized by a living organism when less than 1, 2, 5, 10 or 100 step(s) of their production, such as crystallization of iron oxide, stabilization of the iron oxide mineral, organization of the minerals of magnetic nanoparticles, for example in chains or aggregates, involves or is due to a living organism, a cell, compartment, organelle, or other biological material, such as protein, lipid, enzyme, DNA, or RNA, which is preferentially produced by or originates from an eukaryotic or prokaryotic cell. In this case, this can mean that magnetic nanoparticles are synthesized chemically or are the same as or are similar to chemical nanoparticles.

In one embodiment of the invention, magnetic nanoparticles, in particular magnetosomes, are synthesized by a living organism or prokaryotic cell, which is preferentially a *bacterium*, most preferentially a magnetotactic *bacterium* such as *Magnetospirillum magneticum* strain AMB-1, magnetotactic *coccus* strain MC-1, three facultative anaerobic vibrios strains MV-1, MV-2 and MV-4, the *Magnetospirillum magnetotacticum* strain MS-1, the *Magnetospirillum gryphiswaldense* strain MSR-1, a facultative anerobic magnetotactic spirillum, *Magnetospirillum magneticum* strain MGT-1, and an obligate anaerobe, *Desulfovibrio magneticus* RS-1.

In one embodiment of the invention, a magnetotactic *bacterium* is defined as an organism that is able to produce a magnetic nanoparticle, in particular magnetosome. In one embodiment of the invention, the magnetotactic *bacterium* uses the magnetic nanoparticle, in particular magnetosome, to swim in the direction of the earth magnetic field.

In one embodiment of the invention, a magnetotactic *bacterium* is defined as a *bacterium* able to synthesize magnetic nanoparticles, in particular magnetosomes, wherein these magnetic nanoparticles, in particular magnetosomes, are preferentially characterized by at least one of the following properties: i), they are produced intracellularly, ii), they are magnetic, iii), they comprise a mineral, iv), their core is preferentially composed of a metallic oxide such as iron oxide, v), their core is surrounded by biological material such as lipids, proteins, endotoxins, which is preferentially removed, most preferentially removed by another organism than the magnetotactic *bacterium* such as a human, v), they are arranged in chains, or vi), they produce heat under the application of a laser or irradiation by a laser.

In one embodiment of the invention, the magnetic nanoparticle, in particular the magnetosome, comprises the mineral part synthesized by magnetotactic bacteria, i.e. preferentially the crystallized iron oxide produced by these bacteria. In this case, magnetic nanoparticles, in particular magnetosomes, or the mineral parts of magnetic nanoparticles, in particular magnetosomes, preferentially do not comprise proteins, lipids, endotoxins, or biological materials comprising carbon or carbonaceous material, or more than 0.1, 1, 10, 30, 50, or 75% of carbon, which is/are produced by these bacteria.

In one embodiment of the invention, the magnetic nanoparticle, in particular magnetosome, comprises the mineral part synthetized by magnetotactic bacteria and a substance, which is a carbonaceous biological material synthesized by a magnetotactic *bacterium*. Such substance can preferentially be used in the laser medical or chemical or biological or cosmetic treatment. It may trigger an immune response, preferentially against pathological cells, or target the pathological cells or have a pharmacologic or metabolic or cosmetic effect. When such substance comprises toxic carbonaceous material synthesized by a magnetotactic *bacterium*, such as endotoxins or other types of immunogenic or toxic proteins, lipids, DNA, RNA, synthesized by these bacteria, such substance is preferentially removed or destroyed, most preferentially selectively to avoid the removal of other substances, which are preferentially non-toxic and/or of interest or potential efficacy for/in the laser medical or chemical or biological or cosmetic treatment. When such substance comprises carbonaceous material synthesized by a magnetotactic *bacterium*, which can be used in the laser medical or chemical or biological or cosmetic treatment, which preferentially targets or destroys pathological cells, which is preferentially non-toxic towards healthy cells, such substance is preferentially maintained in/on the magnetic nanoparticle, in particular magnetosome, or at the magnetic nanoparticle, in particular magnetosome, surface or is bound or linked or associated to/with the magnetic nanoparticle, in particular magnetosome, preferentially before or without the irradiation by the laser radiation, preferentially before the administration of the magnetic nanoparticle, in particular magnetosome, in/to the body part.

In one embodiment of the invention, the substance described in the previous embodiment is the compound.

In one embodiment of the invention, pathological cells are cells that are old, preferentially older than $10^{-9}$, $10^{-6}$, $10^{-3}$, 1, $10^3$, $10^6$ minutes, or cells that belong to an old individual, preferentially cells that belong to an individual older than 1, 5, 10, 25, 50, 75, 80, 90, or 100 years, or cells that have entered into an apoptotic or necrotic state, or cells that have a higher or smaller size than a healthy cell, preferentially by a factor of more than 1.1, 1.2, 1.5, 2, 5, 10, $10^3$, or cells that possess organelle(s) that do(es) not work properly, mitochondria producing less energy than they do in a healthy cell, or ribosome linking more or less amino acids than they do in a healthy cell, or cellular membrane not enabling endocytosis or trans-membrane diffusion as they usually do in a healthy cell.

In another embodiment of the invention, pathological cells are cells that lead to an ugly or unusual appearance, where an unusual appearance can be defined as an appearance or condition that is different from that of 1, 5, 10, 50, 75, or 90% of all individuals or of a representative sample of the whole population. An unusual appearance can also be associated to a skin disease, to the presence of plaque, redness, pimple, itch, or blister, on the skin.

In still some other embodiments of the invention, pathological cells are defined as cells that are responsible for diseases, such as cancer, malfunction of the body part, or cells that lead to the death of an individual or to fever or to an increase in the temperature of the individual, preferentially by more than 0.1, 1, 2, 3, 4, 5, 10, 50, or 100° C., preferentially above the physiological temperature, preferentially within a whole individual or a portion of an individual.

In still some other embodiments of the invention, pathological cells are defined as cells that do not divide at a normal speed, or cells that divide at a speed which is 1.1, 2, 5, 10, $10^3$, $10^6$, or $10^9$ higher than the speed of division of a healthy cell.

In still some other embodiments of the invention, pathological cells are defined by their presence in large quantity in the body part, by the presence of more than 1, 10, $10^3$, $10^6$, $10^9$, or $10^{20}$ pathological cells per cm$^3$ of body part.

In still some other embodiments of the invention, pathological cells are defined by their increasing number, preferentially by a factor of more than 1.1, 10, $10^3$, $10^6$, $10^9$, or $10^{20}$ between a time considered before the individual is suffering from a disease, preferentially less than 1, 2, 10, $10^3$, $10^6$, $10^9$, or $10^{40}$ hours before the individual is suffering from a disease, preferentially the disease responsible for the appearance of the pathological cells, and a time after or during the disease of the individual, preferentially more than 1, 2, 10, $10^3$, $10^6$, $10^9$, or $10^{40}$ hours after the starting time of the disease of the individual.

In one embodiment of the invention, pathological cells are bacteria, preferentially pathological bacteria, tumor cells, preferentially benign or malign tumor cells.

In one embodiment of the invention, pathological cells are defined as cells that are in contact, in interaction, with foreign material not belonging to the individual, such as viruses.

In one embodiment of the invention, pathological cells are defined as cells in which viruses have penetrated, or are replicating.

In one embodiment of the invention, pathological cells are assimilated to viruses or to other organisms or entities that colonize cells or target cells or destroy cells or use cells or enter in interaction with cells, preferentially either to enable their own reproduction, multiplication, survival, or death.

In one embodiment of the invention, a pathological cell is defined as a healthy cell that has undergone a transformation, modification, or a healthy cell that is dead, preferentially due to the presence of a virus or to other organisms or entities that colonize cells or use cells or enter in interaction with cells for their own reproduction, multiplication, or survival.

In one embodiment of the invention, the presence in the body part of viruses or of other organisms or entities that colonize cells or use cells or enter in interaction with cells for their reproduction, multiplication, or survival, can be used to deduce the presence of pathological cells in the body part or is responsible for the presence of pathological cells in the body part.

In one embodiment of the invention, the magnetic nanoparticles are chemical nanoparticles, i.e. nanoparticles that have not been synthesized by the synthetizing living organism, most preferentially by a magnetotactic *bacterium*, but possess at least 1, 2, 3, 4, 5, 6, 7, 8, 9, or 10 common property(ies) with the magnetosomes, where these common properties are preferentially a ferrimagnetic behavior, a large size, a crystallization, a mono-domain, a maghemite or magnetite composition, a chain arrangement, a cubic, spherical, cubo-octahedral, cigar-shaped, or elongated geometry, or a ratio between two different dimensions of the magnetosomes that is comprised between $10^{-3}$ and $10^3$.

In one embodiment of the invention, the magnetic nanoparticles can be superparamagnetic or ferrimagnetic nanoparticles, where the magnetic properties of the magnetic nanoparticles are preferentially measured at a temperature higher than 0.1, 1, 5, 10, 50, 100, 200, 300, or 400 K.

In one embodiment of the invention, the magnetic nanoparticles are comprised or composed of a metal or metal oxide or of a majority of metallic atoms or of metallic and oxygen atoms.

In some other embodiments of the invention, the magnetic nanoparticles are comprised or composed of iron oxide such as maghemite or magnetite.

In one embodiment of the invention, magnetic nanoparticles, in particular magnetosomes, are defined by at least one of the properties that result from the application of the laser on them, such as duration of the first or second step, maximum or minimum temperature or maximum or minimum percentage of dissociation, resulting from the sequential irradiation by the laser radiation of the magnetic nanoparticle, in particular magnetosome, or body part.

In one embodiment of the invention, the irradiation by the laser or laser radiation of the magnetosomes can mean that the magnetosomes are irradiated by the laser radiation.

In one embodiment of the invention, the irradiation by the laser radiation is or is due to an electromagnetic wave. The laser radiation can be an electromagnetic wave. The electromagnetic wave or laser radiation is preferentially emitted or generated by a laser equipment or apparatus. The electromagnetic wave is preferentially associated with: i), the propagation of electric and magnetic field waves, ii), waves that do not involve the movement of particles with a mass, or iii), waves comprising photons, or iv), light waves. Preferentially, the magnetic field produced by the electromagnetic wave has a strength lower than $10^{10}$, $10^5$, $10^2$, 10, 1, $10^{-1}$, $10^{-2}$, $10^{-5}$, or $10^{-10}$ T. Preferentially, the electric field produced by the electromagnetic field has a strength lower than $10^{10}$, $10^5$, $10^2$, 10, 1, $10^{-1}$, $10^{-2}$, $10^{-5}$, or $10^{-10}$ V·m$^{-1}$.

In one embodiment of the invention, the electromagnetic wave oscillates in space or time at a frequency that is lower than $10^{10}$, $10^5$, $10^3$, 10, 1, $10^{-1}$, $10^{-3}$, $10^{-5}$, or $10^{-10}$ GHz.

In some other embodiments of the invention, the electromagnetic wave oscillates in space or time at a frequency that is higher than $10^{10}$, $10^5$, $10^3$, 10, 1, $10^{-1}$, $10^{-3}$, $10^{-5}$, or $10^{-10}$ GHz.

In one embodiment of the invention, the laser radiation is monochromatic, i.e. it comprises photons with a single wavelength.

In some other embodiments of the invention, the laser radiation is polychromatic, i.e. it comprises photons with multiple wavelengths, or with more than 1, 2, 5, 10, or $10^3$ wavelength(s).

In one embodiment of the invention, the laser equipment is designated as laser.

In one embodiment of the invention, the laser equipment is a device that emits or generates laser radiation, preferentially through a process of optical amplification based on stimulated emission of electromagnetic radiation. It is preferentially combined or used in combination with: i), a system such as an optical fiber that can carry or transport a laser radiation from this equipment to the body part, ii), a system such as a lens, preferentially convergent or divergent, or a combination of lenses that can focalize or focus or de-focalize or de-focus the laser radiation preferentially on the body part or a specific location of the body part. The combination or association of the laser equipment with a system of light transportation and/or light focusing is designated as laser apparatus in this patent application.

The laser or laser equipment or apparatus is preferentially a: i), gas laser, preferentially a helium-neon, argon, krypton, xenon ion, nitrogen, carbon dioxide or monoxide, or excimer laser, or ii), a chemical laser, preferentially a hydrogen fluoride, deuterium fluoride, chemical oxygen-iodine, or All gas-phase iodine laser, or iii), a dye laser, or iv), a metal-vapor laser, preferentially a helium-cadmium, helium-mercury, helium-selenium, helium-silver, a strontium vapor, a Neon copper, a Copper vapor, gold vapor, or manganese vapor laser, or v), a solid-state laser, preferentially, a ruby, Nd:YAG, NdCrYAG, Er:YAG, Neodymium YLF, Neodymium doped Yttrium orthovanadate, Neodymium doped yttrium calcium oxoborate, Neodymium glass, Titanium sapphire, Thulium YAG, Ytterbium YAG, Ytterbium:$_2$O$_3$, Ytterbium doped glass, Holmium YAG, Cerium doped lithium strontium (or calcium) aluminum fluoride, Promethium 147 doped phosphate glass, Chromium doped chrysoberyl (alexandrite), Erbium doped and erbium-ytterbium codoped glass, Trivalent uranium doped calcium fluoride, or divalent samarium doped calcium fluoride laser, or v), a semi-conductor laser, preferentially a Semiconductor diode, GaN, InGaN, AlGaInP, AlGaAs, InGaAsP, lead salt, Vertical cavity surface emitting, Quantum cascade, or Hybrid silicon laser, or vi), Free electron, Gas dynamic, "Nickel-like" Samarium, Raman, or Nuclear pumped laser. The laser equipment preferentially works in one of the following different ranges of wavelengths: X-rays, ultraviolet, visible, near infrared, mid infrared, and far infrared.

In one embodiment of the invention, the continuous wave laser power can be comprised between $10^{-3}$ mW and $10^3$ kW.

In some other embodiments of the invention, the laser pulse energy is preferentially comprised between 1 mJ and 1 kJ.

In one embodiment of the invention, the laser in monomodal.

In some other embodiments of the invention, the laser is multi-modal.

In one embodiment of the invention, the wavelength $\lambda$ is a monochromatic laser radiation. It is preferentially characterized by a spread or distribution in wavelengths, $\Delta\lambda$, which is lower than $10^3\lambda$, $10\lambda$, $\lambda/1.01$, $\lambda/2$, $\lambda/10$, or $\lambda/10^3$.

In another embodiment of the invention, each of the n different wavelengths $\lambda_i$ ($1<i<n$) of a polychromatic laser radiation is characterized by a spread or distribution in wavelengths, which is such that $\Delta\lambda_i$ is lower than the absolute value of $(\lambda_i-\lambda_j)$, where $\lambda_i$ and $\lambda_j$ are two different wavelengths of the polychromatic laser radiation, preferentially lower by more than $10^9$, $10^6$, $10^3$, 10, or $10^{-1}$ nm.

In one embodiment of the invention, the laser radiation is characterized by or possesses or is associated with or comprises a laser power, laser power density, laser intensity, laser strength, or laser wavelength.

In one embodiment of the invention, the laser radiation is continuous.

In some other embodiments of the invention, the laser radiation is pulsed.

In one embodiment of the invention, the duration of a pulse is smaller than 10, 1, $10^{-1}$, $10^{-3}$, $10^{-6}$, $10^{-9}$ or $10^{-15}$ seconds, preferably smaller than 10 seconds, more preferably smaller than 1 second.

In some other embodiments of the invention, the duration of a pulse is higher than $10^{-50}$, $10^{-20}$, $10^{-10}$, $10^{-5}$, $10^{-1}$ or 1 second, preferably higher than $10^{-50}$ seconds, more preferably higher than $10^{-20}$ seconds.

In one embodiment of the invention, the word laser radiation can designate or mean laser, laser equipment, laser apparatus, laser radiation beam, laser beam, laser energy, laser intensity, laser power, laser power density, laser strength, laser frequency, laser wavelength, or laser pulsation.

In still some other embodiments of the invention, the laser power density can be defined as the laser power divided by the volume, surface, or length, preferentially of the body part, which is preferentially irradiated by laser radiation or onto which laser radiation is preferentially applied.

In one embodiment of the invention, the laser power or laser power density or another parameter of the laser is the laser power or power density or other parameter of the laser measured outside or at some distance, preferentially at a distance that is higher than $10^{-20}$, $10^{-10}$, $10^{-5}$, 1, $10^5$, $10^{10}$, or $10^{20}$ nm, of or from the equipment or apparatus generating the laser radiation.

In one embodiment of the invention, the laser power or laser power density or another parameter of the laser is preferentially measured in the body part or region of magnetic nanoparticle, in particular magnetosome.

In one embodiment of the invention, the laser radiation is not or is different from a magnetic field, an alternating magnetic field, preferentially of strength higher $10^{-9}$, $10^{-6}$, $10^{-3}$, $10^{-1}$, 1, $10^3$, or $10^6$ T, preferentially of frequency higher than $10^{-9}$, $10^{-6}$, $10^{-3}$, $10^{-1}$, 1, 10 kHz, of an acoustic wave, of an ultrasound, of X-rays, of gamma rays, or of waves associated with or inducing or comprising the movement or oscillation, preferentially spatially or temporally, of particles with a non-zero mass or with a mass higher than $10^{-80}$, $10^{-40}$, $10^{-20}$, $10^{-10}$, $10^{-5}$, $10^{-1}$, or 1 gram.

In one embodiment of the invention, a laser radiation medical or chemical or biological or cosmetic treatment, which could be designated as medical or chemical or biological or cosmetic treatment, treatment, or laser treatment, uses the laser radiation or the irradiation by the laser radiation, preferentially applied on magnetic nanoparticle, in particular magnetosome, or body part, to trigger a medical, pharmaceutical, immunological, metabolic, diagnostic, medical device, drug, biological, or cosmetic effect.

In one embodiment of the invention, a medical treatment can be the treatment of an illness or disease, such as an infectious disease, a cancer, or a therapeutic treatment. It can be the treatment of a disease due to the malfunction of an organ or body part. It can lead to or be associated with the destruction, disappearance, of pathological cells, preferentially of more than 1, 5, 10, 50, 75, 80, or 90% of pathological cells, where this percentage can be equal to the ratio between the number of pathological cells, preferentially comprised in the body part, after the medical or chemical or biological or cosmetic treatment, and the number of pathological cells, preferentially comprised in the body part, before the medical treatment. The presence of pathological cells, preferentially in the body part, can be due to the malfunction of a body part of an individual.

In one embodiment of the invention, the medical or chemical or biological or cosmetic treatment is a diagnostic of a disease or a cosmetic treatment.

In one embodiment of the invention, the laser medical or chemical or biological or cosmetic treatment is the treatment of a disease, preferentially an infectious disease, due to or associated with the presence of viruses, bacteria, or other types of organisms or pathological cells than those present in the treated individual before the beginning or appearance of the disease in the individual.

In one embodiment of the invention, the medical or chemical or biological or cosmetic treatment is the treatment of anemia, preferentially the anemia or lack of a substance comprised in the body part, preferentially the anemia or lack in or of iron or of a substance comprised in the compound.

In one embodiment of the invention, the anemia is defined as a concentration in a substance comprised in an individual, which is more than 1.001, 1.01, 1.1, 2, 5, 10, $10^2$, $10^5$, $10^{10}$, or $10^{20}$ times lower in the individual suffering from anemia than in the healthy individual.

In one embodiment, anemia of a substance comprised in the body part is defined as a concentration of a substance comprised in the magnetic nanoparticles, in particular the magnetosomes, or compound, such as iron, oxygen or a substance comprised in the compound, which is lower, preferentially 1.001, 1.01, 1.1, 2, 5, 10, $10^2$, $10^5$, $10^{10}$, or $10^{20}$ times lower, in the body part before administration of the magnetic nanoparticles, in particular the magnetosomes, or without magnetic nanoparticles, in particular magnetosomes, in the body part than after administration of the magnetic nanoparticles, in particular the magnetosomes, or with magnetic nanoparticles, in particular magnetosomes, in the body part.

In an embodiment of the invention, a compound is bound or attached to the magnetic nanoparticle, in particular magnetosome, preferentially before the irradiation by the laser radiation of the magnetic nanoparticles, in particular the magnetosomes.

In one embodiment of the invention, compound(s) or the compound(s) is characterized by an assembly comprising more than 1, 10, $10^2$, $10^3$, $10^5$, $10^{10}$, $10^{20}$, or $10^{50}$ compound(s).

In still another embodiment of the invention, compound(s) or the compound(s) is characterized by an assembly comprising less than 1, 10, $10^2$, $10^3$, $10^5$, $10^{10}$, $10^{20}$, or $10^{50}$ compound(s).

In one embodiment of the invention, the laser radiation is a radiation, which is associated with, or linked with, or which induces, or produces, or results in, or is responsible for, or creates the movement, or vibration, or oscillation of the compound, preferentially after the dissociation of the compound from the magnetic nanoparticle, in particular the magnetosome.

In an embodiment of the invention, the compound is a therapeutic, immunogenic, metabolic, luminescent, fluorescent, radioactive, diagnostic, biologic, or chemical compound, or is a compound that triggers a therapeutic, immunogenic, metabolic, luminescent, fluorescent, radioactive, or diagnostic effect.

In one embodiment of the invention, the compound is part of the magnetic nanoparticle, in particular the magnetosome. In this case, it can be free iron or free oxygen, preferentially in the ionic form, which preferentially dissociates or leaks out or diffuses away from the magnetic nanoparticle, in particular the magnetosome, preferentially under or following the irradiation by the laser radiation of the magnetic nanoparticle, in particular the magnetosome, or body part, preferentially following dissolution of the magnetic nanoparticle, in particular magnetosome, preferentially following administration of the magnetic nanoparticle, in particular magnetosome, in/to the body part.

In one embodiment of the invention, the magnetic nanoparticles, in particular the magnetosomes, are administered to or in the body part, when they are directly administered to the body part or when they are administered close to the body part, preferentially less than 1, $10^{-1}$, $10^{-2}$, $10^{-3}$, $10^{-4}$, $10^{-5}$, $10^{-6}$, or $10^{-9}$ m away from the body part. In this case, the magnetic nanoparticles, in particular the magnetosomes, may not need to be transported or diffuse from the region where they are administered to the body part.

In another embodiment of the invention, the magnetic nanoparticles, in particular the magnetosomes, are administered to or in the body part, when they are administered far from the body part, preferentially more than 1, $10^{-1}$, $10^{-2}$, $10^{-3}$, $10^{-4}$, $10^{-5}$, $10^{-6}$, or $10^{-9}$ m away from the body part. In this case, the magnetic nanoparticles, in particular the magnetosomes, may be transported or diffuse from the region where they are administered to the body part.

In another embodiment of the invention, the magnetic nanoparticles, in particular the magnetosomes, are administered to or in the body part when they are injected in, or mixed with, or introduced in, or inserted in the body part.

In another embodiment of the invention, the magnetic nanoparticles, in particular the magnetosomes, are administered to or in the body part when they occupy more than $10^{-9}, 10^{-7}, 10^{-5}, 10^{-3}, 1, 10, 25, 50,$ or 75% of the body part, where this percentage can be the ratio between the volume of the region occupied by the magnetic nanoparticles, in particular the magnetosomes, in the body part and the volume of the body part, preferentially comprising regions without magnetic nanoparticles, in particular magnetosomes. This occupation can correspond to that measured $10^{-5}, 10^{-3}, 10^{-1}, 1, 10, 10^{3},$ or $10^{5}$ minute(s) following administration of magnetic nanoparticles, in particular magnetosomes.

In one embodiment of the invention, the volume of the region occupied by the magnetic nanoparticles, in particular magnetosomes, in the body part is designated as region of magnetic nanoparticles, in particular magnetosomes. The region of magnetic nanoparticles, in particular magnetosomes, can be the volume occupied by an assembly of magnetic nanoparticles, in particular magnetosomes, in the body part, where the magnetic nanoparticles, in particular magnetosomes, are preferentially separated by less than $10^{9}$, $10^{6}, 10^{3},$ or 10 nm.

In one embodiment of the invention, the separating distance between the magnetic nanoparticles, in particular magnetosomes, within the assembly of magnetic nanoparticle, in particular magnetosome, can correspond to the average or maximum distance separating the magnetic nanoparticles, in particular magnetosomes, within this assembly.

In one embodiment of the invention, the distribution in separating distances between magnetic nanoparticles, in particular magnetosomes, can highlight the presence of a minority of magnetic nanoparticle, in particular magnetosomes, i.e. preferentially less than $50, 10, 1, 10^{-2},$ or $10^{-5}$% of the total number of magnetic nanoparticles, in particular magnetosomes, in the individual, with either small separating distances, i.e separating distances preferentially lower than $10^{9}, 10^{6}, 10^{3},$ or 10 nm, or with large separating distances, i.e. separating distances preferentially higher than $10^{9}, 10^{6}, 10^{3},$ or 10 nm. In this case, the presence of this minority of magnetic nanoparticle, in particular magnetosomes, is preferentially not taken into consideration to estimate the average or maximum separating distance between the magnetic nanoparticles, in particular magnetosomes.

In another embodiment of the invention, the magnetic nanoparticles, in particular magnetosomes, are administered to or in the body part following at least one of the following administration routes: local, enteral, gastrointestinal, parenteral, topical, oral, by inhalation, intramuscular, subcutaneous, intra-tumor, in an organ, in a vein, in arteries, in blood, or in tissue.

In one embodiment of the invention, the body part or a portion of the body part is a pathological site. The pathological site can be defined as an unhealthy site, or a site that is in a different condition from a site of a healthy individual, or the site of an unhealthy individual. It can comprise pathological cells, such as tumor cells, bacteria, eukaryotic or prokaryotic cells, viruses or other pathological material. It can also comprise healthy cells, which are preferentially not arranged or working as they usual do in a healthy individual, most preferentially due to the presence of pathological cells in the pathological site. It can comprise a higher number of pathological than healthy cells. It can lead to a ratio between the number of pathological cells and number of healthy cells, which is preferentially higher than 2, 5, 10, $10^{3}, 10^{6}, 10^{9}, 10^{20},$ or $10^{50}$.

In one embodiment of the invention, pathological cell(s) or the pathological cell(s) can be characterized by an assembly comprising more than $1, 10, 10^{2}, 10^{3}, 10^{5}, 10^{10}, 10^{20},$ or $10^{50}$ pathological cell(s).

In one embodiment of this invention, the body part is divided between a portion of the body part comprising the magnetic nanoparticles, in particular the magnetosomes, also preferentially designated as region of magnetic nanoparticles, in particular magnetosomes, and a portion of the body part not comprising the magnetic nanoparticles, in particular the magnetosomes, also preferentially designated as region of the body part outside of the region of magnetic nanoparticles, in particular magnetosomes.

In one embodiment of the invention, the portion of the body part comprising the magnetic nanoparticles, in particular the magnetosomes, can absorb more than $10^{-9}, 10^{-7}, 10^{-5}, 10^{-3}, 10^{-1}, 1, 5, 10, 25, 50, 75,$ or 80% of the energy or power of the laser and the portion of the body part not comprising the magnetic nanoparticle, in particular the magnetosomes, can preferentially absorb less than $10^{-9}, 10^{-7}, 10^{-5}, 10^{-3}, 10^{-1}, 1, 5, 10, 25, 50, 75,$ or 80% of the energy or power of the laser.

In some other embodiments of the invention, the portion of the body part comprising the magnetic nanoparticle, in particular the magnetosomes, can absorb less than $10^{-9}, 10^{-7}, 10^{-5}, 10^{-3}, 10^{-1}, 1, 5, 10, 25, 50, 75,$ or 80% of the energy of the laser and the portion of the body part not comprising the magnetic nanoparticles, in particular the magnetosomes, can preferentially absorb more than $10^{-9}, 10^{-7}, 10^{-5}, 10^{-3}, 10^{-1}, 1, 5, 10, 25, 50, 75,$ or 80% of the energy of the laser.

In one embodiment of the invention, this percentage can represent the energy or power of the laser radiation absorbed by the magnetic nanoparticles, in particular magnetosomes, divided by the energy or power of the laser radiation generated by the laser equipment or laser apparatus.

In some other embodiments of the invention, this percentage can represent the ratio between the energy or power of the laser radiation absorbed by the portion of the body part comprising the magnetic nanoparticles, in particular magnetosomes, divided by the energy or power of the laser radiation absorbed by the body part, preferentially comprising both the portion of the body part with the magnetic nanoparticles, in particular magnetosomes, and the portion of the body part without the magnetic nanoparticles, in particular magnetosomes.

In one embodiment of this invention, the body part is divided between a portion of the body part comprising the pathological site or the pathological cells and a portion of the body part not comprising the pathological site or the pathological cells.

In one embodiment of the invention, the body part designates the portion of the body part.

In one embodiment of the invention, the portion of the body part designates: i), the portion of the body part comprising the magnetic nanoparticles, in particular magnetosomes, ii), the region of the magnetic nanoparticles, in particular the magnetosomes, or iii), the portion of the body part comprising the pathological cells or pathological site.

In some other embodiments of the invention, the portion of the body part can designate: i), the portion of the body part not comprising the magnetic nanoparticles, in particular the magnetosomes, ii), the region outside of the region of magnetic nanoparticles, in particular magnetosomes, or iii), the portion of the body part not comprising the pathological cells or pathological site.

In this invention, the body part or magnetic nanoparticles, in particular magnetosomes, exposed to the laser radiation or irradiated by the laser radiation can mean that the laser radiation irradiates, covers, targets, is present in, is applied in or on, or is located in at least $10^{-9}$, $10^{-7}$, $10^{-5}$, $10^{-3}$, $10^{-1}$, 1, 5, 10, 25, 50, 75, or 80% of the body part or magnetic nanoparticle(s), in particular magnetosome(s). This percentage can represent the number or volume of magnetic nanoparticle(s), in particular magnetosome(s), or of region of magnetic nanoparticle(s), in particular magnetosome(s), or body part, exposed to the laser radiation or irradiated by the laser radiation divided by the total number or volume of magnetic nanoparticle(s), in particular magnetosome(s), region of magnetic nanoparticles, in particular magnetosomes, or body part, which is(are) both exposed and not irradiated by laser radiation.

In one embodiment of the invention, the laser radiation can also cover, target, be present, be applied in or on, or be located outside of the body part, or magnetic nanoparticle(s), in particular magnetosome(s), or region of magnetic nanoparticle(s), in particular magnetosome(s), preferentially when the laser radiation is of low enough power or energy not to induce toxicity towards healthy cells.

In one embodiment of the invention, healthy cell(s) or the healthy cell(s) can be characterized by an assembly comprising more than 1, 10, $10^2$, $10^3$, $10^5$, $10^{10}$, $10^{20}$, or $10^{50}$ healthy cell(s).

Furthermore, in one embodiment, the body part, or magnetic nanoparticle(s), in particular magnetosome(s), or the region of magnetic nanoparticles, in particular magnetosomes, can be exposed to the laser radiation or can be irradiated by the laser radiation when the laser radiation is applied on or the laser irradiates: i), the body part, or, ii), the magnetic nanoparticle(s), in particular magnetosome(s), or, iii), the region of magnetic nanoparticles, in particular magnetosomes.

In some other embodiments of the invention, the body part, or magnetic nanoparticle(s), in particular magnetosome(s), or the region of magnetic nanoparticles, in particular magnetosomes, can be exposed to the laser radiation or can be irradiated when the body part, or magnetic nanoparticle(s), in particular magnetosome(s), or the region of magnetic nanoparticle(s), in particular magnetosome(s), is(are) irradiated or is(are) subjected to the application of the laser radiation or undergo(es) the effect(s) of the laser radiation or the disturbance created by the laser radiation.

In an embodiment of the invention, the body part comprises more than 1, 2, 5, 10, or 100 similar or different organism(s), apparatus, organ(s), tissue(s), cell(s), or biomolecule(s). The body part can be all or part of the head, neck, shoulder, arm, leg, knee, foot, hand, ankle, elbow, trunk, inferior members, or superior members, preferentially of the individual as defined in this patent application.

In one embodiment of the invention, the body part is or comprises water, an excipient, a solution, a suspension, at least one chemical element, organic material, or gel, which can be synthetic or produced by a living organism.

In an embodiment of the invention, the organ or body part belongs to the musculoskeletal, muscular, digestive, respiratory, urinary, female reproductive, male reproductive, circulatory, cardiovascular, endocrine, circulatory, lymphatic, nervous (peripheral or not), ventricular, enteric nervous, sensory, integumentary system, reproductive organ (internal or external), sensory organ, or endocrine glands. The organ or body part can be or belong to human skeleton, joints, ligaments, tendons, mouth, teeth, tongue, salivary glands, parotid glands, submandibular glands, sublingual glands, pharynx, esophagus, stomach, small intestine, duodenum, jejunum, ileum, large intestine, liver, gallbladder, mesentery, pancreas, nasal cavity, pharynx, larynx, trachea, bronchi, lungs, diaphragm, kidneys, ureters, bladder, urethra, ovaries, fallopian tubes, uterus, vagina, vulva, clitoris, placenta, testes, epididymis, vas deferens, seminal vesicles, prostate, bulbourethral glands, penis, scrotum, pituitary gland, pineal gland, thyroid gland, parathyroid glands, adrenal glands, pancreas, heart, arteries, veins, capillaries, lymphatic vessel, lymph node, bone marrow, thymus, spleen, gut-associated lymphoid tissue, tonsils, brain, cerebrum, cerebral hemispheres, diencephalon, brainstem, midbrain, pons, medulla, oblongata, cerebellum, spinal cord, choroid plexus, nerves, cranial nerves, spinal nerves, ganglia, eye, cornea, iris, ciliary body, lens, retina, ear, outer ear, earlobe, eardrum, middle ear, ossicles, inner ear, cochlea, vestibule of the ear, semicircular canals, olfactory epithelium, tongue, taste buds, mammary glands, or skin. The body part or organ can belong to the circulatory system.

In an embodiment of the invention, the body part designates the body part of an individual.

In one embodiment of the invention, the individual is an organism, preferentially a living organism, a plant, a tree, a flour, a fungus, a mushroom, an archaea, a microbe, an animal, a mammal, a bird, a crustacean, a fish, a vertebrate animal, a *bacterium*, a human, a man, a woman, an elderly man or woman, or a child. In one embodiment of the invention, a distinction is made between the individual that is treated for a disease, preferentially also designated as treated individual, and the individual or organism that is responsible for the disease of the treated individual.

In one embodiment of the invention, the individual can be alive.

In some other embodiments of the invention, the individual can be dead, or be an inactivated or dead organism.

In one embodiment, the body part of the individual is an assembly of cells, preferentially of more than 1, 10, $10^3$, $10^6$, $10^9$, or $10^{20}$ cell(s), that are preferentially comprised in the body part, extracted from the body part, issued from the body part, or resulting in or from the body part. In one embodiment, these cells can be cultivated and amplified to reach a certain number, preferentially more than 1, 10, $10^3$, $10^6$, $10^9$, or $10^{20}$ cell(s).

In an embodiment of the invention, the magnetic nanoparticles, in particular the magnetosomes, according to the invention are drugs, medical devices, cosmetic products, biological products, products used for research purposes, or products used to determine the properties of biological or chemical samples.

In one embodiment of the invention, the compound can dissociate or is dissociated from the magnetic nanoparticles, in particular the magnetosomes, preferentially under the irradiation by the laser radiation.

In one embodiment of the invention, the compound is dissociated from the magnetic nanoparticles, in particular the magnetosomes, when more than $10^{-5}$, $10^{-3}$, $10^{-1}$, 1, 5, 10, 25, 50, 75, 85, or 90% of compounds are dissociated from the magnetic nanoparticles, in particular the magnetosomes, where this percentage can represent the percentage of dissociation.

In one embodiment of the invention, the percentage of dissociation represents the ratio between the quantity of compounds dissociated from the magnetic nanoparticles, in particular the magnetosomes, following or under the irradiation by the laser radiation and the quantity of compounds linked or bound to the magnetic nanoparticles, in particular the magnetosomes, before or without the irradiation by the laser radiation.

In one embodiment of the invention, the number of compounds linked or bound to one magnetic nanoparticle, in particular one magnetosome, can be higher than 1, 2, 5, 10, $10^3$, $10^5$, or $10^{10}$.

In some other embodiments of the invention, the number of compounds linked or bound to one magnetic nanoparticle, in particular one magnetosome, is lower than 2, 5, 10, $10^3$, $10^5$, or $10^{10}$.

In still some other embodiments of the invention, the percentage of compounds dissociated can increase by a factor of at least 1.01, 1.1, 2, 5, 7, 10, $10^2$, or $10^5$ between before and after the irradiation by the laser radiation.

In one embodiment of the invention, the compound cannot dissociate or is not dissociated from the magnetic nanoparticle, in particular magnetosome, preferentially in the absence of irradiation by the laser radiation. Preferentially, less than $10^{-5}$, $10^{-3}$, $10^{-1}$, 1, 5, 10, 25, 50, 75, 85, or 90% of compounds are dissociated from the magnetic nanoparticles, in particular the magnetosomes, when the compounds are not dissociated from the magnetic nanoparticles, in particular the magnetosomes.

In one embodiment of the invention, the compound is linked or bound to the magnetic nanoparticle, in particular magnetosome, or not dissociated from the magnetic nanoparticle, in particular magnetosome, when it is located at a distance of less than $10^9$, $10^5$, $10^3$, 10, or 1 nm from the magnetic nanoparticle, in particular magnetosome. Alternatively, the compound can in one embodiment be linked or bound to the magnetic nanoparticle, in particular magnetosome, or non-dissociated from the magnetic nanoparticle, in particular magnetosome, when the magnetic nanoparticle, in particular magnetosome, and the compound can both or together be attracted by a magnet or both or together move under the application of a magnetic field gradient, of strength per unit distance preferentially higher than $10^{-9}$, $10^{-6}$, $10^{-3}$, $10^{-1}$, or 1 T/m or T/cm or T/mm, where the speed of motion of the compound attached or linked to the magnetic nanoparticle, in particular magnetosome, or non-dissociated from the magnetic nanoparticle, in particular magnetosome, is preferentially higher than $10^{-9}$, $10^{-6}$, $10^{-3}$, $10^{-1}$, 1, 10, or $10^3$ nm/sec or nm/min or nm/hour or nm/day or m/sec or m/min or m/hour or m/day.

In one embodiment of the invention, the compound is not bound, not linked to the magnetic nanoparticle, in particular magnetosome, or is dissociated from the magnetic nanoparticle, in particular magnetosome, when it is located at a distance of more than $10^9$, $10^5$, $10^3$, 10, or 1 nm from the magnetic nanoparticle, in particular magnetosome. Alternatively, the compound can in one embodiment not be bound or linked to the magnetic nanoparticle, in particular magnetosome, or be dissociated from the magnetic nanoparticle, in particular magnetosome, when the compound cannot be attracted by a magnet or move under the application of a magnetic field gradient, of strength per unit length preferentially higher than $10^{-9}$, $10^{-6}$, $10^{-3}$, $10^{-1}$, or 1 T/m or T/cm or T/mm, where the speed of motion of the compound is preferentially lower than $10^{-9}$, $10^{-6}$, $10^{-3}$, $10^{-1}$, 1, 10, or $10^3$ nm/sec or nm/min or nm/hour or nm/day or m/sec or m/min or m/hour or m/day, or where the speed of motion of the compound is preferentially lower, by a factor of more than 1.001, 1.01, 1.1, 2, 5, 10, $10^3$, $10^6$, $10^9$, $10^{15}$, or $10^{20}$, from the speed of motion of the magnetic nanoparticle, in particular magnetosome, or of the compound linked or bound to the magnetic nanoparticle, in particular magnetosome.

In one embodiment of the invention, the percentage of dissociation is between $10^{-20}$% and $10^{20}$%, or between $10^{-10}$% and $10^{10}$%, or between $10^{-5}$% and $10^5$%, or between $10^{-3}$% and $10^3$%, or between $10^{-1}$% and 10%. A percentage of dissociation higher than 100% can in one embodiment be reached, for example when a compound that dissociates from the magnetic nanoparticle, in particular magnetosome, transforms itself or results in several compounds.

In still another embodiment of the invention, the irradiation by the laser radiation designates the irradiation by the laser radiation of the magnetic nanoparticle(s), in particular the magnetosome(s), or region of the magnetic nanoparticle(s), in particular the magnetosome(s), or body part.

In one embodiment of the invention, the irradiation by the laser radiation designates the exposure of the magnetic nanoparticle(s), in particular the magnetosome(s), body part, or region of magnetic nanoparticles, in particular magnetosomes, to the laser radiation.

In another embodiment of the invention, the ratio between the mass, number, or weight, of the compounds, preferentially linked to a single magnetic nanoparticle, in particular magnetosome, and the mas, number, or weight of a single magnetic nanoparticle, in particular magnetosome, is lower than $10^{20}$, $10^9$, $10^5$, $10^2$, 2, 1, $10^{-2}$, $10^{-5}$, $10^{-9}$, or $10^{-20}$.

In another embodiment of the invention, the ratio between the mass, number, or weight, of the compound, preferentially linked to a single magnetic nanoparticle, in particular magnetosome, and the mas, number, or weight of a single magnetic nanoparticle, in particular magnetosome, is higher than $10^{20}$, $10^9$, $10^5$, $10^2$, 1, $10^{-2}$, $10^{-5}$, $10^{-9}$, or $10^{-20}$.

In one embodiment of the invention, a suitable range of values for the number of compounds preferentially linked to a single magnetic nanoparticle, in particular magnetosome, is between 1 and 178, where this minimum value of 1 corresponds to the minimum number of compounds that can be linked to a single magnetosome and the maximum value of 178 corresponds to the number of RhB molecules that was linked to a single magnetosome in patent WO2017/068252 incorporated in reference, and which could dissociate at least in part from a single magnetic nanoparticle, in particular magnetosome. In one embodiment, this maximum value of 178 can be increased, preferentially by a factor of more than 5, 10, $10^3$, $10^7$, $10^{10}$, or $10^{20}$, by: i), decreasing the size, or mass of the compound linked to the magnetic nanoparticle, in particular magnetosome, preferentially by a factor of more than 1.1, 2, 5, 10, $10^3$, $10^7$, $10^{10}$, or $10^{20}$, ii), changing the type of bounds between the compounds and the magnetic nanoparticle, in particular magnetosome, or iii), changing the method for attaching or binding the compound to the magnetic nanoparticle, in particular magnetosome.

In an embodiment of this invention, the magnetic nanoparticle or body part is first irradiated by the laser radiation in a first step. This preferentially means that the body part, preferentially the portion of the body part comprising the magnetic nanoparticle, in particular magnetosome, receives or absorbs the energy or power of the laser, or receives or absorbs at least $10^{-9}$, $10^{-7}$, $10^{-5}$, $10^{-3}$, $10^{-1}$, 1, 5, 10, 25, 50, 75, or 80% of the energy or power of the laser radiation, preferentially emitted or generated by the laser equipment or apparatus. The energy or power of the laser, which is not absorbed by the portion of the body part comprising the magnetic nanoparticle, in particular magnetosome, can be absorbed by the portion of the body part not comprising the magnetic nanoparticle, in particular magnetosome.

In one embodiment of the invention, "in a/the first step" can mean or be equivalent to "during a/the first step."

The first step is preferentially the step during or in which the body part or magnetic nanoparticle, in particular magnetosome, is irradiated by the laser radiation, preferentially of laser power higher than 0 Watt or Watt per cm$^3$ of body part or Watt per gram of nanoparticle. Alternatively, the first step is preferentially the step during or in which the body part or magnetic nanoparticle(s), in particular magnetosome(s), is(are) irradiated by a radiation of power higher than the laser power of the second step, preferentially by a factor of at least 0, 1.1, 1.5, 5, 10, 10$^3$, 10$^5$ or 10$^{10}$.

In one embodiment, preferentially in the first step but possibly also in the second step, the laser power is set at a value that enables to induce a temperature increase of the magnetic nanoparticles, in particular magnetosomes, region of magnetic nanoparticles, in particular magnetosomes, portion of the body part comprising the magnetic nanoparticles, in particular magnetosomes, and preferentially to prevent a temperature increase of the body part not comprising the magnetic nanoparticles, in particular magnetosomes.

In one embodiment of the invention, "in a/the second step" can mean or be equivalent to "during a/the second step."

In one embodiment of the invention, preferentially in the first step but possibly also in the second step, the laser power or laser power density can be maintained below 10$^9$, 10$^6$, 10$^3$, 10$^2$, 10, or 1 W or W/cm or W/cm$^2$ or W/cm$^3$ or W per cm of body part or W per cm$^2$ of body part or W per cm$^3$ of body part.

In one embodiment of the invention, preferentially in the first step but possibly also in the second step, the laser intensity can be maintained below 10$^{20}$, 10$^9$, 10$^6$, 10$^3$, 10$^2$, 10, or 1 mA (milliampere).

In the experimental example, the laser intensity is fixed at 4500 A, and a power density of 2 W/cm$^2$ is used, which is sufficient to induce a temperature increase of the magnetic nanoparticles, in particular magnetosomes, and does not induce a temperature increase of water alone, not comprising the magnetic nanoparticles, in particular magnetosomes. In one embodiment of the invention, it is possible to use laser intensity, which is lower than 4500 mA, preferentially by a factor of more than 1.001, 1.01, 1.1, 1.5, 2, 5, 10, or 10$^3$, and/or a power density, which is lower than 2 W/cm$^2$, preferentially by a factor of more than 1.001, 1.01, 1.1, 1.5, 2, 5, 10, or 10$^3$, and still induce a temperature increase during the heating step. This can preferentially be achieved by: i), increasing the magnetic nanoparticle, in particular magnetosome, concentration, preferentially by a factor of more than 1.001, 1.01, 1.1, 1.5, 2, 5, 10, or 10$^3$, ii), increasing the duration of the heating step, preferentially by a factor of more than 1.001, 1.01, 1.1, 1.5, 2, 5, 10, or 10$^3$, or iii), by reduction the temperature increase or temperature gradient that one wants to achieve during the heating step, preferentially by a factor of more than 1.001, 1.01, 1.1, 1.5, 2, 5, 10, or 10$^3$.

In one embodiment of the invention, the laser intensity can be the strength of the current that produces or induces laser radiation with a certain power. The laser intensity can in one embodiment be related to the laser power and a calibration curve can in one embodiment be established to relate the laser intensity to the laser power.

In one embodiment of the invention, a too high laser power, power density, or laser intensity, is preferentially avoided to prevent toxicity or overheating or a too large percentage of dissociation of compounds from the magnetic nanoparticle, in particular magnetosomes, or to enable cooling during the cooling step.

In some other embodiments of the invention, preferentially in the first step but possibly also in the second step, the laser power is maintained above 10$^{-9}$, 10$^{-6}$, 10$^{-3}$, 10$^{-1}$, 1, 10, 10$^3$, or 10$^5$ W or W/cm or W/cm$^2$ or W/cm$^3$ or W per cm of body part or W per cm$^2$ of body part or W per cm$^3$ of body part.

In still some other embodiments of the invention, preferentially in the first step but possibly also in the second step, the laser intensity is maintained above 10$^{-20}$, 10$^{-9}$, 10$^{-6}$, 10$^{-3}$, 10$^{-1}$, 1, 10, 10$^3$, 10$^5$, or 10$^{10}$ mA.

In the experimental example, the laser intensity is fixed at 4500 A, and a power density of 2 W/cm$^2$ is used, which is sufficient to induce a temperature increase of the magnetic nanoparticles, in particular magnetosomes, and does not induce a temperature increase of water alone, not comprising the magnetic nanoparticles, in particular magnetosomes. In one embodiment, it is possible to use a laser intensity, which is higher than 4500 mA, preferentially by a factor of more than 1.001, 1.01, 1.1, 1.5, 2, 5, 10, or 10$^3$, and/or a power density, which is higher than 2 W/cm$^2$, preferentially by a factor of more than 1.001, 1.01, 1.1, 1.5, 2, 5, 10, or 10$^3$, and induce a temperature increase of the magnetic nanoparticles, in particular magnetosomes, region of magnetic nanoparticles, in particular magnetosomes, or portion of the body part comprising the magnetic nanoparticles, in particular magnetosomes, preferentially without inducing a temperature increase of the portion of the body part not comprising the magnetic nanoparticles, in particular magnetosomes, or of the region outside of the region of the magnetic nanoparticles, in particular magnetosomes. This can preferentially be achieved by: i), decreasing the concentration of the magnetic nanoparticles, in particular magnetosomes, preferentially by a factor of more than 1.001, 1.01, 1.1, 1.5, 2, 5, 10, or 10$^3$, ii), decreasing the duration of the heating step, preferentially by a factor of more than 1.001, 1.01, 1.1, 1.5, 2, 5, 10, or 10$^3$, or iii), by increasing the temperature increase or temperature gradient that one wants to achieve during the heating step, preferentially by a factor of more than 1.001, 1.01, 1.1, 1.5, 2, 5, 10, or 10$^3$.

In sill some other embodiments of the invention, a sufficiently high laser power or laser power density or laser intensity can be desired to be able to heat the magnetic nanoparticles, in particular the magnetosomes, or to produce a sufficiently large percentage of dissociation of the compounds from the magnetic nanoparticle, in particular magnetosomes, preferentially in the first step.

In an embodiment of the invention, the laser power or laser power density or laser intensity is maintained sufficiently large in the first step to produce a temperature increase of the portion of the body part comprising the magnetic nanoparticles, in particular magnetosomes. In one embodiment of the invention, the temperature increase of this body part is higher than 10$^{-6}$, 10$^{-3}$, 10$^{-1}$, 1, 5, 10, 10$^2$, or 10$^{3}$° C.

In some other embodiments of the invention, the temperature increase of this body part is lower than 10$^6$, 10$^3$, 10, 1, or 10$^{-1}$° C.

In one embodiment of the invention, the temperature increase designates the temperature increase of the body part, portion of the body part comprising the magnetic nanoparticles, in particular the magnetosomes, region of the magnetic nanoparticles, in particular the magnetosomes, region, or the magnetic nanoparticles, in particular the magnetosomes. The temperature increase can be assimilated to or correspond to the magnitude of the temperature increase occurring in the first step, which is preferentially the absolute value of the difference between the maximum and minimum temperature reached in the second step, which is also in one embodiment designated as temperature variation or temperature variation during or occurring in the first step.

In another embodiment of the invention, the laser power or power density or laser intensity is maintained sufficiently high in the first step to produce the dissociation of the compounds from the magnetic nanoparticles, in particular the magnetosomes.

In one embodiment of the invention, the percentage of dissociation of the compounds from the magnetic nanoparticles, in particular the magnetosomes, can be higher than $10^{-5}$, $10^{-3}$, $10^{-1}$, 1, 5, 10, 25, 50, 75, or 90%.

In some other embodiments of the invention, the percentage of dissociation of the compounds from the magnetic nanoparticles, in particular the magnetosomes, can be lower than $10^{-5}$, $10^{-3}$, $10^{-1}$, 1, 5, 10, 25, 50, 75, 90, or 99%.

In another embodiment of the invention, the laser power or laser power density or laser intensity is maintained sufficiently low in the first step to prevent a temperature increase of the portion of the body part not comprising the magnetic nanoparticles, in particular the magnetosomes.

In another embodiment of the invention, the laser power or laser power density or laser intensity is maintained sufficiently low in the first step to prevent the dissociation of the compounds from the magnetic nanoparticles, in particular the magnetosomes.

In one embodiment of the invention, the laser wavelength could be designated as or correspond to laser emission wavelength or laser radiation wavelength, In still another embodiment of the invention, in the first step, the laser wavelength is lower or is maintained lower than $10^{20}$, $10^{15}$, $10^{9}$, $10^{7}$, $10^{5}$, $10^{4}$, 1000, 900, 800, 700, 500, 100, 50, 20, 2, or 1 nm.

In still another embodiment of the invention, in the first step, the laser wavelength is higher or is maintained higher than $10^{20}$, $10^{15}$, $10^{9}$, $10^{7}$, $10^{5}$, $10^{4}$, 1000, 900, 800, 700, 500, 100, 50, 20, 2 or 1 nm.

In still another embodiment of the invention, in the first step, the laser wavelength is between or is maintained between 1 nm and 100 000 nm, 1 nm and 10 000 nm, 20 nm and 5000 nm, 50 nm and 2000 nm, or between 100 nm and 1000 nm.

In one embodiment of the invention, the electromagnetic radiation, preferentially associated with or corresponding to laser radiation, comprises more than 1, 2, 5, 10, or $10^{3}$ different frequency(ies) of oscillation.

In still another embodiment of the invention, the electromagnetic radiation, preferentially associated with or corresponding to laser radiation, comprises less than 2, 5, 10, or $10^{3}$ different frequency(ies) of oscillation.

In still another embodiment of the invention, the electromagnetic radiation, preferentially associated with or corresponding to laser radiation, is different from or is not a magnetic field or an alternating magnetic field.

In still another embodiment of the invention, in the first step, the laser wavelength is fixed at a value that corresponds to or leads to or results in a strong absorption of light by the magnetic nanoparticle, in particular magnetosome, i.e. a wavelength that is preferentially lower than 10000, 5000, 2000, 1000, 900, 800, 700, 600, 500, 400, 300, 200, 100, 50, 20, 10, 5, 2, or 1 nm.

In still another embodiment of the invention, preferentially in the first step, the laser wavelength is fixed at a value that corresponds to or leads to or results in a strong absorption or penetration of light in or to the body part or individual, i.e. a wavelength that is preferentially higher than 10000, 5000, 2000, 1000, 900, 800, 700, 600, 500, 400, 300, 200, 100, 50, 20, 10, 5, 2, or 1 nm, or a wavelength that is between 10000 and 1 nm, 5000 and 1 nm, 5000, 10 nm, 5000 and 100 nm, or between 2000 nm and 200 nm.

In still another embodiment of the invention, preferentially in the first step, the laser wavelength is fixed at a wavelength that enables to reach maximum coupling between the surface plasmon wave of the magnetic nanoparticle, in particular magnetosome, and the laser radiation.

In the experimental example, the laser wavelength is fixed at 808 nm.

In one embodiment of the invention, this laser wavelength can be increased, preferentially by a factor of more than 1.001, 1.01, 1.1, 10, $10^{3}$, or $10^{6}$, preferentially to enhance absorption of the laser radiation by the body part, preferentially by a factor of more than 1, 2, 5, 10, $10^{3}$, or $10^{6}$.

In some other embodiments of the invention, this laser wavelength can be decreased, preferentially by a factor of more than 1.001, 1.01, 1.1, 10, $10^{3}$, or $10^{6}$, preferentially to enhance absorption of the laser radiation by the magnetic nanoparticles, in particular magnetosomes, preferentially by a factor of more than 1.001, 1.01, 1.1, 10, $10^{3}$, or $10^{6}$.

In one embodiment of the invention, the percentage of dissociation of the compounds from the magnetic nanoparticles, in particular magnetosomes, reached in the first step can be higher than $10^{-5}$, $10^{-3}$, $10^{-1}$, 1, 5, 10, 25, 50, 75, or 90%.

In some other embodiments of the invention, the percentage of dissociation of the compounds from the magnetic nanoparticles, in particular magnetosomes, reached in the first step can be lower than $10^{-5}$, $10^{-3}$, $10^{-1}$, 1, 5, 10, 25, 50, 75, 90, or 99%.

In still some cases, the percentage of dissociation of the compounds from the magnetic nanoparticles, in particular magnetosomes, reached in the first step can be between $10^{-5}$ and 99%, $10^{-3}$ and 99%, $10^{-1}$ and 99%, 1 and 99%, 10 and 99%, 10 and 90%, or between 25 and 75%.

The second step is preferentially the step during which or in which the body part, or magnetic nanoparticle, preferentially magnetosome, is irradiated by a laser radiation of lower power than in the first step. Alternatively, the second step is preferentially the step during which or in which the body part, or magnetic nanoparticle, preferentially magnetosome, is not irradiated by the laser radiation. Alternatively, the second step is preferentially the step during which or in which no laser irradiation of the magnetic nanoparticles, in particular the magnetosomes, or body part, is performed.

In one embodiment of the invention, the laser power or laser power density or laser intensity is at least 1.1, 1.2, 1.5, 2, 5, 10, $10^{3}$, $10^{6}$, $10^{9}$, or $10^{20}$ times lower in the second step than in the first step.

In the experimental example, the laser is switched off in the second step. It is however possible to maintain the laser switched on during the step, provided the laser power is sufficiently low, preferentially to avoid heating the magnetic nanoparticles, in particular the magnetosomes, or body part. This may in one embodiment be useful to avoid damaging the laser by switching it on and off a too large number of times.

In still another embodiment of the invention, in the second step, the laser wavelength is maintained at a value that differs by less than 100 000, 10 000, 1000, 900, 800, 700, 500, 100, 50, 20, 2, or 1 nm, from the laser wavelength used in the first step.

In still another embodiment of the invention, in the second step, the laser wavelength is maintained at a value that differs by more than 100 000, 10 000, 1000, 900, 800, 700, 500, 100, 50, 20, 2, or 1 nm, from the laser wavelength used in the first step.

In still another embodiment of the invention, in the second step, the laser wavelength is fixed at a value that corresponds to or leads to or results in weak absorption of light by the magnetic nanoparticles, in particular the magnetosomes, i.e. preferentially a wavelength that is higher than 1, 5, 10, 100, 200, 300, 400, 500, 600, 700, 800, 900, 1000, 2000, 5000, or 10000 nm.

In still another embodiment of the invention, in the second step, the laser wavelength is fixed at a wavelength that enables to reach minimum coupling between the surface plasmon waves of the magnetic nanoparticles, in particular magnetosomes, and the laser radiation.

In one embodiment of the invention, the first and/or second step(s) is(are) repeated at least 1, 2, 3, 4, 5, 10, 100, $10^3$, $10^5$, or $10^{10}$ time(s).

In another embodiment of the invention, the first and/or second step(s) is(are) repeated less than 1, 2, 3, 4, 5, 10, 100, $10^3$, $10^5$, or $10^{10}$ time(s).

In still another embodiment of the invention, the first and/or second step(s) is(are) repeated between 2 and $10^{10}$ times, between 2 and $10^5$ times, between 2 and $10^5$ times, between 2 and $10^3$ times, between 5 and $10^3$ times, or between 10 and $10^3$ time(s).

In one embodiment of the invention, the sequence of first step and second step is repeated at least 1, 2, 3, 4, 5, 10, 100, $10^3$, $10^5$, or $10^{10}$ times.

In another embodiment of the invention, the sequence of first step and second step is repeated less than 1, 2, 3, 4, 5, 10, 100, $10^3$, $10^5$, or $10^{10}$ time(s).

In still another embodiment of the invention, the sequence of first step and second step is repeated between 2 and $10^{10}$ times, between 2 and $10^5$ times, between 2 and $10^5$ times, between 2 and $10^3$ times, between 5 and $10^3$ times, or between 10 and $10^3$ time(s).

In one embodiment of the invention, the duration of the first and/or second step(s) is/are higher than $10^{-50}$, $10^{-10}$, $10^{-1}$, 1, 5, 10, 15, 30, 100, $10^3$, $10^5$ or $10^{10}$ minute(s).

In some other embodiments of the invention, the duration of the first and/or second step(s) is/are lower than $10^{50}$, $10^{10}$, 60, 30, 10, 5, 2, 1, $10^{-1}$ or $10^{-5}$ minute(s).

In still some other embodiments of the invention, the duration of the first and/or second step(s) is between $10^{-50}$ and $10^{50}$ minutes, between $10^{-50}$ and $10^3$ minutes, between $10^{-50}$ and 60 minutes, preferably between $10^{-50}$ and 30 minutes, more preferably between $10^{-5}$ and 30 minutes, even more preferably between $10^{-3}$ and 15 minutes, even more preferably between $10^{-1}$ and 10 minutes, or even more preferably between $10^{-1}$ and 5 minutes.

In one embodiment of the invention, the inter-step duration is the duration or lapse of time that separates the first step from the second step.

In one embodiment of the invention, the inter-step duration can be between $10^{-10}$ and $10^{20}$ minute(s), preferably between $10^{-5}$ and $10^5$ minute(s), more preferably between $10^{-5}$ and 10 minute(s), or even more preferably between $10^{-5}$ and 1 minute(s).

In one embodiment of the invention, the inter-step duration can be shorter than $10^5$, $10^3$, 100, 60, 30, 15, 10, 5, 2, 1, $10^{-1}$ or $10^{-3}$ or $10^{-10}$ minute(s).

In some other embodiments of the invention, the inter-step duration can be longer than $10^{-10}$, $10^{-3}$, $10^{-1}$, 1, 5, 10, $10^3$, $10^5$, $10^{10}$ or $10^{20}$ minute(s).

Preferably, the duration of the first step that is sufficiently long to induce a temperature increase and/or to yield the release of at least one compound from the magnetic nanoparticles, preferentially in the body part.

Preferably, the duration of the second step is sufficiently long to induce a temperature decrease and/or to prevent the release of at least one compound from the magnetic nanoparticles, preferentially in the body part.

Preferably, the duration of the first and/or second step(s) is sufficiently long to induce a biological effect such as cellular destruction, immune stimulation, immune suppression, or the production or appearance of biological material such as enzymes, DNA, RNA, or proteins.

Preferably, the duration of the first and/or second step(s) is sufficiently short to avoid that the temperature is maintained at a fixed or stable temperature for: i) more than 1 day, preferentially one minute, most preferentially 1 second, or ii) more than 50% of the duration of the first step, where this percentage is the ratio between the lapse of time during which the temperature is maintained at a fixed temperature and the total duration of the first step.

Preferably, the duration of the first and/or second step(s) is sufficiently short that the first and/or second step(s) can be repeated more than once.

In still some other embodiments, the first step and the second step can be separated by an inter-step duration which may be: the duration between: i) the time $t_1$ where the power of the laser is set to 0 or is decreased to a lower value than that of the first step, preferentially at the beginning of the second step, and the time $t_2$ where the percentage of dissociation of the compound or the temperature increase becomes less important, preferentially by a factor of at least 1.1, 1.2, 1.5, 5, 10, $10^3$, $10^5$ or $10^{10}$ higher than during the first step or ii) the time $t_3$ where the power of the laser is set to a non-zero value or is increased to a higher value than that of the second step, preferentially at the beginning of the first step, and the time $t_4$ where the percentage of dissociation of the compound or the temperature increase becomes more important, preferentially by a factor of at least 1.1, 1.2, 1.5, 5, 10, $10^3$, $10^5$ or $10^{10}$ higher than during the second step. In other words, the inter-step duration may be the lapse of time separating the time at which the laser power is set to a certain value, preferentially at the beginning of the first and/or second step, and the time at which the laser has an effect on the body part and/or nanoparticle, where this effect is preferentially a change in the percentage of dissociation of the compound and/or a change in temperature increase. This effect may be the effect occurring or measured, preferentially in the body part and/or nanoparticle.

In one embodiment of the invention, the inter-step duration can be equal to $t_1$-$t_2$ or $t_3$-$t_4$.

The sequence of the first step and the second step, also designated as the sequence, is the first step followed by the second step.

In one embodiment, the duration of the sequence can be higher than $10^{-50}$, $10^{-10}$, $10^{-1}$, 1, 5, 10, 15, 30, 100, $10^3$, $10^5$ or $10^{10}$ minute(s).

In some other embodiments, the duration of the sequence can be lower than $10^{50}$, $10^{10}$, 60, 30, 10, 5, 2, 1, $10^{-1}$ or $10^{-5}$ minute(s).

In still some other embodiments, the duration of the sequence can be between $10^{-50}$ and $10^{50}$ minutes, preferably between $10^{-50}$ and $10^3$ minutes, more preferably between $10^{-50}$ and 60 minutes, even more preferably between $10^{-50}$ and 30 minutes, even more preferably between $10^{-5}$ and 30 minutes, even more preferably between $10^{-3}$ and 15 minutes, even more preferably between $10^{-1}$ and 10 minutes, or even more preferably between $10^{-1}$ and 5 minutes.

In one embodiment, the duration of the sequence can be longer, preferentially by a factor of at least 0, 1, 1.01, 1.1, 1.5, 2, 5, 10, $10^3$, $10^5$ or $10^{10}$ than the duration of the first and/or second step(s).

Two successive sequences of the first step and the second step can be separated by an inter-sequence duration. The inter-sequence duration can vary or be identical between each sequence.

In one embodiment, the inter-sequence duration can be shorter than $10^5$, $10^3$, 100, 60, 30, 15, 10, 5, 2, 1, $10^{-1}$ or $10^{-3}$ or $10^{-10}$ minutes. This is beneficial when it is needed to rapidly repeat sequences, preferentially to reach medical or antitumor activity.

In some other embodiments, the inter-sequence duration can be longer than $10^{-10}$, $10^{-3}$, $10^{-1}$, 1, 5, 10, $10^3$, $10^5$, $10^{10}$ or $10^{20}$ minute(s). This is beneficial when a patient needs to recover from the treatment or method preferentially between two sequences, for example when the method of treatment uses anesthesia or is combined with or necessitates the use of a difficult to withstand clinical protocol such as surgery, chemotherapy, radiotherapy and/or immunotherapy.

In still some other embodiments, the inter-sequence duration can be between $10^{-10}$ and $10^{20}$ minute(s), between $10^{-5}$ and $10^5$ minute(s), between $10^{-5}$ and 10 minute(s), or between $10^{-5}$ and 1 minute(s).

In one embodiment, the inter-sequence duration is longer by a factor of at least 0, 1, 1.1, 2, 5, 10, $10^3$, $10^5$ or $10^{10}$ than the inter-step duration.

In still some other embodiments, the inter-sequence duration is shorter by a factor of at least 0, 1, 1.1, 2, 5, 10, $10^3$, $10^5$ or $10^{10}$ than the inter-step duration.

Preferably, the duration of the sequence or inter-sequence is sufficiently long to induce a biological effect such as cellular destruction, immune stimulation, immune suppression, or the production or appearance of biological material such as enzymes, DNA, RNA, or proteins.

Preferably, the duration of the sequence or inter-sequence is sufficiently short so that the sequences can be repeated, preferentially a sufficiently large number of times to reach treatment efficacy.

In one embodiment, the duration of at least one sequence is longer, preferentially by a factor of at least 1.1, than the duration of at least one step, and/or the duration of at least one inter-sequence is longer, preferentially by a factor of at least 1.1, than the duration of at least one inter-step.

In still another embodiment of the invention, the number of sequences per unit time is higher than $10^{-50}$, $10^{-20}$, $10^{-10}$, $10^{-5}$, $10^{-3}$, $10^{-1}$, 1, 10, or $10^3$ sequence(s)/sec.

In still another embodiment of the invention, the number of sequences per unit time is lower than $10^{50}$, $10^{20}$, $10^{10}$, $10^5$, $10^3$, 10, 1, $10^{-1}$, $10^{-3}$ sequence(s)/sec.

In the experimental example, the number of sequences per unit time was: 8 $10^{-3}$ sequences per sec. for 0.5 mg/mL of M-CMD, $10^{-2}$ sequences per sec. for 1 mg of M-CMD, and 7 $10^{-3}$ sequences per sec. for 1 mg of N-CMD. In one embodiment, it is possible to increase the number of sequences per unit time, preferentially by a factor of more than 1.001, 1.01, 1.1, 1.5, 2, 5, 10, or $10^3$, by: i), increasing the magnetic nanoparticle, in particular magnetosome, concentration, preferentially by a factor of more than 1.001, 1.01, 1.1, 1.5, 2, 5, 10, or $10^3$, ii), increasing the laser power during the heating step or decreasing the laser power during the cooling step, preferentially by a factor of more than 1.001, 1.01, 1.1, 1.5, 2, 5, 10, or $10^3$, or iii), reducing the temperature increase of the heating step or temperature decrease of the cooling step that one wants to achieve, preferentially by a factor of more than 1.001, 1.01, 1.1, 1.5, 2, 5, 10, or $10^3$. In some other embodiments, it is possible to decrease the number of sequences per unit time, preferentially by a factor of more than 1.001, 1.01, 1.1, 1.5, 2, 5, 10, or $10^3$, by: i), decreasing the magnetic nanoparticle, in particular magnetosome, concentration, preferentially by a factor of more than 1.001, 1.01, 1.1, 1.5, 2, 5, 10, or $10^3$, ii), decreasing the laser power during the heating step or increasing the laser power during the cooling step, preferentially by a factor of more than 1.001, 1.01, 1.1, 1.5, 2, 5, 10, or $10^3$, or iii), increasing the temperature increase of the heating step or temperature decrease of the cooling step that one wants to achieve, preferentially by a factor of more than 1.001, 1.01, 1.1, 1.5, 2, 5, 10, or $10^3$.

A treatment session is the succession of several sequences, preferably more than 1, 2, 5, 10, $10^3$ or $10^5$ sequences.

In one embodiment, the duration between at least two treatment sessions can be longer than the duration between two sequences. This may occur or be necessary, preferentially in or during a clinical protocol, where: i), a patient needs to be treated by the method or treatment according to the invention that requires the use of several sequences that follow each other successively, preferentially to obtain optimal medical activity, ii) at the end of these several sequences, corresponding to a session, the treatment or method needs to be stopped for a sufficiently long time longer than the duration between two sequences, for example because of the suffering or tiring or long anesthesia of the patient treated by the method or treatment or because of the lack of availability of the medical infrastructure or medical team.

In one embodiment, the duration of a treatment session can be longer than $10^{-50}$, $10^{-10}$, $10^{-1}$, 1, 5, 10, 15, 30, 100, $10^3$, $10^5$ or $10^{10}$ minute(s).

In some other embodiments, the duration of a treatment session can be shorter than $10^{50}$, $10^{10}$, 60, 30, 10, 5, 2, 1, $10^{-1}$ or $10^{-5}$ minute(s).

In still some other embodiments, the duration of a treatment session can be between $10^{-50}$ and $10^{50}$ minutes, preferably between $10^{-50}$ and $10^3$ minutes, more preferably between $10^{-50}$ and 60 minutes, even more preferably between $10^{-50}$ and 30 minutes, even more preferably between $10^{-5}$ and 30 minutes, even more preferably between $10^{-3}$ and 15 minutes, between $10^{-1}$ and 10 minutes, or even more preferably between $10^{-1}$ and 5 minutes.

A first treatment session can be separated from a second session by an inter-session duration.

In one embodiment, the inter-session duration can be shorter than $10^5$, $10^3$, 100, 60, 30, 15, 10, 5, 2, 1, $10^{-1}$ or $10^{-3}$ or $10^{-10}$ minutes. This may be the case when it is necessary to rapidly repeat sessions, preferentially to reach medical or antitumor activity.

In some other embodiments, the inter-session duration can be longer than $10^{-10}$, $10^{-3}$, $10^{-1}$, 1, 5, 10, $10^3$, $10^5$, $10^{10}$ or $10^{20}$ minute(s). This may be the case when it is necessary to stop the treatment or method for a certain lapse of time, for example when a patient needs to recover from the treatment or method preferentially between two sessions, for example when the method of treatment uses anesthesia or is combined with or necessitates the use of a difficult to withstand clinical protocol such as surgery, chemotherapy, radiotherapy and/or immunotherapy.

In still some other embodiments, the inter-session duration can be between $10^{-10}$ and $10^{20}$ minute(s), preferably between $10^{-5}$ and $10^5$ minute(s), more preferably between $10^{-5}$ and 10 minute(s), or even more preferably between $10^{-5}$ and 1 minute(s).

In one embodiment, the inter-session duration is higher by a factor of at least 0, 1, 1.1, 2, 5, 10, $10^3$, $10^5$ or $10^{10}$ than the inter-sequence or inter-step duration.

In still some other embodiments, the inter-session duration is lower by a factor of at least 0, 1, 1.1, 2, 5, 10, $10^3$, $10^5$ or $10^{10}$ than the inter-sequence or inter-step duration.

In one embodiment, treatment session can be separated by a duration, which is more than 1.001, 1.01, 1.1, 1.2, 1.5, 2, 5, 10, $10^3$, or $10^5$ times higher than $t_{1a}+t_{2a}$ or $t_{1b}+t_{2b}$.

In one embodiment of the invention, the treatment session is repeated more than 2, 5, 10, 100, or $10^4$ times.

In another embodiment of the invention, the treatment session is repeated less than 5, 10, 100, $10^4$, or $10^5$ times.

In another embodiment of the invention, the number of treatment sessions and/or sequences is adjusted to reach maximum treatment efficacy, i.e. for example to reach the disappearance or destruction of a disease, of the portion of the body part comprising the pathological cells, or of a tumor.

In still another embodiment of the invention, the number of treatment session(s) and/or sequence(s) is adjusted to reach minimal treatment toxicity, i.e. for example to avoid the disappearance or destruction of the portion of the body part comprising the healthy cells.

The sequential laser radiation of the present invention allows a heating temperature of the body part which is lower than with a continuous laser radiation while surprisingly being more efficient and/or having less side effects. The treatment of the present invention preferentially heats the body part at an average heating temperature that is lower than the average temperature reached by continuously irradiating magnetosomes with a laser without carrying out at least the first step and the second step.

In one embodiment, during the first step and/or second step, the heating temperature of the body part resulting from the laser radiation(s) is stable for less than 100%, preferably 50%, more preferably 10% of the duration of the step(s), or for less than $10^5$, preferably $10^3$, more preferably 10 seconds.

In one embodiment, the heating temperature of the body part resulting from the laser radiation(s) is characterized by at least one property selected in the group consisting of:
an average heating temperature that is lower than 100° C.,
an average heating temperature that is lower, preferentially by at least 1° C., than the maximum temperature reached during the treatment,
a maximum heating temperature that is lower than 100° C.,
an average heating temperature that is lower, preferentially by at least 1° C., than the average heating temperature reached by continuously irradiating the magnetic nanoparticles with a laser, and
a number of heating temperature gradients that is higher, preferentially by a factor of at least 2, than the number of heating temperature gradients reached by continuously irradiating the magnetic nanoparticles with a laser,
where the comparison between the methods of sequential and continuous laser irradiation is preferentially made by using the same total time of laser irradiation and/or the same laser power during the time of magnetosome irradiation.

Without wishing to be bound by theory, the sequential laser radiation of the present invention is thus more efficient and/or has less side effects than continuously irradiating magnetosomes with a laser, notably regarding the ratio activated pathological cells/healthy cells.

In one embodiment, the treatment results in a number of activated pathological cells, $N_{pat}$, with at least one property selected in the group consisting of:
A value of $N_{pat}$, which is larger than 1, preferentially 1 per $cm^3$ of body part.
A value of $N_{pat}/N_{health}$, where $N_{health}$ is the number of healthy cells, which is larger than 1, and
A value of $N_{pat}$ or $N_{pat}/N_{health}$, which is larger than that obtained by continuously exposing magnetosomes to a laser radiation,
wherein activated pathological cells are cells with at least one property selected in the group consisting of: i) cells comprised in a pathological site or magnetosome region, ii) cells attracted by or migrating towards or dividing in or proliferating in a pathological site or magnetosome region, iii) cells that are alive preferentially before or without the treatment or when the treatment is not efficient, iv) cells that are dead or destroyed, preferentially through apoptosis or necrosis, preferentially during or after or with the treatment or when the treatment is efficient, v) cells that promote the growth or maintenance of the pathological site, and v) cells that prevent the destruction or disappearance of the pathological site,
wherein healthy cells are cells with at least one property selected in the group consisting of: i) cells comprised in a healthy site or region without magnetosome, ii) cells attracted by or migrating towards or dividing in or proliferating in a healthy site or region without magnetosome, iii) cells that are alive preferentially during or after or with the treatment or when the treatment is efficient, iv) cells that are dead or destroyed, preferentially through apoptosis or necrosis, preferentially before or without the treatment or when the treatment is not efficient, v) cells that promote the growth or maintenance of the healthy site, and vi) cells that prevent the destruction or disappearance of the healthy site.

In one aspect of the invention, the invention relates to magnetic nanoparticles, in particular magnetosomes, for use, wherein the first step is a heating step and/or a dissociation step.

In one aspect of the invention, the invention relates to magnetic nanoparticles, in particular magnetosomes, for use according to the invention, wherein the first step further comprises heating and/or dissociation of at least one compound from the magnetic nanoparticles, in particular magnetosomes.

In one aspect of the invention, the invention relates to the method according to the invention, wherein the first step further comprises heating and/or dissociation of at least one compound from the magnetic nanoparticles, in particular magnetosomes.

In one embodiment of the invention, the heating step has a duration $t_{1a}$, also designated as duration of the heating step or heating time.

In one embodiment, the duration of the heating step corresponds to the duration of the temperature increase of the body part, magnetic nanoparticle(s), in particular magnetosome(s), or the region of the magnetic nanoparticles, in particular magnetosomes. It is preferentially comprised between the time, $t_{i1a}$, of: i), laser start, ii), switching on of the laser equipment or apparatus, or iii), the beginning of irradiation by the laser radiation, preferentially of the body part, magnetic nanoparticle(s), in particular magnetosome,(s), or region of magnetic nanoparticles, in particular magnetosomes, and the time, $t_{f1a}$, of: i), laser stop, ii), switching off of the laser equipment or apparatus, iii), ending of irradiation by the laser radiation, or iv), irradiation by laser radiation with a lower power than at time $t_{ia}$, preferentially of the body part, magnetic nanoparticle(s), in particular magnetosome(s), or region of magnetic nanoparticles, in particular magnetosomes.

In one embodiment, the magnetic nanoparticles, in particular the magnetosomes, will start to produce or induce an increase in temperature of the body part, magnetic nanoparticle(s), in particular magnetosome(s), or region of magnetic nanoparticles, in particular magnetosomes, a certain time $\Delta t_{i1a}$ following $t_{i1a}$.

In one embodiment of the invention, the magnetic nanoparticles, in particular the magnetosomes, will stop producing or inducing an increase in temperature of the body part, magnetic nanoparticle(s), in particular magnetosome(s), or region of magnetic nanoparticles, in particular magnetosomes, a certain time $\Delta t_{f1a}$ following $t_{f1a}$.

In one embodiment of the invention, $\Delta t_{i1a}$ and/or $\Delta t_{f1a}$ is/are higher than $10^{-9}$, $10^{-6}$, $10^{-3}$, $10^{-1}$, 1, or 10 second(s). This long delay may, in one embodiment, be due to the absorption of laser radiation by the body part not comprising the magnetic nanoparticles, in particular magnetosomes, or by other substances than the magnetic nanoparticles, in particular magnetosomes. This long delay may, in some other embodiments, be due to the absorption of laser radiation by the magnetic nanoparticles, in particular magnetosomes, or body part comprising the magnetic nanoparticles, in particular magnetosomes, which is not immediately transformed or transferred into heat.

In some other embodiments of the invention, $\Delta t_{i1a}$ and/or $\Delta t_{f1a}$ is/are lower than $10^{-9}$, $10^{-6}$, $10^{-3}$, $10^{-1}$, 1, or 10 second(s). This short delay may, in one embodiment, be due to the absorption of laser radiation by the magnetic nanoparticles, in particular magnetosomes, and to its rapid transformation or transfer into heat.

In still some other embodiments of the invention, the value(s) of $\Delta t_{i1a}$ and/or $\Delta t_{f1a}$ depend(s) upon organization of magnetic nanoparticles, in particular magnetosomes, transfer of heat from the magnetic nanoparticles, in particular magnetosomes, to the surrounding or environment of the magnetic nanoparticles, in particular magnetosomes, or to the intrinsic properties of the magnetic nanoparticles, in particular magnetosomes, such as size, ferrimagnetic properties, crystallization. In one embodiment, $\Delta t_{i1a}$ and/or $\Delta t_{f1a}$ can be decreased by improving the crystallization of magnetic nanoparticles, in particular magnetosomes, by increasing the size of magnetic nanoparticles, in particular magnetosomes, by reducing the size distribution of magnetic nanoparticles, in particular magnetosomes, or by improving the spatial distribution of magnetic nanoparticles, in particular magnetosomes, preferentially by reducing the aggregation of magnetic nanoparticles, in particular magnetosomes, preferentially in the body part.

In the experimental example, $\Delta t_{f1a}$ is equal to 0 second for 0.5 and 1 mg/mL of M-CMD and between 6 and 16 seconds for N-CMD. It indicates that some nanoparticles, which are preferentially chemically synthesized or which are not well crystallized, continue to heat after the laser has been switched off. This is a property that should usually be avoided since it can yield overheating and prevent an accurate control over the temperature reached during the heating steps. It also indicates that some nanoparticles, which are preferentially produced biologically or by living organisms or are well crystallized, stop heating immediately after the laser has been switched off. This is a property that should usually be sought or looked after since it can prevent overheating and enable an accurate control over the temperature reached during the heating steps.

In one embodiment of the invention, the dissociation step has a duration $t_{1b}$, also designated as duration of the dissociation step or dissociation time.

In one embodiment, the duration of the dissociation step corresponds to the duration of the dissociation of the compound from the magnetic nanoparticle, in particular magnetosome. It is preferentially comprised between the time, $t_{i1b}$, of laser start, switching on of the laser equipment or apparatus, the beginning of irradiation by the laser radiation, preferentially of the body part, magnetic nanoparticle(s), in particular magnetosome(s), or region of magnetic nanoparticles, in particular magnetosomes, and the time, $t_{f1b}$, of laser stop, switching off of the laser equipment or apparatus, or the ending of irradiation by the laser radiation.

In one embodiment, the magnetic nanoparticles, in particular the magnetosomes, will start producing or inducing the dissociation of the compound from the magnetic nanoparticle, in particular magnetosome, at a certain time $\Delta t_{i1b}$ before or following $t_{i1b}$.

In one embodiment of the invention, the magnetic nanoparticle, in particular magnetosome, will stop producing or inducing the dissociation of the compound from the magnetic nanoparticle, in particular magnetosome, at a certain time $\Delta t_{f1b}$ before or following $t_{f1b}$.

In one embodiment of the invention, $\Delta t_{i1b}$ and/or $\Delta t_{f1b}$ is/are higher than $10^{-9}$, $10^{-6}$, $10^{-3}$, $10^{-1}$, 1, or 10 second(s). This long delay may, in one embodiment, be due to the absorption of laser radiation by the body part not comprising the magnetic nanoparticles, in particular magnetosomes, or by other substances than the magnetic nanoparticle, in particular magnetosome. This long delay may, in some other embodiments, be due to the absorption of laser radiation by the magnetic nanoparticle, in particular magnetosome, or body part comprising the magnetic nanoparticles, in particular magnetosomes, which does not immediately induce the dissociation of the compound from the magnetic nanoparticle, in particular magnetosome.

In some other embodiments of the invention, $\Delta t_{i1b}$ and/or $\Delta t_{f1b}$ is/are lower than $10^{-9}$, $10^{-6}$, $10^{-3}$, $10^{-1}$, 1, or 10 second(s). This short delay may, in one embodiment, be due to the absorption of laser radiation by the magnetic nanoparticle, in particular magnetosome, which rapidly leads to the dissociation of the compound from the magnetic nanoparticle, in particular magnetosome.

In still some other embodiments of the invention, the value(s) of $\Delta t_{i1b}$ and/or $\Delta t_{f1b}$ depend(s) upon organization of the magnetic nanoparticle, in particular magnetosome, the strength of the link between the compound and the magnetic nanoparticle, in particular magnetosome, the distance between the compound and the magnetic nanoparticle, in particular magnetosome, the properties of the magnetic nanoparticle, in particular magnetosome, such as size, ferrimagnetic properties, or crystallization. In one embodiment, $\Delta t_{i1b}$ and/or $\Delta t_{f1b}$ can be decreased by improving crystallization of magnetic nanoparticle, in particular magnetosome, by increasing the size of magnetic nanoparticles, in particular magnetosomes, by reducing the size distribution of magnetic nanoparticles, in particular magnetosomes, by improving the spatial distribution of magnetic nanoparticles, in particular magnetosomes, preferentially by reducing the aggregation of magnetic nanoparticles, in particular magnetosomes, preferentially in the body part, by adjusting the strength or distance between the compound and the magnetic nanoparticle, in particular magnetosome, so that the irradiation by the laser radiation induces the dissociation of the compound from the magnetic nanoparticle, in particular magnetosome, rapidly after the irradiation by the laser radiation.

In another embodiment of the invention, the first step has a duration, which is equal to $t_{1a}$ or $t_{1b}$, or which is higher than $t_{1a}$ or $t_{1b}$, or which is lower than $t_{1a}+t_{1b}$.

In one embodiment of the invention, the heating step is the step during which or in which the body part or magnetic nanoparticle, preferentially magnetosome, is heated, preferentially by more than $10^{-6}$, $10^{-3}$, $10^{-1}$, 1, 2, 5, 10, or 15° C., preferentially above physiological temperature or above the temperature of the body part not comprising the magnetic nanoparticle, in particular magnetosome, or above the temperature of the body part reached before the irradiation by the laser radiation or above the temperature of the magnetic nanoparticle before or without the irradiation with the laser radiation.

In one embodiment of the invention, the dissociation step is the step during which or in which the compound dissociates from the magnetic nanoparticle, in particular magnetosome. In one embodiment, the compound dissociates from the magnetic nanoparticle, in particular magnetosome when more than 0.1, 1, 10, 25, 50, 75, or 90% of compounds are dissociated from the magnetic nanoparticle, in particular magnetosome.

Preferentially, the percentage of dissociation means or is the percentage of dissociation of the compounds from the magnetic nanoparticles, in particular magnetosomes, which may also be designated as the percentage of dissociation.

Preferentially, the variation of the percentage of dissociation is the variation with time, most preferentially during the dissociation or non-dissociation step, of the percentage of dissociation.

Preferentially, the gradient of the percentage of dissociation is the slope of the variation with time, most preferentially during the dissociation or non-dissociation step, of the percentage of dissociation. Most preferentially, this gradient is the absolute value of the slope of the variation with time of the percentage of dissociation.

In one embodiment, the percentage of dissociation of the compounds from the magnetic nanoparticle, in particular magnetosome, corresponds to or is the number of compounds not linked or not bound to the magnetic nanoparticle, in particular magnetosome, preferentially following the irradiation by the laser radiation, divided by the number of compounds linked or bound to the magnetic nanoparticle, in particular magnetosome, preferentially before or without the irradiation by the laser radiation.

In embodiment of the invention, the compound dissociated from the magnetic nanoparticles, in particular magnetosomes, belongs to the coating or central part of the magnetic nanoparticle, or is a metallic atom, such as iron. As an example, iron can dissociate from the magnetosomes following irradiation of the magnetosomes. In some embodiments, irradiation directly results in the dissociation of the compound from the magnetic nanoparticle, i.e. the dissociation is not due or not predominantly due to another entity than laser irradiation such as a cell or a specific medium such as an acidic medium. In some other embodiments, irradiation indirectly results in the dissociation of the compound from the magnetic nanoparticle, i.e. an entity different from laser radiation such as a cell or a specific medium can cause the dissociation preferentially after it is activated by the laser or when it dissociates the compound following laser irradiation.

In one embodiment of the invention, the compound comprises at least one substance capable of establishing weak interactions or covalent bonds with the magnetic nanoparticle, in particular magnetosome.

In one embodiment of the invention, the compound comprises at least one compound capable of being chemisorbed or physisorbed on the magnetic nanoparticle, in particular magnetosome, or on the surface of the magnetic nanoparticle, in particular magnetosome.

In one embodiment of the invention, the compound comprises at least one substance capable of establishing interactions or bonds with atoms, ions, or molecules, which may be in or on the surface of the magnetic nanoparticle, in particular magnetosome.

In one embodiment of the invention, the compound comprises at least one substance, atom, ion, or chemical function such as an acid, carboxylic acid, phosphoric acid, or sulfonic acid function, wherein the substance, atom or ion included in the coating is capable of establishing interactions or bonds with the magnetic nanoparticle, in particular magnetosome.

In one embodiment of the invention, the percentage of dissociation is defined as the ratio between the number or mass of compounds that have dissociated following the irradiation by the laser radiation divided by the number or mass of compounds that are linked to the magnetic nanoparticle, in particular magnetosome, before the irradiation by the laser radiation.

In another embodiment of the invention, the compound is dissociated from the magnetic nanoparticle, in particular magnetosome, when the magnetic nanoparticle, in particular magnetosome, is magnetically separated from the compound. In this case, a magnet can preferentially be used to attract the magnetic nanoparticle, in particular magnetosome, preferentially using a magnetic field whose intensity varies spatially, preferentially using a magnet with a lower strength than 10, 1, $10^{-1}$, $10^{-3}$, or $10^{-9}$ T, where this strength is preferentially measured at the surface or near the magnet and decreases with increasing distance away from the magnet. By contrast to the magnetic nanoparticle, in particular magnetosome, the compound is preferentially not attracted by the magnet. Hence, by using magnetic separation, a certain distance, preferentially higher than 1, 10, $10^3$, or $10^5$ nm, can be created between the compound and the magnetic nanoparticle, in particular magnetosome, and the magnetic nanoparticle, in particular magnetosome, can then be separated or isolated from the compound.

In another embodiment of the invention, the compound is dissociated from the magnetic nanoparticle, in particular magnetosome, when the percentage of compounds associated or linked to the magnetic nanoparticle, in particular magnetosome, or located at a distance of less than 10, 1, $10^{-1}$, $10^{-3}$, $10^{-6}$, or $10^{-9}$ cm from the magnetic nanoparticle, in particular magnetosome, is lower than 99, 90, 75, 50, 30, 20, 10, 5, 2, or 1%, where this percentage can represent the ratio between the number or mass of compounds linked or associated to the magnetic nanoparticle, in particular magnetosome, before magnetic separation and the number or mass of compounds linked or associated to the magnetic nanoparticle, in particular magnetosome, after magnetic separation.

In another embodiment of the invention, the compound is not dissociated from the magnetic nanoparticle, in particular magnetosome, or non-dissociated, when the magnetic nanoparticle, in particular magnetosome, cannot be magnetically separated from the compound, preferentially using a magnet with a strength that is lower than 10, 1, $10^{-1}$, $10^{-3}$, or $10^{-9}$ T.

In still another embodiment of the invention, the compound is not dissociated from the magnetic nanoparticle, in particular magnetosome, or non-dissociated when the percentage of compounds associated or linked to the magnetic nanoparticle, in particular magnetosome, or located at a distance of less than 10, 1, $10^{-1}$, $10^{-3}$, $10^{-6}$, or $10^{-9}$ cm from the magnetic nanoparticle, in particular magnetosome, is higher than 99, 90, 75, 50, 30, 20, 10, 5, 2, or 1%, where this percentage can represent the ratio between the number or mass of compounds linked or associated to the magnetic nanoparticle, in particular magnetosome, before magnetic separation and the number or mass of compounds linked or associated to the magnetic nanoparticle, in particular magnetosome, after magnetic separation.

The invention relates to magnetic nanoparticles, in particular magnetosomes, for use, wherein the first step can be divided between a first sub-step during which or in which a first portion of the body part is irradiated by the laser radiation, and a second sub-step during which or in which temperature increase and/or dissociation of a compound from the magnetic nanoparticles, in particular magnetosomes, occurs in another portion of the body part, which has not been irradiated by the laser radiation during the first sub-step.

In one embodiment of this invention, the body part is divided between a portion of the body part irradiated by the laser radiation or irradiated and a portion of the body part not irradiated by the laser radiation or not irradiated.

In still another embodiment of the invention, the portion of the body part irradiated by the laser radiation, also designated in one embodiment as body part or portion of body part, is the region where a first portion of magnetic nanoparticles, in particular magnetosomes, is located preferentially in the body part or individual. It can also be designated in one embodiment as first region of magnetic nanoparticles, in particular magnetosomes.

In one embodiment of the invention, the first region of magnetic nanoparticles, in particular magnetosomes, corresponds to or is the volume comprising less than 99, 90, 80, 70, 50, 40, 20, 10, 5, or 1% of the magnetic nanoparticles, in particular magnetosomes, which have been administered to the individual or body part or are comprised in the body part or individual. This percentage can represent the ratio between the quantity of magnetic nanoparticles, in particular magnetosomes, comprised in the first region of magnetic nanoparticles, in particular magnetosomes, and the quantity of magnetic nanoparticles, in particular magnetosomes, administered to or comprised in the individual or body part.

In one embodiment of the invention, the body part or portion of body part is the region where a second portion of magnetic nanoparticles, in particular magnetosomes, is located preferentially in the individual. It can also be designated in one embodiment as second region of magnetic nanoparticles, in particular magnetosomes.

In one embodiment of the invention, the second region of magnetic nanoparticles, in particular magnetosomes, corresponds to or is the volume comprising more than 99, 90, 80, 70, 50, 40, 20, 10, 5, 1, $10^{-3}$, or $10^{-6}$% of magnetic nanoparticles, in particular magnetosomes, which are not located in the first region of magnetic nanoparticles, in particular magnetosomes, or which are located outside of the first region of magnetic nanoparticles, in particular magnetosomes, or which are located in a different region from the first region of magnetic nanoparticles, in particular magnetosomes. This percentage can represent the ration between the quantity of magnetic nanoparticles, in particular magnetosomes, which are located outside of the first region of magnetic nanoparticles, in particular magnetosomes, or which are located in the second region of magnetic nanoparticles, in particular magnetosomes, divided by the quantity of magnetic nanoparticles, in particular magnetosomes, comprised in or administered to the individual or body part.

In still another embodiment of the invention, the duration between the first and second sub-steps is lower than 1, $10^{-3}$, $10^{-6}$, or $10^{-9}$ second(s).

In still another embodiment of the invention, the mechanism by which the magnetic nanoparticles, in particular the magnetosomes, located in the second region of magnetic nanoparticles, in particular magnetosomes, can be heated or prone to the dissociation of the compound can involve conduction of heat or conduction or transmission of an electromagnetic wave between the first and second regions of magnetic nanoparticles, in particular magnetosomes. In case of large concentrations of magnetic nanoparticles, in particular magnetosomes, or magnetic nanoparticles, in particular magnetosomes, connected to each other, preferentially in chains, or densely packed, heat conduction and/or transmission or conduction of the electromagnetic wave can be favored.

In one embodiment of the invention, heat conduction and/or transmission or conduction of the electromagnetic wave takes place between the magnetic nanoparticles, in particular magnetosomes, and tissues or water comprised in the body part, or between water molecules in the body part, preferentially between moving water molecules, where the movement of water molecules is preferentially increased by heat.

The invention also relates to magnetic nanoparticles, in particular magnetosomes, for use, wherein the second step is a cooling step and/or a non-dissociation step.

In one embodiment of the invention, the cooling step has a duration tea, also designated as duration of the cooling step or cooling time.

In one embodiment of the invention, the duration of the cooling step corresponds to the duration of the temperature decrease of the body part, magnetic nanoparticle(s), in particular magnetosome(s), or region of magnetic nanoparticles, in particular magnetosomes. It is preferentially comprised between the time, $t_{i2a}$, of laser stop, switching off of the laser equipment or apparatus, decrease of the laser power, laser power density, or laser intensity, or the end of irradiation by the laser radiation, and the time, $t_{f2a}$, of laser start, switching on of the laser equipment or apparatus, or the beginning of irradiation by the laser radiation.

In one embodiment of the invention, the temperature decrease designates the temperature decrease of the body part, portion of the body part comprising the magnetic nanoparticles, in particular the magnetosomes, region of the magnetic nanoparticles, in particular the magnetosomes. The temperature decrease can be assimilated to or correspond to the magnitude of the temperature decrease occurring in the second step, which is preferentially the absolute value of the difference between the maximum and minimum temperature reached in the second step, which is also in one embodiment designated as temperature variation or temperature variation during or occurring in the second step.

In one embodiment of the invention, the magnetic nanoparticles, in particular the magnetosomes, will start producing or inducing a decrease in temperature of the body part, magnetic nanoparticle(s), in particular magnetosome(s), or region of magnetic nanoparticles, in particular magnetosomes, a certain time $\Delta t_{i2a}$ following or preceding $t_{i2a}$.

In one embodiment of the invention, the magnetic nanoparticles, in particular magnetosomes, will stop producing or inducing a decrease in temperature of the body part, magnetic nanoparticle(s), in particular magnetosome(s), or region of magnetic nanoparticles, in particular magnetosomes, a certain time $\Delta t_{f2a}$ following or preceding $t_{f2a}$.

In one embodiment of the invention, $\Delta t_{i2a}$ and/or $\Delta t_{f2a}$ is/are higher than $10^{-9}$, $10^{-6}$, $10^{-3}$, $10^{-1}$, 1, or 10 second(s). This long delay may, in one embodiment, be due to the slow or inefficient release or heat transfer from the magnetic nanoparticles, in particular magnetosomes, to the environment or medium surrounding the magnetic nanoparticles, in particular magnetosomes, or to the body part not comprising the magnetic nanoparticles, in particular magnetosomes.

In one embodiment of the invention, this release or transfer of heat can be slower than $10^{-20}$, $10^{-10}$, $10^{-4}$, $10^{-2}$, $10^{-1}$, 1, 10, $10^2$, $10^5$, $10^{10}$, or $10^{20}$° C. per second.

In some other embodiments of the invention, $\Delta t_{i2a}$ and/or $\Delta t_{f2a}$ is/are lower than $10^{-9}$, $10^{-6}$, $10^{-3}$, $10^{-1}$, 1, or 10 second(s). This short delay may, in one embodiment, be due to the fast or efficient release or transfer of heat from the magnetic nanoparticle, in particular magnetosome, to the environment or medium surrounding the magnetic nanoparticle, in particular magnetosome, or to the body part not comprising the magnetic nanoparticle, in particular magnetosome.

In one embodiment of the invention, this release or transfer of heat is faster than $10^{-20}$, $10^{-10}$, $10^{-4}$, $10^{-2}$, $10^{-1}$, 1, 10, $10^2$, $10^5$, $10^{10}$, or $10^{20}$° C. per second.

In still some other embodiments of the invention, the value(s) of $\Delta t_{i2a}$ and/or $\Delta t_{f2a}$ depend(s) upon organization of magnetic nanoparticle, in particular magnetosome, heat transfer from the magnetic nanoparticle, in particular magnetosome, to the surrounding or environment of the magnetic nanoparticle, in particular magnetosome, or to the body part not comprising the magnetic nanoparticle, in particular magnetosome. It can also depend on the properties of the magnetic nanoparticle, in particular magnetosome, such as size, ferrimagnetic properties, crystallization. In one embodiment of the invention, $\Delta t_{i2a}$ and/or $\Delta t_{f2a}$ can be decreased by improving crystallization of magnetic nanoparticle, in particular magnetosome, increasing the size of magnetic nanoparticles, in particular magnetosomes, reducing the size distribution of magnetic nanoparticles, in particular magnetosomes, improving the spatial distribution of magnetic nanoparticles, in particular magnetosomes, preferentially by reducing aggregation of magnetic nanoparticles, in particular magnetosomes, preferentially in the body part.

In the experimental example, $\Delta t_{f2a}$ is equal to 0 second for 0.5 and 1 mg/mL of M-CMD and between 6 and 25 seconds for N-CMD. It indicates that some nanoparticles, which are preferentially chemically synthesized or which are not well crystallized, do not cool down within the same period of time as that of laser switch off. This is a property that should usually be avoided since it can yield overcooling and prevents an accurate control over the temperature reached during the cooling steps. It also indicates that some nanoparticles, which are preferentially produced biologically or by living organisms or are well crystallized, cool down within the same period of time as that of laser switch off. This is a property that should usually be sought after since it can prevent overcooling and enable an accurate control over the temperature reached during the cooling steps.

In one embodiment of the invention, the non-dissociation step has a duration $t_{2b}$, also designated as duration of the non-dissociation step or non-dissociation time.

In one embodiment of the invention, the duration of the non-dissociation step corresponds to the duration of the non-dissociation of the compound from the magnetic nanoparticle, in particular magnetosome. It is preferentially comprised between the time, $t_{i2b}$, of laser stop, switching off of the laser equipment or apparatus, the end of irradiation by the laser radiation, and the time, $t_{f2b}$, of laser start, switching on of the laser equipment or apparatus, the beginning of irradiation by the laser radiation.

In one embodiment of the invention, the magnetic nanoparticle, in particular magnetosome, will start producing or inducing the non-dissociation of the compound from the magnetic nanoparticle, in particular magnetosome, a certain time $\Delta t_{i2b}$ following or preceding $t_{i2b}$.

In one embodiment of the invention, the magnetic nanoparticle, in particular magnetosome, will stop producing or inducing the non-dissociation of the compound from the magnetic nanoparticle, in particular magnetosome, a certain time $\Delta t_{f2b}$ following or preceding $t_{f2b}$.

In one embodiment of the invention, $\Delta t_{i2b}$ and/or $\Delta t_{f2b}$ is/are higher than $10^{-9}$, $10^{-6}$, $10^{-3}$, $10^{-1}$, 1, or 10 second(s). This long delay may for $\Delta t_{i2b}$ be due to the continuation of the dissociation of the compound from the magnetic nanoparticle, in particular magnetosome, a long time after the laser has been switched off or reduced in power. This long delay may for $\Delta t_{f2b}$ be due to the beginning of the dissociation of the compound a long time after the laser has been switched on.

In some other embodiments of the invention, $\Delta t_{i2b}$ and/or $\Delta t_{f2b}$ is/are lower than $10^{-9}$, $10^{-6}$, $10^{-3}$, $10^{-1}$, 1, or 10 second(s). This short delay may for $\Delta t_{i2b}$ be due to the end of the dissociation of the compound from the magnetic nanoparticle, in particular magnetosome, a short time after the laser has been switched off or reduced in power. This sort delay may for $\Delta t_{f2b}$ be due to the beginning of the dissociation of the compound a short time after the laser has been switched on.

In still some other embodiments of the invention, the value(s) of $\Delta t_{i2b}$ and/or $\Delta t_{f2b}$ depend upon the organization of magnetic nanoparticles, in particular magnetosomes, the strength of the link between the compound and the magnetic nanoparticle, in particular magnetosome, the distance between the compound and the magnetic nanoparticle, in particular magnetosome, the properties of the magnetic nanoparticle, in particular magnetosome, such as size, ferrimagnetic properties, or crystallization.

In one embodiment of the invention, $\Delta t_{i2b}$ and/or $\Delta t_{f2b}$ is/are decreased by improving crystallization of magnetic nanoparticles, in particular magnetosomes, increasing the size of magnetic nanoparticles, in particular magnetosomes, reducing the size distribution of magnetic nanoparticles, in particular magnetosomes, improving the spatial distribution of magnetic nanoparticles, in particular magnetosomes, preferentially by reducing aggregation of magnetic nanoparticles, in particular magnetosomes, preferentially in the body part, by adjusting the strength or distance between the compound and the magnetic nanoparticle, in particular magnetosome, so that the end of irradiation by the laser radiation stops the dissociation or induces the non-dissociation of the compound from the magnetic nanoparticle, in particular magnetosome, a short time after the end of irradiation by the laser radiation.

In another embodiment of the invention, the second step has a duration, which is equal to $t_{2a}$ or $t_{2b}$, or which is higher than $t_{2a}$ or $t_{2b}$, or which is lower than $t_{2a}+t_{2b}$.

In one embodiment of the invention, the cooling step is the step during which or in which the body part or magnetic nanoparticle is cooled or decreased in temperature, preferentially by more than $10^{-6}$, $10^{-3}$, $10^{-1}$, 1, 2, 5, 10, or 15° C., preferentially below the maximum temperature reached during the heating step.

In one embodiment of the invention, the non-dissociation step is the step during which or in which the compound does not dissociate from the magnetic nanoparticle, in particular magnetosome.

In one embodiment of the invention, the compound does not dissociate from the magnetic nanoparticle, in particular magnetosome, when the percentage of dissociation is lower than 0.1, 1, 10, 25, 50, 75, or 90%.

In another embodiment of the invention, the time $t_{1a}$, $t_{1b}$, $t_{2a}$, or $t_{2b}$, is shorter than $10^{-3}$, $10^{-2}$, $10^{-1}$, 1, 10, $10^2$, or $10^3$ minute(s).

In one embodiment of the invention, $t_{1a}$, $t_{1b}$, $t_{2a}$, or $t_{2b}$, is shorter than $10^{-9}$, $10^{-7}$, $10^{-5}$, $10^{-3}$, $10^{-1}$, 1, 10, $10^3$, $10^5$, $10^7$, or $10^9$ second(s).

In still another embodiment of the invention, the time $t_{1a}$, $t_{1b}$, $t_{2a}$, or $t_{2b}$, is longer than $10^{-3}$, $10^{-2}$, $10^{-1}$, 1, 10, $10^2$, or $10^3$ minute(s).

In one embodiment of the invention, $t_{1a}$, $t_{1b}$, $t_{2a}$, or $t_{2b}$, is longer than $10^{-9}$, $10^{-7}$, $10^{-5}$, $10^{-3}$, $10^{-1}$, 1, 10, $10^3$, $10^5$, $10^7$, or $10^9$ second(s).

In one embodiment of the invention, the time $t_{1a}$, $t_{1b}$, $t_{2a}$, or $t_{2b}$, is shorter than the time of a laser pulse, preferably by a factor of at least 1.1, 1.5, 2, 5, 10, $10^2$, $10^3$, $10^5$, $10^7$, $10^9$, $10^{12}$, $10^{15}$, or $10^{20}$.

In still another embodiment of the invention, the time $t_{1a}$, $t_{1b}$, $t_{2a}$, or $t_{2b}$, is longer than the time of a laser pulse, preferably by a factor of at least 1.1, 1.5, 2, 5, 10, $10^2$, $10^3$, $10^5$, $10^7$, $10^9$, $10^{12}$, $10^{15}$, or $10^{20}$.

In still another embodiment of the invention, the pulse is defined as the irradiation by the laser radiation, preferentially on magnetic nanoparticle(s), in particular magnetosome,(s), body part, or region of magnetic nanoparticles, in particular magnetosomes, during a time shorter than $10^6$, $10^3$, 1, $10^{-3}$, $10^{-6}$, $10^{-9}$, $10^{-12}$, $10^{-15}$, or $10^{-20}$ second(s).

In one embodiment of the invention, the ratio $t_{1a}/t_{2a}$ or $t_{1b}/t_{2b}$ is smaller than $10^{-9}$, $10^{-6}$, $10^{-3}$, $10^{-1}$, 1, 10, $10^3$, $10^6$, or $10^9$.

In still another embodiment of the invention, the ratio $t_{1a}/t_{2a}$ or $t_{1b}/t_{2b}$ is higher than $10^{-9}$, $10^{-6}$, $10^{-3}$, $10^{-1}$, 1, 10, $10^3$, $10^6$, or $10^9$.

In the experimental example, $t_{1a}$ is comprised between 35 sec. and 150 sec. for 0.5 mg/mL of M-CMD, 21 sec. and 80 sec. for 1 mg/mL M-CMD, and 22 sec. and 45 sec. for N-CMD.

In one embodiment of the invention, it is possible to decrease $t_{1a}$, preferentially by a factor of more than 1.001, 1.01, 1.1, 1.5, 2, 5, 10, or $10^3$, and still induce a temperature increase during the heating step. This can preferentially be achieved by: i), increasing the concentration of magnetic nanoparticles, in particular magnetosomes, preferentially by a factor of more than 1.001, 1.01, 1.1, 1.5, 2, 5, 10, or $10^3$, ii), increasing the laser power, laser power density, or laser intensity, preferentially by a factor of more than 1.001, 1.01, 1.1, 1.5, 2, 5, 10, or $10^3$, or iii), by reducing the temperature increase or temperature gradient that one wants to achieve during the heating step, preferentially by a factor of more than 1.001, 1.01, 1.1, 1.5, 2, 5, 10, or $10^3$.

In still some other embodiments of the invention, it is possible to increase $t_{1a}$, preferentially by a factor of more than 1.001, 1.01, 1.1, 1.5, 2, 5, 10, or $10^3$, and induce a temperature increase during the heating steps, preferentially without inducing a temperature increase of the body part not comprising the magnetic nanoparticles, in particular magnetosomes. This can preferentially be achieved by: i), decreasing the concentration of the magnetic nanoparticles, in particular magnetosomes, preferentially by a factor of more than 1.001, 1.01, 1.1, 1.5, 2, 5, 10, or $10^3$, ii), decreasing the laser power, laser power density, or laser intensity, preferentially by a factor of more than 1.001, 1.01, 1.1, 1.5, 2, 5, 10, or $10^3$, or iii), by increasing the temperature increase or temperature gradient that one wants to achieve during the heating step, preferentially by a factor of more than 1.001, 1.01, 1.1, 1.5, 2, 5, 10, or $10^3$.

In the experimental example, $t_{2a}$ is comprised between 60 sec. and 75 sec. for 0.5 mg/mL of M-CMD, 65 sec. and 90 sec. for 1 mg/mL of M-CMD, and 89 sec. and 105 sec. for N-CMD.

In one embodiment of the invention, it is possible to decrease $t_{2a}$, preferentially by a factor of more than 1.001, 1.01, 1.1, 1.5, 2, 5, 10, or $10^3$, and still induce a temperature decrease during the cooling step. This can preferentially be achieved by: i), decreasing the concentration of magnetic nanoparticle, in particular magnetosome, preferentially by a factor of more than 1.001, 1.01, 1.1, 1.5, 2, 5, 10, or $10^3$, ii), decreasing the laser power, laser power density, or laser intensity, preferentially by a factor of more than 1.001, 1.01, 1.1, 1.5, 2, 5, 10, or $10^3$, or iii), by reducing the temperature decrease or temperature gradient that one wants to achieve during the cooling step, preferentially by a factor of more than 1.001, 1.01, 1.1, 1.5, 2, 5, 10, or $10^3$.

In still some other embodiments of the invention, it is possible to increase $t_{2a}$, preferentially by a factor of more than 1.001, 1.01, 1.1, 1.5, 2, 5, 10, or $10^3$, and induce a temperature decrease during the cooling steps, preferentially without inducing a temperature decrease of the body part not comprising the magnetic nanoparticles, in particular magnetosomes. This can preferentially be achieved by: i), increasing the concentration of magnetic nanoparticles, in particular magnetosomes, preferentially by a factor of more than 1.001, 1.01, 1.1, 1.5, 2, 5, 10, or $10^3$, ii), increasing the laser power, laser power density, or laser intensity, preferentially by a factor of more than 1.001, 1.01, 1.1, 1.5, 2, 5, 10, or $10^3$, or iii), by decreasing the temperature decrease or temperature gradient that one wants to achieve during the cooling steps, preferentially by a factor of more than 1.001, 1.01, 1.1, 1.5, 2, 5, 10, or $10^3$.

In the experimental example, not taking into consideration the first sequence, $t_{1a}/t_{2a}$ is comprised between 0.6 and 0.7 for 0.5 mg of M-CMD, equal to 0.3 for 1 mg of M-CMD, and comprised between 0.2 and 0.4 for 1 mg of N-CMD.

In one embodiment of the invention, the ratio $t_{1a}/t_{2a}$ can be increased, preferentially by a factor higher than 1.001, 1.01, 1.1, 1.5, 2, 5, 10, or $10^3$, preferentially by: i), decreasing the concentration of magnetic nanoparticles, in particular magnetosomes, preferentially by a factor of more than 1.001, 1.01, 1.1, 1.5, 2, 5, 10, or $10^3$, ii), decreasing the laser power, preferentially by a factor of more than 1.001, 1.01, 1.1, 1.5, 2, 5, 10, or $10^3$.

In some other embodiments of the invention, the ratio $t_{1a}/t_{2a}$ can be decreased, preferentially by a factor higher than 1.001, 1.01, 1.1, 1.5, 2, 5, 10, or $10^3$, preferentially by: i), increasing the concentration of magnetic nanoparticles, in particular magnetosomes, preferentially by a factor of more than 1.001, 1.01, 1.1, 1.5, 2, 5, 10, or $10^3$, ii), increasing the laser power, preferentially by a factor of more than 1.001, 1.01, 1.1, 1.5, 2, 5, 10, or $10^3$.

In still another embodiment of the invention, the cooling time is more than 1.001, 1.01, 1.1, 1.5, 2, 5, 10, or $10^3$ higher in the absence than in the presence of the magnetic nanoparticles, in particular magnetosomes.

In still another embodiment of the invention, the heating time is more than 1.001, 1.01, 1.1, 1.5, 2, 5, 10, or $10^3$ higher in the presence than in the absence of the magnetic nanoparticles, in particular magnetosomes.

In one aspect of the invention, the invention relates to magnetic nanoparticles, preferentially magnetosomes, for use according to the invention, wherein the heating of the first step is performed at a heating temperature characterized by at least one property selected in the group consisting of:
- an average heating temperature that is lower than 100° C.,
- an average heating temperature that is lower, preferentially by at least 1° C., than the maximum temperature reached during the treatment,
- a maximum heating temperature that is lower than 100° C.,
- an average heating temperature reached by sequentially irradiating the magnetic nanoparticles, in particular the magnetosomes, with a laser after two steps comprising irradiation that is lower, preferentially by at least 1° C., than an average heating temperature reached by continuously irradiating the magnetic nanoparticles, in particular the magnetosomes, with a laser,
- a number of heating temperature gradients that is larger than 2, and
- a number of heating temperature gradients reached by sequentially irradiating the magnetic nanoparticles, in particular the magnetosomes, with a laser after two steps comprising irradiation that is larger, preferentially by a factor of at least 2, than a number of heating temperature gradients reached by continuously irradiating the magnetic nanoparticles, in particular the magnetosomes, with a laser, wherein a heating temperature gradient is a temperature increase of the heating in the first step, which is preferentially larger than $10^{-1}$, 1, 5 or 10° C.

In one aspect of the invention, the invention relates to the method according to the invention, wherein the heating of the first step is performed at a heating temperature characterized by at least one property selected in the group consisting of:
- an average heating temperature that is lower than 100° C.,
- an average heating temperature that is lower than the maximum temperature reached during the treatment,
- a maximum heating temperature that is lower than 100° C.,
- an average heating temperature reached by sequentially irradiating the magnetic nanoparticles, in particular the magnetosomes, with a laser after at least two steps comprising irradiation that is lower than an average heating temperature reached by continuously irradiating the magnetic nanoparticles, in particular the magnetosomes, with a laser,
- a number of heating temperature gradients that is larger than 2, and
- a number of heating temperature gradients reached by sequentially irradiating the magnetic nanoparticles, in particular the magnetosomes, with a laser after at least two steps comprising irradiation that is larger than a number of heating temperature gradients reached by continuously irradiating the magnetic nanoparticles, in particular the magnetosomes, with a laser, wherein a heating temperature gradient is a temperature increase of the heating in the first step.

In one embodiment of the invention, the heating temperature of the at least one first step is any temperature or at least one temperature that is reached during the at least one first step.

In one embodiment of the invention, the average heating temperature, preferentially of the at least one first step, is $(THS_{max}+THS_{min})/2$ or $(THS_1+THS_2+\ldots THS_i)/i$, where $1<i<n$, $T_i$ is a heating temperature of the heating step, $THS_{min}$ is the minimum heating temperature of the heating step, $THS_{max}$ is the maximum heating temperature of the heating step, and i is an integer comprised between 1 and n.

In one embodiment of the invention, the average heating temperature, preferentially of the at least one first step, is lower than $10^{10}$, $10^7$, $10^5$, $10^3$, 500, 250, 150, 100, 70, 50 or 20° C.

In one embodiment of the invention, the average heating temperature, preferentially of the at least one first step, is larger than −273, −200, −100, −50, 0, 5, 10, 20, 37, 40, 42, 50, 55, 60, 70 or 90° C.

In one embodiment of the invention, the average heating temperature, preferentially of the at least one first step, is comprised between −273 and $10^{10}$° C., between −100 and $10^5$° C., between 0 and $10^3$° C., between 20 and $10^3$° C., between 37 and $10^3$° C., or between 37 and 100° C.

In one embodiment of the invention, the average heating temperature is the average heating temperature or average temperature of at least one step, of at least one sequence, of at least one session or of the whole treatment, comprising step(s), sequence(s) and session(s).

In one embodiment of the invention, the maximum heating temperature is the maximum heating temperature or maximum temperature of at least one step, of at least one sequence, of at least one session or of the whole treatment, comprising step(s), sequence(s) and session(s).

In one embodiment of the invention, the minimum heating temperature is the minimum heating temperature or minimum temperature of at least one step, of at least one sequence, of at least one session or of the whole treatment, comprising step(s), sequence(s) and session(s).

In one embodiment of the invention, the average heating temperature, preferentially of the at least one first step, is lower, preferentially by at least $10^{-5}$, 1, 5 or 10° C., than the maximum temperature reached during the treatment, the at least one heating step, the at least one sequence, or the at least one session.

In one embodiment of the invention, the temperature, preferentially the maximum heating temperature, preferentially of the at least one first step, is lower than $10^5$, $10^3$, 500, 250, 100, 75 or 50° C.

In one embodiment of the invention, the temperature, preferentially the maximum heating temperature, preferentially of the at least one first step, is larger than −273, −200, −100, −50, −20, −10, −5, 0, 5, 10, 20 or 37° C.

In one embodiment of the invention, the temperature, preferentially the maximum heating temperature, preferentially of the at least one first step, is between −273 and $10^5$, −100 and $10^3$, 0 and 100, 37 and 70, or 30 and 60° C.

In one embodiment of the invention, the minimum heating temperature, preferentially of the at least one first step, is lower, preferentially by at least $10^{-10}$, $10^{-5}$, $10^{-3}$, $10^{-1}$, 1, 5, 10 or 50° C., than the maximum heating temperature, preferentially of the at least one first step.

In one embodiment of the invention, the minimum heating temperature, preferentially of the at least one first step, is lower, preferentially by less than $10^{10}$, $10^5$, $10^3$, 100, 50, 20, 10, 5 or 1° C., than the maximum heating temperature, preferentially of the least one first step.

In one embodiment of the invention, the average heating temperature reached by sequentially irradiating the magnetic nanoparticles with a laser is lower, preferentially by at least $10^{-10}$, $10^{-5}$, $10^{-1}$, 1, 5 or 10° C., than the average heating temperature reached by continuously irradiating the magnetic nanoparticles with a laser. The average heating temperature reached by continuously irradiating the magnetic nanoparticles with a laser can be $(T_{max}+T_{min})/2$ or $(T_1+$ $T_2+ \ldots T_i)/i$, where $1<i<n$, $T_i$ is a temperature of the continuous treatment session, $T_{min}$ is the minimum temperature of the continuous treatment session, $T_{max}$ is the maximum temperature of the continuous treatment session, and i is an integer comprised between 1 and n.

In one embodiment of the invention, the number of heating temperature gradients, preferentially of the at least one first step, preferentially comprised in at least one sequence, in at least one session, or in the whole treatment, is larger than 2, 5, 10, $10^3$ or $10^5$. The heating temperature gradient can be the temperature increase of the at least one first step.

In one embodiment of the invention, the number of heating temperature gradients, preferentially of the at least one first step, preferentially comprised in at least one sequence, in at least one session, or in the whole treatment, is lower than $10^{10}$, $10^5$, $10^3$, 500, 250, 100, 50, 20, 10, 5 or 2.

In one embodiment of the invention, the number of heating temperature gradients, preferentially of the at least one first step, preferentially comprised in at least one sequence, in at least one session, or in the whole treatment, is between 2 and $10^{10}$, between 2 and $10^5$, between 2 and $10^3$ or between 2 and 100.

In one embodiment of the invention, the number of heating temperature gradients reached by sequentially irradiating the magnetic nanoparticles with a laser is larger, preferentially by a factor of at least 1.1, 1.5, 2, 5, 10 or $10^3$, than the number of heating temperature gradients reached by continuously irradiating the magnetic nanoparticles with a laser.

In one embodiment of the invention, the comparison between the sequential and continuous treatments is made by comparing at least one treatment session of the sequential treatment or method with at least one treatment session of the continuous treatment or method.

In one embodiment of the invention, the heating temperature gradient is the temperature increase of the heating step, preferentially at least one temperature increase of the heating step, where the temperature increase of the heating step can be defined as a variation of temperature with time occurring during the heating step, where the variation is only or is continuously a temperature increase or where the variation is not a temperature decrease.

In one embodiment of the invention, a variation of temperature with time is a temperature increase, where such variation is larger than $10^{-5}$, $10^{-3}$, $10^{-1}$, 1, 5 or 10° C. in magnitude.

In one aspect of the invention, the invention relates to magnetic nanoparticles, in particular the magnetosomes, for use according to the invention, wherein the second step comprises cooling and/or non-dissociation of at least one compound from the magnetic nanoparticles, in particular the magnetosomes.

In one aspect of the invention, the invention relates to the method according to the invention, wherein the second step is performed and comprises cooling and/or non-dissociation of at least one compound from the magnetic nanoparticles, in particular magnetosomes.

In one aspect of the invention, the invention relates to magnetic nanoparticles, in particular the magnetosomes, for use according to the invention, wherein the cooling of the second step is performed at a cooling temperature characterized by at least one property selected in the group consisting of:

an average cooling temperature that is larger than 0° C., and a number of cooling temperature gradients that is larger than 2, wherein a cooling temperature gradient is a temperature decrease of the cooling step, which is preferentially larger than $10^{-1}$, 1, 5 or 10° C.

In one aspect of the invention, the invention relates to the method according to the invention, wherein the cooling of the second step is performed at a cooling temperature characterized by at least one property selected in the group consisting of:

an average cooling temperature that is larger than 0° C., and a number of cooling temperature gradients that is larger than 2, wherein a cooling temperature gradient is a temperature decrease of the cooling of the second step, which is preferentially larger than $10^{-1}$, 1, 5 or 10° C.

In one embodiment of the invention, the cooling temperature of the at least one second step is any temperature or at least one temperature that is reached during the at least one second step.

In one embodiment of the invention, the average cooling temperature, preferentially of the at least one second step, is $(TCS_{max}+TCS_{min})/2$ or $(TCS_1+TCS_2+ \ldots TCS_i)/i$, where $1<i<n$, $TCS_i$ is a cooling temperature of the cooling step, $TCS_{min}$ is the minimum cooling temperature of the cooling step, $TCS_{max}$ is the maximum cooling temperature of the cooling step, and i is an integer comprised between 1 and n.

In one embodiment of the invention, the average cooling temperature, preferentially of the at least one second step, is lower than $10^{10}$, $10^7$, $10^5$, $10^3$, 500, 250, 150, 100, 70, 50 or 20° C.

In one embodiment of the invention, the average cooling temperature, preferentially of the at least one second step, is larger than −273, −200, −100, −50, 0, 5, 10, 20, 37, 40, 42, 50, 55, 60, 70 or 90° C.

In one embodiment of the invention, the average cooling temperature, preferentially of the at least one second step, is comprised between −273 and $10^{10}$° C., between −100 and $10^5$° C., between 0 and $10^3$° C., between 20 and $10^3$° C., between 37 and $10^3$° C., or between 37 and 100° C.

In one embodiment of the invention, the average cooling temperature is the average cooling temperature or average temperature of at least one step, of at least one sequence, of at least one session or of the whole treatment, comprising step(s), sequence(s) and session(s).

In one embodiment of the invention, the maximum cooling temperature is the maximum cooling temperature or maximum temperature of at least one step, of at least one sequence, of at least one session or of the whole treatment, comprising step(s), sequence(s) and session(s).

In one embodiment of the invention, the minimum cooling temperature is the minimum cooling temperature or minimum temperature of at least one step, of at least one sequence, of at least one session or of the whole treatment, comprising step(s), sequence(s) and session(s).

In one embodiment of the invention, the average cooling temperature, preferentially of the at least one second step, is larger, preferentially by at least $10^{-5}$, 1, 5 or 10° C., than the minimum temperature reached during the treatment, the at least one cooling step, the at least one sequence, or the at least one session.

In one embodiment of the invention, the temperature, preferentially the minimum cooling temperature, preferentially of the at least one second step, is larger than −273, −200, −100, −50, 0, 5, 10, 20, 37, 10 or 45° C.

In one embodiment of the invention, the temperature, preferentially the minimum cooling temperature, preferentially of the at least one second step, is smaller than 100, 70, 60, 55, 50, 45, 40, 37, 30, 20, 0, −10, −50 or −100° C.

In one embodiment of the invention, the temperature, preferentially the minimum cooling temperature, preferentially of the at least one second step, is between −273 and $10^5$, −100 and $10^3$, 0 and 100, 37 and 70, or 30 and 60° C.

In one embodiment of the invention, the maximum cooling temperature, preferentially of the at least one second step, is larger, preferentially by at least $10^{-10}$, $10^{-5}$, $10^{-3}$, $10^{-1}$, 1, 5, 10 or 50° C., than the minimum cooling temperature, preferentially of the at least one second step.

In one embodiment of the invention, the maximum cooling temperature, preferentially of the at least one second step, is larger, preferentially by less than $10^{10}$, $10^5$, $10^3$, 100, 50, 20, 10, 5 or 1° C., than the minimum cooling temperature, preferentially of the least one second step.

In one embodiment of the invention, the number of cooling temperature gradients, preferentially of the at least one second step, preferentially comprised in at least one sequence, in at least one session, or in the whole treatment, is larger than 2, 5, 10, $10^3$ or $10^5$. The cooling temperature gradient can be the temperature decrease of the at least one second step.

In one embodiment of the invention, the number of cooling temperature gradients, preferentially of the at least one second step, preferentially comprised in at least one sequence, in at least one session, or in the whole treatment, is lower than $10^{10}$, $10^5$, $10^3$, 500, 250, 100, 50, 20, 10, 5 or 2.

In one embodiment of the invention, the number of cooling temperature gradients, preferentially of the at least one second step, preferentially comprised in at least one sequence, in at least one session, or in the whole treatment, is between 2 and $10^{10}$, between 2 and $10^5$, between 2 and $10^3$ or between 2 and 100.

In one embodiment of the invention, the cooling temperature gradient is the temperature decrease of the cooling step, preferentially at least one temperature decrease of the cooling step, where the temperature decrease of the cooling step can be defined as a variation of temperature with time occurring during the cooling step, where the variation is only or is continuously a temperature decrease or where the variation is not a temperature increase.

In one embodiment of the invention, a variation of temperature with time is a temperature decrease, where such variation is larger than $10^{-5}$, $10^{-3}$, $10^{-1}$, 1, 5 or 10° C. in magnitude.

The invention also relates to magnetic nanoparticles, in particular magnetosomes, for use, wherein the heating step produces a temperature increase of more than 1° C. of the body part.

In one embodiment of the invention, the heating step produces a temperature increase of/in the body part, magnetic nanoparticle, in particular magnetosome, or region of magnetic nanoparticle, in particular magnetosome, of more than $10^{-9}$, $10^{-6}$, $10^{-3}$, $10^{-1}$, 1, 2, 5, or 10° C., preferentially above the physiological temperature, or preferentially above the temperature of the body part before or without irradiation by the laser radiation.

In the experimental example, apart from the first sequence, the temperature increase reached during the second to eight heating steps, which is equal to the maximum temperature minus the minimum temperature of the heating steps, is equal to an average of: i), 8° C. for 0.5 and 1 mg/mL of M-CMD, and ii) 12° C. for 1 mg/mL of N-CMD, where M-CMD and N-CMD are exposed to a laser power density of 2 W/cm².

In one embodiment of the invention, it is possible to reach higher values of temperature increase, preferentially by a factor of more than 1.001, 1.01, 1.1, 1.5, 2, 5, 10, or $10^3$, by: i), increasing the concentration of magnetic nanoparticles, in particular magnetosomes, preferentially by a factor of more than 1.001, 1.01, 1.1, 1.5, 2, 5, 10, or $10^3$, ii), increasing the duration of the heating step, preferentially by a factor of more than 1.001, 1.01, 1.1, 1.5, 2, 5, 10, or $10^3$, iii), by increasing the temperature increase or temperature gradient that one wants to achieve during the heating step, preferentially by a factor of more than 1.001, 1.01, 1.1, 1.5, 2, 5, 10, or $10^3$, or, iv), by using magnetic nanoparticles, in particular magnetosomes, that continue to heat, preferentially by more than $10^{-9}$, $10^{-6}$, $10^{-3}$, $10^{-1}$, 1, 10, $10^3$, or $10^{6\circ}$ C., after the laser has been switched off, preferentially more $10^{-9}$, $10^{-6}$, $10^{-3}$, $10^{-1}$, 1, 10, $10^3$, or $10^6$ second(s) after the laser has been switched off.

In one embodiment of the invention, the heating step produces a temperature gradient of/in the body part preferentially comprising the magnetic nanoparticles, in particular magnetosomes, measured at any given time of the heating step, $(\Delta T/\delta t)t_{1a}$, which is higher than $10^{-9}$, $10^{-6}$, $10^{-3}$, $10^{-1}$, 1, 2, 5, or 10° C./sec, or which is preferentially higher, most preferentially higher by a factor of more than 1.1, 1.2, 2, 5, 10, 50, $10^2$, $10^3$, or $10^5$, than any temperature gradient occurring in the body part without the magnetic nanoparticles, in particular magnetosomes.

In one embodiment of the invention, $(\Delta T/\delta t)t_{1a}$ is defined as the slope of the tangent of the temperature variation with time occurring during the heating step.

In one embodiment of the invention, $(\Delta T/\delta t)t_{1a}$ and $(\Delta T/\delta t)t_{2a}$ are the absolute values of the slopes of the tangent of the temperature variation with time, measured at $t_{1a}$ and $t_{1b}$, respectively.

In one embodiment of the invention, $(\Delta T/\delta t)t_{1a}$ decreases, preferentially by a factor of more than 1.001, 1.01, 1.1, 1.5, 2, 5, 10, or 100, when $t_{1a}$ increases, preferentially by a factor of more than 1.001, 1.01, 1.1, 1.5, 2, 5, 10, or 100. This can mean that $(\Delta T/\delta t)t_{1a}$ is higher at the beginning than at the end of the first step. This can mean that the initial slope of the temperature variation with time, measured at the beginning of the heating step, is the largest value of $(\Delta T/\delta t)t_{1a}$.

In one embodiment of the invention, the laser power, laser power density, laser intensity, and/or concentration of magnetic nanoparticles, in particular magnetosomes, can be increased, preferentially by a factor of more than 1.001, 1.01, 1.1, 1.2, 1.5, 2, 5, 10, or 100, to decrease the variation between the different values of $(\Delta T/\delta t)t_{1a}$, measured during the heating step. In one embodiment, $(\Delta T/\delta t)t_{1a}$ varies by less than 99, 90, 85, 75, 60, 50, 30, 20, 10, 5, 2, 1, or $10^{-1}$%. This percentage can be equal to $[(\Delta T/\delta t)t_{1a1}-(\Delta T/\delta t)t_{1a2}]/(\Delta T/\delta t)t_{1a1}$, where $(\Delta T/\delta t)t_{1a1}$ and $(\Delta T/\delta t)t_{1a2}$ are the temperature gradients measured at two different times $t_{1a1}$ and $t_{1a2}$ of the heating step.

In still another embodiment of the invention, the average temperature gradient of the heating step is the average value of $(\Delta T/\delta t)t_{1a}$ measured at different times $t_{1a}$, where the different values of $t_{1a}$ used to measure this average value are preferentially separated by similar durations, or by durations that are longer than $10^{-9}$, $10^{-6}$, $10^{-3}$, $10^{-1}$, 1, 5, 10, 50, or 100 second(s). The average value of $(\Delta T/\delta t)t_{1a}$ is designated as $\text{Av}[(\Delta T/\delta t)t_{1a}]$.

In one embodiment of the invention, $\text{Av}[(\Delta T/\delta t)t_{1a}]$ is higher than $10^{-9}$, $10^{-6}$, $10^{-3}$, $10^{-1}$, 1, 2, 5, or 10° C./sec.

In some other embodiments of the invention, $Av[(\Delta T/\delta t)t_{1a}]$ is lower than $10^6$, $10^3$, 10, 5, 2, 1, or $10^{-3}$° C./sec.

In the experimental example, the average temperature gradient of the heating step is comprised between 0.13 and 0.21° C./sec. for 0.5 mg of M-CMD, 0.22 and 0.4° C./sec. for 1 mg of M-CMD, and 0.33 and 0.56° C./sec. for N-CMD.

In one embodiment of the invention, the temperature gradient or average temperature gradient of the heating step can be increased, preferentially by a factor of more than 1.001, 1.01, 1.1, 1.5, 2, 5, 10, or $10^3$, by: i), increasing the concentration of the magnetic nanoparticle, in particular magnetosome, preferentially by a factor of more than 1.001, 1.01, 1.1, 1.5, 2, 5, 10, or $10^3$, or ii), increasing the laser power or laser power density, preferentially by a factor of more than 1.001, 1.01, 1.1, 1.5, 2, 5, 10, or $10^3$.

In some other embodiments of the invention, the temperature gradient or average temperature gradient of the heating step is decreased, preferentially by a factor of more than 1.001, 1.01, 1.1, 1.5, 2, 5, 10, or $10^3$, by: i), decreasing the concentration of the magnetic nanoparticle, in particular magnetosome, preferentially by a factor of more than 1.001, 1.01, 1.1, 1.5, 2, 5, 10, or $10^3$, or ii), decreasing the laser power or laser power density, preferentially by a factor of more than 1.001, 1.01, 1.1, 1.5, 2, 5, 10, or $10^3$.

The invention also relates to magnetic nanoparticles, in particular magnetosomes, for use, wherein the cooling step produces a temperature decrease of more than 1° C. of the body part.

In one embodiment of the invention, the cooling step produces a temperature decrease of more than $10^{-9}$, $10^{-6}$, $10^{-3}$, $10^{-1}$, 1, 2, 5, or 10° C. of the body part, magnetic nanoparticle(s), in particular magnetosome(s), or region of magnetic nanoparticles, in particular magnetosomes, preferentially below the maximum temperature reached during the heating step.

In the experimental example, the temperature decrease reached during the cooling steps, which is equal to the absolute value of the minimum temperature minus the maximum temperature of the cooling steps, is equal to an average of: i), 8° C. for 0.5 and 1 mg/mL of M-CMD, and ii) 12° C. for 1 mg/mL of N-CMD, where M-CMD and N-CMD are not irradiated by the laser radiation during the cooling steps.

In one embodiment of the invention, it is possible to reach higher values of temperature decrease, preferentially by a factor of more than 1.001, 1.01, 1.1, 1.5, 2, 5, 10, or $10^3$, by: i), increasing or decreasing the concentration of the magnetic nanoparticles, in particular magnetosomes, preferentially by a factor of more than 1.001, 1.01, 1.1, 1.5, 2, 5, 10, or $10^3$, ii), increasing the duration of the cooling step, preferentially by a factor of more than 1.001, 1.01, 1.1, 1.5, 2, 5, 10, or $10^3$, or iii), by increasing the temperature decrease or temperature gradient that one wants to achieve during the cooling step, preferentially by a factor of more than 1.001, 1.01, 1.1, 1.5, 2, 5, 10, or $10^3$.

In one embodiment of the invention, the cooling step produces a temperature gradient of/in the body part, measured at any given time of the cooling step, $(\Delta T/\delta t)t_{2a}$ or the absolute value of $(\Delta T/\delta t)t_{2a}$, which is higher than $10^{-9}$, $10^{-6}$, $10^{-3}$, $10^{-1}$, 1, 2, 5, or 10° C./sec, or which is preferentially higher, most preferentially higher by a factor of more than 1.1, 1.2, 2, 5, 10, 50, $10^2$, $10^3$, or $10^5$, than any temperature gradient occurring in the body part without the magnetic nanoparticles, in particular magnetosomes. In one embodiment, $(\Delta T/\delta t)t_{2a}$ can be defined as the slope or the absolute value of the slope of the tangent of the temperature variation with time occurring during the cooling step.

In one embodiment of the invention, $(\Delta T/\delta t)t_{2a}$ decreases, preferentially by a factor of more than 1.001, 1.01, 1.1, 1.5, 2, 5, 10, or 100, when $t_{2a}$ increases, preferentially by a factor of more than 1.001, 1.01, 1.1, 1.5, 2, 5, 10, or 100. This can mean that $(\Delta T/\delta t)t_{2a}$ is higher at the beginning than at the end of the second or cooling step. This can mean that the initial slope of the temperature variation with time, measured at the beginning of the cooling step, is the largest value of $(\Delta T/\delta t)t_{2a}$.

In one embodiment of the invention, the laser power, laser power density, laser intensity, and/or concentration of magnetic nanoparticles, in particular magnetosomes, can be increased, preferentially by a factor of more than 1.001, 1.01, 1.1, 1.2, 1.5, 2, 5, 10, or 100, to decrease the variation between the different values of $(\Delta T/\delta t)t_{2a}$, measured during different times of the cooling step.

In one embodiment of the invention, $(\Delta T/\delta t)t_{2a}$ varies by less than 99, 90, 85, 75, 60, 50, 30, 20, 10, 5, 2, 1, or $10^{-1}$%. This percentage can be equal to $[(\Delta T/\delta t)t_{2a1}-(\Delta T/\delta t)t_{2a2}]/(\Delta T/\delta t)t_{2a1}$, where $(\Delta T/\delta t)t_{2a1}$ and $(\Delta T/\delta t)t_{2a2}$ are the temperature gradients measured at two different times $t_{2a1}$ and $t_{2a2}$ of the cooling step.

In still another embodiment of the invention, the average temperature gradient of the cooling step is the average value of $(\Delta T/\delta t)t_{2a}$ measured at different times $t_{2a}$, where the different values of $t_{2a}$ used to measure this average value are preferentially separated by similar durations, or by durations that are longer than $10^{-9}$, $10^{-6}$, $10^{-3}$, $10^{-1}$, 1, 5, 10, 50, or 100 second(s). The average value of $(\Delta T/\delta t)t_{2a}$ is designated as $Av[(\Delta T/\delta t)t_{2a}]$.

In one embodiment of the invention, $Av[(\Delta T/\delta t)t_{2a}]$ is higher than $10^{-9}$, $10^{-6}$, $10^{-3}$, $10^{-1}$, 1, 2, 5, or 10° C./sec.

In some other embodiments of the invention, $Av[(\Delta T/\delta t)t_{2a}]$ is lower than $10^6$, $10^3$, 10, 5, 2, 1, or $10^{-3}$° C./sec.

In the experimental example, the average temperature gradient of the cooling step is comprised between 0.11 and 0.13° C./sec. for 0.5 mg of M-CMD, 0.09 and 0.12° C./sec. for 1 mg of M-CMD, and 0.11 and 0.14° C./sec. for N-CMD.

In one embodiment of the invention, the temperature gradient or average temperature gradient of the cooling step can be increased, preferentially by a factor of more than 1.001, 1.01, 1.1, 1.5, 2, 5, 10, or $10^3$, by: i), decreasing the concentration of magnetic nanoparticles, in particular magnetosomes, preferentially by a factor of more than 1.001, 1.01, 1.1, 1.5, 2, 5, 10, or $10^3$, or ii), decreasing the laser power or laser power density, preferentially by a factor of more than 1.001, 1.01, 1.1, 1.5, 2, 5, 10, or $10^3$.

In some other embodiments of the invention, the temperature gradient or average temperature gradient of the heating step can be decreased, preferentially by a factor of more than 1.001, 1.01, 1.1, 1.5, 2, 5, 10, or $10^3$, by: i), increasing the concentration of magnetic nanoparticles, in particular magnetosomes, preferentially by a factor of more than 1.001, 1.01, 1.1, 1.5, 2, 5, 10, or $10^3$, or ii), increasing the laser power or laser power density, preferentially by a factor of more than 1.001, 1.01, 1.1, 1.5, 2, 5, 10, or $10^3$.

In one embodiment of the invention, the magnitudes of the temperature increase reached during the heating step, $\Delta T_{HS}$, and the magnitude of the temperature decrease reached during the cooling step, $\Delta T_{CS}$, differ by less than $10^6$, $10^3$, $10^2$, 10, or 1%, where this percentage can be equal to the absolute values of $(\Delta T_{HS}-\Delta T_{CS})/\Delta T_{HS}$ or $(\Delta T_{CS}-\Delta T_{HS})/\Delta T_{CS}$.

In still another embodiment of the invention, the largest temperature gradient is that reached at the beginning of the heating or cooling step.

The invention also relates to magnetic nanoparticles, in particular magnetosomes, for use, wherein the dissociation step produces a percentage of dissociation of the compounds from the magnetic nanoparticles, in particular magnetosomes, which is higher than $10^{-4}$%.

In one embodiment of the invention, the dissociation step produces a percentage of dissociation of the compounds from the magnetic nanoparticles, in particular magnetosomes, which is higher than $10^{-20}$, $10^{-10}$, $10^{-4}$, $10^{-1}$, 1, 5, 10, or 50%.

In one embodiment of the invention, the dissociation step produces a gradient of the percentage of dissociation, preferentially of/in the body part comprising the magnetic nanoparticles, in particular magnetosomes, measured at any given time of the dissociation step, $(\Delta D/\delta t)t_{1b}$, which is higher than $10^{-9}$, $10^{-6}$, $10^{-3}$, $10^{-1}$, 1, 2, 5, or 10%./sec.

In one embodiment of the invention, $(\Delta D/\delta t)t_{1b}$ can be defined as the slope of the tangent of the variation with time of the percentage of dissociation occurring during the dissociation step.

In one embodiment of the invention, $(\Delta D/\delta t)t_{1b}$ decreases, preferentially by a factor of more than 1.001, 1.01, 1.1, 1.5, 2, 5, 10, or 100, when $t_{1b}$ increases, preferentially by a factor of more than 1.001, 1.01, 1.1, 1.5, 2, 5, 10, or 100. This can mean that $(\Delta D/\delta t)t_{1b}$ is higher at the beginning than at the end of the dissociation step. This can mean that the initial slope of the variation of the percentage of dissociation with time, measured at the beginning of the dissociation step, is the largest value of $(\Delta D/\delta t)t_{1b}$.

In one embodiment of the invention, the laser power, laser power density, laser intensity, and/or concentration of the magnetic nanoparticles, in particular magnetosomes, can be increased, preferentially by a factor of more than 1.001, 1.01, 1.1, 1.2, 1.5, 2, 5, 10, or 100, to decrease the variation between the different values of $(\Delta D/\delta t)t_{1b}$, measured at different times of the dissociation step.

In one embodiment of the invention, $(\Delta D/\delta t)t_{1b}$ varies by less than 99, 90, 85, 75, 60, 50, 30, 20, 10, 5, 2, 1, or $10^{-1}$%. This percentage can be equal to $[(\Delta D/\delta t)t_{1b1}-(\Delta D/\delta t)t_{1b2}]/(\Delta D/\delta t)t_{1b1}$, where $(\Delta D/\delta t)t_{1b1}$ and $(\Delta D/\delta t)t_{1b2}$ are the gradients in the percentages of dissociation measured at two different times $t_{1b1}$ and $t_{1b2}$ of the dissociation step.

In still another embodiment of the invention, the average gradient of the percentage of dissociation, measured during the dissociation step, is the average value of $(\Delta D/\delta t)t_{1b}$ measured at different times $t_{1b}$, where the different values of $t_{1b}$ used to measure this average value are preferentially separated by similar durations, or by durations that are longer than $10^{-9}$, $10^{-6}$, $10^{-3}$, $10^{-1}$, 1, 5, 10, 50, or 100 second(s). The average value of $(\Delta D/\delta t)t_{1b}$ is designated as $Av[(\Delta D/\delta t)t_{1b}]$.

In one embodiment of the invention, $Av[(\Delta D/\delta t)t_{1b}]$ is higher than $10^{-9}$, $10^{-6}$, $10^{-3}$, $10^{-1}$, 1, 2, 5, or 10%/sec. In some other embodiments of the invention, $Av[(\Delta D/\delta t)t_{1b}]$ is lower than $10^6$, $10^3$, 10, 5, 2, 1, or $10^{-3}$%/sec.

The invention also relates to magnetic nanoparticles, in particular magnetosomes, for use, wherein the non-dissociation step produces a percentage of dissociation of the compounds from the magnetic nanoparticles, in particular magnetosomes, which is lower than 99%.

In one embodiment of the invention, the non-dissociation step produces a percentage of dissociation of the compounds from the magnetic nanoparticles, in particular magnetosomes, which is lower than 99.9, 99, 90, 80, 50, 40, 20, 10, 5, 2, or 1%.

In one embodiment of the invention, the non-dissociation step produces a gradient of the percentage of dissociation, preferentially of/in the body part comprising the magnetic nanoparticles, in particular magnetosomes, measured at any given time of the non-dissociation step, $(\Delta D/\delta t)t_{2b}$, which is lower than $10^{-9}$, $10^{-6}$, $10^{-3}$, $10^{-1}$, 1, 2, 5, or 10%/sec.

In one embodiment of the invention, $(\Delta D/\delta t)t_{2b}$ can be defined as the slope of the tangent of the variation with time of the percentage of dissociation occurring during the non-dissociation step.

In still another embodiment of the invention, the average gradient of the percentage of dissociation, measured during the non-dissociation step, is the average value of $(\Delta D/\delta t)t_{2b}$ measured at different times $t_{2b}$, where the different values of $t_{2b}$ used to measure this average value are preferentially separated by similar durations, or by durations that are longer than $10^{-9}$, $10^{-6}$, $10^{-3}$, $10^{-1}$, 1, 5, 10, 50, or 100 second(s). The average value of $(\Delta D/\delta t)t_{2b}$ is designated as $Av[(\Delta D/\delta t)t_{2b}]$.

In one embodiment of the invention, $Av[(\Delta D/\delta t)t_{2b}]$ can be lower than $10^{-9}$, $10^{-6}$, $10^{-3}$, $10^{-1}$, 1, 2, 5, or 10%/sec.

In some other embodiments of the invention, $Av[(\Delta D/\delta t)t_{2b}]$ can be lower than $10^6$, $10^3$, 10, 5, 2, 1, or $10^{-3}$%/sec.

In one embodiment of the invention, the percentage of dissociation reached during the dissociation step, $P_{DS}$, and the percentage of dissociation reached during the non-dissociation step, $P_{NDS}$, differ by more than $10^{-6}$, $10^{-3}$, $10^{-2}$, $10^{-1}$, or 1%, where this percentage can be equal to the absolute values of $(P_{DS}-P_{NDS})/P_{DS}$ or $(P_{NDS}-P_{DS})/P_{NDS}$.

In one aspect of the invention, the invention also relates to magnetic nanoparticles, in particular the magnetosomes, for use according to the invention, wherein the second step is carried out in the presence of a substance or equipment that decreases the temperature of the body part or magnetic nanoparticle, in particular the magnetosomes, wherein:

i) the duration of the second step is preferentially shorter in the presence than in the absence of such substance or equipment, ii) the difference between a maximum and minimum temperature of the second step is preferentially larger in the presence than in the absence of such substance or equipment, iii) the laser power that irradiates the magnetic nanoparticles, in particular the magnetosomes, during the first step is preferentially lower in the presence than in the absence of such substance or equipment, iv) the concentration of the magnetic nanoparticle, in particular the magnetosomes, preferentially comprised in the body part, is preferentially smaller in the presence than in the absence of such substance or equipment, and/or v) the number of sequences that is carried out during the at least one session is preferentially larger in the presence than in the absence of such substance or equipment.

In one aspect of the invention, the invention relates to the method according to the invention, wherein the second step is carried out in the presence of a substance or equipment that decreases the temperature of the body part or magnetic nanoparticle, wherein:

i) the duration of the second step is preferentially shorter in the presence than in the absence of such substance or equipment, ii) the difference between the maximum and minimum temperatures of the second step is preferentially larger in the presence than in the absence of such substance or equipment, iii) the laser power that irradiates the magnetic nanoparticles during the first step is preferentially lower in the presence than in the absence of such substance or equipment, iv) the concentration of the magnetic nanoparticle, preferentially comprised in the body part, is preferentially smaller in the presence than in the absence of such substance or equipment, and/or v) the number of sequences that is carried out during the at least one session is preferentially larger in the presence than in the absence of such substance or equipment.

In one embodiment of the invention, the substance or equipment that decreases the temperature of the body part or magnetic nanoparticle is selected in the group consisting of: i) a probe that decreases the temperature of the body part or magnetic nanoparticle, ii) a cryogenic probe, iii) ice, iv) water, v) blood, and vi) a substance or equipment that is in contact or proximity of the magnetic nanoparticle or body part and that is at a lower temperature than the temperature of the magnetic nanoparticle or body part measured before the magnetic nanoparticle or body part is in contact or in proximity with this substance or equipment.

In one embodiment of the invention, the duration of the second step is shorter in the presence than in the absence of such substance or equipment, preferentially by a factor of at least 0, 1, 1.1, 2, 5, 10 or $10^3$ or by at least 0, $10^{-50}$, $10^{-1}$, 1, 5, 10 or $10^3$ seconds.

In one embodiment of the invention, the difference between the maximum and minimum temperatures of the second step is larger in the presence than in the absence of such substance or equipment, preferentially by a factor of at least 0, 1, 1.1, 2, 5, 10 or $10^3$ or by at least 0, $10^{-50}$, $10^{-1}$, 1, 5, 10 or $10^{3}$° C.

In one embodiment of the invention, the laser power that irradiates the magnetic nanoparticles during the first step is lower in the presence than in the absence of such substance or equipment, preferentially by a factor of at least 0, 1, 1.1, 2, 5, 10 or $10^3$ or by at least 0, $10^{-50}$, $10^{-1}$, 1, 5, 10 or $10^3$ Watt or Watt per $cm^3$, per $cm^2$ or per cm, preferentially of the body part.

In one embodiment of the invention, the concentration of the magnetic nanoparticle, preferentially comprised in the body part, is smaller in the presence than in the absence of such substance or equipment, preferentially by a factor of at least 0, 1, 1.1, 2, 5, 10 or $10^3$ or by at least 0, $10^{-50}$, $10^{-1}$, 1, 5, 10 or $10^3$ mg of magnetic nanoparticles, preferentially per $cm^3$, per $cm^2$ or per cm, most preferably per $cm^3$, per $cm^2$ or per cm of the body part.

In another embodiment of the invention, the number of sequences that is carried out during the at least one session is preferentially larger in the presence than in the absence of such substance or equipment, preferentially by a factor of at least 0, 1, 1.1, 2, 5, 10 or $10^3$ or by at least 0, 1, 5, 10, $10^2$ or $10^3$ sequence(s).

In one aspect of the invention, the invention also relates to magnetic nanoparticles, preferentially magnetosomes, for use according to the invention, wherein the first step comprises heating and the second step comprises cooling, and a heating temperature of the first step and/or a cooling temperature of the second step is/are stable or varies by less than $10^5$, $10^3$, 10, 1 or $10^{-1}$° C., for less than 99.9%, preferably 50%, more preferably 10% of the duration of the first step and/or second step, and/or for less than $10^5$ seconds, preferably $10^3$ seconds, more preferably 10 seconds.

In one aspect of the invention, the invention relates to the method according to the invention, wherein the first step comprises heating and the second step comprises cooling, and a heating temperature of the first step and/or a cooling temperature of the second step is/are stable or varies by less than $10^5$, $10^3$, 10, 1 or $10^{-1}$° C., for less than 99.9% of the duration of the first step and/or second step, and/or for less than $10^5$ seconds.

In one embodiment of the invention, the heating temperature of the at least one first step is stable. The heating temperature can be stable when: i) the heating temperature varies by less than $10^5$, $10^3$, 10 or 1° C., preferentially per hour, minute or second, ii) the heating temperature remains constant, iii) the heating temperature has reached a plateau, preferentially at the end of the first step, or iv) the heating temperature is that of the beginning or end of the first step.

In one embodiment of the invention, the heating temperature of the at least one first step is unstable. The heating temperature can be unstable when: i) the heating temperature varies by more than $10^{-10}$, $10^{-5}$, $10^{-1}$, 1, 5 or 10° C., preferentially per hour, minute or second, ii) the heating temperature does not remain constant, iii) the heating temperature belongs to the range of temperatures that gives rise to the heating temperature gradient, or iv) the heating temperature is that of the middle of the first step.

In one embodiment of the invention, the heating temperature of the first step is stable for less than 100, 99.9, 95, 90, 80, 70, 50, 20, 10, 1, $10^{-1}$, $10^{-2}$ or $10^{-5}$% of the duration of the at least one first step. This percentage can be the ratio $D_{SFS}/D_{FS}$, where $D_{SFS}$ is the lapse of time during which the temperature is stable or varies by less than 0.5° C. or 0.5° C. per second during the first step and $D_{FS}$ is the duration of the first step.

In one embodiment of the invention, the heating temperature of the first step is stable or varies by less than 0.5° C. or 0.5° C. per second for less than $10^{50}$, $10^{20}$, $10^{10}$, $10^5$, $10^3$, 100, 10, 5, 2 or 1 second(s), preferentially of the first step.

In one embodiment of the invention, the heating temperature of the first step is stable for more than $10^{-5}$, $10^{-3}$, $10^{-1}$, 1, 5, 10, 50 or 75% of the duration of the at least one first step.

In one embodiment of the invention, the heating temperature of the first step is stable or varies by less than 0.5° C. or 0.5° C. per second for less than $10^{50}$, $10^{20}$, $10^{10}$, $10^5$, $10^3$, 100, 10, 5, 2 or 1 second(s), preferentially of the first step.

In the experimental example, when 0.5 mg/mL of M-CMD is exposed to a laser power of 2 W/$cm^2$, the lapse of time during which the temperature increase is stable or smaller than 0.5° C. is shorter than 10 seconds (10/160=6% of the first step) (FIG. 1(a)). In some embodiments, this lapse of time is longer when: i) one considers that the temperature is stable when it varies by more than 0.5° C., ii) the laser power or power density is decreased, and/or iii) the nanoparticle concentration is decreased. In some other embodiments, this lapse of time is shorter when: i) one considers that the temperature is stable when it varies by less than 0.5° C., ii) the laser power or power density is increased, and/or iii) the nanoparticle concentration is increased.

In one embodiment of the invention, the heating temperature of the first step is unstable for less than 100, 99.9, 95, 90, 80, 70, 50, 20, 10, 1, $10^{-1}$, $10^{-2}$ or $10^{-5}$% of the duration of the at least one first step. This percentage can be the ratio $D_{USFS}/D_{FS}$, where $D_{USFS}$ is the lapse of time during which the temperature is unstable or varies by more than 0.5° C. or 0.5° C. per second during the first step and $D_{FS}$ is the duration of the first step.

In one embodiment of the invention, the heating temperature of the first step is unstable or varies by more than 0.5° C. or 0.5° C. per second for less than $10^{50}$, $10^{20}$, $10^{10}$, $10^5$, $10^3$, 100, 10, 5, 2 or 1 second(s), preferentially of the first step.

In one embodiment of the invention, the heating temperature of the first step is unstable for more than $10^{-5}$, $10^{-3}$, $10^{-1}$, 1, 5, 10, 50 or 75% of the duration of the at least one first step.

In one embodiment of the invention, the heating temperature of the first step is unstable or varies by less than 0.5° C. or 0.5° C. per second for less than $10^{50}$, $10^{20}$, $10^{10}$, $10^5$, $10^3$, 100, 10, 5, 2 or 1 second(s), preferentially of the first step.

In the experimental example, when 0.5 mg/mL of M-CMD is sequentially exposed to a laser power of 2 W/cm², the lapse of time during which the temperature increase is unstable or larger than 0.5° C. is larger than 150 seconds (150/160=94% of the first step) (FIG. 1(a)). In some embodiments, this lapse of time is longer when: i) one considers that the temperature is unstable when it varies by less than 0.5° C., ii) the laser power or power density is increased, and/or iii) the nanoparticle concentration is increased. In some other embodiments, this lapse of time is shorter when: i) one considers that the temperature is unstable when it varies by more than 0.5° C., ii) the laser power or power density is decreased, and/or iii) the nanoparticle concentration is decreased.

In one embodiment of the invention, the heating temperature of the first step is unstable during a lapse of time $D_{USFS}$, which is at least 1.1, 1.5, 2, 5, 10, $10^3$ or $10^5$ than the lapse of time $D_{SFS}$ during which the temperature is stable during the first step.

In one embodiment of the invention, the cooling temperature of the at least one second step is stable. The cooling temperature can be stable when: i) the cooling temperature varies by less than $10^5$, $10^3$, 10 or 1° C., preferentially per hour, minute or second, ii) the cooling temperature remains constant, iii) the cooling temperature has reached a plateau, preferentially at the end of the second step, or iv) the cooling temperature is that of the beginning or end of the second step.

In one embodiment of the invention, the cooling temperature of the at least one second step is unstable. The cooling temperature can be unstable when: i) the cooling temperature varies by more than $10^{-10}$, $10^{-5}$, $10^{-1}$, 1, 5 or 10° C., preferentially per hour, minute or second, ii) the cooling temperature does not remain constant, iii) the cooling temperature belongs to the range of temperatures that gives rise to the cooling temperature gradient, or iv) the cooling temperature is that of the middle of the cooling step.

In one embodiment of the invention, the cooling temperature of the second step is stable for less than 100, 99.9, 95, 90, 80, 70, 50, 20, 10, 1, $10^{-1}$, $10^{-2}$ or $10^{-5}$% of the duration of the at least one second step. This percentage can be the ratio $D_{SSS}/D_{SS}$, where $D_{SSS}$ is the lapse of time during which the temperature is stable or varies by less than 0.5° C. or 0.5° C. per second during the second step and $D_{SS}$ is the duration of the second step.

In one embodiment of the invention, the cooling temperature of the second step is stable or varies by less than 0.5° C. or 0.5° C. per second for less than $10^{50}$, $10^{20}$, $10^{10}$, $10^5$, $10^3$, 100, 10, 5, 2 or 1 second(s), preferentially of the second step.

In one embodiment of the invention, the cooling temperature of the second step is stable for more than $10^{-5}$, $10^{-3}$, $10^{-1}$, 1, 5, 10, 50 or 75% of the duration of the at least one second step.

In one embodiment of the invention, the cooling temperature of the second step is stable or varies by less than 0.5° C. or 0.5° C. per second for less than $10^{50}$, $10^{20}$, $10^{10}$, $10^5$, $10^3$, 100, 10, 5, 2 or 1 second(s), preferentially of the second step.

In the experimental example, when 0.5 mg/mL of M-CMD is sequentially exposed to a laser power of 2 W/cm², the lapse of time during which the temperature decreases during the second step by less than 0.5° C. is shorter than 10 seconds (FIG. 1(a)). In some embodiments, this lapse of time can be shorter when: i) an equipment or substance is used to cool down the magnetic nanoparticles during the second step, ii) the maximum temperature of the first and/or second step(s) is decreased, and/or iii) the minimum temperature of the first and/or second step(s) is increased.

In one embodiment of the invention, the cooling temperature of the second step is unstable for less than 100, 99.9, 95, 90, 80, 70, 50, 20, 10, 1, $10^{-1}$, $10^{-2}$ or $10^{-5}$% of the duration of the at least one second step. This percentage can be the ratio $D_{USSS}/D_{SS}$, where $D_{USSS}$ is the lapse of time during which the temperature is unstable or varies by more than 0.5° C. or 0.5° C. per second during the second step and $D_{SS}$ is the duration of the second step.

In one embodiment of the invention, the cooling temperature of the second step is unstable or varies by more than 0.5° C. or 0.5° C. per second for less than $10^{50}$, $10^{20}$, $10^{10}$, $10^5$, $10^3$, 100, 10, 5, 2 or 1 second(s), preferentially of the second step.

In one embodiment of the invention, the cooling temperature of the second step is unstable or varies by more than 0.5° C. or 0.5° C. per second for more than $10^{-5}$, $10^{-3}$, $10^{-1}$, 1, 5, 10, 50 or 75% of the duration of the at least one second step.

In one embodiment of the invention, the cooling temperature of the second step is unstable or varies by more than 0.5° C. or 0.5° C. per second for less than $10^{50}$, $10^{20}$, $10^{10}$, $10^5$, $10^3$, 100, 10, 5, 2 or 1 second(s), preferentially of the second step.

In the experimental example, when 0.5 mg/mL of M-CMD is sequentially exposed to a laser power of 2 W/cm², the lapse of time during which the temperature decrease is unstable or larger than 0.5° C. is larger than 150 seconds (180/190=95% of the second step) (FIG. 1(a)). In some embodiments, this lapse of time is longer when: i) one considers that the temperature is unstable when it varies by less than 0.5° C., ii) the nanoparticle concentration is varied, increased or decreased, or iii) an equipment or substance is used to cool down the magnetic nanoparticle during the second step.

It should be noted that depending on the way in which it is used, the equipment or substance used to cool down the magnetic nanoparticles during the second step can in some embodiments increase the rate at which the temperature is decreased during the second step, in some other embodiments enable to maintain the temperature stabilized during the second step.

In one embodiment of the invention, the cooling temperature of the second step is unstable during a lapse of time $D_{USSS}$, which is at least 1.1, 1.5, 2, 5, 10, $10^3$ or $10^5$ larger than the lapse of time $D^{SSS}$ during which the temperature is stable during the second step.

In another aspect of the invention, the invention relates to magnetic nanoparticles, preferentially magnetosomes, for use according to the invention, wherein the first step and/or second step(s) is/are characterized by at least one property selected in the group consisting of:

a duration of between $10^{-50}$ and $10^{50}$ minutes, preferably of between $10^{-50}$ and $10^3$ minutes, more preferably of between $10^{-50}$ and 60 minutes, even more preferably of between $10^{-50}$ and 30 minutes, even more preferably of between $10^{-5}$ and 30 minutes, even more preferably of between $10^{-3}$ and 15 minutes, even more preferably of between $10^{-1}$ and 10 minutes, or even more preferably of between $10^{-1}$ and 5 minutes, and an inter-step duration separating the first step from the second step that is: i) between $10^{-10}$ and $10^{20}$ minute(s), preferably between $10^{-5}$ and $10^{5}$ minute(s), more preferably between $10^{-5}$ and 10 minute(s), or even more preferably between $10^{-5}$ and 1 minute(s), or ii) shorter than the duration of the first and/or second step(s).

In one aspect of the invention, the invention relates to the method according to the invention, wherein the first step and/or second step(s) is/are characterized by at least one property selected in the group consisting of:

a duration of between $10^{-50}$ and $10^{50}$ minutes, and an inter-step duration separating the first step from the second step that is: i) between $10^{-10}$ and $10^{20}$ minutes, or ii) shorter than the duration of the first and/or second step(s).

In one embodiment of the invention, the inter-step duration is the lapse of time during which the temperature switches from a temperature increase, preferentially of more than $10^{-5}$, $10^{-3}$, $10^{-1}$ or 1° C. per second, to a temperature decrease, preferentially of more than $10^{-5}$, $10^{-3}$, $10^{-1}$ or 1° C. per second.

In one embodiment of the invention, the duration between the first and second steps or inter-step duration is at least 1.1, 2, 5, 10 or $10^{3}$ shorter than the duration of the first or second step. In the experimental example (FIG. 1(a)), the lapse of time to increase the temperature from 44.5° C. to 45° C. is 5 seconds at the end of the first step and the lapse of time to decrease the temperature from 45 to 44.5° C. is 5 seconds at the beginning of the second step. The duration between the first and second steps is ~10 seconds, whereas the duration of the first and/or second step(s) is larger than 35 seconds. The inter-step duration can be shorter if one considers that the inter-step duration occurs within a smaller temperature interval than 44.5-45° C., i.e. for example 44.9-45° C. The inter-step duration can be longer if one considers that the inter-step duration occurs within a larger temperature interval than 44.5-45° C., i.e. for example 44-45° C.

In the experimental example (table 2, 0.5 mg M-CMD), the duration of the heating step is between 35 seconds and 150 seconds. In some embodiments, this duration can be decreased by: i) increasing the laser power, ii) increasing the nanoparticle concentration, iii) increasing the minimum temperature of the heating step, and/or iv) decreasing the maximum temperature of the heating step. In some embodiments, this duration can be increased by: i) decreasing the laser power, ii) decreasing the nanoparticle concentration, iii) decreasing the minimum temperature of the heating step, and/or iv) increasing the maximum temperature of the heating step.

In the experimental example (table 2, 0.5 mg M-CMD), the duration of the cooling step is between 60 and 75 seconds. In some embodiments, this duration can be decreased by using an equipment or substance that cools down the magnetic nanoparticle or body part or by varying, increasing or decreasing, the nanoparticle concentration. In some other embodiments, this duration can be increased by varying, decreasing or increasing the nanoparticle concentration, or by limiting blood circulation in the body part, or by limiting heat exchanges between the magnetic nanoparticle or body part and the environment of the magnetic nanoparticle or body part.

In one embodiment of the invention, the duration of the first step ($D_{FS}$) is similar to the duration of the second step ($D_{SS}$). In some embodiments $D_{FS}/D_{SS}$ is smaller than 100, 50, 40, 10, 5, 2, 1.5 or 1.1.

In some embodiments, $D_{FS}/D_{SS}$ is larger than $10^{-50}$, $10^{-10}$, $10^{-1}$, 1, 5, 10, 50 or 100.

Another aspect of the invention relates to magnetic nanoparticles, preferentially magnetosomes, for use according to the invention, wherein the at least one sequence comprising the first step and second step is characterized by at least one property selected in the group consisting of:

a duration of the sequence that is between $10^{-50}$ and $10^{50}$ minutes, preferably between $10^{-50}$ and $10^{3}$ minutes, more preferably between $10^{-50}$ and 60 minutes, more preferably between $10^{-50}$ and 30 minutes, even more preferably between $10^{-5}$ and 30 minutes, even more preferably between $10^{-3}$ and 15 minutes, even more preferably between $10^{-1}$ and 10 minutes, or even more preferably between $10^{-1}$ and 5 minutes, a duration between two successive sequences or inter-sequence duration that is between $10^{-10}$ and $10^{20}$ minutes, preferably between $10^{-5}$ and $10^{5}$ minutes, more preferably between $10^{-5}$ and 10 minutes, or even more preferably between $10^{-5}$ and 1 minutes, and a duration of at least one sequence that is longer, preferentially by a factor of at least 0, 1.1, 1.5 or 2 than the duration of at least one step.

In one aspect of the invention the invention relates to the method according to the invention, wherein the at least one sequence comprising the first step and second step is characterized by at least one property selected in the group consisting of:

a duration of the sequence that is between $10^{-50}$ and $10^{50}$ minutes, a duration between two successive sequences or inter-sequence duration that is between $10^{-10}$ and $10^{20}$ minutes, a duration of at least one sequence that is longer than a duration of at least one step, and a duration of at least one inter-sequence that is shorter than a duration of at least one sequence or a duration of at least one step.

In one embodiment of the invention, the duration of at least one sequence or of at least one first step or of at least one second step is longer than $10^{-100}$, $10^{-50}$, $10^{-10}$, $10^{-5}$, $10^{-1}$, 1, 5, 10 or 100 minute(s).

In another embodiment of the invention, the duration of at least one sequence or of at least one first step or of at least one second step is shorter than $10^{100}$, $10^{50}$, $10^{20}$, $10^{10}$, $10^{5}$, $10^{3}$, 100, 75, 50, 20, 10, 5, 2, 1 or $10^{-1}$ minute(s).

In the experimental example, the duration of a sequence is comprised between 95 and 225 seconds (table 2, 0.5 mg M-CMD). In some embodiments, the duration of a sequence can be decreased by: i) increasing the laser power, ii) increasing the nanoparticle concentration, iii) decreasing the maximum temperature reached during the first and/or second step, iv) increasing the minimum temperature reached during the first and/or second step, and/or v) using an equipment or substance to cool the magnetic nanoparticle or body part during the cooling step. In some embodiments, he duration of a sequence can be increased by: i) decreasing the laser power, ii) decreasing the nanoparticle concentration, iii) increasing the maximum temperature reached during the first and/or second step, and/or iv) decreasing the minimum temperature reached during the first and/or second step.

In an embodiment of the invention, the duration of a sequence or of the first and/or second step(s) is sufficiently long to enable a stimulation of the immune system. It is preferentially longer than the time of a laser pulse, which is typically much shorter than 1 second.

In an embodiment of the invention, the duration of a sequence or of the first and/or second step(s) is sufficiently short to avoid burning the body part or inducing side effects on the body part.

In an embodiment of the invention, the duration of at least one sequence is longer than the duration of the at least one first step or of the at least one second step, preferably by a factor of at least 0, 0.5, 1, 1.1, 1.5, 2, 5, 10 or $10^3$.

In an embodiment of the invention, the duration between two different sequences, also designated as inter-sequence duration, is longer, preferentially by a factor of at least 0, 1, 1.1, 1.5, 2, 5, 10 or $10^3$ than the duration of at least one inter-step.

In another embodiment of the invention, the duration between two different sequences, is shorter, preferentially by a factor of at least 0, 1, 1.1, 1.5, 2, 5, 10 or $10^3$ than the duration of at least one sequence or the duration of at least one step.

In another aspect, the invention relates to magnetic nanoparticles, in particular magnetosomes, for use according to the invention, wherein the succession of at least one sequences is a treatment session, wherein a treatment session is characterized by at least one property selected in the group consisting of:
  each treatment session has a duration that is between $10^{-50}$ and $10^{50}$ minutes, preferably between $10^{-50}$ and $10^3$ minutes, more preferably between $10^{-50}$ and 60 minutes, even more preferably between $10^{-50}$ and 30 minutes, even more preferably between $10^{-5}$ and 30 minutes, even more preferably between $10^{-3}$ and 15 minutes, between $10^{-1}$ and 10 minutes, or even more preferably between $10^{-1}$ and 5 minutes, there is an inter-session duration between two treatment sessions which is between $10^{-10}$ and $10^{20}$ minute(s), preferably between $10^{-5}$ and $10^5$ minute(s), more preferably between $10^{-5}$ and 10 minute(s), or even more preferably between $10^{-5}$ and 1 minute(s),
  at least one session has a duration that is longer than the duration of at least one sequence, preferentially by a factor of at least 1.1, and
  there is at least one inter-session between two treatment sessions that has a duration that is longer, preferentially by a factor of at least 1.1, than a duration of at least one sequence.

The invention also relates to the method according to the invention, wherein a succession of at least one sequence is a treatment session, wherein a treatment session is characterized by at least one property selected in the group consisting of:
  each treatment session has a duration that is between $10^{-50}$ and $10^{50}$ minutes,
  there is an inter-session duration between two treatment sessions which is between $10^{-10}$ and $10^{20}$ minute(s)
  at least one session has a duration that is longer than a duration of at least one sequence, and
  there is at least one inter-session between two treatment sessions that has duration that is longer than a duration of at least one sequence.

In one embodiment of the invention, the duration of at least one session or inter-session is longer than $10^{-100}$, $10^{-50}$, $10^{-10}$, $10^{-5}$, $10^{-1}$, 1, 5, 10, $10^3$ or $10^5$ minute(s).

In one embodiment of the invention, the duration of at least one session or inter-session is longer, preferentially by a factor of at least 0, 1, 5, 10, $10^3$ or $10^5$ than the duration of at least one sequence or inter-sequence.

In one embodiment of the invention, the duration of at least one inter-session is longer, preferentially by a factor of at least 0, 1, 1.1, 2, 5, 10, $10^3$ or by at least $10^{-50}$, $10^{-3}$, 0, 1, 10, 100 or $10^3$ minutes than the duration of at least one sequence, one step, one inter-sequence, one session.

In another embodiment of the invention, the duration of at least one session or inter-session is shorter than $10^{100}$, $10^{50}$, $10^{10}$, $10^5$, $10^3$, $10^2$, 50, 20, 10, 5, 2 or 1 minute(s).

Figure 2:
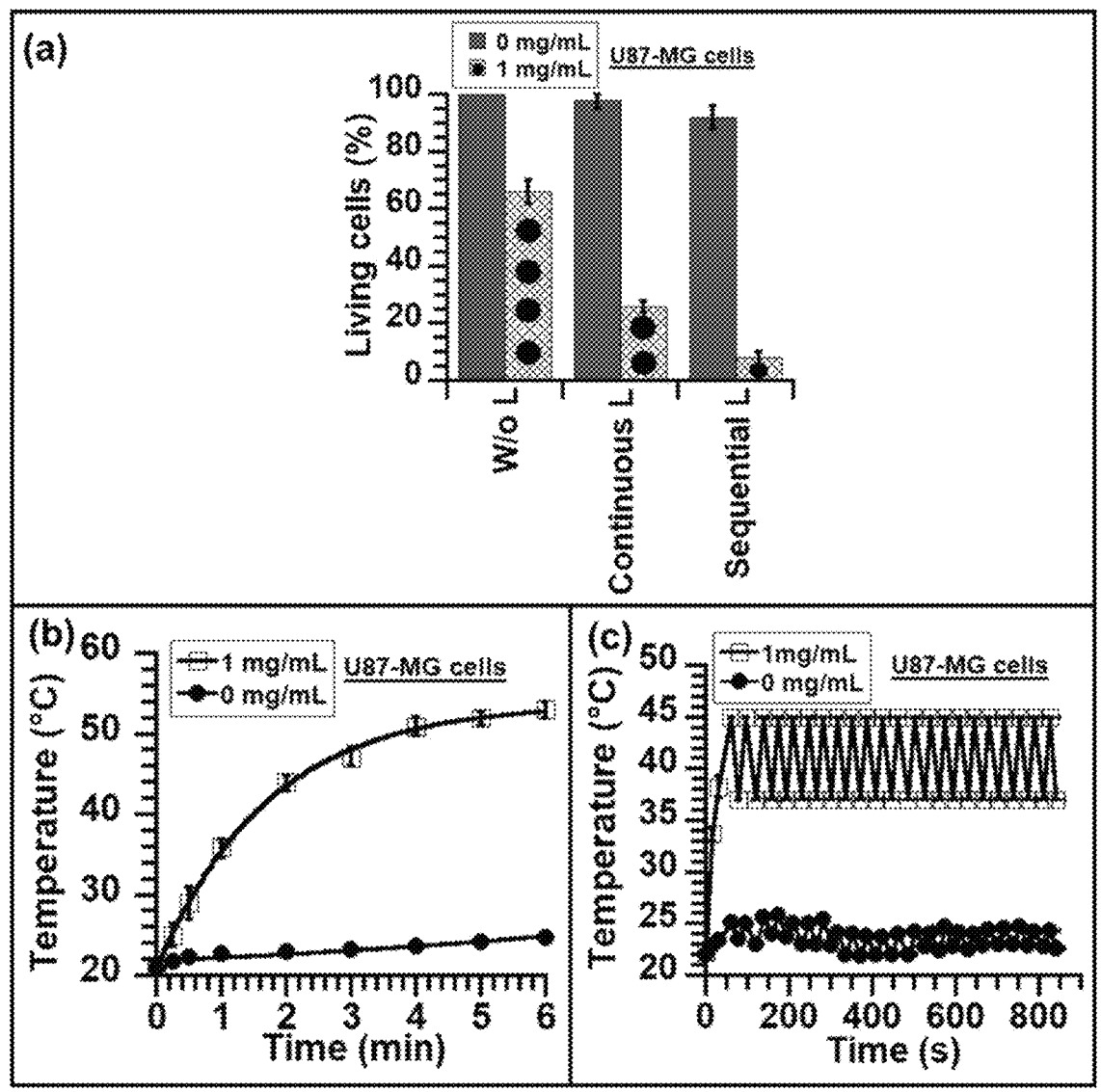
FIG. 2: (a) Percentage of living cells after the following treatment: U87-MG cells are brought into contact with 1 mg/mL in iron of magnetosomes or not brought into contact with magnetosomes (0 mg/mL) and either not exposed to the laser (W/o L), exposed sequentially to the laser with an average power at 3 W/cm$^2$, where the details of the sequences are given in the legend of (c) (Sequential L), or exposed continuously to the laser with an average power at 3 W/cm$^2$ during 6 minutes (continuous L). (b) Variation as a function of time of the temperature of U87-MG cells brought into contact with 0 mg/mL and 1 mg/mL of magnetosomes and exposed continuously to a laser with an average power at 3 W/cm$^2$ during 6 minutes. (c) Variation as a function of time of the temperature of U87-MG cells brought into contact with 0 mg/mL and 1 mg/mL of magnetosomes and sequentially exposed to a laser of average power at 3 W/cm$^2$.
Figure 3:
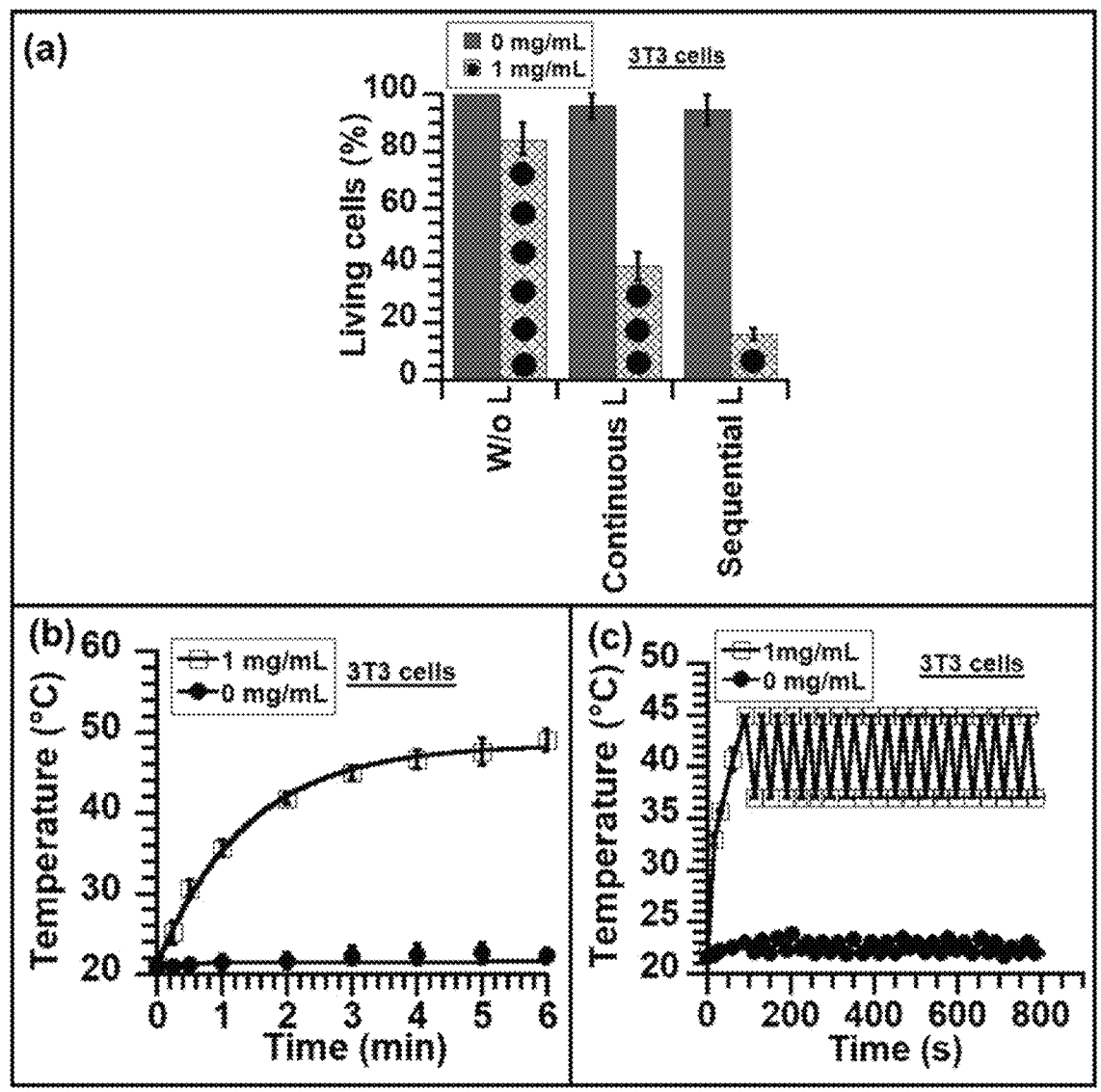
FIG. 3: (a) Percentage of living cells after the following treatment: 3T3 cells are brought into contact with 1 mg/mL in iron of magnetosomes or not brought into contact with magnetosomes (0 mg/mL) and either not exposed to the laser (W/o L), exposed sequentially to the laser with an average power at 3 W/cm$^2$, where the details of the sequences are given in the legend of (c) (Sequential L), or exposed continuously to the laser with an average power at 3 W/cm$^2$ during 6 minutes (continuous L). (b) Variation as a function of time of the temperature of 3T3 cells brought into contact with 0 mg/mL and 1 mg/mL of magnetosomes and exposed continuously to a laser with an average power at 3 W/cm$^2$ during 6 minutes. (c) Variation as a function of time of the temperature of 3T3 cells brought into contact with 0 mg/mL and 1 mg/mL of magnetosomes and sequentially exposed to a laser an average power at 3 W/cm$^2$.
Figure 4:
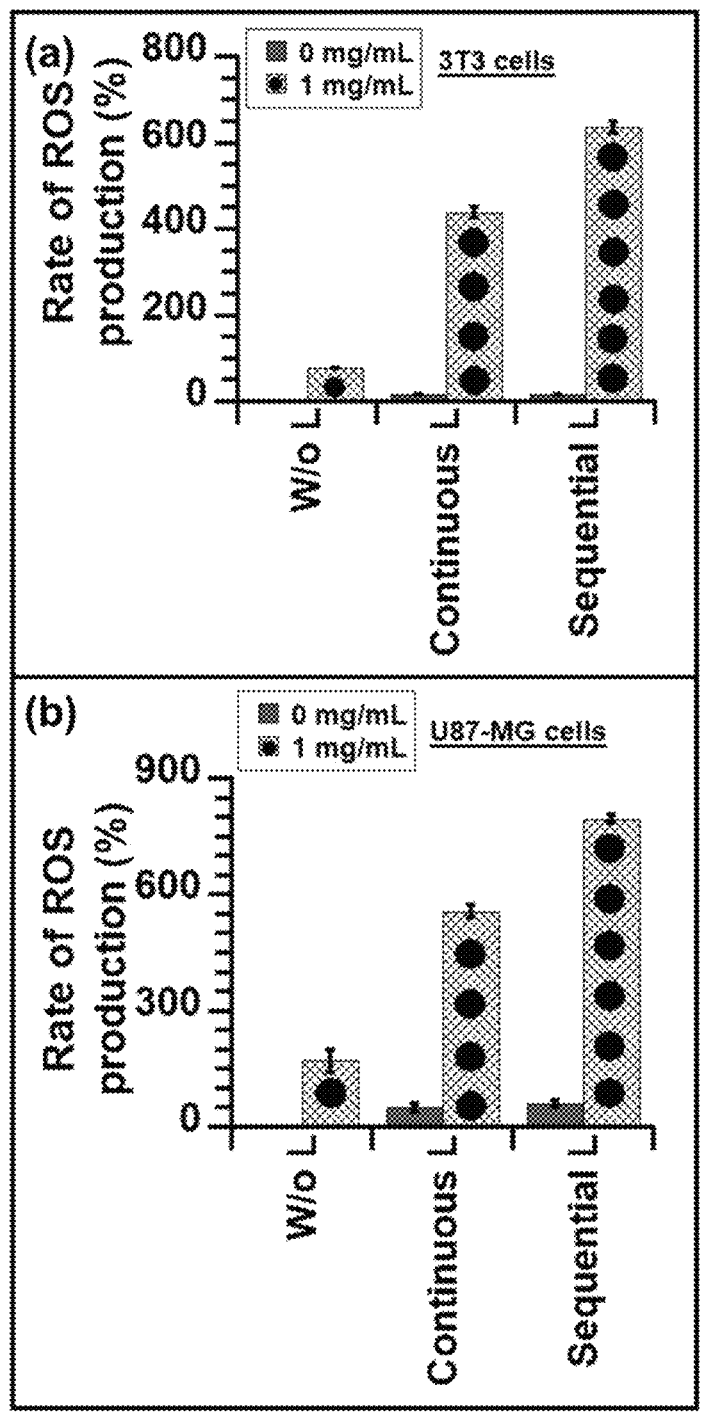
FIG. 4: (a), Rate of ROS production after the following treatment: 3T3 cells are brought into contact with 1 mg/mL in iron of magnetosomes (M-CMD) or not brought into contact with magnetosomes (0 mg/mL) and either not exposed to the laser (W/o L), or exposed continuously to the laser with average power of 3 W/cm$^2$ during 6 minutes, or exposed sequentially to the laser with an average power at 3 W/cm$^2$, where the details of the sequences are given in the legend FIG. 2(c). (b), Rate of ROS production after the following treatment: U87-MG cells are brought into contact with 1 mg/mL in iron of magnetosomes or not brought into contact with magnetosomes (0 mg/mL) and either not exposed to the laser (W/o L), exposed continuously to the laser with an average power at 3 W/cm$^2$ during 6 minutes, exposed sequentially to the laser with an average power at 3 W/cm², where the details of the sequences are given in FIG. 3(c).
Figure 5:
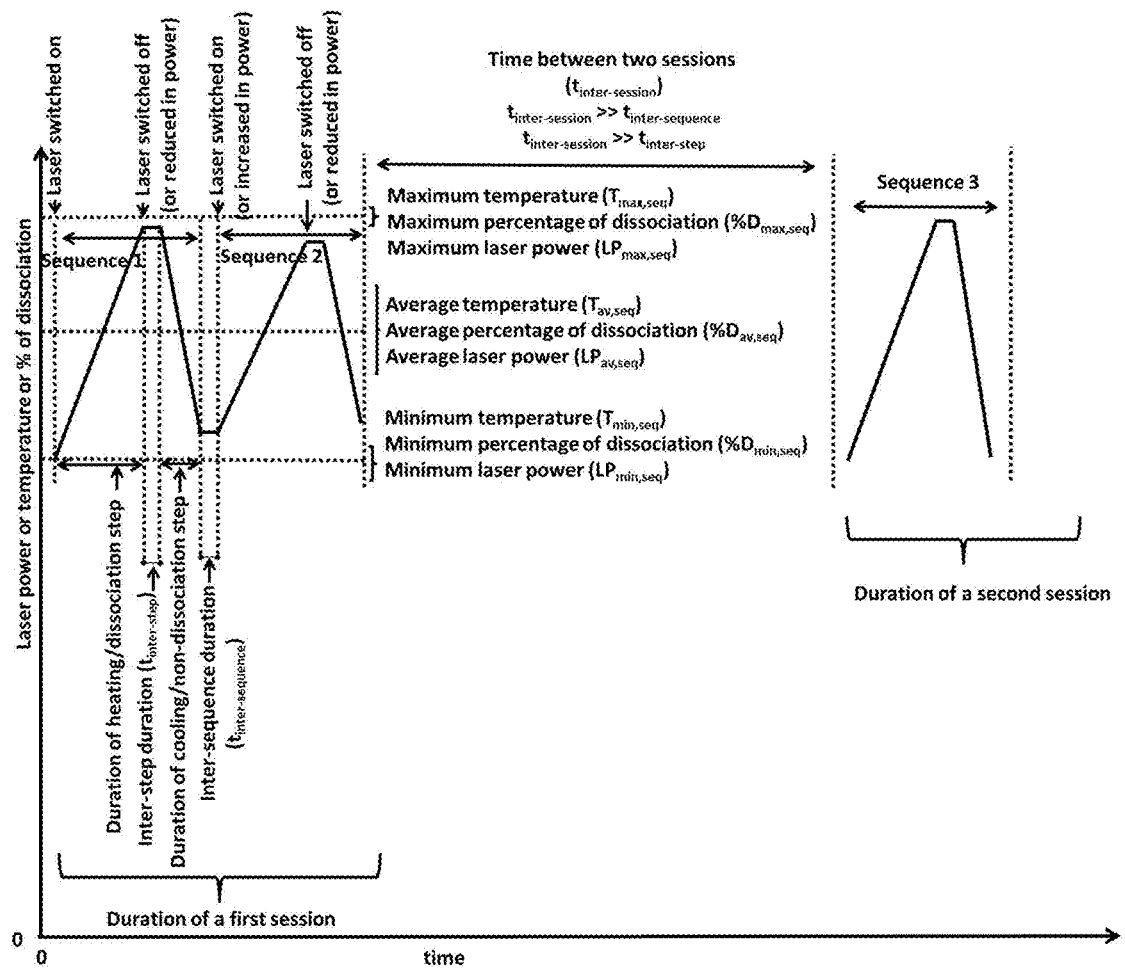
FIG. 5: Schematic diagram illustrating how the method of sequential laser radiation could be implemented. It shows different steps of the sequential method of laser irradiation, the heating and cooling steps, 3 different sequences, as well as two sessions separated by a certain lapse of time. The time between two sessions is higher than the time between two steps or than the time between two sequences. The maximum temperature reached with the sequential method of laser radiation is $T_{max,seq}$. The maximum percentage of dissociation reached with the sequential method of laser radiation is % $D_{max,seq}$. The maximum laser power reached with the sequential method of laser radiation is $LP_{max,seq}$. The average temperature reached with the sequential method of laser radiation is $T_{av,seq}$. The average percentage of dissociation reached with the sequential method of laser radiation is % $D_{av,seq}$. The average laser power used in the sequential method of laser irradiation is $LP_{av,seq}$. The minimum temperature reached with the sequential method of laser radiation is $T_{min,seq}$. The minimum percentage of dissociation reached with the sequential method of laser radiation is % $D_{min,seq}$. The minimum laser power reached with the sequential method of laser radiation is $LP_{min,seq}$.
Figure 6:
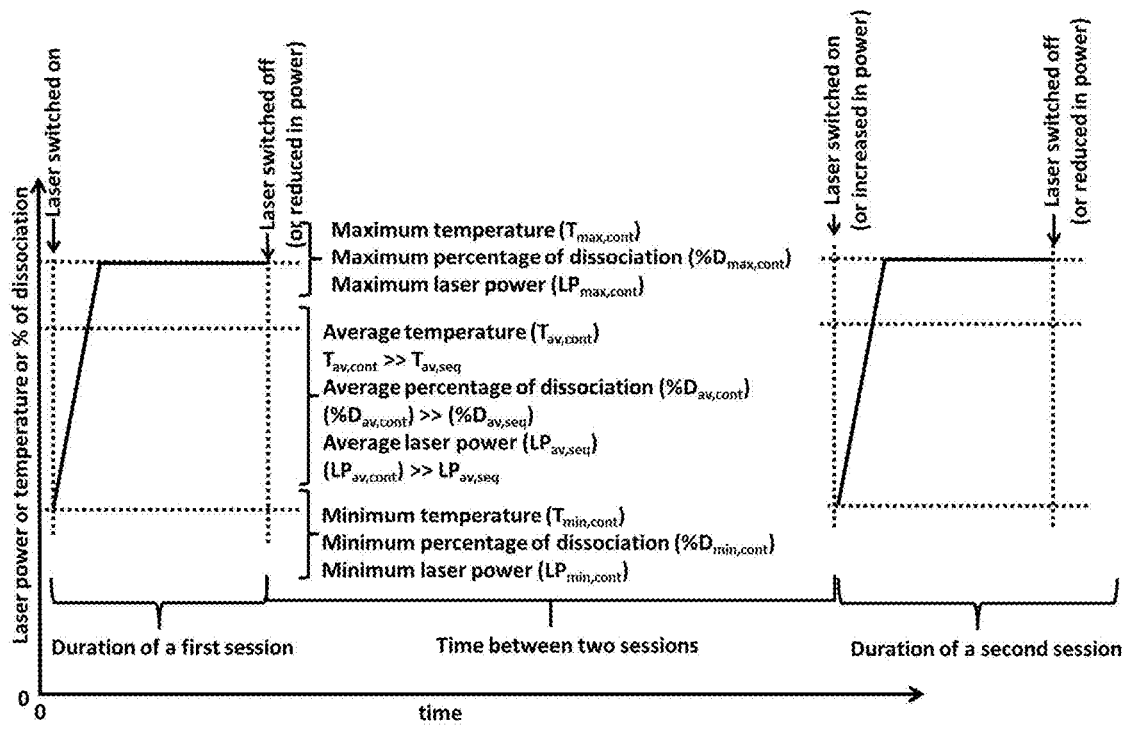
FIG. 6: Schematic diagram illustrating how a method of continuous laser radiation could be implemented. It shows two different sessions of a continuous method of laser irradiation. Compared with the sequential method of laser irradiation, i) there is not any step or sequence, ii) the average temperature is higher in the continuous than in the sequential method, iii) the maximum temperature is reached over a higher percentage of the heating cycle in the continuous than in the sequential method, iv) the number of temperature gradient is lower in the continuous method (only 2 at the beginning of each session) than the number of temperature gradient in the sequential method (where it is higher than 2). The maximum temperature reached with the continuous method of laser radiation is $T_{max,cont}$. The maximum percentage of dissociation reached with the continuous method of laser radiation is % $D_{max,cont}$. The maximum laser power reached with the continuous method of laser radiation is $LP_{max,cont}$. The average temperature reached with the continuous method of laser radiation is $T_{av,cont}$. The average percentage of dissociation reached with the continuous method of laser radiation is % $D_{av,cont}$. The average laser power used in the continuous laser irradiation is $LP_{av,cont}$. The minimum temperature reached with the continuous method of laser radiation is $T_{min,cont}$. The minimum percentage of dissociation reached with the continuous method of laser radiation is % $D_{min,cont}$. The minimum laser power reached with the continuous method of laser radiation is $LP_{min,cont}$.

In the experimental example, the duration of a session is 6 minutes (FIGS. 2 and 3) and comprises 22 sequences (FIG. 2(c)) and 19 sequences (FIG. 3(c)).

The details of the sequences of FIG. 2 are as follows: First sequence: i) application of the laser of average power at 3 W/cm² during 60 seconds until the temperature reaches 45° C., ii) non-application of the laser during 18 seconds resulting in a temperature decrease from 45° C. to 37° C.; Second sequence: i) application of the laser of average power at 3 W/cm² during 17.5 seconds resulting in a temperature increase from 37° C. to 45° C., ii) non-application of the laser during resulting in a temperature decrease from 45° C. to 37° C. during 24 seconds; Third sequence: i), application of the laser of average power at 3 W/cm² during 17.5 seconds resulting in a temperature increase from 37° C. to 45° C., ii) non-application of the laser during resulting in a temperature decrease from 45° C. to 37° C. during 20 seconds; Fourth sequence: i) application of the laser of average power at 3 W/cm² during 15.5 seconds resulting in a temperature increase from 37° C. to 45° C., ii) non-application of the laser during resulting in a temperature decrease from 45° C. to 37° C. during 20.5 seconds; Fifth sequence: i) application of the laser of average power at 3 W/cm² during 15 seconds resulting in a temperature increase from 37° C. to 45° C., ii) non-application of the laser during 21.5 seconds resulting in a temperature decrease from 45° C. to 37° C.; sixth sequence: i) application of the laser of average power at 3 W/cm² during 14.5 seconds resulting in a temperature increase from 37° C. to 45° C., ii) non-application of the laser during 21.5 seconds resulting in a temperature decrease from 45° C. to 37° C.; seventh sequence: i) application of the laser of average power at 3 W/cm² during 15 seconds resulting in a temperature increase from 37° C. to 45° C., ii) non-application of the laser during 20 seconds resulting in a temperature decrease from 45° C. to 37° C.; eighth sequence: i) application of the laser of average power at 3 W/cm² during 13.5 seconds resulting in a temperature increase from 37° C. to 45° C., ii) non-application of the laser during 22 seconds resulting in a temperature decrease from 45° C. to 37° C.; ninth sequence: i) application of the laser of average power 3 W/cm² during 13 seconds resulting in a temperature increase from 37° C. to 45° C., ii) non-application of the laser during 21 seconds resulting in a temperature decrease from 45° C. to 37° C.; tenth sequence: i) application of the laser of average power 3 W/cm² during 15 seconds resulting in a temperature increase from 37° C. to 45° C., ii), non-application of the laser during 23 seconds resulting in a temperature decrease from 45° C. to 37° C.; eleventh sequence: i) application of the laser of average power 3 W/cm² during 14.5 seconds resulting in a temperature increase from 37° C. to 45° C., ii) non-application of the laser during 23 seconds resulting in a temperature decrease from 45° C. to 37° C.; twelfth sequence: i) application of the laser of average power at 3 W/cm² during 15 seconds resulting in a temperature increase from 37° C. to 45° C., ii) non-application of the laser during 25 seconds resulting in a temperature decrease from 45° C.

to 37° C.; thirteenth sequence: i) application of the laser of average power at 3 W/cm² during 14.5 seconds resulting in a temperature increase from 37° C. to 45° C., ii) non-application of the laser during 24.5 seconds resulting in a temperature decrease from 45° C. to 37° C.; fourteenth sequence: i) application of the laser of average power 3 W/cm² during 12.5 seconds resulting in a temperature increase from 37° C. to 45° C., ii) non-application of the laser during 24 seconds resulting in a temperature decrease from 45° C. to 37° C.; fifteenth sequence: i) application of the laser of average power 3 W/cm² during 12.5 seconds resulting in a temperature increase from 37° C. to 45° C., ii) non-application of the laser during 18.5 seconds resulting in a temperature decrease from 45° C. to 37° C.; sixteenth sequence: i) application of the laser of average power 3 W/cm² during 15 seconds resulting in a temperature increase from 37° C. to 45° C., ii), non-application of the laser during 23 seconds resulting in a temperature decrease from 45° C. to 37° C.; seventeenth sequence: i) application of the laser of average power 3 W/cm² during 12.5 seconds resulting in a temperature increase from 37° C. to 45° C., ii) non-application of the laser during 22.5 seconds resulting in a temperature decrease from 45° C. to 37° C.; eighteenth sequence: i) application of the laser of average power 3 W/cm² during 13.5 seconds resulting in a temperature increase from 37° C. to 45° C., ii) non-application of the laser during 24 seconds resulting in a temperature decrease from 45° C. to 37° C.; nineteenth sequence: i) application of the laser of average power 3 W/cm² during 13.5 seconds resulting in a temperature increase from 37° C. to 45° C., ii) non-application of the laser during 21.5 seconds resulting in a temperature decrease from 45° C. to 37° C.; twentieth sequence: i) application of the laser of average power 3 W/cm² during 14 seconds resulting in a temperature increase from 37° C. to 45° C., ii) non-application of the laser during 21 seconds resulting in a temperature decrease from 45° C. to 37° C.; twenty first sequence: i) application of the laser of average power 3 W/cm² during 14.5 seconds resulting in a temperature increase from 37° C. to 45° C., ii) non-application of the laser during 23 seconds resulting in a temperature decrease from 45° C. to 37° C.; twenty second sequence: i) application of the laser of average power 3 W/cm² during 14 seconds resulting in a temperature increase from 37° C. to 45° C., ii) non-application of the laser during 16 seconds resulting in a temperature decrease from 45° C. to 37° C. The total duration of laser application was 6 min 2 sec.

The details of the sequences of FIG. 3 are as follows: First sequence: i) application of the laser of average power at 3 W/cm² during 90 seconds until the temperature reaches 45° C., ii) non-application of the laser during 21 seconds resulting in a temperature decrease from 45° C. to 37° C.; Second sequence: i) application of the laser of average power 3 W/cm² during 17.5 seconds resulting in a temperature increase from 37° C. to 45° C., ii) non-application of the laser during 22 seconds resulting in a temperature decrease from 45° C. to 37° C.; Third sequence: i) application of the laser of average power at 3 W/cm² during 17.5 seconds resulting in a temperature increase from 37° C. to 45° C., ii) non-application of the laser during 20.5 seconds resulting in a temperature decrease from 45° C. to 37° C.; Fourth sequence: i) application of the laser of average power 3 W/cm² during 14.5 seconds resulting in a temperature increase from 37° C. to 45° C., ii) non-application of the laser during 20.5 seconds resulting in a temperature decrease from 45° C. to 37° C.; Fifth sequence: i) application of the laser of average power 3 W/cm² during 15.5 seconds resulting in a temperature increase from 37° C. to 45° C., ii) non-application of the laser during 19 seconds resulting in a temperature decrease from 45° C. to 37° C.; sixth sequence: i) application of the laser of average power 3 W/cm² during 15.5 seconds resulting in a temperature increase from 37° C. to 45° C., ii) non-application of the laser during 19.5 seconds resulting in a temperature decrease from 45° C. to 37° C.; seventh sequence: i) application of the laser of average power 3 W/cm² during 18.5 seconds resulting in a temperature increase from 37° C. to 45° C., ii) non-application of the laser during 20 seconds resulting in a temperature decrease from 45° C. to 37° C.; eighth sequence: i) application of the laser of average power 3 W/cm² during 18.5 seconds resulting in a temperature increase from 37° C. to 45° C., ii) non-application of the laser during 21 seconds resulting in a temperature decrease from 45° C. to 37° C.; ninth sequence: i) application of the laser of average power 3 W/cm² during 20 seconds resulting in a temperature increase from 37° C. to 45° C., ii) non-application of the laser during 20 seconds resulting in a temperature decrease from 45° C. to 37° C.; tenth sequence: i) application of the laser of average power 3 W/cm² during 18.5 seconds resulting in a temperature increase from 37° C. to 45° C., ii) non-application of the laser during 19.5 seconds resulting in a temperature decrease from 45° C. to 37° C.; eleventh sequence: i) application of the laser of average power 3 W/cm² during 17.5 seconds resulting in a temperature increase from 37° C. to 45° C., ii) non-application of the laser during 18.5 seconds resulting in a temperature decrease from 45° C. to 37° C.; twelfth sequence: i) application of the laser of average power at 3 W/cm² during 18 seconds resulting in a temperature increase from 37° C. to 45° C., ii) non-application of the laser during 19.5 seconds resulting in a temperature decrease from 45° C. to 37° C.; thirteenth sequence: i) application of the laser of average power 3 W/cm² during 17.5 seconds resulting in a temperature increase from 37° C. to 45° C., ii) non-application of the laser during 18.5 seconds resulting in a temperature decrease from 45° C. to 37° C.; fourteenth sequence: i) application of the laser of average power 3 W/cm² during 17.5 seconds resulting in a temperature increase from 37° C. to 45° C., ii) non-application of the laser during 18.5 seconds resulting in a temperature decrease from 45° C. to 37° C.; fifteenth sequence: i) application of the laser of average power 3 W/cm² during 19.5 seconds resulting in a temperature increase from 37° C. to 45° C., ii) non-application of the laser during 21.5 seconds resulting in a temperature decrease from 45° C. to 37° C.; sixteenth sequence: i) application of the laser of average power 3 W/cm² during 18 seconds resulting in a temperature increase from 37° C. to 45° C., ii) non-application of the laser during 19.5 seconds resulting in a temperature decrease from 45° C. to 37° C.; seventeenth sequence: i) application of the laser of average power 3 W/cm² during 17.5 seconds resulting in a temperature increase from 37° C. to 45° C., ii) non-application of the laser during 19.5 seconds resulting in a temperature decrease from 45° C. to 37° C.; eighteenth sequence: i) application of the laser of average power 3 W/cm² during 17.5 seconds resulting in a temperature increase from 37° C. to 45° C., ii) non-application of the laser during 20 seconds resulting in a temperature decrease from 45° C. to 37° C.; nineteenth sequence: i) application of the laser of average power 3 W/cm² during 19 seconds resulting in a temperature increase from 37° C. to 45° C., ii) non-application of the laser during 18.5 seconds resulting in a temperature decrease from 45° C. to 37° C.

In some embodiments, the duration of the session is increased, for example to increase the number of sequences in each session. In some other embodiments, the duration of the session is decreased, for example to decrease the number of sequences in each session.

In one aspect of the invention, the invention relates to magnetic nanoparticles, preferentially magnetosomes, for use according to the invention, wherein the first step and/or second step is/are ended when a given percentage of dissociation of at least one compound from magnetic nanoparticles, preferentially magnetosomes, is reached and/or when a given temperature of the first step, $GT_{FS}$, and/or a given temperature of the second step, $GT_{SS}$, is reached, wherein $GT_{SS}$ and $GT_{FS}$ are characterized by at least one property selected from the group consisting of:

- $GT_{SS}$ is above $GT_{FS}$,
- ($GT_{SS}$–$GT_{FS}$) is between 0 and $10^{5\circ}$ C., between $10^{-5}$ and $10^{5\circ}$ C., between $10^{-3}$ and $10^{3\circ}$ C., between $10^{-1}$ and $10^{2\circ}$ C., between $10^{-1}$ and $50°$ C., between $10^{-1}$ and $20°$ C., between $10^{-1}$ and $10°$ C., or between $10^{-1}$ and $5°$ C.,
- $GT_{SS}$ and/or $GT_{FS}$ is/are comprised between $-273$ and $10^{3\circ}$ C., preferably between $-100$ and $10^{3\circ}$ C., more preferably between 0 and $100°$ C., most preferably between 30 and $70°$ C., most preferably between 30 and $60°$ C., most preferably between 37 and $55°$ C.,
- $GT_{SS}$ is within the range of temperatures reached during a hyperthermia treatment, i.e. preferentially within the range of 37 to $70°$ C., most preferentially within the range of 37 to $60°$ C.,
- $GT_{FS}$ is preferably above: i) the cryogenic temperature or $-40°$ C., ii) $0°$ C. or the temperature of ice formation, or iii) physiological temperature or $37°$ C., and
- $GT_{SS}$ and $GT_{FS}$ are preferably below: i) the boiling temperature of water or tissue or $100°$ C., or ii) the ablative temperature or $70°$ C., and
- $GT_{SS}$ and $GT_{FS}$ are preferably less than $10^5$, $10^3$, 10, 5, 2 or $1°$ C. above $37°$ C. or physiological temperature.

In one aspect of the invention, the invention also relates to the method according to the invention, wherein the first step and/or the second step(s) is/are ended when a given percentage of dissociation of at least one compound from magnetic nanoparticles, in particular magnetosomes, is reached and/or when a given temperature of the first step, $GT_{FS}$, and/or a given temperature of the second step, $GT_{SS}$, is reached, wherein $GT_{SS}$ and $GT_{FS}$ are characterized by at least one property selected from the group consisting of:

- $GT_{SS}$ is above $GT_{FS}$,
- ($GT_{SS}$–$GT_{FS}$) is between $10^{-5}$ and $10^{5\circ}$ C.,
- $GT_{SS}$ and/or $GT_{FS}$ are comprised between $-273$ and $10^{3\circ}$ C.,
- $GT_{SS}$ is within a range of temperatures reached during a hyperthermia treatment,
- $GT_{FS}$ is above: i) $-40°$ C., ii) $0°$ C., or iii) $37°$ C. or physiological temperature,
- $GT_{SS}$ and $GT_{FS}$ are below: i) $100°$ C., or ii) $70°$ C., and
- $GT_{SS}$ and $GT_{FS}$ are less than $10^5$, $10^3$, 10, 5, 2 or $1°$ C. above $37°$ C. or physiological temperature.

In one embodiment temperature, the ablative temperature is the temperature that leads to the removal or destruction of the body part or pathological cells, preferably without the predominant involvement of the immune system or apoptosis, preferentially by burning the body part.

In one embodiment of the invention, the first step is ended by switching off the laser and/or by reducing laser power.

In one embodiment of the invention, the second step ended by switching on the laser and/or by increasing laser power.

In one embodiment of the invention, the given temperature is the temperature that one desires to reach or that is reached at the end of the first or second step. In some embodiments, it corresponds to the maximum temperature of the first step or to the minimum temperature of the second step.

In one embodiment of the invention, the given percentage of dissociation is the percentage of dissociation that one desires to reach or that is reached at the end of the first or second step. In some embodiments, it corresponds to the maximum percentage of dissociation of the first step or to the minimum percentage of dissociation of the second step.

In one embodiment of the invention, $GT_{SS}$ and/or $GT_{FS}$ is/are larger than $-273$, $-100$, $-50$, $-10$, 0, 5, 10, 20, 37, 40, 41, 45, 50 or $60°$ C.

In one embodiment of the invention, $GT_{SS}$ and/or $GT_{FS}$ is/are lower than $10^{20}$, $10^{10}$, $10^5$, $10^3$, 100, 90, 80, 70, 60, 55, 50, 45, 43, 42, 41, 40, 39, 38, 37, 36, 35, 30, 20, 10 or $0°$ C.

In the experimental example, $GT_{FS}$ is between ~45 and ~50° C., while $GT_{SS}$ is ~37° C. (FIG. 1, FIG. 2(c), FIG. 3(c)). $GT_{FS}$ can be higher when one wishes to heat the body part or magnetic nanoparticles at a higher temperature. $GT_{FS}$ can be lower when one wishes to heat the body part or magnetic nanoparticles at a lower temperature.

In one aspect of the invention, the invention also relates to magnetic nanoparticles, in particular magnetosomes, for use, wherein the first and/or second step(s) is/are ended when a given percentage of dissociation is reached and/or when a given temperature is reached, preferably between $-273$ and $10^{5\circ}$ C. for the at least one first step and/or at least one second step, more preferably between 0 and $10^{3\circ}$ C. for the at least one first step and/or at least one second step, most preferably between 0 and $70°$ C. for the at least one first step and/or at least one second step.

In one embodiment of the invention, the first and/or second step(s) is/are ended when a temperature higher than $-273$, $-270$, $-150$, $-100$, $-50$, $-20$, 0, 5, 10, 15, 20, 37, 40, 41, 43, 45, 50, 55, 60, 70, 80, 90, 100, 200, 500, or $1000°$ C., is reached.

In another embodiment of the invention, the first and/or second step(s) is/are ended when a temperature lower than $-273$, $-270$, $-150$, $-100$, $-50$, $-20$, 0, 5, 10, 15, 20, 37, 40, 41, 43, 45, 50, 55, 60, 70, 80, 90, 100, 200, 500, or $1000°$ C., is reached.

In one embodiment of the invention, the first and/or second step(s) is/are ended when a percentage of dissociation higher than $10^{-20}$, $10^{-10}$, $10^{-5}$, $10^{-3}$, $10^{-1}$, 1, 5, 10, $10^3$, $10^5$, $10^{10}$, or $10^{20}$%, is reached.

In one embodiment of the invention, the first and/or second step(s) is/are ended when a percentage of dissociation lower than $10^{-20}$, $10^{-10}$, $10^{-5}$, $10^{-3}$, $10^{-1}$, 1, 5, 10, $10^3$, $10^5$, $10^{10}$, or $10^{20}$%, is reached.

In one embodiment of the invention, the first and/or second step(s) is/are ended: i), by switching off or stop the laser or laser power or laser intensity or laser equipment or laser apparatus, or, ii), by decreasing the laser power or laser intensity by a factor, which is preferentially higher than 1.001, 1.01, 1.1, 1.5, 2, 5, 10, 50, $10^2$, $10^3$, $10^6$, or $10^9$, preferentially between the first and second step.

The invention also relates to magnetic nanoparticles, in particular magnetosomes, for use, wherein the concentration of the magnetic nanoparticles, in particular magnetosomes, and/or the duration(s) of the first and/or second step(s) and/or the laser power or laser power density or laser intensity is(are) adjusted to reach the desired variation(s) or gradient(s) of temperature and/or percentage of dissociation occurring during the first and/or second step(s).

In one embodiment of the invention, the concentration of the magnetic nanoparticle, in particular magnetosome, preferentially in the body part, is adjusted to a value above $10^{-9}$, $10^{-6}$, $10^{-3}$, $10^{-2}$, $10^{-1}$, 1, 10, 100, or $10^3$ mg of magnetic nanoparticles, in particular magnetosomes, per $cm^3$ or mg of magnetic nanoparticle, in particular magnetosome, per $cm^3$ of body part. A sufficiently large concentration of magnetic nanoparticle, in particular magnetosome, can enable to heat locally the body part, preferentially at the nanometer scale.

In the experimental example, for M-CMD, the increase in concentration from 0.5 to 1 mg per mL produces an increase of the average temperature gradient during the heating step by a factor comprised between 1.6 and 2.2. In some case, it is possible to reduce the concentration of the magnetic nanoparticles, in particular magnetosomes, preferentially by a factor of more than 1.001, 1.01, 1.1, 2, 5, 10, or $10^3$, and reach an average temperature gradient during the heating step, which is decreased, preferentially by a factor a factor of more than 1.001, 1.01, 1.1, 2, 5, 10, or $10^3$.

In some other embodiments of the invention, it is possible to increase the concentration of magnetic nanoparticles, in particular magnetosomes, preferentially by a factor of more than 1.001, 1.01, 1.1, 2, 5, 10, or $10^3$, and reach an average temperature gradient during the heating step, which is increased, preferentially by a factor a more than 1.001, 1.01, 1.1, 2, 5, 10, or $10^3$.

In the experimental example, for M-CMD, the increase in concentration from 0.5 to 1 mg per mL produces a decrease of the average temperature gradient during the cooling step by a factor comprised between 1.1 and 1.3. In some case, it is possible to reduce the magnetic nanoparticle, in particular magnetosome, concentration, preferentially by more than a factor of 1.001, 1.01, 1.1, 2, 5, 10, or $10^3$, and reach an average temperature gradient during the cooling step, which is increased, preferentially by a factor a factor of 1.001, 1.01, 1.1, 2, 5, 10, or $10^3$.

In some other embodiments of the invention, it is possible to increase the magnetic nanoparticle, in particular magnetosome, concentration, preferentially by more than a factor of 1.001, 1.01, 1.1, 2, 5, 10, or $10^3$, and reach an average temperature gradient during the cooling step, which is decreased, preferentially by a factor a factor of 1.001, 1.01, 1.1, 2, 5, 10, or $10^3$.

In one embodiment of the invention, a sufficiently large magnetic nanoparticle, in particular magnetosome, concentration can be looked for to reach a sufficiently large magnetic nanoparticle, in particular magnetosome, absorption rate, $SAR_M$.

In one embodiment of the invention, $SAR_M$ can be higher than $10^{-20}$, $10^{-10}$, $10^{-5}$, $10^{-2}$, $10^{-1}$, 1, 5, 10, $10^2$, or $10^3$ Watt per gram of magnetic nanoparticle, in particular magnetosome, or Watt per gram of iron oxide comprised in the magnetic nanoparticle, in particular magnetosome, or Watt per gram of iron comprised in the magnetic nanoparticle, in particular magnetosome.

In still another embodiment of the invention, $SAR_M$ does not vary or decrease or increase by more than $10^5$, 500, 90, 70, 50, 25, 10, 5, or 2% between different concentrations of magnetic nanoparticles, in particular magnetosomes, where this percentage can represent $SAR_{MC2}-SAR_{MC1}/SAR_{MC1}$, where $SAR_{MC1}$ and $SAR_{MC2}$ are two different concentrations of magnetic nanoparticles, in particular magnetosomes.

In one embodiment of the invention, this situation occurs when the concentration of magnetic nanoparticle, in particular magnetosome, is between $10^{-6}$ and $10^6$, $10^{-5}$ and $10^5$, $10^{-3}$ and $10^3$, or between $10^{-2}$ and $10^2$ mg per mL or mg per $cm^3$ of body part. In some other embodiments, this situation can occur when the concentration of magnetic nanoparticle, in particular magnetosome, is lower than 1000, 100, 10, 1, 0.1, or 0.01 mg per mL or mg per $cm^3$ of body part.

In still some other embodiments, this situation occurs when the concentration of magnetic nanoparticles, in particular magnetosomes, is higher than 1000, 100, 10, 1, 0.1, or 0.01 mg per mL or mg per $cm^3$ of body part.

In one embodiment of the invention, $SAR_M$ is the specific absorption rate of the magnetic nanoparticles, in particular magnetosomes, comprised, mixed or inserted in the body part. It can be expressed in a power unit such as Watt divided by a mass unit such as gram or in a power unit divided by a length, surface area, or volume unit such as cm, $cm^2$, or $cm^3$. $SAR_M$ is preferentially measured under the application of a radiation that produces a temperature increase, preferentially in the presence of the magnetic nanoparticle, in particular magnetosomes. In one embodiment, this radiation can be a laser, preferentially of power or power density higher than $10^{-9}$, $10^{-5}$, $10^{-3}$, $10^{-1}$, 1, 10, or $10^3$ W or W/cm or W/$cm^2$ or W/$cm^3$.

In some other embodiments of the invention, this radiation is an acoustic wave, preferentially of power or power density higher than $10^{-9}$, $10^{-5}$, $10^{-3}$, $10^{-1}$, 1, 10, or $10^3$ W/cm or W/$cm^2$ or W/$cm^3$, preferentially of frequency higher than $10^{-6}$, $10^{-3}$, $10^{-1}$, 1, 10, $10^3$, or $10^6$ MHz.

In still some other embodiments of the invention, this radiation is an alternating magnetic field, preferentially of frequency higher than $10^{-9}$, $10^{-6}$, $10^{-3}$, 1, $10^3$, $10^6$, or $10^9$ kHz, preferentially of strength higher than $10^{-9}$, $10^{-6}$, $10^{-3}$, $10^{-1}$, 1, 10, $10^3$, or $10^6$ mT. $SAR_M$ is preferentially measured in adiabatic conditions or in conditions in which heat exchanges are minimized, preferentially between: i), the portion of the body part comprising the magnetic nanoparticles, in particular magnetosomes, and the portion of the body part not comprising the magnetic nanoparticles, in particular the magnetosomes, or the region outside the body part comprising the magnetic nanoparticles, in particular the magnetosomes, or ii), the container or tube containing the magnetic nanoparticles, in particular the magnetosomes, and the exterior of this container or tube. Heat exchanges are minimized when they produce a temperature decrease of less than 75, 60, 50, 25, 10, 5, 2, 1, or 0.1° C.

In one embodiment of the invention, $SAR_M$ is proportional to the difference between the initial slope of the temperature variation with time of the body part, medium, water, tissue comprising the magnetic nanoparticles, in particular magnetosomes, $(\Delta T/\delta t)_{(M)}$, minus the initial slope of the temperature variation with time of body part, medium, water, tissue, not comprising the magnetic nanoparticles, in particular magnetosomes, $(\Delta T/\delta t)_{(WM)}$, where $(\Delta T/\delta t)_{(M)}$ and $(\Delta T/\delta t)_{(WM)}$ are preferentially estimated in ° C./sec. $SAR_M$ is preferentially estimated using to the formula: $SAR_M = \alpha_{real}[(\Delta T/\delta t)_{(M)}-(\Delta T/\delta t)_{(WM)}]$, where $\alpha_{real}$ is a proportionality coefficient. In one embodiment, $SAR_M = [(\Delta T/\delta t)_{(M)}-(\Delta T/\delta t)_{(WM)}] \cdot C_v/C_{mag}$, where $C_v$ is the specific heat capacity, preferentially of the body part, tissue, water, medium comprising the magnetic nanoparticle, in particular magnetosomes, and $C_{mag}$ is the concentration of magnetic nanoparticles, in particular magnetosomes, or quantity or number of magnetic nanoparticles, in particular magnetosomes, preferentially comprised in the body part.

In another embodiment of the invention, $SAR_M$ is the specific absorption rate of the magnetic nanoparticles, in particular magnetosomes, estimated without subtracting $(\Delta T/\delta t)_{(WM)}$ to $(\Delta T/\delta t)_{(M)}$. This can be the case when $(\Delta T/\delta t)_{(WM)}$ is small, preferentially smaller than $10^{-9}$, $10^{-6}$, $10^{-3}$, $10^{-1}$, 1, 10, or 20° C./sec.

In one embodiment of the invention, $SAR_M$ is proportional to the initial slope of the temperature variation with time of the magnetic nanoparticles, in particular magnetosomes, comprised in the body part, $(\Delta T/\delta t)_{(M)}$, preferentially estimated in ° C./sec, preferentially leading to the formula: $SAR_M = \alpha_M \cdot (\Delta T/\delta t)_{(M)}$, where $\alpha_M$ is a proportionality coefficient.

In some other embodiments of the invention, $SAR_M = (\Delta T/\delta t)_{(M)} \cdot C_v/C_{mag}$, where $C_v$ is the specific heat capacity, preferentially of the body part, tissue, water, medium comprising the magnetic nanoparticles, in particular magnetosomes, and $C_{mag}$ is the concentration of the magnetic nanoparticles, in particular magnetosomes, or quantity or number of magnetic nanoparticles, in particular magnetosomes, preferentially comprised in the body part.

In still another embodiment of the invention, the SAR measured by applying the laser on the magnetic nanoparticles, in particular magnetosomes, or body part, designated as $SAR_{laser}$, is different from the SAR measured by applying an alternating magnetic field on the magnetic nanoparticles, in particular magnetosomes, or body part, designated as $SAR_{AMF}$. In one embodiment of the invention, $SAR_{laser}$ differs from $SAR_{AMF}$ by at least $10^{-9}$, $10^{-7}$, $10^{-5}$, $10^{-3}$, $10^{-1}$, 1, 10, $10^3$, $10^5$, $10^7$, or $10^9$%, where this percentage can be equal to $(SAR_{laser} - SAR_{AMF})/SAR_{laser}$, where this percentage is preferentially measured at a given concentration of magnetic nanoparticles, in particular magnetosomes.

In one embodiment of the invention, the concentration of magnetic nanoparticles, in particular magnetosomes, is comprised between $10^{-9}$ and $10^9$, $10^{-7}$ and $10^7$, $10^{-5}$ and $10^5$, $10^{-3}$ and $10^3$, or between $10^{-1}$ and 10 mg of magnetic nanoparticles, in particular magnetosomes, per mL or between $10^{-1}$ and 10 mg of magnetic nanoparticles, in particular magnetosomes, per $cm^3$ of body part. In some other embodiments, the concentration of the magnetic nanoparticles, in particular magnetosomes, is lower than $10^9$, $10^7$, $10^5$, $10^3$, 10, 1, $10^{-3}$, $10^{-5}$, $10^{-7}$, or $10^{-9}$ mg of magnetic nanoparticles, in particular magnetosomes, per mL or mg of magnetic nanoparticle, in particular magnetosomes, per $cm^3$ of body part.

In still some other embodiments of the invention, the concentration of magnetic nanoparticles, in particular magnetosomes, is higher than $10^9$, $10^7$, $10^5$, $10^3$, 10, 1, $10^{-3}$, $10^{-5}$, $10^{-7}$, or $10^{-9}$ mg of magnetic nanoparticles, in particular magnetosomes, per mL or $10^{-9}$ mg of magnetic nanoparticles, in particular magnetosomes, per $cm^3$ of body part.

In another embodiment of the invention, the concentration of magnetic nanoparticles, in particular magnetosomes, preferentially in the body part, is adjusted to a value below $10^9$, $10^6$, $10^3$, $10^2$, 1, $10^{-1}$, or $10^{-3}$ mg of magnetic nanoparticles, in particular magnetosomes, per $cm^3$ or mg of magnetic nanoparticles, in particular magnetosomes, per $cm^3$ of body part. A sufficiently low concentration of magnetic nanoparticles, in particular magnetosomes, can be sought after or looked for to avoid toxicity of magnetic nanoparticles, in particular magnetosomes.

In another embodiment of the invention, a too low concentration of magnetic nanoparticles, in particular magnetosomes, may prevent sufficient local heating and possibly result in macroscopic heating, i.e. heating at a scale that is preferentially higher than 1, 10, $10^3$, $10^6$, or $10^9$ nm. In this case, a too low concentration of magnetic nanoparticles, in particular magnetosomes, may be avoided.

In one embodiment of the invention, local heating or local temperature increase is defined as heating at a local scale or heating that can be measured at a local scale or locally, where a local scale can designate a scale that is below $10^9$, $10^7$, $10^5$, $10^3$, 10, 1, $10^{-1}$, or $10^{-3}$ nm, or a scale that is close to the nanometer scale or to the size of a single magnetic nanoparticle, in particular magnetosome, or to the size of an assembly of magnetic nanoparticles, in particular magnetosomes.

In one embodiment of the invention, macroscopic heating or macroscopic temperature increase is defined as heating at a macroscopic scale or heating that can be measured at a macroscopic scale or macroscopically, where a macroscopic scale can designate a scale that is above $10^9$, $10^7$, $10^5$, $10^3$, 10, 1, $10^{-1}$, or $10^{-3}$ nm, or a scale that is above the nanometer scale or above the size of a single magnetic nanoparticle, in particular magnetosome, or of the size of an assembly of magnetic nanoparticles, in particular magnetosomes.

In one embodiment of the invention, an increase in concentration of magnetic nanoparticles, in particular magnetosomes, preferentially by a factor of more than 1.001, 1.01, 1.1, 1.2, 1.5, 2, 5, 10, $10^3$, or $10^6$, or preferentially above $10^{-6}$, $10^{-3}$, $10^{-1}$, 1, 5, or 10 mg of magnetic nanoparticle(s), in particular magnetosome(s), per $cm^3$ of body part, can increase the temperature gradient, average temperature gradient, or temperature variation, occurring during the first and/or second step(s), preferentially by a factor of more than 1.001, 1.01, 1.1, 1.2, 1.5, 2, 5, 10, $10^3$, or $10^6$, or preferentially by more than $10^{-6}$, $10^{-3}$, $10^{-1}$, 1, 5, 10, or $10^{3}$° C.

In another embodiment of the invention, an increase in concentration of magnetic nanoparticles, in particular magnetosomes, by a factor of more than 1.001, 1.01, 1.1, 1.2, 1.5, 2, 5, 10, $10^3$, or $10^6$, or preferentially above $10^{-6}$, $10^{-3}$, $10^{-1}$, 1, 5, or 10 mg of magnetic nanoparticle(s), in particular magnetosome,(s), per $cm^3$ of body part, can increase the percentage of dissociation occurring in the first step, preferentially by a factor of more than 1.001, 1.01, 1.1, 1.2, 1.5, 2, 5, 10, $10^3$, or $10^6$, or preferentially above $10^{-6}$, $10^{-3}$, $10^{-1}$, 1, 5, 10, 25, 50, 75, 80, or 90%.

In another embodiment of the invention, a decrease in $t_{1a}$ and/or $t_{2a}$, preferentially by a factor of more than 1.001, 1.01, 1.1, 1.2, 1.5, 2, 5, 10, $10^3$, or $10^6$, or preferentially below $10^{20}$, $10^{10}$, $10^5$, $10^3$, $10^2$, 50, 10, or 1 second(s), can increase the average temperature gradient, the temperature gradient, or the temperature variation, occurring during the first and/or second step(s), preferentially by a factor of more than 1.001, 1.01, 1.1, 1.2, 1.5, 2, 5, 10, $10^3$, or $10^6$, or preferentially by more than $10^{-6}$, $10^{-3}$, $10^{-1}$, 1, 5, 10, or $10^{3}$° C.

In an embodiment of the invention, a decrease in $t_{1b}$ and/or $t_{2b}$ by a factor of more than 1.001, 1.01, 1.1, 1.2, 1.5, 2, 5, 10, $10^3$, or $10^6$, or preferentially below $10^{20}$, $10^{10}$, $10^5$, $10^3$, $10^2$, 50, 10, or 1 second(s), can increase the percentage of dissociation, the average percentage of dissociation, the gradient of the percentage of dissociation, the average gradient of the percentage of dissociation, occurring during the first and/or second steps(s), preferentially by a factor of more than 1.001, 1.01, 1.1, 1.2, 1.5, 2, 5, 10, $10^3$, or $10^6$, or preferentially above $10^{-6}$, $10^{-3}$, $10^{-1}$, 1, 5, 10, 25, 50, 75, 80, or 90%.

In one embodiment of the invention, the first step is carried out to reach a maximum temperature, i.e. a temperature that is preferentially above the temperature reached before or without irradiation by the laser radiation, preferentially by more than $10^{-3}$, 1, 5, 10, or 50° C.

In some other embodiments of the invention, the first step is carried out to reach a maximum percentage of dissociation, i.e. a percentage of dissociation that is preferentially above, preferentially by more than $10^{-3}$, $10^{-1}$, 1, 10, or 25%, the percentage of dissociation reached before or without the irradiation by the laser radiation.

In one embodiment of the invention, the first step is carried out to reach a maximum quantity or concentration of radical species, i.e. a quantity or concentration of radical species that is above, preferentially by at least $10^{-6}$, $10^{-3}$, 1, 10, $10^3$ or $10^6$ µM of radical species preferentially per $cm^3$ of body part or per mg of magnetic nanoparticles, the quantity or concentration of radical species reached before or without the irradiation by the laser radiation.

In one embodiment of the invention, the temperature of the first step, preferentially the maximum or minimum temperature of the first step, most preferentially the maximum temperature that one desires to reach in the first step, is higher than $-273, -150, -100, -50, -20, -10, -5, -3, -1, 5, 10, 50, 10^2$, or $10^{3\circ}$ C.

In some other embodiments of the invention, the percentage of dissociation of the first step, preferentially the maximum or minimum percentage of dissociation of the first step, most preferentially the maximum percentage of dissociation that one desires to reach in the first step, is higher than 90, 80, 70, 50, 25, 10, 5, 2, or 1%.

In one embodiment of the invention, the quantity or concentration of radical species of the first step, preferentially the maximum or minimum percentage of radical species of the first step, most preferentially the maximum quantity or concentration of radical species that one desires to reach in the first step, is higher than $10^{-50}, 10^{-10}, 10^{-5}, 10^{-2}, 1, 5,$ or 10 µM of radical species preferentially per $cm^3$ of body part or per mg of magnetic nanoparticles.

In one embodiment of the invention, the temperature of the first step, preferentially the minimum or maximum temperature of the first step, most preferentially the maximum temperature that one desires to reach in the first step, is lower than $-273, -150, -100, -50, -20, -10, -5, -3, -1, 5, 10, 50, 10^2$, or $10^{3\circ}$ C.

In some other embodiments of the invention, the percentage of dissociation of the first step, preferentially the maximum or minimum percentage of dissociation of the first step, most preferentially the maximum percentage of dissociation that one desires to reach in the first step, is lower than 90, 80, 70, 50, 25, 10, 5, 2, or 1%.

In one embodiment of the invention, the quantity or concentration of radical species of the first step, preferentially the maximum or minimum percentage of radical species of the first step, most preferentially the maximum quantity or concentration of radical species that one desires to reach in the first step, is lower than $10^{50}, 10^{10}, 10^5, 10^2, 10, 5, 2, 1$ or $10^{-3}$ µM of radical species preferentially per $cm^3$ of body part or per mg of magnetic nanoparticles.

In one embodiment of the invention, the second step can be carried out to reach a minimum temperature, i.e. a temperature that is preferentially below, preferentially by more than $10^{-3}, 1, 5, 10,$ or $50°$ C., the maximum temperature reached in the first step.

In some other embodiments of the invention, the second step is carried out to reach a minimum percentage of dissociation, i.e. a percentage of dissociation that is preferentially below, preferentially by more than $10^{-3}, 10^{-1}, 1, 10,$ or 25%, the percentage of dissociation reached in the first step.

In one embodiment of the invention, the second step is carried out to reach a minimum quantity or concentration of radical species, i.e. a quantity or concentration of radical species that is below, preferentially by at least $10^{-6}, 10^{-3}, 1, 10, 10^3$ or $10^6$ µM of radical species preferentially per $cm^3$ of body part or per mg of magnetic nanoparticles, the quantity or concentration of radical species reached before or without the irradiation by the laser radiation.

In one embodiment of the invention, the temperature of the second step, preferentially the maximum or minimum temperature of the second step, most preferentially the minimum temperature that one desires to reach in the second step, is higher than $-273, -150, -100, -50, -20, -10, -5, -3, -1, 5, 10, 50, 10^2$, or $10^{3\circ}$ C.

In some other embodiments of the invention, the percentage of dissociation of the second step, preferentially the maximum or minimum percentage of dissociation of the second step, most preferentially the minimum percentage of dissociation that one desires to reach in the second step, is higher than 90, 80, 70, 50, 25, 10, 5, 2, or 1%.

In one embodiment of the invention, the quantity or concentration of radical species of the second step, preferentially the maximum or minimum percentage of radical species of the second step, most preferentially the maximum quantity or concentration of radical species that one desires to reach in the second step, is higher than $10^{-50}, 10^{-10}, 10^{-5}, 10^{-2}, 1, 5,$ or 10 µM of radical species preferentially per $cm^3$ of body part or per mg of magnetic nanoparticles.

In one embodiment of the invention, the temperature of the second step, preferentially the minimum or maximum temperature of the second step, most preferentially the minimum temperature that one desires to reach in the second step, is lower than $-273, -150, -100, -50, -20, -10, -5, -3, -1, 5, 10, 50, 10^2$, or $10^{3\circ}$ C.

In some other embodiments of the invention, the percentage of dissociation of the second step, preferentially the maximum or minimum percentage of dissociation of the second step, most preferentially the maximum percentage of dissociation that one desires to reach in the second step, is lower than 90, 80, 70, 50, 25, 10, 5, 2, or 1%.

In one embodiment of the invention, the quantity or concentration of radical species of the second step, preferentially the maximum or minimum percentage of radical species of the second step, most preferentially the maximum quantity or concentration of radical species that one desires to reach in the second step, is lower than $10^{50}, 10^{10}, 10^5, 10^2, 10, 5, 2, 1$ or $10^{-3}$ µM of radical species preferentially per $cm^3$ of body part or per mg of magnetic nanoparticles.

In one embodiment of the invention, the minimum temperature that one desires to reach in the second step is at lease 1, 5, 10, 50, 100, $10^3$, or $10^{5\circ}$ C. lower than the maximum temperature that one desires to reach in the first step.

In some other embodiments of the invention, the minimum percentage of dissociation that one desires to reach in the second step is at least 1, 5, 10, 50, 75, 80, or 90% lower than the maximum percentage of dissociation that one desires to reach in the first step.

In one embodiment of the invention, the minimum temperature that one desires to reach in the second step is lower than $273, -150, -100, -50, -20, -10, -5, -3, -1, 5, 10, 50, 10^2$, or $10^{3\circ}$ C.

In some other embodiments of the invention, the minimum percentage of dissociation that one desires to reach in the second step is lower than 1, 5, 10, 50, 75, 80, or 90%.

In still some other embodiments of the invention, the maximum or minimum temperature or percentage of dissociation that one desires to reach during the first or second step can be the same as the maximum or minimum temperature or percentage of dissociation that is reached during the first or second step.

In still some other embodiments of the invention, the maximum or minimum temperature or percentage of dissociation that one desires to reach during the first or second step can be different from the maximum or minimum temperature or percentage of dissociation that is reached during the first or second step, preferentially by a factor of more than 1.001, 1.01, 1.1, 1.5, 2, 5, 10, or $10^3$.

In still another embodiment of the invention, the absolute value of the variation or gradient of temperature occurring in the first step does not differ by a factor of more than 1.1, 1.2, 1.5, 2, 5, 10, or $10^3$, from the absolute value of the variation or gradient of temperature occurring in the second step.

In still another embodiment of the invention, the percentage of dissociation occurring in the first step differs by a factor of more than 1.1, 1.2, 1.5, 2, 5, 10, or $10^3$, from the percentage of dissociation occurring in the second step.

The invention also relates to magnetic nanoparticles, in particular magnetosomes, for use, wherein the duration(s) of the first and/or second step(s) is/are between $10^{-9}$ seconds and $10^3$ hours.

In one embodiment of the invention, the duration of the first and/or second step(s) is between $10^{-20}$ seconds and $10^{20}$ hours, or between $10^{-9}$ seconds and $10^{10}$ hours, or between $10^{-3}$ seconds and 1 hour, or between $10^{-3}$ seconds and $10^3$ seconds, or between $10^{-2}$ seconds and $10^3$ seconds, or between $10^{-1}$ seconds and 10 seconds, or between 1 second and $10^3$ seconds, or between 1 second and $10^2$ seconds, or between 1 second and 50 seconds.

The invention also relates to magnetic nanoparticles, in particular magnetosomes, for use, wherein the ratio between the duration of the first step and the duration of the second step is between $10^{-20}$ and $10^{20}$.

In one embodiment of the invention, the ratio between the duration of the first step and the duration of the second step is between $10^{-20}$ and $10^{20}$, $10^{-10}$ and $10^{10}$, $10^{-5}$ and $10^5$, $10^{-3}$ and $10^3$, $10^{-1}$ and 10, 0.5 and 5, or between 0.5 and 2.

In one aspect of the invention, the invention relates to magnetic nanoparticles, in particular magnetosomes, for use according to the invention, wherein the application of at least one sequences is associated with at least one property selected in the group consisting of: i) a decrease in magnetic nanoparticles, in particular magnetosomes, diffusion outside of the portion of the body part comprising the magnetic nanoparticles, in particular magnetosomes, ii) an increase of the percentage of dissociation of at least one compound from the magnetic nanoparticles, in particular magnetosomes, iii) an increase of the number of temperature gradients or variations, and iv) a decrease of the average temperature reached during treatment. In some embodiments, these decreases and increases are established by comparison with the method of continuous laser irradiation and/or by comparison with the situation before or without the method or treatment.

In one aspect of the invention, the invention relates to the method according to the invention, wherein the application of the at least one sequence is associated with at least one property selected in the group consisting of: i) a decrease in magnetic nanoparticles diffusion outside of the portion of the body part comprising the magnetic nanoparticles, in particular magnetosomes, ii) an increase of the percentage of dissociation of at least one compound from the magnetic nanoparticles, in particular magnetosomes, iii) an increase of the number of temperature gradients or variations, and iv) a decrease of an average temperature reached during treatment.

The invention also relates to magnetic nanoparticles, in particular magnetosomes, for use, wherein the application of sequences enables to decrease diffusion of magnetic nanoparticles, in particular magnetosomes, outside of the portion of the body part comprising the magnetic nanoparticles, in particular the magnetic nanoparticles, in particular magnetosomes.

In one embodiment of the invention, the portion of the body part comprising the magnetic nanoparticles, in particular the magnetosomes, is the portion of the body part that has received the magnetic nanoparticle, in particular the magnetosomes, more than $10^{-9}$, $10^{-6}$, $10^{-3}$, 1, $10^3$, $10^6$, or $10^9$ second(s) following administration in the body part of magnetic nanoparticles, in particular magnetosomes.

In another embodiment of the invention, the portion of the body part comprising the magnetic nanoparticles, in particular the magnetosomes, is the portion of the body part that has received the magnetic nanoparticle, in particular the magnetosomes, less than $10^{-9}$, $10^{-6}$, $10^{-3}$, 1, $10^3$, $10^6$, or $10^9$ second(s) following administration in the body part of the magnetic nanoparticles, in particular magnetosomes.

In another embodiment of the invention, the portion of the body part comprises pathological cells, or a majority of pathological cells, or more than $10^{-20}$, $10^{-10}$, $10^{-5}$, $10^{-3}$, $10^{-1}$, 1, 5, 10, 25, 50, 75, or 90% of pathological cells, where this percentage represents the ratio between the number of pathological cells comprised in the body part and the total number of cells or the sum of the numbers of healthy and pathological cells comprised in the body part.

In one embodiment of the invention, the body part is or comprises or includes the portion of the body part.

In one embodiment of the invention, the portion of the body part is the portion of the body part comprising the magnetic nanoparticle, in particular magnetosomes.

In some other embodiments of the invention, the portion of the part is the portion of the body part not comprising the magnetic nanoparticle, in particular magnetosomes.

In still some other embodiments of the invention, the portion of the body parts is the portion of the body part comprising pathological cells.

In still some other embodiments of the invention, the portion of the body part is the portion of the body part not comprising the pathological cells.

In still some other embodiments of the invention, the portion of the body part is the portion of the body part not comprising the healthy cells.

In still some other embodiments of the invention, the portion of the body part is the portion of the body part not comprising the healthy cells.

In one embodiment of the invention, the application of sequences enables to reach a percentage of magnetic nanoparticles, in particular magnetosomes, diffusing outside of the portion of the body part comprising the magnetic nanoparticles, in particular magnetosomes, which is lower than 95, 90, 80, 70, 50, 30, 20, 10, 5, 2, or 1%. Considering a portion of the body part with numbers of magnetic nanoparticles, in particular magnetosomes, $N_1$ at a time $t_1$ and $N_2$ at a time $t_2$, preferentially following administration in the body part of magnetic nanoparticles, in particular magnetosomes, this percentage can be equal to $(N_2-N_1)/N_1$.

In one embodiment of the invention, the application of sequences enables to heat the magnetic nanoparticles, in particular magnetosomes, or to dissociate the compound from the magnetic nanoparticle, in particular magnetosome, during an overall time, which preferentially includes the duration of all sessions, which is 2, 5, 10, or 100 times longer than without the application of sequences.

In another embodiment of the invention, the application of sequences enables to heat the magnetic nanoparticles, in particular magnetosomes, or to dissociate the compound from the magnetic nanoparticles, in particular magnetosomes, during more than 1 minute, 1 hour, 1 day, 1 week, 1 month, or 1 year, following administration, preferentially in the body part, of the magnetic nanoparticles, in particular magnetosomes.

The invention also relates to magnetic nanoparticles, in particular magnetosomes, for use, wherein the application of sequences enables to increase the percentage of dissociation of the compound from the magnetic nanoparticle, in particular magnetosome, and/or to increase the number of temperature gradients or variations and/or to decrease the average temperature reached during treatment.

In one embodiment of the invention, the application of sequences enables to decrease the average temperature reached during treatment, preferentially by a factor of more than 1.001, 1.01, 1.1, 1.2, 1.5, 2, 5, 10, $10^3$, or $10^6$, preferentially below $10^6$, $10^3$, 100, 90, 70, 50, 49, 48, 47, 46, 45, 44, 43, 42, 41, 40, 39, 38, 37, 35, 20, 10, 5, 2° C.

In still another embodiment of the invention, the application of sequences enables to reach an average temperature reached during treatment, which is lower than $10^6$, $10^3$, 100, 90, 70, 50, 49, 48, 47, 46, 45, 44, 43, 42, 41, 40, 39, 38, 37, 35, 20, 10, 5, 2° C.

In the experimental example of the invention, the average temperature reached during treatment can be equal to (45+37)/2=41° C. for 0.5 and 1 mg/mL of M-CMD, and to (49+37)/2=43° C. for 1 mg/mL of N-CMD.

In one embodiment of the invention, it is possible to decrease the average temperature reached during treatment, preferentially by a factor of more than 1.001, 1.01, 1.1, 1.5, 2, 5, 10, or $10^3$, by decreasing the temperature increase and/or temperature decrease that one wants to achieve during the heating and/or cooling step(s), respectively, preferentially by a factor of more than 1.001, 1.01, 1.1, 1.5, 2, 5, 10, or $10^3$.

In some other embodiments of the invention, it is possible to increase the average temperature reached during treatment, preferentially by a factor of more than 1.001, 1.01, 1.1, 1.5, 2, 5, 10, or $10^3$, by increasing the temperature increase and/or temperature decrease that one wants to achieve during the heating and/or cooling step(s), respectively, preferentially by a factor of more than 1.001, 1.01, 1.1, 1.5, 2, 5, 10, or $10^3$.

In one embodiment of the invention, the average temperature reached during treatment is an average value of the maximum and minimum temperatures reached in the first step, or is the average value of the maximum and minimum temperature reached in the second step.

In one embodiment of the invention, the average temperature reached during treatment is the average value of the two average values estimated for the different heating and cooling steps.

In some other embodiments of the invention, the average temperature reached during treatment is the average of the average values estimated for each of the various sequences or sessions.

In still another embodiment of the invention, the average temperature reached during treatment is the temperature that is reached during the longest period of time of the treatment.

In one embodiment of the invention, the saturating temperature or the temperature that reaches a plateau during the heating or cooling step, i.e. the temperature that varies by less than $10^6$, $10^3$, 10, 5, 2, 1, $10^{-3}$, $10^{-6}$, $10^{-9}$, or $10^{-20}$° C./sec could be considered as the average temperature reached during treatment.

In some other embodiments of the invention, the average temperature reached during treatment can be deduced from the average temperature variations of the heating and cooling steps, being preferentially the average value of the temperature variations of the heating and cooling steps divided by a certain factor, preferentially a factor of 2.

In some other embodiments of the invention, the average temperature reached during treatment can be deduced from the average temperature gradients of the heating and cooling steps.

In one embodiment of the invention, the application of sequences enables to increase, preferentially by a factor of more than 1.1, 1.2, 1.5, 2, 5, 10, $10^3$, or $10^5$, the percentage of dissociation and/or the number of temperature gradients or variations, compared with a continuous application of the laser, i.e. an irradiation by the laser radiation without sequences or sessions or with less than $10^3$, $10^2$, 10, 5, or 2 sequences or sessions. A continuous application can be defined as the continuous irradiation by the laser radiation during a sufficiently long time, preferentially during more than $10^{-3}$, 1, $10^3$, $10^6$, or $10^9$ second(s), without switching off the laser or without reducing the laser power or laser power density or laser intensity by a factor of more than 1.1, 1.2, 1.5, 2, 5, 10, $10^3$, or $10^6$, or below $10^{20}$, $10^{10}$, $10^5$, $10^3$, 10, 1, $10^{-3}$, or $10^{-5}$ W or W/cm or W/cm$^2$ or W/cm$^3$, or below $10^{20}$, $10^{10}$, $10^5$, $10^3$, 10, 1, $10^{-3}$, or $10^{-5}$ mA.

The invention also relates to magnetic nanoparticles, in particular magnetosomes, for use, in which the sequences are carried out in such a way that: i), the maximum temperature or maximum percentage of dissociation that one desires to reach in the first step and the minimum temperature or minimum percentage of dissociation that one desires to reach in the second step are determined, ii), a parameter of the laser is set or fixed at a first value to reach the maximum temperature and/or maximum percentage of dissociation in the first step and then a parameter of the laser is set or fixed at a second value to reach the minimum temperature and/or minimum percentage of dissociation in the second step, optionally, iii), the duration(s) of the first and/or second step(s) required to reach the maximum or minimum temperature and/or the maximum or minimum percentage of dissociation are measured, and optionally, and/or iv), the first and/or second step(s) is(are) repeated during the measured duration(s) of the first and/or second step(s).

The invention relates to magnetic nanoparticles, in particular magnetosomes, for use according to the invention, wherein the at least one sequence is carried out following at least one of the following steps:

i) determining a maximum temperature or maximum percentage of dissociation in the first step and a minimum temperature or minimum percentage of dissociation in the second step prior to treating, ii) setting or fixing a parameter of the laser at a first value to reach the maximum temperature and/or maximum percentage of dissociation in the first step and then setting or fixing a parameter of the laser at a second value to reach the minimum temperature and/or minimum percentage of dissociation in the second step, iii) optionally, measuring the duration(s) of the first and/or second step(s) required to reach these maximum or minimum temperature and/or the maximum or minimum percentage of dissociation, and iv) optionally, repeating the first and/or second step(s) during the measured duration(s) of the first and/or second step(s).

In one aspect of the invention, the invention relates to the method according to the invention, wherein the at least one sequence is carried out following at least one of the following steps:

i) determining a maximum temperature or maximum percentage of dissociation in the first step and a minimum temperature or minimum percentage of dissociation in the second step prior to treating, ii) setting or fixing a parameter of the laser at a first value to reach the maximum temperature and/or maximum percentage of dissociation in the first step and then setting or fixing a parameter of the laser at a second value to reach the minimum temperature and/or minimum percentage of dissociation in the second step, iii) optionally, measuring the duration(s) of the first and/or second step(s) required to reach these maximum or minimum temperature and/or the maximum or minimum percentage of dissociation, and iv) optionally, repeating the first and/or second step(s) during the measured duration(s) of the first and/or second step(s).

In one aspect of the invention, the invention relates to the method according to the invention, wherein the method is for medically treating a body part having a disease selected from a cancer, a tumor, and an infection.

In one aspect of the invention, the invention relates to the method according to the invention, wherein the method is for treating, preferentially cosmetically, the body part by repairing, replacing, coloring, imaging, curing, healing and/or contrasting the body part.

In one embodiment of the invention, the maximum temperature and/or maximum percentage of dissociation that one wants to reach in the first step is(are) set or fixed at one or several given value(s), designated as $g_{max}$.

In one embodiment of the invention, the maximum temperature and/or maximum percentage of dissociation that one wants to reach in the first step is(are) different from the maximum temperature and/or maximum percentage of dissociation reached in the first step by a factor of more than 1.1, 1.5, 10, $10^3$, $10^6$, $10^9$, or $10^{20}$.

In some other embodiments of the invention, the maximum temperature and/or maximum percentage of dissociation that one wants to reach in the first step is/are different from the maximum temperature and/or maximum percentage of dissociation reached in the first step by a factor of less than 1.1, 1.5, 10, $10^3$, $10^6$, $10^9$, or $10^{20}$.

In one embodiment of the invention, the minimum temperature and/or minimum percentage of dissociation that one wants to reach in the second step is(are) set at one or several given value(s), designated as $g_{min}$.

In one embodiment of the invention, the minimum temperature and/or minimum percentage of dissociation that one wants to reach in the second step is(are) different from the minimum temperature and/or minimum percentage of dissociation reached in the first step by a factor of more than 1.1, 1.5, 10, $10^3$, $10^6$, $10^9$, or $10^{20}$.

In some other embodiments of the invention, the minimum temperature and/or minimum percentage of dissociation that one wants to reach in the second step is(are) different from the minimum temperature and/or minimum percentage of dissociation reached in the first step by a factor of less than 1.1, 1.5, 10, $10^3$, $10^6$, $10^9$, or $10^{20}$.

In one embodiment of the invention, $g_{max}$, $g_{min}$, the duration of the first or second step, the number of sequences or sessions, or the laser parameter, is chosen to reach the maximum laser treatment efficacy or minimum laser treatment toxicity.

In one embodiment of the invention, maximum laser treatment efficacy and/or minimum laser treatment toxicity can be reached when the treatment involves direct effects, where direct effects can be defined as effects that cause the destruction or disappearance of the disease or pathological cells without involving substances such as immune cells, immune-attractants, T cells, B Cells, cytokines, which are preferentially different from the magnetic nanoparticle, in particular magnetosome, or the compound. For example, a direct effect can be the destruction of a pathological cell by the heat produced by the magnetic nanoparticle, in particular magnetosome, or by the toxicity of the compound towards pathological cells.

In some other embodiments of the invention, maximum laser treatment efficacy and/or minimum laser treatment toxicity can be reached when the treatment involves indirect effects, where indirect effects can be defined as effects that cause the destruction or disappearance of the disease or pathological cells by involving substances such as immune cells, immune-attractants, T cells, B Cells, cytokines, which are different from the magnetic nanoparticle, in particular magnetosome, or the compound. For example, an indirect effect can be the destruction of a pathological cell by an immune cell, or the destruction of a pathological cell at a distance from the magnetic nanoparticles, in particular magnetosomes, or body part comprising the magnetic nanoparticles, in particular magnetosomes, which is preferentially higher than 1, 5, 10, 100, $10^3$, $10^5$, $10^7$, or $10^9$ nm. An indirect effect is preferentially an effect that is not a direct effect.

In one embodiment of the invention, the parameter of the laser used to reach the maximum temperature and/or maximum percentage of dissociation in the first step is different, preferentially by a factor of more than 1.1, 1.5, 2, 5, 10, $10^3$, $10^6$, or $10^{10}$, from the parameter of the laser used to reach the minimum temperature and/or minimum percentage of dissociation in the second step.

In another embodiment of the invention, the duration(s) of the first and/or second step(s) required to reach maximum or minimum temperature and/or maximum or minimum percentage of dissociation are measured.

In one embodiment of the invention, the duration of the first step is measured by preferentially starting from the minimum temperature or minimum percentage of dissociation, preferentially reached at the beginning of the first step, by irradiating magnetic nanoparticle, in particular magnetosome, or body part, with laser radiation and by measuring the time that it takes for magnetic nanoparticles, in particular magnetosomes, or body part to reach the maximum temperature or maximum percentage of dissociation, preferentially reached at the end of the first step.

In some other embodiments of the invention, the duration of the second step is measured by preferentially starting from the maximum temperature or maximum percentage of dissociation, preferentially reached at the beginning of the second step, by not irradiating by laser radiation or by irradiating with laser radiation of lower power than in the first step, and by measuring the time it takes to reach the minimum temperature or minimum percentage of dissociation, preferentially reached at the end of the second step.

In one embodiment of the invention, the duration(s) of the first and/or second step(s) is(are) measured for magnetic nanoparticles, in particular magnetosomes, comprised in the body part.

In some other embodiments of the invention, the durations of the first and/or second step(s) is(are) measured for magnetic nanoparticles, in particular magnetosomes, comprised outside of the body part, for example for magnetic nanoparticles, in particular magnetosomes, mixed in water or in a matrix or medium that preferentially mimics the body part.

In still some other embodiments of the invention, the duration(s) of the first and/or second step(s) is(are) measured during the first sequences, preferentially during less than 2, 5, 10, $10^2$, $10^3$, or $10^5$ sequences that preferentially belong to a treatment session.

In still some other embodiments of the invention, the duration(s) of the first and/or second step(s) is(are) measured during the first sessions, preferentially during less than 2, 5, 10, $10^2$, $10^3$, or $10^5$ sessions.

In still some other embodiments of the invention, the duration(s) of the first and/or second step(s) is(are) measured during the first sequences or sessions and the average value(s) of the duration(s) of this/these step(s) is/are estimated. This/these average value(s) is/are preferentially used to carry out sequences or sessions that follow the first sequences or sessions, preferentially without measuring or without needing to measure: i), the duration(s) of the first and/or second step(s), ii), the temperature, or iii), the percentage of dissociation.

In one embodiment of the invention, the first and second steps are repeated, preferentially more than 2, 5, 10, $10^2$, $10^3$, or $10^6$ times, preferentially during the duration(s) of the first and/or second step(s), which have been measured.

In another embodiment of the invention, the first and second steps are repeated until a therapeutic effect, such as the destruction of the body part or pathological cells, is achieved.

The invention also relates to magnetic nanoparticles, in particular magnetosomes, for use, wherein the parameter of the laser is selected from the group consisting of laser power, power density, intensity, amplitude, strength, frequency, and pulsation time.

In one embodiment of the invention, the laser power corresponds to the power of laser radiation generated by the equipment or apparatus generating laser radiation before laser radiation reaches or travels through the body part.

In still some other embodiments of the invention, the laser power corresponds to the power of laser radiation generated by the equipment or apparatus generating laser radiation after or while laser radiation reaches or travels through the body part.

In one embodiment of the invention, the laser power is higher than $10^{-20}$, $10^{-10}$, $10^{-5}$, $10^{-2}$, $10^{-1}$, 1, 5, 10, $10^2$, $10^3$, or $10^5$ W (Watt).

In another embodiment of the invention, the laser power is lower than $10^{-20}$, $10^{-10}$, $10^{-5}$, $10^{-2}$, $10^{-1}$, 1, 5, 10, $10^2$, $10^3$, or $10^5$ W (Watt).

In still another embodiment of the invention, the laser power density is the ratio between the laser power and the volume, surface, length of body part through which laser radiation travels or of body part that laser radiation reaches.

In one embodiment of the invention, the laser power density is higher than $10^{-20}$, $10^{-10}$, $10^{-5}$, $10^{-2}$, $10^{-1}$, 1, 5, 10, $10^2$, $10^3$, or $10^5$ W per cm$^3$ of body part.

In another embodiment of the invention, the laser intensity is lower than $10^{-20}$, $10^{-10}$, $10^{-5}$, $10^{-2}$, $10^{-1}$, 1, 5, 10, $10^2$, $10^3$, $10^5$, $10^{10}$, or $10^{10}$ mA.

In one embodiment of the invention, the laser intensity is higher than $10^{-20}$, $10^{-10}$, $10^{-5}$, $10^{-2}$, $10^{-1}$, 1, 5, 10, $10^2$, $10^3$, $10^5$, $10^{10}$ mA.

In one embodiment of the invention, a similar temperature increase or percentage of dissociation can be reached by increasing the laser power, laser power density, or laser intensity, preferentially by a factor of more than 1.001, 1.01, 1.1, 1.2, 1.5, 2, 5, 10, $10^3$, $10^6$, or $10^9$, while decreasing the magnetic nanoparticle, in particular magnetosome, concentration, preferentially in the body part, preferentially by a factor of more than 1.001, 1.01, 1.1, 1.2, 1.5, 2, 5, 10, $10^3$, $10^6$, or $10^9$.

In some other embodiments of the invention, a similar temperature increase or percentage of dissociation can be reached by decreasing the laser power, laser power density, or laser intensity, preferentially by a factor of more than 1.001, 1.01, 1.1, 1.2, 1.5, 2, 5, 10, $10^3$, $10^6$, or $10^9$, while increasing the concentration of the magnetic nanoparticle, in particular magnetosome, preferentially in the body part, preferentially by a factor of more than 1.001, 1.01, 1.1, 1.2, 1.5, 2, 5, 10, $10^3$, $10^6$, or $10^9$.

In one embodiment of the invention, the laser amplitude can be or be proportional to the amplitude of the laser radiation or of the electromagnetic wave associated with the laser radiation, preferentially measured at a given time of the oscillation of this wave or of laser radiation, or preferentially measured at a given wavelength of the laser radiation.

In one embodiment of the invention, the laser amplitude can correspond to or be or be proportional to the laser intensity or laser power.

In one embodiment of the invention, the laser frequency is the frequency of oscillation of the electromagnetic wave associated with the laser radiation, or is the frequency at which the laser radiation is generated, or is generated with sufficient intensity, power, or amplitude. The laser frequency is preferentially associated with a temporal or spatial laser frequency.

In one embodiment of the invention, the laser frequency is lower than $10^{20}$, $10^{15}$, $10^{12}$, $10^{10}$, $10^8$, $10^6$, $10^5$, $10^3$, $10^2$, 10, or 1 Hz.

In some other embodiments of the invention, the frequency is higher than $10^{20}$, $10^{15}$, $10^{12}$, $10^{10}$, $10^8$, $10^6$, $10^5$, $10^3$, $10^2$, 10, or 1 Hz.

In still some other embodiments of the invention, the frequency is between 1 and $10^{20}$, $10^3$ and $10^{15}$, or between $10^8$ and $10^{12}$ Hz.

In one embodiment of the invention, the laser pulsation time can be the time of pulsation of the laser radiation.

In one embodiment of the invention, the laser pulsation time is lower than $10^3$, $10^1$, $10^{-1}$, $10^{-3}$, $10^{-5}$, $10^{-10}$, $10^{-12}$, $10^{-15}$, $10^{-20}$, $10^{-40}$ second(s).

In some other embodiments of the invention, the laser pulsation time is higher than $10^3$, $10^1$, $10^{-1}$, $10^{-3}$, $10^{-5}$, $10^{-10}$, $10^{-12}$, $10^{-15}$, $10^{-20}$, $10^{-40}$ second(s). In still some other embodiments, it can be between $10^{-40}$ and $10^3$ sec., between $10^{-20}$ and 10 sec., between $10^{-20}$ and $10^{-3}$ sec., or between $10^{-10}$ and $10^{-20}$ sec.

The invention also relates to magnetic nanoparticles, in particular magnetosomes, for use, for the prevention or treatment of a disease selected from a cancer, a tumor, and an infection.

In one embodiment of the invention, a disease is a health condition of an individual in which the body part comprises more than 1, 10, $10^3$, $10^6$, $10^9$, $10^{15}$, or $10^{20}$ pathological cells or less than 1, 10, $10^3$, $10^6$, $10^9$, $10^{15}$, or $10^{20}$ healthy cells.

In one embodiment of the invention, a disease is a health condition of an individual in which the body part malfunctions or does not work or function as in a healthy individual.

In still some other embodiments of the invention, a disease is characterized by an increase of the number of pathological cells in the individual by a factor of more than 1.001, 1.1, 1.2, 1.5, 10, $10^3$, $10^6$, $10^9$, or $10^{20}$, compared with the number of pathological cells in this individual before he had the disease or in another individual without the disease.

In one embodiment of the invention, the disease is a disorder or malfunction of the body part, an infectious disease, an auto-immune disease, a neuropathology, a cancer, a cutaneous condition, an endocrine disease, an eye disease or disorder, an intestinal disease, a communication disorder, a genetic disorder, a neurological disorder, a voice disorder, a vulvovaginal disorder, a liver disorder, a heart disorder, a heating disorder, a mood disorder, or a personality disorder.

In one embodiment of the invention, the disease is selected from the group consisting of: a tumor, a cancer, a brain tumor, cervical cancer, colorectal cancer, cutaneous tumor, endometrial cancer, stomach cancer, liver cancer, gastrointestinal stromal tumor, malignant hemopathy, leukemia, multiple myeloma, lymphoma, Hodgkin's disease, non-Hodgkin's lymphoma, hepatocellular carcinoma, Kaposi's sarcoma, laryngeal cancer, mesothelioma, cancer of the esophagus, osteosarcoma, ovarian cancer, pancreatic cancer, skin cancer, oral cancer, lung cancer, small cell lung carcinoma, prostate cancer, rhabdomyosarcoma, kidney cancer, breast cancer, testicular cancer, thyroid cancer, soft tissue sarcoma, bladder carcinoma, myeloma (bone cancer), plasmacytoma, myeloma, germ cell cancer, neuroblastoma, osteosarcoma, retinoblastoma, cancer of the central nervous system, wilms tumor and nephroblastoma.

In one aspect of the invention, the invention relates to magnetosomes, in particular magnetosomes, for use in a composition.

In one aspect of the invention, the invention also relates to magnetic nanoparticles, in particular magnetosomes, for use in a cosmetic composition or cosmetic treatment.

In one embodiment of the invention, a cosmetic composition is a composition that is used in a cosmetic treatment.

In one embodiment of the invention, a cosmetic treatment is used to repair or replace damaged body part, or a body part that comprises more than 1, 10, $10^3$, $10^6$, or $10^9$ pathological cells.

In one embodiment of the invention, a cosmetic treatment is a treatment that yields a percentage of pathological cells in the body part, which is lower than $10^{-6}$, $10^{-3}$, 1, 5, 10, 25, 50, 75, or 90%. This percentage is preferentially the ratio between the number of pathological cells and the total number of the cells in the body part.

In one embodiment of the invention, a cosmetic treatment is a treatment that changes or modifies the color of the body part, for example by making it darker or lighter, by making the body part color switch from an orange, yellow, white, gray, green, blue, or red color, or a mixture of any of these colors without the magnetic nanoparticles, in particular magnetosomes, to another color, orange, yellow, white, gray, green, blue, red color, or a different mixture of these colors with the magnetic nanoparticles, in particular magnetosomes. In one embodiment, this change in color can be accentuated or more pronounced or different in the presence than in the absence of the laser. In still some other embodiments, this change in color or can be absent without laser irradiation or without the heat or compound dissociation that it induces and occur in the presence of laser irradiation or in the presence of heat or dissociation of the compound that laser induces.

In one aspect of the invention, the invention relates to a method for sequentially irradiating magnetic nanoparticles, in particular magnetosomes, with a laser, comprising:

i) performing a first step comprising irradiating the magnetic nanoparticles, in particular magnetosomes, by laser radiation at a first power;

ii) optionally performing a second step comprising not irradiating the irradiated magnetic nanoparticles, in particular magnetosomes, obtained from the first step or irradiating the irradiated magnetic nanoparticles, in particular magnetosomes, obtained from the first step by laser radiation at a second power lower than the first power; and iii) repeating the step or steps as at least once sequence.

In at least one embodiment of the invention, the method for sequentially irradiating magnetic nanoparticles, in particular magnetosomes, with a laser, may be performed using a system that allows for the control of the power of the laser radiation and timing for each step based on one or more measured conditions. For example, the power of the laser radiation applied at a given step and the time at which step occurs may be determined based on the parameter measured by a sensor located proximate to the magnetic nanoparticles, in particular magnetosomes. Such as system may comprise:

i) a laser for applying radiation to magnetic nanoparticles, in particular magnetosomes, by sequential application of power;

ii) magnetic nanoparticles, in particular magnetosomes;

iii) a parameter sensor for measuring at least one parameter selected in the group consisting of: temperature of magnetic nanoparticles, percentage of compounds released from the magnetic nanoparticles, and radical species produced by magnetic nanoparticles;

iv) a control unit which is in communication with the laser and the parameter sensor and, based on the parameter measurement received by the parameter sensor, controls the power applied to the laser and radiation of the magnetic particles, in particular magnetosomes.

In this example, the system allows for application of laser radiation at the first power $P_1$ to increase the value of the at least one parameter of or during the first step:

from: i) a minimum temperature, ii) a minimum percentage of dissociation of the compounds from the magnetic nanoparticles, in particular the magnetosomes, or iii) a minimum concentration or quantity of radical species produced by magnetic nanoparticles, in particular the magnetosomes, up to: iv) a maximum temperature, v) a maximum percentage of dissociation of the compounds from the magnetic nanoparticles, in particular the magnetosomes, or iv) a maximum concentration or quantity of radical species produced by magnetic nanoparticles, in particular the magnetosomes.

Once the parameter sensor measures the maximum value of the at least one parameter of or during the first step, the control unit turns off the power of the laser or reduces the power of the laser or changes the power of the laser from the power $P_1$ of the first step to the power $P_2$ of the second step, and the value of the at least one parameter of or during the second step is allowed to decrease:

from: i) a maximum temperature, ii) a maximum percentage of dissociation of the compounds from the magnetic nanoparticles, in particular the magnetosomes or iii) a maximum concentration or quantity or radical species produced by magnetic nanoparticles, in particular the magnetosomes, down to: i) a minimum temperature, ii) a minimum percentage of dissociation of the compounds from the magnetic nanoparticles, in particular the magnetosomes, or iii) a minimum concentration or quantity or radical species produced by magnetic nanoparticles, in particular the magnetosomes.

Once the parameter sensor measures the minimum value of the at least one parameter of the second step, the control unit initiates the application of laser radiation on the magnetic nanoparticles at the first power P1. The system allows for the repeating of the application of laser radiation for a number of sequences or time, which is in particular predetermined.

In one embodiment of the invention, radical species are selected in the group consisting of: reactive oxygen species (ROS), reactive nitrogen species (RNS), superoxide, hydroxyl, alkoxyl radical, peroxyl radical, Hydrogen peroxide, Singlet oxygen, Organic peroxide, Hypochlorous acid, Hypobromous acid, Nitric oxide, Nitrogen dioxide, Peroxynitrite, Nitrosyl cation, Nitroxyl anion, Dinitrogen trioxide, Dinitrogen tetraoxide, Nitrous acid, and any derivative of these compounds.

In one embodiment of the invention, the magnetic nanoparticles, in particular the magnetosomes, are used in the method.

In some embodiments of the invention, the method according to the invention comprises an additional step of administering the magnetic nanoparticles to the body part.

In some embodiments of the invention, the method according to the invention does not comprise an additional step of administering the magnetic nanoparticles to the body part.

In some embodiments of the invention, the method according to the invention in the sequential laser radiation medical or chemical or biological or cosmetic treatment.

In some other embodiments of the invention, the method according to the invention is different from the sequential laser radiation medical or chemical or biological or cosmetic treatment.

The invention relates to irradiated magnetic nanoparticles, in particular irradiated magnetosomes, obtained by the method according to the invention, said irradiated magnetic nanoparticles, in particular irradiated magnetosomes, having at least one property selected in the group consisting of:
- a size of the irradiated magnetic nanoparticles, in particular irradiated magnetosomes, that is smaller than the size of the non-irradiated magnetic nanoparticles, in particular non-irradiated magnetosomes, preferentially by a percentage between $10^{-3}$% and 99.99%, where this percentage is preferentially $S_I/S_{NI}$ or $(S_{NI}-S_I)/S_{NI}$, where $S_{NI}$ and $S_I$ are the sizes of the non-irradiated and irradiated magnetic nanoparticles, in particular non-irradiated and irradiated magnetosomes, respectively,
- a number of irradiated compounds bound to the irradiated magnetic nanoparticle, in particular irradiated magnetosomes, $n_I$, that is smaller than the number of compounds bound to the non-irradiated magnetic nanoparticle, in particular non-irradiated magnetosomes, $n_{NI}$, where $n_{NI}/n_I$ is between 1 and $10^{10}$.
- a binding strength of least one bond between the irradiated compound and the irradiated nanoparticle, in particular irradiated magnetosomes, $S_I$, that is smaller than the binding strength of at least one bond between the non-irradiated compound and the non-irradiated nanoparticle, in particular non-irradiated magnetosomes, $S_{NI}$,
- a breaking of at least one bond between the irradiated compound and the irradiated nanoparticle, in particular irradiated magnetosome,
- a bond-dissociation energy between the irradiated compound and the irradiated magnetic nanoparticle, in particular irradiated magnetosome, $Ed_I$, that is smaller than the bond-dissociation energy between the non-irradiated compound and the non-irradiated magnetic nanoparticle, in particular non-irradiated magnetosome, $Ed_{NI}$,
- a coating thickness of the irradiated magnetic nanoparticle, in particular irradiated magnetosomes, $CT_I$, that is smaller than the coating thickness of the non-irradiated magnetic nanoparticle, in particular non-irradiated magnetosomes, $CT_{NI}$,
- a percentage in mass of organic material or carbon of the irradiated magnetic nanoparticle, in particular irradiated magnetosomes, that is smaller than the percentage in mass of organic material or carbon of the non-irradiated magnetic nanoparticle, in particular non-irradiated magnetosomes,
- a cluttering of the irradiating compound bound to the irradiated magnetic nanoparticle, in particular irradiated magnetosomes, that is smaller than the cluttering of the non-irradiated compound bound to the non-irradiated nanoparticle, in particular non-irradiated magnetosomes, and
- a number of irradiated compounds $N_{1I}$ that prevent the release of irradiated compounds $N_{2I}$ from the irradiated magnetic nanoparticle, in particular irradiated magnetosomes, that is smaller than the number of non-irradiated compounds $N_{1NI}$ that prevent the release of non-irradiated compounds $N_{2NI}$ from the non-irradiated magnetic nanoparticle, in particular non-irradiated magnetosomes, wherein the non-irradiated magnetic nanoparticle, in particular non-irradiated magnetosomes, is either a magnetic nanoparticle, in particular magnetosomes, that is not subjected to laser irradiation or a magnetic nanoparticle, in particular magnetosomes, that is subjected to continuous laser irradiation.

In one embodiment of the invention, the irradiation is or results in or is associated with a decrease in nanoparticle size, preferentially from the size of the non-irradiated nanoparticle down to the size of the irradiated nanoparticle, where this decrease is preferentially such that $S_I/S_{NI}$ or $(S_{NI}-S_I)/S_{NI}$ is between $10^{-3}$% and 99.99%, where $S_I$ and $S_{NI}$ are the sizes of the irradiated and non-irradiated nanoparticles, respectively.

In some cases, $S_I/S_{NI}$ or $(S_{NI}-S_I)/S_{NI}$ can be larger than $10^{-50}$, $10^{-20}$, $10^{-10}$, $10^{-5}$, $10^{-1}$, 1, 5, 10, 50, $10^2$, $10^3$, $10^5$ or $10^{10}$%.

In some other cases, $S_I/S_{NI}$ or $(S_{NI}-S_I)/S_{NI}$ can be lower than $10^{50}$, $10^{20}$, $10^{10}$, $10^5$, 10, 5, 2, 1, $10^{-3}$, $10^{-5}$, $10^{-10}$ or $10^{-50}$%.

In still some other embodiments, $S_I/S_{NI}$ or $(S_{NI}-S_I)/S_{NI}$ can be between $10^{-50}$ and $10^{50}$%, between $10^{-3}$ and $10^3$%, between $10^{-3}$ and 99.99%, between $10^{-2}$ and 99%, between $10^{-1}$ and 90%, between 1 and 85%, or between 5 and 60%.

In one embodiment of the invention, the irradiation is or results in or is associated with a decrease in nanoparticle size from the size of the non-irradiated nanoparticle larger than $10^{-3}$, 0.1, 1, 5, 10 or 100 nm, down to the size of the irradiated nanoparticle smaller than $10^5$, $10^3$, 100, 50, 20, 10, 5, 3, 2 or 1 nm.

In another embodiment of the invention, the irradiation is or results in or is associated with a decrease in nanoparticle size from the size of the non-irradiated nanoparticle to the size of the irradiated nanoparticle by a quantity $S_{NI}-S_I$, which is larger than $10^{-5}$, $10^{-1}$, 1, 5, 10 or $10^3$ nm.

In another embodiment of the invention, the irradiation is or results in or is associated with a decrease in nanoparticle size from the size of the non-irradiated nanoparticle to the size of the irradiated nanoparticle by a quantity $S_{NI}-S_I$, which is smaller than $10^5$, 10, 5, 1 or $10^{-1}$ nm.

In one embodiment of the invention, the irradiation is associated with, corresponds to, results in, or leads to a size-reduction of the nanoparticle, where the size reduction of the nanoparticle is preferentially a decrease in size of the nanoparticle, which is due to irradiation or occurs or is measured during irradiation or between before and after irradiation.

In some embodiments, the size-reduction of the nanoparticle can be larger than $10^{-50}$, $10^{-10}$, $10^{-5}$, $10^{-1}$, 1, 5, 10, 50, 70, 80, 90, 95, 99, 100, $10^2$, $10^5$, $10^{10}$ or $10^{100}$%.

In some embodiments, the percentage of size reduction resulting from irradiation can be equal to $(S_{NBI}-S_{NAI})/S_{NBI}$, $S_{NAI}/S_{NBI}$, or $(S_{NAI}-S_{NBI})/S_{NBI}$, where $S_{NBA}$ and $S_{NAI}$ are the sizes of the nanoparticle before and after irradiation, respectively.

In another embodiment of the invention, the size-reduction of the nanoparticle is smaller than $10^{100}$, $10^{50}$, $10^{10}$, $10^5$, 100, 99.9, 99, 95, 90, 80, 70, 50, 30, 20, 10, 5, 2, 1 or $10^{-3}$%, In still another embodiment of the invention, the size-reduction of the nanoparticle is between $10^{-100}$ and $10^{100}$%, or between $10^{-5}$ to 99.9%.

In another embodiment of the invention, the irradiation is associated with, corresponds to, results in, or leads to the decrease of the number of compounds attached or bound to the nanoparticle, preferentially in the following manner: i) by a factor of at least 1.001, 1.1, 1.5, 2, 5, 10, $10^3$, $10^5$, $10^{10}$, or ii) from more than 1, 5, 10, $10^3$, $10^5$, $10^{10}$ or $10^{50}$ non-irradiated compound(s), preferentially per non-irradiated nanoparticle, attached or bound to the non-irradiated nanoparticle before irradiation to less than $10^{50}$, $10^{10}$, $10^5$, $10^3$, 10, 5 or 1 irradiated compound(s), preferentially per irradiated nanoparticle, attached or bound to the irradiated nanoparticle during or after irradiation.

In still another embodiment of the invention, the irradiation is, results in, or is associated with a size-reduction of the nanoparticle down to a size that is such that at least one compound remains attached or bound to at least one nanoparticle.

In still another embodiment of the invention, the irradiation is a size-reduction of the nanoparticles down to a threshold size, preferentially a threshold size of the irradiated nanoparticle.

In some embodiments, the threshold size can be the size that is such that at least one compound remains attached or bound to at least one nanoparticle, preferentially irradiated nanoparticle. Preferentially, above the threshold size, at least one compound remains or is bound to the nanoparticle, preferentially the irradiated nanoparticle, while below the threshold size no compound is bound to the nanoparticle, preferentially the irradiated nanoparticle.

In still some other embodiments, the threshold size can be the size that is such that between above and below the threshold size, the number of compounds, preferentially irradiated compounds, bound to the nanoparticle, preferentially irradiated nanoparticle, is lower, preferentially by: i) a factor of more than 1.1, 1.2, 1.5, 2, 5, 10, $10^3$ or $10^5$ or ii) more than 1, 2, 3, 5, 10, $10^3$ or $10^5$ compound(s), preferentially irradiated compound(s), preferentially per nanoparticle, most preferentially per irradiated nanoparticle.

In still some other embodiments, a size that is above the threshold size is a size that is at least $10^{-5}$, $10^{-1}$, 1, 5, 10, $10^3$, $10^5$ or $10^{10}$ nm above the threshold size.

In still some other cases, a size that is below the threshold size is a size that is at least $10^{-5}$, $10^{-1}$, 1, 5, 10, $10^3$, $10^5$ or $10^{10}$ nm below the threshold size In one embodiment of invention, the threshold size is larger than $10^{-10}$, $10^{-5}$, $10^{-3}$, $10^{-1}$, 1, 10, $10^3$, $10^5$ or $10^{10}$ nm.

In another embodiment of the invention, the threshold size is smaller than $10^{10}$, $10^5$, $10^3$, 10, 5, 2, 1, $10^{-1}$ or $10^{-3}$ nm.

In still another embodiment of the invention, the threshold size is between $10^{-5}$ and $10^{10}$, between $10^{-1}$ and $10^5$ nm, or between $10^{-1}$ and 10 nm.

In one embodiment of the invention, the irradiation is or results in or is associated with an increase in nanoparticle size, preferentially from the size of the non-irradiated nanoparticle up to the size of the irradiated nanoparticle, where this increase is preferentially such that $S_{NI}/S_I$ or $(S_1-S_{NI})/S_I$ is between $10^{-3}$% and 99.99%, where $S_I$ and $S_{NI}$ are the sizes of the irradiated and non-irradiated nanoparticles, respectively.

In some embodiments, $S_{NI}/S_I$ or $(S_I-S_{NI})/S_I$ is larger than $10^{-50}$, $10^{-20}$, $10^{-10}$, $10^{-5}$, $10^{-1}$, 1, 5, 10, 50, $10^2$, $10^3$, $10^5$ or $10^{10}$%.

In some other embodiments, $S_{NI}/S_I$ or $(S_I-S_{NI})/S_I$ is lower than $10^{50}$, $10^{20}$, $10^{10}$, $10^5$, 10, 5, 2, 1, $10^{-3}$, $10^{-5}$, $10^{-10}$ or $10^{-50}$%.

In still some other embodiments, $S_{NI}/S_I$ or $(S_I-S_{NI})/S_I$ is between $10^{-50}$ and $10^{50}$%, between $10^{-3}$ and $10^3$%, between $10^{-3}$ and 99.99%, between $10^{-2}$ and 99%, between $10^{-1}$ and 90%, between 1 and 85%, or between 5 and 60%.

In one embodiment of the invention, the alteration is or results in or is associated with an increase in nanoparticle size from the size of the non-irradiated nanoparticle smaller than $10^5$, $10^3$, 100, 50, 20, 10, 5, 3, 2 or 1 nm up to a size of the irradiated nanoparticle larger than $10^{-3}$, 0.1, 1, 5, 10 or 100 nm.

In another embodiment of the invention, the irradiation is or results in or is associated with an increase in nanoparticle size from the size of the non-irradiated nanoparticle to the size of the irradiated nanoparticle by a quantity $S_I-S_{NI}$, which is larger than $10^{-5}$, $10^{-1}$, 1, 5, 10 or $10^3$ nm.

In another embodiment of the invention, the irradiation is or results in or is associated with an increase in nanoparticle size from the size of the non-irradiated nanoparticle to the size of the irradiated nanoparticle by a quantity $S_I-S_{NI}$, which is smaller than $10^5$, 10, 5, 1 or $10^{-1}$ nm.

In one embodiment of the invention, the irradiation is or results in or is associated with a decrease in FWHM or width W of the nanoparticle size distribution, preferentially from the FWHM or width W of the size distribution of the non-irradiated nanoparticle down to the FWHM or width W of the size distribution of the irradiated nanoparticle, where this decrease is such that $FWHM_I/FWHM_{NI}$, $(FWHM_{NI}-FWHM_I)/FWHM_{NI}$, $W_I/W_{NI}$, or $(W_{NI}-W_I)/W_{NI}$ is between $10^{-3}$% and 99.99%, where $FWHM_I$ and $FWHM_{NI}$ are the full width half maximum of the size distribution of the irradiated and non-irradiated nanoparticles, respectively, where $W_I$ and $W_{NI}$ are the width of the size distribution of the irradiated and non-irradiated nanoparticles, respectively.

In one embodiment of the invention, the irradiation is or results in or is associated with an increase in FWHM or width W of the nanoparticle size distribution, preferentially from the FWHM or width W of the size distribution of the non-irradiated nanoparticle up to the FWHM or width W of the size distribution of the irradiated nanoparticle, where this increase is such that $FWHM_{NI}/FWHM_I$, $(FWHM_I-FWHM_{NI})/FWHM_I$, $W_{NI}/W_I$, or $(W_I-W_{NI})/W_I$ is between $10^{-3}\%$ and $99.99\%$, where $FWHM_I$ and $FWHM_{NI}$ are the full width half maximum of the size distribution of the irradiated and non-irradiated nanoparticles, respectively, where $W_I$ and $W_{NI}$ are the width of the size distribution of the irradiated and non-irradiated nanoparticles, respectively.

In some embodiments, the number or concentration of non-irradiated compounds exists before or without irradiation.

In some other embodiments, the number or concentration of irradiated compounds exists during or after irradiation.

In one embodiment of the invention, the alteration is or results in or is associated with a decrease in the number or concentration of compounds bound to the nanoparticle, from a number $n_{NI}$ of non-irradiated compounds bound to the non-irradiated nanoparticle down to a number $n_I$ of irradiated compounds bound to the irradiated nanoparticle, where $n_{NI}/n_I$ is preferentially between 1 and $10^{10}$.

In one embodiment of the invention, $n_{NI}$, $n_I$, or $n_{NI}-n_I$ is larger than $10^{-50}$, $10^{-20}$, $10^{-10}$, $10^{-5}$, $10^{-2}$, $10^{-1}$, 1, 5, 10, $10^3$ or $10^5$ compounds or mg of compounds or compounds per nanoparticle or mg of compounds per mg of nanoparticle. In some other cases, $n_{NI}/n_I$ is larger than 1, 2, 5, 10, $10^3$, $10^5$, $10^{10}$ or $10^{50}$. This can occur when the irradiation results in a large decrease of the number of compounds bound to the nanoparticle.

In some other embodiments, $n_{NI}$, $n_I$, $n_{NI}-n_I$ is smaller than $10^{100}$, $10^{50}$, $10^{20}$, $10^{10}$, $10^5$, $10^2$, 10, 5, 2, 1, $10^{-1}$, $10^{-5}$, $10^{-10}$ or $10^{-50}$ compounds or mg of compounds or compounds per nanoparticle or mg of compounds per mg of nanoparticle. In some other cases, $n_{NI}/n_I$ is smaller than $10^{50}$, $10^{10}$, $10^5$, $10^3$, 10, 5, 2 or 1. This can occur when the alteration results in a small decrease of the number of compounds bound to the nanoparticle.

In still some other embodiments, $n_{NI}/n_I$ is between $10^{-50}$ and $10^{50}$, $10^{-10}$ and $10^{20}$, $10^{-5}$ and $10^{20}$, $10^{-3}$ and $10^{20}$, $10^{-1}$ and $10^{10}$, or between 1 and $10^{10}$.

In one embodiment of the invention, the irradiation is or results in or is associated with a decrease of the number or concentration of compounds bound to the nanoparticle from a number $n_{NI}$ larger than $10^{-50}$, $10^{-20}$, $10^{-10}$, $10^{-5}$, $10^{-2}$, $10^{-1}$, 1, 5, 10, $10^3$ or $10^5$ compounds or mg of compounds or compounds per nanoparticle or mg of compounds per mg of nanoparticles down to a number $n_I$ lower than $10^{100}$, $10^{50}$, $10^{20}$, $10^{10}$, $10^5$, $10^2$, 10, 5, 2, 1, $10^{-1}$, $10^{-5}$, $10^{-10}$ or $10^{-50}$ compounds or mg of compounds or compounds per nanoparticle or mg of compounds per mg of nanoparticles.

In some embodiments, the decrease in number or concentration of compounds bond to the nanoparticle can be or be associated with an increase in the number or concentration of compounds released from the nanoparticle.

In one embodiment of the invention, the irradiation is or results in or is associated with the increase in the number or concentration of compounds released from the nanoparticles. The number or concentration of compounds released from the nanoparticle can increase from a number $n_{RNI}$ before irradiation, where $n_{RNI}$ is preferentially the number of non-irradiated compounds released from the non-irradiated nanoparticle, up to a number $n_{RI}$, where $n_{RI}$ is preferentially the number of irradiated compounds released from the irradiated nanoparticle.

In some embodiments, $n_{RNI}$ is smaller than $10^{100}$, $10^{50}$, $10^{20}$, $10^{10}$, $10^5$, $10^2$, 10, 5, 2, 1, $10^{-1}$, $10^{-5}$, $10^{-10}$ or $10^{-50}$ compounds or mg of compounds or compounds per nanoparticle or mg of compounds per mg of nanoparticles. Most preferentially, $n_{RNI}$ is equal to 0.

In some other embodiments, $n_{RI}$ is larger than $10^{-50}$, $10^{-20}$, $10^{-10}$, $10^{-5}$, $10^{-2}$, $10^{-1}$, 1, 5, 10, $10^3$ or $10^5$ compounds or mg of compounds or compounds per nanoparticle or mg of compounds per mg of nanoparticles.

In still some other embodiments, $abs(n_{RI}-n_{RNI})$, $n_{RI}/n_{RNI}$, $n_{RNI}/n_{RI}$, $abs(n_{RI}-n_{RNI})/n_{RI}$ or $abs(n_{RI}-n_{RNI})/n_{RNI}$ is larger than $10^{-50}$, $10^{-20}$, $10^{-10}$, $10^{-5}$, $10^{-1}$, 1, 5, 10, $10^3$, $10^5$, $10^{10}$ or $10^{50}$. Abs can designate the absolute value.

In still some other embodiments, $abs(n_{RI}-n_{RNI})$, $n_{RI}/n_{RNI}$, $n_{RNI}/n_{RI}$, $abs(n_{RI}-n_{RNI})/n_{RI}$ or $abs(n_{RI}-n_{RNI})/n_{RNI}$ is lower than $10^{50}$, $10^{20}$, $10^{10}$, $10^5$, $10^3$, 10, 5, 1, $10^{-1}$, $10^{-5}$, $10^{-10}$ or $10^{-50}$.

In one embodiment of the invention, the irradiation results in a percentage of compounds released from the nanoparticles larger than $10^{-50}$, $10^{-20}$, $10^{-10}$, $10^{-5}$, $10^{-1}$, 1, 5, 10, $10^3$, $10^5$, $10^{10}$ or $10^{50}\%$. This percentage can be equal to $N_R/(N_R+N_{NR})$, where $N_R$ and $N_{NR}$ are the concentration or number of compounds released from the nanoparticles, and the concentration or number of compounds not released from the nanoparticles or bond to the nanoparticle, respectively.

In some embodiments, the percentage of compounds released from the nanoparticles is larger after, during or with irradiation than before or without irradiation, preferentially by a factor of at least 1.001, 1.1, 1.2, 1.5, 2, 5, 10, $10^3$, $10^5$ or $10^{10}$.

In some embodiments, the strength of at least one bond between the compound and the nanoparticle can be the binding strength or the strength with which the compound is bound to the nanoparticle.

In one embodiment of the invention, the irradiation is or results in or is associated with a decrease of the strength of at least one bond between the compound and the nanoparticle, from a strength $S_{NI}$ of at least one bond between the non-irradiated compound and the non-irradiated nanoparticle to a strength $S_I$ of at least one bond between the irradiated compound and the irradiated nanoparticle.

In some cases, $S_{NI}$ and $S_I$ can be the strengths of at least one bond that link(s) at least one compound to at least one nanoparticle.

In some other cases, $S_{NI}$ and $S_I$ can be the energies of at least one bond that link(s) at least one compound to at least one nanoparticle.

In some cases, $S_I$ can be lower than $S_{NI}$ if: i) at least one irradiated compound is linked to at least one irradiated nanoparticles via a number of bonds that is lower than the number of bonds that link at least one non-irradiated compound to at least one non-irradiated nanoparticle ii) at least one non-irradiated compound is linked to at least one non-irradiated nanoparticles via strong bonds and/or iii) at least one irradiated compound is linked to at least one irradiated nanoparticle via weak bonds.

In some cases, weak bonds can be Van der Waals interactions, dipole-dipole interactions, London dispersion force, and/or hydrogen bonding.

In some other embodiments, strong bonds can be covalent, ionic, and/or metallic bonds.

In some embodiments, $S_{NI}$ and/or $S_I$ is larger than $10^{-50}$, $10^{-20}$, $10^{-10}$, $10^{-5}$, $10^{-1}$, 1, 5, 10, $10^3$, $10^5$, $10^{10}$, $10^{20}$, $10^{50}$ or $10^{100}$ eV, KJ, or Kcal, preferentially as measured per: i) mol of nanoparticle, compound, or bond, or ii) nanoparticle, compound, or bond.

In some other embodiments, $S_{NI}$ and/or $S_I$ is lower than $10^{50}$, $10^{20}$, $10^{10}$, $10^5$, 10, 5, 2, 1, $10^{-1}$, $10^{-3}$, $10^{-5}$, $10^{-10}$ or $10^{-20}$ eV, KJ, or Kcal, preferentially as measured per: i) mol of nanoparticle, compound, or bond, or ii) nanoparticle, compound, or bond.

In still some other embodiments, $S_{NI}/S_I$ is larger than $10^{-50}$, $10^{-20}$, $10^{-10}$, $10^{-5}$, $10^{-1}$, 1, 5, 10, 20, 50, $10^2$, $10^3$, $10^5$ or $10^{10}$.

In one embodiment of the invention, the irradiation is or results in or is associated with the breaking of at least one bond between the altered compound and the altered nanoparticle. In some embodiments, the irradiation can be the release of at least one compound from at least one nanoparticle.

In one embodiment of the invention, the irradiation is or results in or is associated with the weakening of at least one bond between the irradiated compound and the irradiated nanoparticle.

In some embodiments, the weakening of the bond between the compound and the nanoparticle can be a decrease of the bond forces, bond energies, interaction forces, or interaction energies between the compound and the nanoparticle.

In some embodiments, the breaking of the bond between the compound and the nanoparticle can be or be due to the removal or annihilation or decrease of the bond forces, bond energies, interaction forces, or interaction energies between the compound and the nanoparticle In some embodiments, the weakening of the bond between the compound and the nanoparticle can be a decrease of the dissociation energy of the bond between the compound and the nanoparticle.

In some embodiments, the breaking of the bond between the compound and the nanoparticle can be or be due to the removal or annihilation or decrease of the dissociation energy of the bond between the compound and the nanoparticle.

In some embodiments, the bond forces, bond energies, interaction forces, or interaction energies between the compound and the nanoparticle can be equal, proportional to, or related to the dissociation energy of the bond.

In some embodiments, the larger or the stronger the dissociation energy of the bond, the larger or the stronger the bond forces, bond energies, interaction forces, or interaction energies between said nanoparticles and said compound.

In some other embodiments, the lower or the weaker the dissociation energy of the bond, the lower or the weaker the bond forces, bond energies, interaction forces, or interaction energies between said nanoparticles and said compound.

In still some other embodiments, the dissociation energy of the bond can be the energy that needs to be provided or brought to or absorbed by or received by or transferred to the bond, or nanoparticle, preferentially an energy due to or originating from or provided by the radiation to dissociate the compound and/or bond from the nanoparticle.

In one embodiment of the invention, the types of bonds that are weakened or broken by alteration are strong bonds.

In another embodiment of the invention, the types of bonds that are not weakened or not broken by alteration are strong bonds.

In one embodiment of the invention, the types of bonds that are weakened or broken by alteration are weak bonds.

In one embodiment of the invention, the types of bonds that are not weakened or not broken by alteration are weak bonds.

In another embodiment of the invention, the number of bonds that is broken or weakened by irradiation is larger than 1, 5, 10, $10^3$, $10^5$ or $10^{10}$ bonds per nanoparticle or per mg of nanoparticle or per $cm^3$ of body part or altering medium.

In another embodiment of the invention, the number of bonds that is broken or weakened by irradiation is smaller than $10^{10}$, $10^5$, 10, 5, 3 or 1 bonds per nanoparticle or per mg of nanoparticle or per $cm^3$ of body part or altering medium.

In one embodiment of the invention, the irradiation is or results in or is associated with a decrease of the bond-dissociation energy between the compound and the nanoparticle, preferentially from a bond-dissociation energy $E_{dNI}$ between the non-irradiated compound and the non-irradiated nanoparticle down to a bond-dissociation energy $E_{dI}$ between the irradiated compound and the irradiated nanoparticle.

In some embodiments, $E_{dNI}$ and/or $E_{dI}$ is/are larger than $10^{-50}$, $10^{-20}$, $10^{-10}$, $10^{-5}$, $10^{-1}$, 1, 5, 10, $10^3$, $10^5$, $10^{10}$, $10^{20}$, $10^{50}$ or $10^{100}$ eV, KJ, or Kcal, preferentially as measured per: i) mol of nanoparticle, compound, or bond, or ii) nanoparticle, compound, or bond.

In some other embodiments, $E_{dNI}$ and/or $E_{dI}$ is/are lower than $10^{50}$, $10^{20}$, $10^{10}$, $10^5$, 10, 5, 1, $10^{-1}$, $10^{-3}$, $10^{-5}$, $10^{-10}$ or $10^-$ eV, KJ, or Kcal, preferentially as measured per: i) mol of nanoparticle, compound, or bond, or ii) nanoparticle, compound, or bond.

In still some other cases, $E_{dNI}/E_{dI}$ is lower than $10^{50}$, $10^{10}$, $10^5$, 10, 5, 2, 1, $10^{-5}$, $10^{-10}$ or $10^{-50}$. This can be the case when the compound is more strongly bound after irradiation than before irradiation.

In still come other cases, $E_{dNI}/E_{dI}$ is larger than $10^{-50}$, $10^{-10}$, $10^{-5}$, $10^{-1}$, 1, 5, 10, $10^5$, $10^{10}$ or $10^{50}$. This can be the case when the compound is less strongly bound after irradiation than before irradiation.

In one embodiment of the invention, the alteration is or results in or is associated with an increase of the bond-dissociation energy between the compound and the nanoparticle, preferentially from a bond-dissociation energy $E_{dNI}$ between the non-irradiated compound and the non-irradiated nanoparticle up to a bond-dissociation energy $E_{dI}$ between the irradiated compound and the irradiated nanoparticle.

In still another embodiment of the invention, the irradiation is or results in or is associated with a decrease of the thickness of the coating of said nanoparticle.

In some embodiments, the coating thickness is not uniform or the coating only partly surrounds the nanoparticles.

In some other embodiments, the coating thickness is uniform or the coating fully surrounds the nanoparticles.

In some embodiments, the coating thickness can be the thickness of the coating measured at least one site of the nanoparticle(s).

In some embodiments, the coating thickness can be the average thickness of the coatings of the nanoparticle(s).

In some embodiments, the coating thickness can be larger than $10^{-1}$, 1, 5, 10, $10^3$ or $10^5$ nm, preferentially in the non-irradiated nanoparticle, preferentially before or without irradiation.

In some other embodiments, the coating thickness can be smaller than $10^5$, $10^3$, 10, 5, 1 or $10^{-1}$ nm, preferentially in the irradiated nanoparticle, preferentially during, after or with irradiation.

In still some other embodiments, the coating thickness decreases, preferentially by a factor of at least 1.001, 1.1, 1.5, 2, 5, 10, $10^3$ or $10^5$ between before and after irradiation.

In one embodiment of the invention, the irradiation is or results in or is associated with a decrease of the coating thickness of the nanoparticle, from a coating thickness $CT_{NI}$ of the non-irradiated nanoparticle down to a coating thickness $CT_I$ of the irradiated nanoparticle.

In some cases, the coating thickness can decrease from $CT_{NI}$ larger than $10^{-3}$, 0.1, 1, 5, 10 or 100 nm down to $CT_I$ smaller than $10^5$, 103, 100, 50, 20, 10, 5, 3, 2 or 1 nm.

In some other embodiments, the coating thickness can decrease between before and after irradiation by a quantity of at least $10^{-5}$, $10^{-1}$, 1, 5, 10 or $10^3$ nm.

In some embodiments, $CT_{NI}$ is larger than $10^{-10}$, $10^{-5}$, $10^{-1}$, 1, 5, 10, $10^3$ or $10^5$ nm or is larger than $\alpha \cdot S_{NI}$, where $\alpha$ is a proportionality coefficient preferentially larger than $10^{-10}$, $10^{-5}$, $10^{-1}$, 1, 5, 10, $10^3$ or $10^5$, and $S_{NI}$ is the size of the non-irradiated nanoparticle preferentially larger than $10^{-10}$, $10^{-5}$, $10^{-1}$, 1, 5, 10, $10^3$ or $10^5$ nm.

In some other embodiments, $CT_I$ is larger than $10^{-10}$, $10^{-5}$, $10^{-1}$, 1, 5, 10, $10^3$ or $10^5$ nm or is larger than $\alpha \cdot S_I$, where $\alpha$ is a proportionality coefficient preferentially larger than $10^{-10}$, $10^{-5}$, $10^{-1}$, 1, 5, 10, $10^3$ or $10^5$, and $S_I$ is the size of the irradiated nanoparticle preferentially larger than $10^{-10}$, $10^{-5}$, $10^{-1}$, 1, 5, 10, $10^3$ or $10^5$ nm.

In some embodiments, $CT_{NI}$ is smaller than $10^{50}$, $10^{10}$, $10^5$, 10, 5, 2, 1, $10^{-1}$, $10^{-3}$ or $10^{-5}$ nm or is smaller than $\alpha \cdot S_{NI}$, where $\alpha$ is a proportionality coefficient preferentially larger than $10^{-10}$, $10^{-5}$, $10^{-1}$, 1, 5, 10, $10^3$ or $10^5$, and $S_{NI}$ is the size of the non-irradiated nanoparticle preferentially smaller than $10^{50}$, $10^{10}$, $10^5$, 10, 5, 2, 1, $10^{-1}$, $10^{-3}$ or $10^{-5}$ nm.

In some other embodiments, $CT_{NI}$ is smaller than $10^{50}$, $10^{10}$, $10^5$, 10, 5, 2, 1, $10^{-1}$, $10^{-3}$ or $10^{-5}$ nm or is larger than $\alpha \cdot S_I$, where $\alpha$ is a proportionality coefficient preferentially larger than $10^{-10}$, $10^{-5}$, $10^{-1}$, 1, 5, 10, $10^3$ or $10^5$, and $S_I$ is the size of the irradiated nanoparticle preferentially smaller than $10^{50}$, $10^{10}$, $10^5$, 10, 5, 2, 1, $10^{-1}$, $10^{-3}$ or $10^{-5}$ nm.

In still some other embodiments, $CT_{NI}/CT_I$ is larger than $10^{-50}$, $10^{-20}$, $10^{-10}$, $10^{-5}$, $10^{-1}$, 1, 5, 10, $10^3$, $10^5$, $10^{10}$ or $10^{20}$.

In still some other embodiments, $CT_{NI}/CT_I$ is smaller than $10^{50}$, $10^{10}$, $10^5$, 1, $10^{-5}$, $10^{-10}$ or $10^{-50}$.

In still some other embodiments, $CT_{NI}/CT_I$ is between $10^{-50}$ and $10^{50}$, between $10^{-10}$ and $10^{10}$, between $10^{-5}$ and $10^5$, between $10^{-3}$ and $10^3$, between $10^{-1}$ and 10, or between 0.2 and 5.

In one embodiment of the invention, the irradiation is or results in or is associated with an increase of the coating thickness of the nanoparticle, from a coating thickness $CT_{NI}$ of the non-irradiated nanoparticle up to a coating thickness $CT_I$ of the irradiated nanoparticle.

In some embodiments, the coating thickness increases from a value of $CT_{NI}$ smaller than $10^5$, $10^3$, 100, 50, 20, 10, 5, 3, 2 or 1 nm, to a value of $CT_I$ larger than $10^{-3}$, 0.1, 1, 5, 10 or 100 nm.

In still some other embodiments, the coating thickness can increase by a quantity of at least $10^{-5}$, $10^{-1}$, 1, 5, 10 or $10^3$ nm between before and after irradiation.

In one embodiment of the invention, the irradiation is or results in or is associated with a decrease of the cluttering of the compound bound to the nanoparticle, from a large cluttering of the non-irradiated compound bound to the non-irradiated nanoparticle down to a low cluttering of the irradiated compound bound to the irradiated nanoparticle. In some embodiments, a large cluttering of the non-irradiated compound bound to the non-irradiated nanoparticle can represent a large level of cluttering of these compounds, which can be due to the large number or concentration of these compounds, preferentially located in the coating or at the surface of the nanoparticle, where the cluttering of these compounds can be considered as large relatively to the cluttering of the irradiated compounds. In some other cases, a low cluttering of the irradiated compound bound to the irradiated nanoparticle can represent a low level of cluttering of these compounds, which can be due to the small number or concentration of these compounds, preferentially located in the coating or at the surface of the nanoparticle, where the cluttering of these compounds can be considered as low relatively to the cluttering of the non-irradiated compounds.

In still another embodiment of the invention, the irradiation is a decrease of the cluttering of the compounds bond to the nanoparticle. In some embodiments, the decrease of the cluttering of the compound bound to the nanoparticle can be or correspond to or result in or lead to or be associated with: i) a decrease in the number or concentration of compound bound to the nanoparticle that imped or block the release of the compound from the nanoparticle, or ii) an increased faculty of the nanoparticle to release the compound from the nanoparticle due to a lower number of compounds bound to the nanoparticle that block or imped such release.

In one embodiment of the invention, the irradiation is or results in or is associated with an increase of the cluttering of the compound bound to the nanoparticle, from a small cluttering of the non-irradiated compound bound to the non-irradiated nanoparticle up to a large cluttering of the irradiated compound bound to the irradiated nanoparticle.

In one embodiment of the invention, the irradiation is or results in or is associated with a decrease of the number or concentration of compounds $N_1$ that prevent the release of compounds $N_2$ from the nanoparticle, from a number of non-irradiated compounds $N_{1i}$ that prevent the release of non-irradiated compounds $N_{2NI}$ from the non-irradiated nanoparticle down to a number of irradiated compounds $N_{1I}$ that prevent the release of irradiated compounds $N_{2a}$ from the irradiated nanoparticle.

In some embodiments, the sum of $N_{1NI}+N_{2NI}$ is the total number or concentration of compounds bound to the non-irradiated nanoparticle.

In some embodiments, the sum $N_{1I}+N_{2I}$ is the total number or concentration of compounds bound to the irradiated nanoparticle.

In some embodiments, $N_{1NI}$ and/or $N_{1I}$ can be smaller than $10^{100}$, $10^{50}$, $10^{20}$, $10^{10}$, $10^5$, $10^2$, 10, 5, 2, 1, $10^{-1}$, $10^{-5}$, $10^{-10}$ or $10^{-50}$ compounds or mg of compounds or compounds per nanoparticle or mg of compounds per mg of nanoparticles.

In some other embodiments, $N_{1NI}$ and/or $N_{1I}$ can be larger than $10^{-50}$, $10^{-20}$, $10^{-10}$, $10^{-5}$, $10^{-2}$, $10^{-1}$, 1, 5, 10, $10^3$ or $10^5$ compounds or mg of compounds or compounds per nanoparticle or mg of compounds per mg of nanoparticles.

In still some other embodiments, $abs(N_{1I}-N_{1NI})/N_{1NI}$, $N_{1NI}/N_{1I}$, $abs(N_{1I}-N_{1NI})/N_{1I}$ or $abs(N_{1I}-N_{1NI})/N_{1NI}$ is larger than $10^{-50}$, $10^{-20}$, $10^{-10}$, $10^{-5}$, $10^{-1}$, 1, 5, 10, $10^3$, $10^5$, $10^{10}$ or $10^{50}$.

In still some other embodiments, $abs(N_{1I}-N_{1NI})/N_{1NI}$, $N_{1NI}/N_{1I}$, $abs(N_{1I}-N_{1NI})/N_{1I}$ or $abs(N_{1I}-N_{1NI})/N_{1NI}$ is lower than $10^{50}$, $10^{20}$, $10^{10}$, $10^5$, $10^3$, 10, 5, 1, $10^{-1}$, $10^{-5}$, $10^{-10}$ or $10^{-50}$.

In one embodiment of the invention, the irradiation is or results in or is associated with a modification of the chemical composition of the nanoparticle, also designated as chemical modification.

In some other embodiments, the chemical modification is the change of more than 1, 2, 5, 10, $10^3$, $10^5$, $10^{10}$, $10^{20}$, $10^{50}$ or $10^{100}$ chemical element(s) comprised in the nanoparticle, between before and after irradiation.

In some other embodiments, the chemical modification is the change of less than $10^{100}$, $10^{50}$, $10^{20}$, $10^{10}$, $10^5$, $10^3$, 10, 5, 2 or 1 chemical element(s) comprised in the nanoparticle, between before and after irradiation.

In some other embodiments, the chemical modification is the change of more than $10^{-50}$, $10^{-10}$, $10^{-1}$, 1, 5, 10, 20, 50, 75, 80, 90 or 99%, preferentially by mass or volume, of the chemical elements comprised in the nanoparticle between before after irradiation. This percentage can be the ratio between the number or concentration or mass of chemical elements comprised in the irradiated nanoparticle divided by the number or concentration or mass of chemical elements comprised in the non-irradiated nanoparticle.

In some other embodiments, the chemical modification is the change of less than 100, 99, 90, 70, 60, 50, 20, 10, 5, 2, 1 or $10^{-3}$% preferentially by mass or volume, of the chemical elements comprised in the nanoparticle between before after irradiation.

In still some other embodiments, the chemical modification is the replacement of at least one chemical element by another chemical element in the nanoparticle or the loss or release of at least one chemical element by the nanoparticle or the gain of at least one chemical element by the nanoparticles, preferentially between before and after irradiation.

In some embodiments, a chemical element can be an atom or an ion.

In some embodiments, the chemical modification can be a change from a metallic to a non-metallic composition of the nanoparticle, between before and after irradiation.

In some embodiments, the chemical modification can be a change from a more metallic composition before irradiation to a less metallic composition after irradiation.

In some other embodiments, the chemical modification can be change from a composition comprising more than 1, 5, 10, $10^3$, $10^5$, $10^{10}$, $10^{50}$ or $10^{100}$ metallic atom(s), preferentially per nanoparticle, before irradiation, to a composition comprising less than $10^{100}$, $10^{50}$, $10^{10}$, $10^5$, $10^3$, 10, 5 or 1 metallic atom(s), preferentially per nanoparticle, after irradiation.

In some other embodiments, the chemical modification can be a change from a composition comprising more than $10^{-50}$, $10^{-10}$, 1, 5, 10, 50, 75, 90 or 99% of metallic atom(s), preferentially by mass, number or volume, preferentially per nanoparticle, before irradiation, to a composition comprising less than 99, 90, 75, 50, 10, 5, 1 or $10^{-3}$% of metallic atom(s), preferentially by mass, number, or volume, preferentially per nanoparticle, after irradiation. This percentage may be the ratio between the number, concentration, mass or volume of metallic atom(s) comprised in the nanoparticle and the number, concentration, mass or volume of all atom(s) in the nanoparticle.

In some other embodiments, the chemical modification can be a change from a metallic to a non-metallic composition of the nanoparticle.

In some other embodiments, the chemical modification can be a change from a non-metallic to a metallic composition of the nanoparticle.

In some embodiments, a metallic composition can be a composition, preferentially of the nanoparticle, in which the nanoparticle comprise more than $10^{-50}$, $10^{-10}$, $10^{-5}$, 1, 5, 10, 50, 70, 90 or 99%, preferentially by mass, number, or volume, of metallic atoms, preferentially per nanoparticle. This percentage may be the ratio between the number of metallic atoms in the nanoparticle and the total number of atoms in the nanoparticle.

In some other embodiments, a non-metallic composition can be a composition, in which the nanoparticle comprises less than $10^{50}$, $10^{10}$, $10^5$, $10^3$, 10, 5, 2, 1, $10^{-2}$ or $10^{-5}$%, preferentially by mass, number, or volume, of metallic atoms, preferentially per nanoparticle.

In one embodiment of the invention, the chemical modification is the change from a non-immunogenic to an immunogenic composition of the nanoparticle or from an immunogenic to a non-immunogenic composition of the nanoparticle. In some cases, a non-immunogenic composition is a composition that triggers the appearance, preferentially in the body part, of a number of immune cells (T cells, B cells, dendritic cells, antigen presenting cells, macrophages) or other immune entities such as chemokines or interleukins that is lower than $10^{50}$, $10^{10}$, $10^5$, 10, 1, $10^{-1}$, $10^{-5}$ or $10^{-10}$ preferentially per cm$^3$ or mL of body part. In some other cases, an immunogenic composition is a composition that triggers the appearance, preferentially in the body part, of more than $10^{-50}$, $10^{-10}$, $10^{-5}$, 1, 10, $10^5$ or $10^{10}$ immune cells or other immune entities such as chemokines or interleukins, preferentially per cm$^3$ or mL of body part.

In one embodiment of the invention, the chemical modification is the change from a non-pharmacological to a pharmacological composition or from a pharmacological to a non-pharmacological composition. In some cases, a non-pharmacological composition is a composition that comprises less than $10^{50}$, $10^{10}$, $10^5$, 10, 1, $10^{-1}$, $10^{-5}$ or $10^{-10}$ pharmacological compounds or mg of pharmacological compounds, preferentially per nanoparticle or per mg of nanoparticle. In some other cases, a pharmacological composition is a composition that comprises more $10^{-50}$, $10^{-10}$, $10^{-5}$, 1, 1, 10, $10^5$ or $10^{10}$ pharmacological compounds or mg of pharmacological compounds, preferentially per nanoparticle or per mg of nanoparticle. In some cases, a pharmacological compound can have a pharmacological activity, preferentially when it is activated, preferentially after it is released from the nanoparticle, such as an activity against pathological or tumor cells. In some other cases, a pharmacological compound can be non-pharmacologically active, preferentially when it is bound to the nanoparticle.

In one embodiment of the invention, the chemical modification is the change from a non-metabolic to a metabolic composition or from a metabolic to a non-metabolic composition. In some cases, a non-metabolic composition is a composition that comprises less than $10^{50}$, $10^{10}$, $10^5$, 10, 0, 1, $10^{-1}$, $10^{-5}$ or $10^{-10}$ metabolic compounds or mg of metabolic compounds, preferentially per nanoparticle or per mg of nanoparticle. In some other cases, a metabolic composition is a composition that comprises more $10^{-50}$, $10^{-10}$, $10^{-5}$, 0, 1, 10, $10^5$ or $10^{10}$ metabolic compounds or mg of metabolic compounds, preferentially per nanoparticle or per mg of nanoparticle. In some cases, a metabolic compound can have a metabolic activity, preferentially when it is activated, preferentially after it is released from the nanoparticle, such as an activity against pathological or tumor cells. In some other cases, a metabolic compound can be non-metabolically active, preferentially when it is bound to the nanoparticle.

In one embodiment of the invention, the chemical modification is the change from a non-immunogenic to an immunogenic composition or from an immunogenic to a non-immunogenic composition. In some cases, a non-immunogenic composition is a composition that comprises less than $10^{50}$, $10^{10}$, $10^5$, 10, 1, $10^{-1}$, $10^{-5}$ or $10^{-10}$ immunogenic compounds or mg of immunogenic compounds, preferentially per nanoparticle or per mg of nanoparticle. In some other cases, an immunogenic composition is a composition that comprises more $10^{-50}$, $10^{-10}$, $10^{-5}$, 1, 1, 10, $10^5$ or $10^{10}$ immunogenic compounds or mg of immunogenic compounds, preferentially per nanoparticle or per mg of nanoparticle. In some cases, an immunogenic compound can have an immunogenic activity, preferentially when it is activated, preferentially after it is released from the nanoparticle, such as an activity against pathological or tumor cells. In some other cases, an immunogenic compound can be non-immunogenically active, preferentially when it is bound to the nanoparticle.

In another embodiment of the invention, the irradiation is or results in or is associated with a decrease of the surface charge or zeta potential of the nanoparticle, preferentially from a surface charge of the non-irradiated nanoparticle $SC_{NI}$ or zeta potential of the non-irradiated nanoparticle $ZP_{NI}$ down to a surface charge of the irradiated nanoparticle $SC_I$ or zeta potential of the irradiated nanoparticle $ZP_I$.

In some embodiments, the property of the nanoparticle such as the surface charge or zeta potential of the nanoparticle exists before or without irradiation.

In some other embodiments, the property of the nanoparticle such as the surface charge or zeta potential of the nanoparticle exists during or after or with irradiation.

In some embodiments, $SC_{NI}$, $ZP_{NI}$, $SC_I$, and/or $ZP_I$ can be smaller than $10^{50}$, $10^{10}$, $10^5$, $10^3$, 100, 50, 20, 10, 5, 2, 1, 0, −5, −10, −50 or −100 mV.

In some other embodiments, $SC_{NI}$, $ZP_{NI}$, $SC_I$, and/or $ZP_I$ can be larger than $-10^{10}$, $-10^5$, $-10^3$, −100, −50, −20, −10, −5, −1, 0, 2, 5, 10, 50, $10^2$ or $10^5$ mV.

In still some other embodiments, $SC_{NI}$, $ZP_{NI}$, $SC_I$, and/or $ZP_I$ is/are be between $-10^{50}$ mV and $10^{50}$ mV, between $-10^{10}$ mV and $10^{10}$ mV, between $-10^5$ mV and $10^5$ mV, between $-10^3$ mV and $10^3$ mV, between −100 mV and 100 mV, between −50 mV and 50 mV, or between −20 mV and 20 mV.

In still some other embodiments, $SC_{NI}/SC_I$ or $ZP_{NI}/ZP_I$ is/are larger than $10^{-50}$, $10^{-10}$, $10^{-5}$, $10^{-3}$, 0, 1, 2, 5, 10, $10^3$, $10^5$ or $10^{10}$.

In still some other embodiments, the zeta potential and/or surface charge can decrease from $ZP_{NI}$ or $SC_{NI}$ larger than $-10^5$, $-10^3$, −100, −50, −20, −10, −5, −2, −1, 0, 1, 2, 5, 10, 20 or 50 mV, preferentially before or without irradiation to $SC_I$ or $ZP_I$ smaller than $10^{10}$, $10^5$, $10^3$, 10, 5, 2, 1, 0, −1, −5, −10, −50 or −100 mV, preferentially during, after or with irradiation.

In still some other embodiments, the zeta potential and/or surface charge can decrease between before and after irradiation by a magnitude or value larger than $10^{-20}$, $10^{-5}$, $10^{-1}$, 1, 5, 10, 20 or 100 mV.

In still some other embodiments, the zeta potential and/or surface charge can increase from $ZP_{NI}$ or $SC_{NI}$ smaller than $10^5$, $10^3$, 500, 100, 50, 20 or 10 mV up to $SC_I$ or $ZP_I$ larger than $-10^5$, $-10^3$, $-10^{-1}$, 0, 1, 5, 10, 50 or 100 mV.

In still some other embodiments, the zeta potential and/or surface charge can increase between before and after irradiation by a magnitude or value larger than $10^{-20}$, $10^{-5}$, $10^{-1}$, 1, 5, 10, 20 or 100 mV.

In still another embodiment of the invention, the irradiation is or results in or is associated with a modification, preferentially a decrease, of the percentage in mass of organic material or carbon of the nanoparticle.

In some embodiments, the percentage in mass of organic material or carbon of the nanoparticle can be larger than $10^{-100}$, $10^{-50}$, $10^{-10}$, $10^{-5}$, $10^{-1}$, 1, 5, 10, 50, 70 or 99%, preferentially before or without irradiation.

In some other embodiments, the percentage in mass of organic material or carbon of the nanoparticle can be smaller than 100, 99, 70, 50, 10, 5, 2, 1, $10^{-1}$ or $10^{-5}$%, preferentially during, after or with irradiation.

In still some other embodiments, the percentage in mass of organic material or carbon of the nanoparticle decreases, preferentially by a factor of at least 1.001, 1.1, 1.5, 2, 5, 10, $10^3$ or $10^5$ between before and after irradiation.

In another embodiment of the invention, the irradiation is or results in or is associated with a decrease of the mass or weight of the nanoparticle. In some cases, this decrease is a decrease from a mass or weight of the non-irradiated nanoparticle larger than $10^{-50}$, $10^{-10}$, $10^{-5}$, $10^{-1}$, 1, 5, 10, 100 or $10^5$ mg of nanoparticle or mg of nanoparticle per $cm^3$ of assembly of nanoparticle or mg of nanoparticle per $cm^3$ of body part, preferentially before or without irradiation, down to a mass or weight of the irradiated nanoparticle smaller than $10^{100}$, $10^{50}$, $10^{10}$, $10^5$, $10^2$, 10, 5, 2, 1, $10^{-5}$ or $10^{-10}$ mg of nanoparticle or mg of nanoparticle per $cm^3$ of assembly of nanoparticle or mg of nanoparticle per $cm^3$ of body part, preferentially after, during or with irradiation. In some other cases, this decrease is a decrease by at least $10^{-50}$, $10^{-10}$, $10^{-5}$, $10^{-1}$, 1, 5, 10, 25, 50, 70 or 90% between before and after irradiation. This percentage can equal to $abs(M_I-M_{NI})/M_{NI}$, $M_I/M_{NI}$, where $M_I$ and $M_{NI}$ are the mass or weight of the irradiated and non-irradiated nanoparticles, respectively.

In another embodiment of the invention, the irradiation is or results in or is associated with an increase of the mass or weight of the nanoparticle. In some cases, this increase is an increase from a mass or weight of the non-irradiated nanoparticle lower than $10^{50}$, $10^{10}$, $10^5$, 10, 5, 1, $10^{-1}$ or $10^{-5}$ mg of nanoparticle or mg of nanoparticle per $cm^3$ of assembly of nanoparticle or mg of nanoparticle per $cm^3$ of body part, preferentially before or without irradiation, up to a mass or weight of the irradiated nanoparticle larger than $10^{-100}$, $10^{-50}$, $10^{-10}$, $10^{-2}$, 0, 1, 5, 10, $10^5$ or $10^{10}$ mg of nanoparticle or mg of nanoparticle per $cm^3$ of assembly of nanoparticle or mg of nanoparticle per $cm^3$ of body part, preferentially during, after or with irradiation. In some other cases, this increase is an increase by at least $10^{-50}$, $10^{-10}$, $10^{-5}$, $10^{-1}$, 1, 5, 10, 25, 50, 70 or 90% between before and after irradiation. This percentage can equal to $abs(M_I-M_{NI})/M_I$, $M_{NI}/M_I$, where $M_I$ and $M_{NI}$ are the mass or weight of the irradiated and non-irradiated nanoparticles, respectively.

In an embodiment of the invention, the irradiation is or results in or is associated with a modification of the magnetic properties of the nanoparticle. Such change can be a change: i) from a diamagnetic property of the non-irradiated nanoparticle to a paramagnetic, superparamagnetic, ferromagnetic, and/or ferromagnetic property of the irradiated nanoparticle, ii) from a paramagnetic property of the initial nanoparticle to a diamagnetic, superparamagnetic, ferromagnetic, and/or ferromagnetic property of the altered nanoparticle, iii) from a superparamagnetic property of the non-irradiated nanoparticle to a diamagnetic, paramagnetic, ferromagnetic, and/or ferromagnetic property of the irradiated nanoparticle, iv) from a ferromagnetic property of the non-irradiated nanoparticle to a diamagnetic, paramagnetic, superparamagnetic, and/or ferromagnetic property of the irradiated nanoparticle, and/or v) from a ferromagnetic property of the non-irradiated nanoparticle to a diamagnetic, paramagnetic, superparamagnetic, and/or ferromagnetic property of the irradiated nanoparticle.

In another embodiment of the invention, the modification of the magnetic properties of the nanoparticle is an increase of at least one of the following magnetic parameters: i) the coercivity of the nanoparticle, preferentially from a coercivity of the non-irradiated nanoparticle lower than $10^{50}$, $10^{10}$, $10^5$, $10^3$, 10, 1, $10^{-1}$, $10^{-5}$ or $10^{-10}$ Oe, preferentially before or without irradiation, up to a coercivity of the irradiated nanoparticle larger than $10^{-10}$, $10^{-5}$, $10^{-1}$, 1, 5, 10, $10^3$, $10^5$, $10^{10}$ or $10^{50}$ Oe, preferentially during, after or with irradiation, ii) the remanent magnetization of the nanoparticle, preferentially from a remanent magnetization of the non-irradiated nanoparticle lower than 1, 0.99, 0.9, 0.8, 0.7, 0.6, 0.5, 0.4, 0.3, 0.2 or 0.1, preferentially measured before or without irradiation, up to a remanent magnetization of the irradiated nanoparticle larger than $10^{-50}$, $10^{-10}$, $10^{-5}$, $10^{-1}$, 0.1, 0.2, 0.3, 0.4, 0.5, 0.6, 0.7, 0.8 or 0.9, during, after or with irradiation, iii) the saturating magnetization of the nanoparticle, from a saturating magnetization of the non-irradiated nanoparticle lower than $10^{50}$, $10^{20}$, $10^{10}$, $10^5$, $10^3$, 10, 5, 2, 1, $10^{-2}$, $10^{-5}$, $10^{-10}$ or $10^{-50}$ emu or emu per gram or milligram of nanoparticle, preferentially before or without irradiation, up to a saturating magnetization of the irradiated nanoparticle larger than $10^{-50}$, $10^{-20}$, $10^{-10}$, $10^{-1}$, 1, 5, 10, 100, $10^5$ or $10^{10}$ emu or emu per gram or milligram of nanoparticle, preferentially during, after or with alteration. In some cases, the magnetic parameters can exist or be measured at a temperature larger than 0, 0.1, 5, 10, $10^3$, $10^5$, $10^{10}$ or $10^{20}$ K (Kelvin). In some other cases, the magnetic parameters can exist or be measured at temperatures lower than $10^{100}$, $10^{50}$, $10^{20}$, $10^{10}$, $10^5$, $10^3$, 100, 50, 20, 10, 5, 2, 1 or 0.1 K.

In another embodiment of the invention, the modification of the magnetic properties of the nanoparticle is a decrease of at least one of the following magnetic parameters: i) the coercivity of the nanoparticle, preferentially from a coercivity of the non-irradiated nanoparticle larger than $10^{-10}$, $10^{-5}$, $10^{-1}$, 1, 5, 10, $10^3$, $10^5$, $10^{10}$ or $10^{50}$ Oe, preferentially before or without irradiation, down to a coercivity of the irradiated nanoparticle lower than $10^{50}$, $10^{10}$, $10^5$, $10^3$, 10, 1, $10^{-1}$, $10^{-5}$ or $10^{-10}$ Oe, preferentially after or with irradiation, ii) the remanent magnetization of the nanoparticle, preferentially from a remanent magnetization of the non-irradiated nanoparticle larger than $10^{-50}$, $10^{-10}$, $10^{-5}$, $10^{-1}$, 0.1, 0.2, 0.3, 0.4, 0.5, 0.6, 0.7, 0.8 or 0.9, preferentially before or without irradiation, down to a remanent magnetization of the irradiated nanoparticle smaller than 1, 0.99, 0.9, 0.8, 0.7, 0.6, 0.5, 0.4, 0.3, 0.2 or 0.1, preferentially during, after or with irradiation, iii) the saturating magnetization of the nanoparticle, preferentially from a saturating magnetization of the non-irradiated nanoparticle larger than $10^{-50}$, $10^{-20}$, $10^{-10}$, $10^{-1}$, 1, 5, 10, 100, $10^5$ or $10^{10}$ emu or emu per gram or milligram of nanoparticle, preferentially before or without irradiation, down to a saturating magnetization of the irradiated nanoparticle smaller than $10^{50}$, $10^{20}$, $10^{10}$, $10^5$, $10^3$, 100, 10, 5, 2, 1, $10^{-2}$, $10^{-5}$, $10^{-10}$ or $10^{-50}$ emu or emu per gram or milligram of nanoparticle, preferentially during, after or with irradiation.

In one embodiment of the invention, the irradiation is or results in or is associated with a modification of a property of assembly, organization, and/or distribution of the nanoparticles. Such modification can be selected from the group consisting of: i) an organization of non-irradiated nanoparticle in chains, preferentially existing or measured before or without irradiation, to an organization of irradiated nanoparticle that is not in chains, preferentially existing or measured during, after, or with irradiation, ii) an organization of non-irradiated nanoparticle in aggregates, preferentially existing or measured before or without irradiation, to an organization of irradiated nanoparticle that is not in aggregates, preferentially existing or measured during, after or with irradiation, iii) an organization of non-irradiated nanoparticle in a geometric figure such as a circle, preferentially existing or measured before or without irradiation, to an organization of irradiated nanoparticle that is not in a geometric figure, preferentially existing or measured during, after or with irradiation, and/or iv) an homogenous distribution of the non-irradiated nanoparticle, preferentially existing or measured before or without irradiation, to a non-homogenous distribution of the irradiated nanoparticle, preferentially existing or measured during, after or with irradiation.

In one embodiment of the invention, the modification of a property of assembly, organization, and/or distribution of the nanoparticle is selected from the group consisting of: i) an organization of non-irradiated nanoparticle that is not in chains, preferentially existing or measured before or without irradiation, to an organization of irradiated nanoparticle in chains, preferentially existing or measured during, after or with irradiation, ii) an organization of non-irradiated nanoparticle that is not in aggregates, preferentially existing or measured before or without irradiation, to an organization of irradiated nanoparticle in aggregates, preferentially existing or measured during, after or with irradiation, iii) an organization of non-irradiated nanoparticle that is not in a geometric figure, preferentially existing or measured before or without irradiation, to an organization of irradiated nanoparticle in a geometric figure, preferentially existing or measured during, after or with irradiation, and/or iv) a non-homogenous distribution of the non-irradiated nanoparticle, preferentially existing or measured before or without irradiation, to a homogenous distribution of the irradiated nanoparticle, preferentially existing or measured during, after or with irradiation.

In some embodiments, at least two nanoparticles can be organized in chains, when the at least two nanoparticles are: i) bound together by some binding material, ii) close to each other, preferentially separated by less than $10^5$, $10^3$, 10, 5, 2 or 1 nm, or iii) in interaction or bound with each other.

In some other embodiments, at least two nanoparticles are not organized in chains when the at least two nanoparticles are: i) not bound together by some binding material, ii) far from each other, preferentially separated by more than $10^{-5}$, $10^{-1}$, 1, 5, 10, $10^2$ or $10^5$ nm, or iii) in interaction with each other.

In some embodiments, at least two nanoparticles are organized in aggregates when they are close to each other, preferentially separated by a distance of less than $10^5$, $10^3$, 100, 50, 20, 10, 5 or 1 nm, or when they are in interactions with each other.

In some other cases, at least two nanoparticles are not organized in aggregates when they are not close to each other, preferentially separated by a distance of more than $10^{-2}$, $10^{-1}$, 1, 5, 10, $10^3$ or $10^5$ nm, or when they are not in interactions with each other.

In some embodiments, an aggregate can be an assembly of at least two chains of nanoparticles.

In some embodiments, at least two nanoparticles are organized in a geometric figure.

In some embodiments, a geometric figure is selected from the group consisting of: a Balbis, Concave polygon, Constructible polygon, Convex polygon, Cyclic polygon, Equiangular polygon, Equilateral polygon, Penrose tile, Polyform, Regular polygon, Simple polygon, Tangential polygon, Polygons with specific numbers of sides, Henagon, Digon, Triangle, Acute triangle, Equilateral triangle, Heptagonal triangle, Isosceles triangle, Obtuse triangle, Rational triangle, Right triangle, Kepler triangle, Scalene triangle, Quadrilateral, Cyclic quadrilateral, Kite, Parallelogram, Rhombus, Lozenge, Rhomboid, Rectangle, Square, Tangential quadrilateral, Trapezoid, Isosceles trapezoid, Pentagon, Hexagon, Lemoine hexagon, Heptagon, Octagon, Nonagon, Decagon, Hendecagon, Dodecagon, Tridecagon, Tetradecagon, Pentadecagon, Hexadecagon, Heptadecagon, Octadecagon, Enneadecagon, Icosagon, Swastika, Star polygon, Pentagram—star polygon, Hexagram, Star of David, Heptagram, Octagram, Star of Lakshmi, Decagram—star polygon, Annulus, Arbelos, Circle, Archimedes' twin circles, Bankoff circle, Circumcircle, Disc, Incircle and excircles of a triangle, Nine-point circle, Circular sector, Circular segment, Crescent, Indalo, Lens, Lune, Reuleaux polygon, Reuleaux triangle, Salinon, Semicircle, Tomahawk, Triquetra, Heart, Archimedean spiral, Astroid, Cardioid, Deltoid, Ellipse, Heart, Heartagon, Various lemniscates, Oval, Cartesian oval, Cassini oval, Oval of Booth, Ovoid, Superellipse, Taijitu, Tomoe, and Magatama.

In some other embodiments, the at least two nanoparticles are not organized in a geometric figure.

In some embodiments, the irradiation is the sequential irradiation of the magnetic nanoparticle or body part or compound by the method or treatment according to the invention.

In some embodiments, the irradiation may be an alteration of the nanoparticle or compound.

In one aspect, the invention relates to the irradiated magnetic nanoparticles according to the invention, wherein the magnetic nanoparticle is a magnetic nanoparticle synthesized by a living organism, preferentially a magnetosome.

In one aspect, the invention relates to irradiated magnetosomes according to the invention, wherein the irradiated magnetosomes are synthesized by a living organism, preferentially a magnetotactic *bacterium*.

In one aspect, the invention relates to a composition, preferentially a cosmetic or medical or diagnosis composition, comprising the irradiated magnetic nanoparticles, in particular magnetosomes, according to the invention, and at least one color or contrasting agent or imaging agent or diagnosis agent or therapeutic agent, for modifying at least one property of the body part selected in the group consisting of:
  i) color of the body part,
  ii) contrast of the body part,
  iii) imaging capacity of the body part, and
  iv) healing or repair capacity of the body part.

In some embodiments, modifying the contrast of the body part, or modifying the imaging, healing, or repair capacity of the body part is: i), improving by the method the contrast of the body part, or ii), improving by the method, the imaging, healing, or repair capacity of the body part.

In still another embodiment of the invention, the step(s), sequence(s), and/or session(s) can follow each other in any order.

In still another embodiment of the invention, the property(ies) or features, preferentially of the nanoparticle or method or step or sequence or session, preferentially described in each individual embodiment or section or sentence of this patent application can be combined to result in a combination of property(ies) or features, preferentially of the nanoparticle or method or step or sequence or session.

In still another embodiment of the invention, when an entity such as the nanoparticle, radiation, laser, compound, step, sequence or session has a property with a value of $P_1$ that is higher, longer, or higher by a factor a than a property, preferentially of this entity, with a value of $P_2$, it means that: $P_1 = \alpha \cdot P_2$ ($\alpha$ preferentially higher than 1) or $P1 = \alpha + P_2$ ($\alpha$ preferentially higher than 0).

In still another embodiment of the invention, when an entity such as the nanoparticle, radiation, laser, compound, step, sequence or session has a property with a value of $P_1$ that is lower, smaller, or shorter by a factor β than a property, preferentially of this entity, with a value of $P_2$, it means that: $P_1 = \beta \cdot P_2$ (β preferentially smaller than 1), $P_1 = P_2/\beta$ (β preferentially higher than 1), $P_1 = P_2 - \beta$ (β preferentially higher than 0) or $P_1 = \beta - P_2$.

In one embodiment of the invention, $P_1$, $P_2$, $\alpha \cdot P_2$, $\alpha + P_2$, $\beta \cdot P_2$, $P_2/\beta$, $P_2 - \beta$, and/or $\beta - P_2$ can be or designate the absolute values of $P_1$, $P_2$, $\alpha \cdot P_2$, $\alpha + P_2$, $\beta \cdot P_2$, $P_2/\beta$, $P_2 - \beta$, and/or $\beta - P_2$.

The invention will be further described by the following non-limiting examples.

EXAMPLE

Example 1: Sequential Application of a Laser on Suspensions Comprising CMD Coated Magnetosome Minerals and CMD Coated Chemically Synthesized Nanoparticles Material and Method:

Magnetosome minerals coated with carboxymethyldextran (M-CMD) were prepared according to a protocol slightly modified from that of example 8 of patent PCT/FR2016/000095 incorporated in reference. In this example, the word naked indicates that the nanoparticles are devoid of most carbonaceous material and mainly comprise iron oxide mineral in the form of maghemite.

Briefly, to fabricate M-CMD and N-CMD, we first prepared: i), powder 1 comprising naked magnetosome minerals, i.e. comprising the central part of the magnetosomes with a low percentage of carbonaceous material surrounding the magnetosome, mineral core (also designated as magnetosome, central part) as defined and described in patent PCT/FR2016/000095 incorporated in reference (example 4), ii), powder 2 comprising naked chemical iron oxide nanoparticles purchased from Sigma Aldrich (reference Sigma: 637106), iii), a solution 2 containing carboxy-methyl-dextran (ref SIGMA ALDRICH: 86524-50G-F; lot #BCBQ7420V). The suspensions 1 and 2 were mixed, using an Iron to CMD molar ratio of 20.

First, we collected 40 mg of naked dried magnetosome mineral powder and naked dried chemical nanoparticle powder (ref Sigma: 637106) using a balance, where these weighted powders comprise 20 mg of iron.

Then, we harvested 400 mg of CMD powder using a balance (corresponding to a mass of CMD 20 times higher than the mass of iron in the nanoparticle powders) and we mixed these 400 mg of CMD in 20 ml of Milli-Q water.

Afterwards, we mixed the two different naked dried nanoparticle powders with CMD solutions and we adjusted the pH of the two resulting suspensions to 4.65 with a 2M hydrochloric acid solution. We sonicated these suspensions using a sonic bath (reference Transsonic T460: FY 7864596; frequency: 50-60 Hz; power: 67 W) during 15 hours.

After sonication, we did a first washing by centrifugation in eppendorf tubes (14500 rpm) for 10 minutes. Then, we removed with a pipette the coating in excess from the eppendorf, contained in the supernatant of coated nanoparticles. We added 2 ml of Milli Q water to the pellet containing the coated nanoparticles and repeated centrifugation again (14500 rpm), removal of supernate, and re-suspension in water. We then obtained M-CMD and N-CMD suspensions.

Finally, we used an iron dosage to estimate the iron concentration of the N-CMD and M-CMD suspensions. The concentration of the two suspensions of CMD coated nanoparticles mixed in water was adjusted to 0.5 mg/mL and 1 mg/mL for M-CMD and 1 mg/mL for N-CMD.

N-CMD and M-CMD were determined to be mainly composed of a core of maghemite, to have an average size between 35 and 41 nm, respectively, to have a distribution in sizes comprised between 10 and 75 nm for N-CMD and between 20 and 75 nm for M-CMD and to have a stability of 100% for both types of nanoparticles (table 1). To determine the stability of both types of nanoparticles, we measured the percentage of absorption decrease, measured at 480 nm, of 1 mL of suspensions comprising 1 mg/mL of both types of nanoparticles between the time of nanoparticle homogenization by hand checking and 12 hours afterwards.

We carried out a series of heating steps by exposing the suspension of M-CMD and N-CMD to the laser of power density 2 W/cm$^2$. We started the heating steps by switching on the laser (the laser intensity is set at 4500 mA). We ended the heated steps by switching off the laser (the laser intensity is set at 0 A) when the temperature reached 45° C. For N-CMD, when we switched off the laser, the temperature continued to increase up to 49° C. The heating steps were followed by cooling steps in which suspensions of N-CMD and M-CMD were not exposed to the laser. We started the cooling steps by switching off the laser (the laser intensity is

TABLE 1

Properties of N-CMD (Sigma nanoparticles, reference 637106, coated with CMD) and M-CMD (magnetosome minerals coated with CMD) mixed in water; endotoxin concentration in Endotoxin unit (EU) per mL of suspension per mg of nanoparticles in iron; coating thickness; size distribution; mean size of N-CMD and M-CMD in nm as determined by Transmission electron microscopy; hydrodynamic sizes of N-CMD and M-CMD determined by dynamic light scattering measurements; Isoelectric point and zeta potential of N-CMD and M-CMD mixed in suspension; stability in suspension of N-CMD and M-CMD determined by measuring the percentage of decrease of the absorption at 480 nm of suspensions comprising 1 mg/mL of N-CMD and M-CMD, between the time just after homogenization of these suspensions and 12 hours afterwards.

| Properties of the different samples | | Endotoxin concentration EU/mL/ | Coating thickness | Iso-electric point | Size distribution | Mean size | Hydro-dynamic size | Stability in suspension (% variation | Zeta potential (mV) | | | | | | CHNS analysis (before coating) | |
|---|---|---|---|---|---|---|---|---|---|---|---|---|---|---|---|---|
| Sample type | Coating | mg in iron) | (nm) | (pH) | (nm) | (nm) | (nm) | abs) | pH 2 | pH 4 | pH 6 | pH 8 | pH 10 | pH 12 | % C | % N |
| N-Sigma (ref: 637106) | CMD | 16-38 | 1-4 | 9.5 | 10-75 | 35 | 117 | 0% | 17 | -19 | -37 | -40 | -40 | -40 | 2.4 | 0 |
| M-CMD | CMD | 19-46 | 1-7 | ND | 20-75 | 41 | ND | 0% | 32 | -18 | -36 | -44 | -43 | -44 | 6.4 | 0 |

The suspensions of N-CMD (100 μg of N-CMD mixed in water introduced in a 100 μl well) and M-CMD (50 μg or 100 μg of M-CMD mixed in water introduced in a 100 μL well) were exposed (or not) to a laser (reference: SHANGHAI DREAM LASER TECHNOLOGY: SDL-LM-5000T), which was connected to an optical fiber (diameter: 0.5 mm, reference: SMA905/LD80) that transported laser radiation from the laser equipment or unit to a fixed position, which is 1 cm away from the bottom of the well comprising the nanoparticle suspensions. The power of the laser was measured using a power meter (Spectra Physics: Model 407A) with a distance of 1 cm between the fiber end and the power meter detector surface. We made a calibration curve to relate the laser intensity to the laser power, measured 1 cm away from the fiber end. The power density of the laser was measured by dividing the power of the laser estimated 1 cm away from the fiber end and the surface of illumination of the laser, which was estimated by eyes as corresponding to an illuminated surface area of 1 cm$^2$. For the experiments, the laser power density was estimated as 2 W/cm$^2$ when the laser was switched on. This laser power density was chosen because it produced a temperature increase in the presence of M-CMD (0.5 and 1 mg/mL) and N-CMD (1 mg/mL), while it did induce a low temperature increase in the absence of the nanoparticles (~0.007° C./sec.)

To irradiate (or not) the nanoparticle suspensions with laser radiation, we prepared suspensions comprising 100 μL of N-CMD or M-CMD at 1 mg/ml in iron that we inserted in wells of 96 microwell plate. We measured the temperature within the wells using an infrared camera and the duration of the different steps using a timer.

set at 0 A). We ended the cooling steps by switching on the laser (the laser intensity is set at 4500 mA) when the temperature reached 37° C.

Results and Discussion:

Within a lapse of time of 1000 seconds, we have been able to carry out 8 and 10 sequences, using 0.5 mg/mL and 1 mg/mL of M-CMD, respectively. By increasing the concentration of M-CMD from 0.5 mg/mL to 1 mg/mL, we were able to increase the number of sequences from 8 to 10 (FIG. 1). Within a lapse of time of 1000 seconds, we have been able to carry out 10 sequences with 1 mg of M-CMD and 7 sequences by using N-CMD. By using the magnetosome minerals coated with CMD, we were able to increase the number of sequences compared with chemically synthesized nanoparticles coated with M-CMD (FIG. 1).

Considering the heating steps following the first one, for the concentration of 0.5 mg/mL of M-CMD, the heating times were between 40 sec. and 50 sec., while the cooling times were between 60 sec. and 75 sec (table 2). For the first sequence, the heating step lasts 150 sec., twice longer than the duration of the cooling step of 75 sec. (table 2). For the other sequences, the heating times were shorter than the cooling times, with a ratio between the cooling and the heating times comprised between 1.33 and 1.71 (table 2).

For the concentration of 1 mg/mL of M-CMD, the heating times were between 20 sec. and 80 sec (table 2). They were between 1.6 and 2.2 times shorter than the heating times measured for 0.5 mg of M-CMD at the same sequence numbers (table 2). The cooling times were between 65 sec. and 90 sec. for 1 mg/mL of M-CMD, while the cooling times were between 1 min and 1 min 15 s for 0.5 mg/mL of M-CMD. By increasing the concentration of M-CMD from 0.5 mg/mL to 1 mg/mL, we: i), decreased the duration of the heating steps by a factor comprised between 1.6 and 2.2 depending on the heating step, and ii), increased the duration of the cooling steps by a factor comprised between 1.01 and 1.2.

For the concentration of 1 mg/mL of N-CMD, the heating times were between 22 sec. and 45 sec., while the cooling times were between 89 sec. and 105 sec (table 2). Compared with 1 mg of M-CMD, the heating times of N-CMD were either shorter or longer than the heating time of M-CMD depending on the sequence with a ratio between the heating times of N-CMD and those of M-CMD comprised between 0.6 and 1.8 (table 2). Compared with 1 mg of M-CMD, the cooling times were globally higher with 1 mg of N-CMD with a ratio between the cooling times of N-CMD and those of M-CMD comprised between 0.99 and 1.5 (table 2). The longer cooling times observed with N-CMD could explain why we could carry out a lower number of sequences per unit time (1000 seconds for example) with N-CMD than with M-CMD.

TABLE 2

Heating times of heating steps and ($t_{1ai}$, 1 < i < 10) cooling times of cooling steps ($t_{2ai}$, 1 < i < 10), measured for suspensions comprising 0.5 mg of M-CMD, 1 mg of M-CMD, or 1 mg of N-CMD, which are irradiated by the laser radiation of power density 2 W/cm² during 10 heating steps and not irradiated by the laser radiation during 10 cooling steps.

|  | M-CMD (0.5 mg) | M-CMD (1 mg) | N-CMD (1 mg) |
| --- | --- | --- | --- |
| $t_{1a1}$ | 150 s | 80 s | 45 s |
| $t_{2a1}$ | 75 s | 90 s | 89 s |
| $t_{1a2}$ | 48 s | 30 s | 36 s |
| $t_{2a2}$ | 69 s | 80 s | 105 s |
| $t_{1a3}$ | 39 s | 22 s | 35 s |
| $t_{2a3}$ | 60 s | 77 s | 105 s |
| $t_{1a4}$ | 45 s | 21 s | 35 s |
| $t_{2a4}$ | 69 s | 70 s | 90 s |
| $t_{1a5}$ | 45 s | 24 s | 25 s |
| $t_{2a5}$ | 69 s | 72 s | 105 s |
| $t_{1a6}$ | 45 s | 20 s | 28 s |
| $t_{2a6}$ | 68 s | 65 s | 100 s |
| $t_{1a7}$ | 45 s | 22 s | 27 s |
| $t_{2a7}$ | 60 s | 65 s | 100 s |
| $t_{1a8}$ | 35 s | 21 s | 26 s |
| $t_{2a8}$ | 60 s | 71 s | 101 s |
| $t_{1a9}$ | 37 s | 25 s | 22 s |
| $t_{2a9}$ | 60 s | 75 s | 103 s |
| $t_{1a10}$ | 41 s | 22 s | 23 s |
| $t_{2a10}$ | 60 s | 70 s | 100 s |

For the concentration of 0.5 mg/mL of M-CMD, the ratio between the temperature increase of the heating step and the heating time was comprised between 0.14° C./sec. and 0.24° C./sec, while the ratio between the temperature decrease of the cooling step and the cooling time was comprised between 0.11° C./sec. and 0.13° C./sec (table 3). This suggests that the average rate at which the temperature increases during the heating step or the average temperature gradient of the heating step is higher than the average rate at which temperature decreases during the cooling step or the average temperature gradient of the cooling step.

For the concentration of 1 mg/mL of M-CMD, the ratio between the temperature increase of the heating step and the heating time was comprised between 0.22° C./sec. and 0.4° C./sec, while the ratio between the temperature decrease of the cooling step and the cooling time was comprised between 0.09° C./sec. and 0.12° C./sec (table 3). Compared with 0.5 mg/mL of M-CMD, the ratio between the temperature increase of the heating step and the heating time increased by a factor comprised between 1.6 and 2 for 1 mg/mL of M-CMD. This suggests that the rate at which temperature increases during the heating step is more important at 1 mg than at 0.5 mg of M-CMD. Compared with 0.5 mg/mL of M-CMD, the ratio between the temperature decrease of the cooling step and the cooling time decreased by a factor of 1.1-1.2 (table 3). This suggests that the rate at which temperature decreases is more important at 0.5 mg than at 1 mg of M-CMD.

For the concentration of 1 mg/mL of N-CMD, the ratio between the temperature increase of the heating step and the heating time was comprised between 0.33° C./sec. and 0.56° C./sec, while the ratio between the temperature decrease of the cooling step and the cooling time was comprised between 0.11° C./sec. and 0.14° C./sec (table 3). Between 1 mg of M-CMD and 1 mg of N-CMD, the ratio between the temperature increase of the heating step and the heating time increased (except for the third step) by a factor comprised between 1.02 and 2.3. This increase could be explained by the maximum temperature reached at the end of each heating step of 49° C., which is 4° C. above the desired temperature of 45° C. (table 6 and FIG. 1). Between 1 mg of M-CMD and 1 mg of N-CMD, the ratio between the temperature decrease of the cooling step and the cooling time did not change very significantly as a whole (table 3). Even so there is an increase in the rate of temperature increase for 1 mg/mL of N-CMD, it does not result as a whole in a higher number of sequences since the maximum temperature reached during treatment is higher than the desired temperature.

TABLE 3

Ratio between the variations of temperature of the heating steps and the heating times ($t_{1ai}$, 1 < i < 10) as well as ratio between the variations of temperature of the cooling step and the cooling times ($t_{2ai}$, 1 < i < 10), measured for suspensions comprising 0.5 mg of M-CMD, or 1 mg of M-CMD, or 1 mg of N-CMD, which are irradiated by the laser radiation of power density 2 W/cm² during 10 heating steps and not irradiated by the laser radiation during 10 cooling steps.

|  | M-CMD (0.5 mg) | M-CMD (1 mg) | N-CMD (1 mg) |
| --- | --- | --- | --- |
| $\Delta T/t_{1a1}$ | 0.14 | 0.22 | 0.51 |
| $\Delta T/t_{2a1}$ | 0.11 | 0.09 | 0.14 |
| $\Delta T/t_{1a2}$ | 0.17 | 0.27 | 0.33 |
| $\Delta T/t_{2a2}$ | 0.11 | 0.1 | 0.11 |
| $\Delta T/t_{1a3}$ | 0.21 | 0.36 | 0.35 |
| $\Delta T/t_{2a3}$ | 0.13 | 0.1 | 0.14 |
| $\Delta T/t_{1a4}$ | 0.18 | 0.38 | 0.47 |
| $\Delta T/t_{2a4}$ | 0.12 | 0.11 | 0.11 |
| $\Delta T/t_{1a5}$ | 0.18 | 0.33 | 0.43 |
| $\Delta T/t_{2a5}$ | 0.12 | 0.11 | 0.12 |
| $\Delta T/t_{1a6}$ | 0.18 | 0.4 | 0.41 |
| $\Delta T/t_{2a6}$ | 0.13 | 0.12 | 0.11 |
| $\Delta T/t_{1a7}$ | 0.18 | 0.36 | 0.47 |
| $\Delta T/t_{2a7}$ | 0.13 | 0.12 | 0.12 |
| $\Delta T/t_{1a8}$ | 0.24 | 0.38 | 0.56 |
| $\Delta T/t_{2a8}$ | 0.13 | 0.11 | 0.12 |
| $\Delta T/t_{1a9}$ | 0.22 | 0.37 | 0.53 |
| $\Delta T/t_{2a9}$ | 0.13 | 0.11 | 0.12 |
| $\Delta T/t_{1a10}$ | 0.18 | 0.36 | 0.53 |
| $\Delta T/t_{2a10}$ | 0.13 | 0.11 | 0.11 |

Interestingly, the heating times were the same as the durations of irradiation by the laser radiation during the heating steps and the cooling times were the same as the durations of non-irradiation by the laser radiation during the cooling steps for 0.5 mg/mL and 1 mg/mL of M-CMD (tables 2 and 4). By contrast, for 1 mg/mL of N-CMD, the heating times were higher by a factor comprised between 1.4 and 1.8 than the durations of irradiation by the laser radiation during the heating steps and the cooling times were higher by a factor comprised between 1.1 and 1.3 than the durations of non-irradiation by the laser radiation during the cooling steps (tables 2 and 4). Consequently, for 0.5 mg and 1 mg of M-CMD, we found that: i), the ratio between the temperature increases during the heating steps and the heating times were the same as the ratio between the temperature increases during the heating steps and the duration of irradiation by the laser radiation during the various heating sequences, and ii), the ratio between the temperature decreases during the cooling steps and the cooling times were the same as the ratio between the temperature decreases during the cooling steps and the duration of non-irradiation by the laser radiation during the various cooling sequences, (tables 3 and 5). By contrast, for 1 mg/mL of N-CMD, we found that: i), the ratio between the temperature increases during the heating steps and the heating times were lower than the ratio between the temperature increases during the heating steps and the duration of irradiation by the laser radiation during the various heating sequences, and ii), the ratio between the temperature decreases during the cooling steps and the cooling times were higher than the ratio between the temperature decreases during the cooling steps and the duration of non-irradiation by the laser radiation during the various cooling sequences. The behavior observed with N-CMD could be explained by the fact that N-CMD continue to produce heat after the laser has been switched off at the end of each heating step, hence increasing the heating time and decreasing the cooling time.

TABLE 4

Durations of irradiation by the laser radiation with power density of 2 W/cm² during the various heating steps (tON-OFFi, 1 < i < 10), as well as durations of the non-irradiation by the laser radiation during the various cooling steps (tOFF-ONi, 1 < i < 10), measured for suspensions comprising 0.5 mg of M-CMD, 1 mg of M-CMD, or 1 mg of N-CMD, which are irradiated by the laser radiation of power density 2 W/cm² during 10 heating steps and not irradiated by the laser radiation during 10 cooling steps.

| | M-CMD (0.5 mg) | M-CMD (1 mg) | N-CMD (1 mg) |
|---|---|---|---|
| $t_{ON-OFF1}$ | 150 s | 80 s | 30 s |
| $t_{OFF-ON1}$ | 75 s | 90 s | 104 s |
| $t_{ON-OFF2}$ | 48 s | 30 s | 20 s |
| $t_{OFF-ON2}$ | 69 s | 80 s | 119 s |
| $t_{ON-OFF3}$ | 39 s | 22 s | 20 s |
| $t_{OFF-ON3}$ | 60 s | 77 s | 120 s |
| $t_{ON-OFF4}$ | 45 s | 21 s | 20 s |
| $t_{OFF-ON4}$ | 69 s | 70 s | 115 s |
| $t_{ON-OFF5}$ | 45 s | 24 s | 15 s |
| $t_{OFF-ON5}$ | 69 s | 72 s | 115 s |
| $t_{ON-OFF6}$ | 45 s | 20 s | 18 s |
| $t_{OFF-ON6}$ | 60 s | 65 s | 110 s |
| $t_{ON-OFF7}$ | 45 s | 22 s | 17 s |
| $t_{OFF-ON7}$ | 60 s | 65 s | 110 s |
| $t_{ON-OFF8}$ | 35 s | 21 s | 16 s |
| $t_{OFF-ON8}$ | 60 s | 71 s | 111 s |
| $t_{ON-OFF9}$ | 37 s | 25 s | 16 s |
| $t_{OFF-ON9}$ | 60 s | 75 s | 109 s |
| $t_{ON-OFF10}$ | 41 s | 22 s | 15 s |
| $t_{OFF-ON10}$ | 60 s | 70 s | 108 s |

TABLE 5

Ratio between the variations of temperature of the heating steps and the durations of irradiation by the laser radiation with power density of 2 W/cm² during the various heating steps ($t_{ON-OFFi}$, 1 < i < 10), as well as ratio between the variations of temperature of the cooling steps and durations of the non-irradiation by the laser radiation during the various cooling steps ($t_{OFF-ONi}$, 1 < i < 10), measured for suspensions comprising 0.5 mg of M-CMD, 1 mg of M-CMD, or 1 mg of N-CMD, which are irradiated by the laser radiation of power density 2 W/cm² during 10 heating steps and not irradiated by the laser radiation during 10 cooling steps.

| | M-CMD (0.5 mg) | M-CMD (1 mg) | N-CMD (1 mg) |
|---|---|---|---|
| $\Delta T/t_{ON-OFF1}$ | 0.14 | 0.22 | 0.61 |
| $\Delta T/t_{OFF-ON1}$ | 0.11 | 0.09 | 0.08 |
| $\Delta T/t_{ON-OFF2}$ | 0.17 | 0.27 | 0.4 |
| $\Delta T/t_{OFF-ON2}$ | 0.11 | 0.1 | 0.07 |
| $\Delta T/t_{ON-OFF3}$ | 0.21 | 0.36 | 0.4 |
| $\Delta T/t_{OFF-ON3}$ | 0.13 | 0.1 | 0.07 |
| $\Delta T/t_{ON-OFF4}$ | 0.18 | 0.38 | 0.4 |
| $\Delta T/t_{OFF-ON4}$ | 0.12 | 0.11 | 0.08 |
| $\Delta T/t_{ON-OFF5}$ | 0.18 | 0.33 | 0.5 |
| $\Delta T/t_{OFF-ON5}$ | 0.12 | 0.11 | 0.07 |
| $\Delta T/t_{ON-OFF6}$ | 0.18 | 0.4 | 0.44 |
| $\Delta T/t_{OFF-ON6}$ | 0.13 | 0.12 | 0.08 |
| $\Delta T/t_{ON-OFF7}$ | 0.18 | 0.36 | 0.47 |
| $\Delta T/t_{OFF-ON7}$ | 0.13 | 0.12 | 0.07 |
| $\Delta T/t_{ON-OFF8}$ | 0.24 | 0.38 | 0.5 |
| $\Delta T/t_{OFF-ON8}$ | 0.13 | 0.11 | 0.07 |
| $\Delta T/t_{ON-OFF9}$ | 0.22 | 0.37 | 0.5 |
| $\Delta T/t_{OFF-ON9}$ | 0.13 | 0.11 | 0.07 |
| $\Delta T/t_{ON-OFF10}$ | 0.18 | 0.36 | 0.5 |
| $\Delta T/t_{OFF-ON10}$ | 0.13 | 0.11 | 0.07 |

TABLE 6

Desired temperature and average temperature reached during the various steps for suspensions comprising 0.5 mg of M-CMD, 1 mg of M-CMD, or 1 mg of N-CMD, which are irradiated by the laser radiation of power density 2 W/cm².

| Steps | | Desired temperature (° C.) | Reached temperature (° C.) (averaged over the different steps) |
|---|---|---|---|
| 0.5 mg M-CMD | Heating steps | 45°C. | 45°C. |
| | Cooling steps | 37°C. | 37°C. |
| 1 mg M-CMD | Heating steps | 45°C. | 45°C. |
| | Cooling steps | 37°C. | 37°C. |
| 1 mg N-CMD | Heating steps | 45°C. | 45°C. |
| | Cooling steps | 37°C. | 37°C. |

We can Draw the Following Conclusions from this Example:

i) By increasing the concentration of M-CMD irradiated by laser radiation from 0.5 mg/mL to 1 mg/mL, we could increase the number of sequences from 8 to 10 within 1000 sec. of laser radiation application. This suggests that the number of sequences per unit time can be adjusted by varying nanoparticle, in particular magnetosome, concentration, preferentially the number of sequence can be increased by increasing nanoparticle, in particular magnetosome, concentration.

ii) At equivalent concentration of 1 mg/mL and for the same laser power density of 2 W/cm², M-CMD led to a higher number of sequences of 10 within 1000 seconds compared with N-CMD that resulted in 7 sequences within 1000 seconds of irradiation by laser radiation. This suggests that M-CMD can produce a higher number of sequences per unit time than N-CMD.

iii) Increasing the concentration of M-CMD irradiated by laser radiation of 2 W/cm² from 0.5 mg/mL to 1 mg/mL resulted in a decrease in heating time by a factor comprised between 1.6 and 2.2 and in an increase in cooling time by a factor comprised between 1.01 and 1.2. This suggests that the heating and cooling times can be tuned by varying the nanoparticle, in particular magnetosome, concentration, and that optimal nanoparticle, in particular magnetosome, concentration can correspond to a concentration resulting in the smallest heating times while possibly avoiding a too large increase in cooling times.

iv) The rate at which temperature increases during the heating steps is higher for 1 mg/mL than for 0.5 mg/mL of M-CMD irradiated by the laser radiation, while the rate at which temperature decreases during the cooling steps is higher for 0.5 mg/mL than for 1 mg/mL of M-CMD irradiated by the laser radiation. This suggests that increasing the nanoparticle, in particular magnetosome, concentration decreases the heating time and increases the cooling time, possibly due a different mechanism of heat transfer during the heating and cooling steps. During the heating steps, laser radiations can be directly or immediately coupled to or absorbed by magnetosomes, resulting in immediate heating. It can result to a rate of temperature increase that increases with increasing magnetic, in particular magnetosome, concentration. During the cooling steps, heat may be transferred from the magnetosomes to their surrounding such as body part at a rate or speed that decreases with increasing magnetosome concentration, possibly due to the fact that with increasing magnetosome concentration, heat is maintained for a longer period of time in the magnetosomes without being transferred to the surrounding medium or body part of the magnetosomes.

v) Interestingly, for both 0.5 mg/mL and 1 mg/mL of M-CMD, the heating and cooling times were the same as the durations of application and non-irradiation by the laser radiation, respectively. The desired maximum temperature of the heating steps and minimum temperature of the cooling steps were also the same as the temperatures reached during the heating and cooling steps, respectively. This suggests an optimal coupling between laser radiation and the magnetosomes. This is an advantageous property for the laser medical or chemical or biological or cosmetic treatment. On the one hand it enables to reach a maximum temperature during the heating step and minimum temperature during the cooling step that are the same as those that one wants reaching. On the other hand it prevents overheating or overcooling and potential side effects that can result from them.

vi) By contrast, for 1 mg/mL of N-CMD, the heating and cooling times were different from the durations of applications and non-irradiation by the laser radiation, respectively. The desired maximum temperatures of the heating steps (45° C.) were also different from the maximum temperatures reached during the heating steps (49° C.). This suggests non-optimal coupling between laser radiation and the N-CMD. This is a disadvantageous property for the laser medical or chemical or biological or cosmetic treatment. On the one hand, it does not enable to reach a maximum temperature during the heating step that is the same as the temperature that one wants to reach. On the other hand, it leads to overheating and potential side effects that can result from it.

vii) For the second to tenth sequence, the duration of sequences (heating step+cooling step), was between 1.3 to 1.5 longer for 1 mg/mL of N-CMD than for 1 mg/mL of M-CMD. This explains why we could carry out a lower number of sequences per unit time for N-CMD than for M-CMD (FIG. 1).

viii) The better match between desired and reached maximum/minimum temperatures of the heating/cooling steps, the smaller heating times observed for M-CMD compared with N-CMD could be explained by the better crystallization, more homogenous organization, better faceted, higher coercivity or remanent magnetization, higher size, or lower size distribution, of M-CMD compared with N-CMD. This could also be explained by the arrangement in chains, which is present in M-CMD and absent in N-CMD.

Example 2: Cellular Toxicity and Temperature Measurement of Cells Brought into Contact with Magnetosomes and Subjected (or not) to the Continuous or Sequential Application of the Laser Materials and Methods:

Magnetosomes used in this example ate M-CMD. U87-MG glioblastoma cells were purchased from ATCC (ATCC® HTB-14) and cultivated in High-Glucose Dulbecco's Modified Eagle's Medium (DMEM), supplemented with 1 mM pyruvate, 10% fetal calf serum, 100 units/mL of penicillin and 100 µg/mL of streptomycin. The cells were seeded in a T175 flask with culture medium. When 80-90% confluence was reached, the supernatant was removed and replaced with PBS to rinse the cells. Subsequently, the PBS solution was removed and replaced with a volume of 5 mL of 0.25% trypsin-EDTA. The cells were incubated for 5 minutes at 37° C. with 5% carbon dioxide in an incubator with a humidity of 90-95%. The cells were then harvested. A volume of 10 ml of culture medium was added to deactivate the action of trypsin and the cells were homogenized. A volume of 30 µL of cells was collected and mixed with 30 µL of 4% trypan blue to count the cells using a cell counter (Countess™ II FL Automated Cell Counter (Thermo Fisher scientific)) and thus to determine the cell concentration of the initial suspension. A volume of 100 µL of $10^4$ cells was inserted in each well of a 96 well plate and the cells were incubated at 37° C. with 5% CO2 for 24 hours so that the cells adhere at the surface of well. The cell medium was then removed and replaced either by a new medium without magnetosomes or a new medium containing magnetosomes at a concentration of 1 mg/mL in iron of magnetosomes.

BALB/3T3 clone A31 fibroblast cells were purchased from ATCC (ATCC®CCL-163)) and cultivated in High-Glucose Dulbecco's Modified Eagle's Medium (DMEM), supplemented with 1 mM pyruvate, 10% bovine calf serum, 100 units/mL of penicillin and 100 µg/mL of streptomycin. The cells were seeded in a T175 flask with culture medium. When 80-90% confluence was reached, the supernatant was removed and replaced with PBS to rinse the cells. Subsequently, the PBS solution was removed and replaced with a volume of 5 mL of 0.25% trypsin-EDTA. The cells were incubated for 5 minutes at 37° C. with 5% carbon dioxide in an incubator with a humidity of 90-95%. The cells were then harvested. A volume of 10 ml of culture medium was added to deactivate the action of trypsin and the cells were homogenized. A volume of 30 µL of cells was collected and mixed with 30 µL of 4% trypan blue to count the cells using a cell counter (Countess™ II FL Automated Cell Counter (Thermo Fisher scientific)) and thus to determine the cell concentration of the initial suspension. A volume of 100 µL of $10^4$ cells was deposited in each well of a 96 well plate and the cells were incubated at 37° C. with 5% $CO_2$ for 24 hours so that the cells adhere at the surface of well. The cell medium was then removed and replaced either by a new medium without magnetosomes or a new medium containing magnetosomes at a concentration of 1 mg/mL in iron of magnetosomes.

U87-MG or 3T3 cells, treated as described above, were then either continuously exposed to a laser of average power 3 W/cm² during 6 minutes or sequentially exposed to the laser. The power of the laser used was ~3 W/cm², where the power is the ratio between the laser power at the end of the fiber and the exposed surface (the surface of the well). The wavelength of the laser was 808 nm. The beam of laser light was focused at the bottom of the well containing cells with/without magnetosomes.

The laser light was applied as follows:

For the continuous application of the laser, the laser was applied continuously during 6 minutes.

For the sequential application of the laser, two conditions were tested. In condition 1, the cells were brought into contact with 1 mg/mL of magnetosomes and exposed sequentially to a laser in the following way: (a) for U87-MG cells: First sequence: i) application of the laser of average power 3 W/cm² during 60 seconds until the temperature reaches 45° C., ii) non-application of the laser during 18 seconds resulting in a temperature decrease from 45° C. to 37° C.; Second sequence: i) application of the laser of average power 3 W/cm² during 17.5 seconds resulting in a temperature increase from 37° C. to 45° C., ii) non-application of the laser during 24 seconds resulting in a temperature decrease from 45° C. to 37° C.; Third sequence: i) application of the laser of average power 3 W/cm² during 17.5 seconds resulting in a temperature increase from 37° C. to 45° C., ii) non-application of the laser during 20 seconds resulting in a temperature decrease from 45° C. to 37° C.; Fourth sequence: i) application of the laser of average power 3 W/cm² during 15.5 seconds resulting in a temperature increase from 37° C. to 45° C., ii) non-application of the laser during 20.5 seconds resulting in a temperature decrease from 45° C. to 37° C.; Fifth sequence: i) application of the laser of average power 3 W/cm² during 15 seconds resulting in a temperature increase from 37° C. to 45° C., ii) non-application of the laser during 21.5 seconds resulting in a temperature decrease from 45° C. to 37° C.; sixth sequence: i) application of the laser of average power 3 W/cm² during 14.5 seconds resulting in a temperature increase from 37° C. to 45° C., ii) non-application of the laser during 21.5 seconds resulting in a temperature decrease from 45° C. to 37° C.; seventh sequence: i) application of the laser of average power 3 W/cm² during 15 seconds resulting in a temperature increase from 37° C. to 45° C., ii) non-application of the laser during 20 seconds resulting in a temperature decrease from 45° C. to 37° C.; eighth sequence: i) application of the laser of average power 3 W/cm² during 13.5 seconds resulting in a temperature increase from 37° C. to 45° C., ii) non-application of the laser during 22 seconds resulting in a temperature decrease from 45° C. to 37° C.; ninth sequence: i) application of the laser of average power at 3 W/cm² during 13 seconds resulting in a temperature increase from 37° C. to 45° C., ii) non-application of the laser during 21 seconds resulting in a temperature decrease from 45° C. to 37° C.; tenth sequence: i) application of the laser of average power 3 W/cm² during 15 seconds resulting in a temperature increase from 37° C. to 45° C., ii) non-application of the laser during 23 seconds resulting in a temperature decrease from 45° C. to 37° C.; eleventh sequence: i) application of the laser of average power at 3 W/cm² during 14.5 seconds resulting in a temperature increase from 37° C. to 45° C., ii) non-application of the laser during 23 seconds resulting in a temperature decrease from 45° C. to 37° C.; twelfth sequence: i) application of the laser of average power 3 W/cm² during 15 seconds resulting in a temperature increase from 37° C. to 45° C., ii) non-application of the laser during 25 seconds resulting in a temperature decrease from 45° C. to 37° C.; thirteenth sequence: i) application of the laser of average power 3 W/cm² during 14.5 seconds resulting in a temperature increase from 37° C. to 45° C., ii) non-application of the laser during 24.5 seconds resulting in a temperature decrease from 45° C. to 37° C.; fourteenth sequence: i) application of the laser of average power 3 W/cm² during 12.5 seconds resulting in a temperature increase from 37° C. to 45° C., ii) non-application of the laser during 24 seconds resulting in a temperature decrease from 45° C. to 37° C.; fifteenth sequence: i) application of the laser of average power 3 W/cm² during 12.5 seconds resulting in a temperature increase from 37° C. to 45° C., ii) non-application of the laser during 18.5 seconds resulting in a temperature decrease from 45° C. to 37° C.; sixteenth sequence: i) application of the laser of average power 3 W/cm² during 15 seconds resulting in a temperature increase from 37° C. to 45° C., ii) non-application of the laser during 23 seconds resulting in a temperature decrease from 45° C. to 37° C.; seventeenth sequence: i) application of the laser of average power 3 W/cm² during 12.5 seconds resulting in a temperature increase from 37° C. to 45° C., ii) non-application of the laser during 22.5 seconds resulting in a temperature decrease from 45° C. to 37° C.; eighteenth sequence: i) application of the laser of average power 3 W/cm² during 13.5 seconds resulting in a temperature increase from 37° C. to 45° C., ii) non-application of the laser during 24 seconds resulting in a temperature decrease from 45° C. to 37° C.; nineteenth sequence: i) application of the laser of average power 3 W/cm² during 13.5 seconds resulting in a temperature increase from 37° C. to 45° C., ii) non-application of the laser during 21.5 seconds resulting in a temperature decrease from 45° C. to 37° C.; twentieth sequence: i) application of the laser an average power at 3 W/cm² during 14 seconds resulting in a temperature increase from 37° C. to 45° C., ii) non-application of the laser during 21 seconds resulting in a temperature decrease from 45° C. to 37° C.; twenty first sequence: i) application of the laser of average power 3 W/cm² during 14.5 seconds resulting in a temperature increase from 37° C. to 45° C., ii) non-application of the laser during 23 seconds resulting in a temperature decrease from 45° C. to 37° C.; twenty second sequence: i) application of the laser of average power 3 W/cm² during 14 seconds resulting in a temperature increase from 37° C. to 45° C., ii) non-application of the laser during 16 seconds resulting in a temperature decrease from 45° C. to 37° C. The total duration of the application of the laser is 6 min 2 sec. (b), for 3T3 cells: First sequence: i) application of the laser of average power 3 W/cm² during 90 seconds until the temperature reaches 45° C., ii) non-application of the laser during 21 seconds resulting in a temperature decrease from 45° C. to 37° C.; Second sequence: i) application of the laser of average power 3 W/cm² during 17.5 seconds resulting in a temperature increase from 37° C. to 45° C., ii) non-application of the laser during 22 seconds resulting in a temperature decrease from 45° C. to 37° C.; Third sequence: i) application of the laser of average power 3 W/cm² during 17.5 seconds resulting in a temperature increase from 37° C. to 45° C., ii) non-application of the laser during 20.5 seconds resulting in a temperature decrease from 45° C. to 37° C.; Fourth sequence: i) application of the laser of average power 3 W/cm² during 14.5 seconds resulting in a temperature increase from 37° C. to 45° C., ii) non-application of the laser during 20.5 seconds resulting in a temperature decrease from 45° C. to 37° C.; Fifth sequence: i) application of the laser of average power 3 W/cm2 during 15.5 seconds resulting in a temperature increase from 37° C. to 45° C., ii) non-application of the laser during 19 seconds resulting in a temperature decrease from 45° C. to 37° C.; sixth sequence: i) application of the laser of average power 3 W/cm$^2$ during 15.5 seconds resulting in a temperature increase from 37° C. to 45° C., ii) non-application of the laser during 19.5 seconds resulting in a temperature decrease from 45° C. to 37° C.; seventh sequence: i) application of the laser of average power 3 W/cm$^2$ during 18.5 seconds resulting in a temperature increase from 37° C. to 45° C., ii) non-application of the laser during 20 seconds resulting in a temperature decrease from 45° C. to 37° C.; eighth sequence: i) application of the laser of average power 3 W/cm$^2$ during 18.5 seconds resulting in a temperature increase from 37° C. to 45° C., ii) non-application of the laser during 21 seconds resulting in a temperature decrease from 45° C. to 37° C.; ninth sequence: i) application of the laser of average power 3 W/cm$^2$ during 20 seconds resulting in a temperature increase from 37° C. to 45° C., ii) non-application of the laser during 20 seconds resulting in a temperature decrease from 45° C. to 37° C.; tenth sequence: i) application of the laser of average power 3 W/cm$^2$ during 18.5 seconds resulting in a temperature increase from 37° C. to 45° C., ii) non-application of the laser during 19.5 seconds resulting in a temperature decrease from 45° C. to 37° C.; eleventh sequence: i) application of the laser of average power 3 W/cm2 during 17.5 seconds resulting in a temperature increase from 37° C. to 45° C., ii) non-application of the laser during 18.5 seconds resulting in a temperature decrease from 45° C. to 37° C.; twelfth sequence: i) application of the laser of average power 3 W/cm$^2$ during 18 seconds resulting in a temperature increase from 37° C. to 45° C., ii) non-application of the laser during 19.5 seconds resulting in a temperature decrease from 45° C. to 37° C.; thirteenth sequence: i) application of the laser of average power 3 W/cm$^2$ during 17.5 seconds resulting in a temperature increase from 37° C. to 45° C., ii) non-application of the laser during 18.5 seconds resulting in a temperature decrease from 45° C. to 37° C.; fourteenth sequence: i) application of the laser of average power 3 W/cm$^2$ during 17.5 seconds resulting in a temperature increase from 37° C. to 45° C., ii) non-application of the laser during 18.5 seconds resulting in a temperature decrease from 45° C. to 37° C.; fifteenth sequence: i) application of the laser of average power 3 W/cm$^2$ during 19.5 seconds resulting in a temperature increase from 37° C. to 45° C., ii) non-application of the laser during 21.5 seconds resulting in a temperature decrease from 45° C. to 37° C.; sixteenth sequence: i) application of the laser of average power 3 W/cm$^2$ during 18 seconds resulting in a temperature increase from 37° C. to 45° C., ii) non-application of the laser during 19.5 seconds resulting in a temperature decrease from 45° C. to 37° C.; seventeenth sequence: i) application of the laser of average power 3 W/cm$^2$ during 17.5 seconds resulting in a temperature increase from 37° C. to 45° C., ii) non-application of the laser during 19.5 seconds resulting in a temperature decrease from 45° C. to 37° C.; eighteenth sequence: i) application of the laser of average power 3 W/cm$^2$ during 17.5 seconds resulting in a temperature increase from 37° C. to 45° C., ii) non-application of the laser during 20 seconds resulting in a temperature decrease from 45° C. to 37° C.; nineteenth sequence: i) application of the laser of average power 3 W/cm$^2$ during 19 seconds resulting in a temperature increase from 37° C. to 45° C., ii) non-application of the laser during 18.5 seconds resulting in a temperature decrease from 45° C. to 37° C. In condition 2, the cells were not brought into contact with the magnetosomes and sequentially exposed to the laser using the same sequence durations those of condition 1.

During the application of the laser, the heating temperature was measured using the infra-red camera EasyIR-2 from the company Guide Infrared, which was positioned 20 cm above the well.

24 hours after the treatments, the medium with and without magnetosomes was removed and then replaced with a PBS buffer solution. The cells were washed twice with this buffer solution and then 100 µl of a solution of bromide of 3-(4,5-dimethylthiazol-2-yl)-2,5-diphenyl-tetrazolium at 1 mg/ml was brought into contact with the cells during 4 hours, the tetrazolium salt was removed and then replaced with 100 µL of isopropanol. After gentle stirring, absorbance was measured at 620 nm using a microplate spectrophotometer system. The percentage of living cells was determined by measuring the ratio between the optical density for the cells treated with laser and magnetosomes and the optical density measured for the cells treated alone without magnetosomes without the application of the laser, and the ratio was multiplied by 100.

Results:

FIGS. 2(b) and 3(b) show the temperature variations obtained when U87-Luc and 3T3 cells are not brought into contact with magnetosomes or are brought into contact with 1 mg/mL of magnetosomes and continuously exposed to the laser of average power 3 W/cm$^2$ during 6 minutes. The initial temperature before laser application is 21° C. For the concentration of 1 mg/mL a temperature of 48-52° C. is reached after 6 minutes of laser application, while in the absence of magnetosomes, a temperature of 21-24° C. is reached.

FIGS. 2(c) and 3(c) show the temperature variations obtained when U87-Luc and 3T3 cells are either brought into contact with 1 mg/mL of magnetosomes or are not brought into contact with the magnetosomes, and are then sequentially exposed to a laser of average power 3 W/cm$^2$. The total heating time for the continuous application of the laser is the similar to the total heating time of the sequential application.

The details of the sequences are as follows for U87-MG cells: First sequence: i) application of the laser of average power 3 W/cm$^2$ during 60 seconds until the temperature reaches 45° C., ii) non-application of the laser during 18 seconds resulting in a temperature decrease from 45° C. to 37° C.; Second sequence: i) application of the laser of average power 3 W/cm$^2$ during 17.5 seconds resulting in a temperature increase from 37° C. to 45° C., ii) non-application of the laser during 24 seconds resulting in a temperature decrease from 45° C. to 37° C.; Third sequence: i) application of the laser of average power 3 W/cm$^2$ during 17.5 seconds resulting in a temperature increase from 37° C. to 45° C., ii) non-application of the laser during 20 seconds resulting in a temperature decrease from 45° C. to 37° C.; Fourth sequence: i) application of the laser of average power at 3 W/cm$^2$ during 15.5 seconds resulting in a temperature increase from 37° C. to 45° C., ii) non-application of the laser during resulting in a temperature decrease from 45° C. to 37° C. during 20.5 seconds; Fifth sequence: i) application of the laser of average power 3 W/cm$^2$ during 15 seconds resulting in a temperature increase from 37° C. to 45° C., ii) non-application of the laser during resulting in a temperature decrease from 45° C. to 37° C. during 21.5 seconds; sixth sequence: i) application of the laser of average power 3 W/cm$^2$ during 14.5 seconds resulting in a temperature increase from 37° C. to 45° C., ii) non-application of the laser during 21.5 seconds resulting in a temperature decrease from 45° C. to 37° C.; seventh sequence: i) application of the laser of average power 3 W/cm² during 15 seconds resulting in a temperature increase from 37° C. to 45° C., ii) non-application of the laser during 20 seconds resulting in a temperature decrease from 45° C. to 37° C.; eighth sequence: i) application of the laser of average power 3 W/cm² during 13.5 seconds resulting in a temperature increase from 37° C. to 45° C., ii) non-application of the laser during 22 seconds resulting in a temperature decrease from 45° C. to 37° C.; ninth sequence: i) application of the laser of average power 3 W/cm² during 13 seconds resulting in a temperature increase from 37° C. to 45° C., ii) non-application of the laser during 21 seconds resulting in a temperature decrease from 45° C. to 37° C.; tenth sequence: i) application of the laser of average power 3 W/cm² during 15 seconds resulting in a temperature increase from 37° C. to 45° C., ii) non-application of the laser during 23 seconds resulting in a temperature decrease from 45° C. to 37° C.; eleventh sequence: i) application of the laser of average power 3 W/cm² during 14.5 seconds resulting in a temperature increase from 37° C. to 45° C., ii) non-application of the laser during 23 seconds resulting in a temperature decrease from 45° C. to 37° C.; twelfth sequence: i) application of the laser of average power 3 W/cm² during 15 seconds resulting in a temperature increase from 37° C. to 45° C., ii) non-application of the laser during 25 seconds resulting in a temperature decrease from 45° C. to 37° C.; thirteenth sequence: i) application of the laser of average power 3 W/cm² during 14.5 seconds resulting in a temperature increase from 37° C. to 45° C., ii) non-application of the laser during 24.5 seconds resulting in a temperature decrease from 45° C. to 37° C.; fourteenth sequence: i) application of the laser of average power 3 W/cm² during 12.5 seconds resulting in a temperature increase from 37° C. to 45° C., ii) non-application of the laser during 24 seconds resulting in a temperature decrease from 45° C. to 37° C.; fifteenth sequence: i) application of the laser of average power 3 W/cm² during 12.5 seconds resulting in a temperature increase from 37° C. to 45° C., ii) non-application of the laser during 18.5 seconds resulting in a temperature decrease from 45° C. to 37° C.; sixteenth sequence: i) application of the laser of average power 3 W/cm² during 15 seconds resulting in a temperature increase from 37° C. to 45° C., ii) non-application of the laser during 23 seconds resulting in a temperature decrease from 45° C. to 37° C.; seventeenth sequence: i) application of the laser of average power 3 W/cm² during 12.5 seconds resulting in a temperature increase from 37° C. to 45° C., ii) non-application of the laser during 22.5 seconds resulting in a temperature decrease from 45° C. to 37° C.; eighteenth sequence: i) application of the laser of average power 3 W/cm² during 13.5 seconds resulting in a temperature increase from 37° C. to 45° C., ii) non-application of the laser during 24 seconds resulting in a temperature decrease from 45° C. to 37° C.; nineteenth sequence: i) application of the laser of average power 3 W/cm² during 13.5 seconds resulting in a temperature increase from 37° C. to 45° C., ii) non-application of the laser during 21.5 seconds resulting in a temperature decrease from 45° C. to 37° C.; twentieth sequence: i) application of the laser of average power 3 W/cm² during 14 seconds resulting in a temperature increase from 37° C. to 45° C., ii) non-application of the laser during 21 seconds resulting in a temperature decrease from 45° C. to 37° C.; twenty first sequence: i) application of the laser of average power 3 W/cm² during 14.5 seconds resulting in a temperature increase from 37° C. to 45° C., ii) non-application of the laser during 23 seconds resulting in a temperature decrease from 45° C. to 37° C.; twenty second sequence: i) application of the laser of average power 3 W/cm² during 14 seconds resulting in a temperature increase from 37° C. to 45° C., ii) non-application of the laser during 16 seconds resulting in a temperature decrease from 45° C. to 37° C. The total duration of laser application is 6 min 2 sec.

The details of the sequences are as follows for 3T3 cells. First sequence: i) application of the laser an average power at 3 W/cm² during 90 seconds until the temperature reaches 45° C., ii) non-application of the laser during 21 seconds resulting in a temperature decrease from 45° C. to 37° C.; Second sequence: i) application of the laser of average power at 3 W/cm² during 17.5 seconds resulting in a temperature increase from 37° C. to 45° C., ii) non-application of the laser during 22 seconds resulting in a temperature decrease from 45° C. to 37° C.; Third sequence: i) application of the laser of average power 3 W/cm² during 17.5 seconds resulting in a temperature increase from 37° C. to 45° C., ii) non-application of the laser during 20.5 seconds resulting in a temperature decrease from 45° C. to 37° C.; Fourth sequence: i) application of the laser of average power 3 W/cm² during 14.5 seconds resulting in a temperature increase from 37° C. to 45° C., ii) non-application of the laser during 20.5 seconds resulting in a temperature decrease from 45° C. to 37° C.; Fifth sequence: i) application of the laser of average power 3 W/cm² during 15.5 seconds resulting in a temperature increase from 37° C. to 45° C., ii) non-application of the laser during 19 seconds resulting in a temperature decrease from 45° C. to 37° C.; sixth sequence: i) application of the laser of average power at 3 W/cm² during 15.5 seconds resulting in a temperature increase from 37° C. to 45° C., ii) non-application of the laser during 19.5 seconds resulting in a temperature decrease from 45° C. to 37° C.; seventh sequence: i) application of the laser of average power 3 W/cm² during 18.5 seconds resulting in a temperature increase from 37° C. to 45° C., ii) non-application of the laser during 20 seconds resulting in a temperature decrease from 45° C. to 37° C.; eighth sequence: i) application of the laser of average power 3 W/cm² during 18.5 seconds resulting in a temperature increase from 37° C. to 45° C., ii) non-application of the laser during 21 seconds resulting in a temperature decrease from 45° C. to 37° C.; ninth sequence: i) application of the laser of average power 3 W/cm² during 20 seconds resulting in a temperature increase from 37° C. to 45° C., ii) non-application of the laser during 20 seconds resulting in a temperature decrease from 45° C. to 37° C.; tenth sequence: i) application of the laser of average power 3 W/cm² during 18.5 seconds resulting in a temperature increase from 37° C. to 45° C., ii) non-application of the laser during 19.5 seconds resulting in a temperature decrease from 45° C. to 37° C.; eleventh sequence: i) application of the laser of average power 3 W/cm² during 17.5 seconds resulting in a temperature increase from 37° C. to 45° C., ii) non-application of the laser during 18.5 seconds resulting in a temperature decrease from 45° C. to 37° C.; twelfth sequence: i) application of the laser of average power 3 W/cm² during 18 seconds resulting in a temperature increase from 37° C. to 45° C., ii) non-application of the laser during 19.5 seconds resulting in a temperature decrease from 45° C. to 37° C.; thirteenth sequence: i) application of the laser of average power 3 W/cm² during 17.5 seconds resulting in a temperature increase from 37° C. to 45° C., ii) non-application of the laser during 18.5 seconds resulting in a temperature decrease from 45° C. to 37° C.; fourteenth sequence: i) application of the laser of average power 3 W/cm² during 17.5 seconds resulting in a temperature increase from 37° C. to 45° C., ii) non-application of the laser during 18.5 seconds resulting in a temperature decrease from 45° C. to 37° C.; fifteenth sequence: i) application of the laser of average power 3 W/cm² during 19.5 seconds resulting in a temperature increase from 37° C. to 45° C., ii) non-application of the laser during 21.5 seconds resulting in a temperature decrease from 45° C. to 37° C.; sixteenth sequence: i) application of the laser of average power 3 W/cm² during 18 seconds resulting in a temperature increase from 37° C. to 45° C., ii) non-application of the laser during 19.5 seconds resulting in a temperature decrease from 45° C. to 37° C.; seventeenth sequence: i) application of the laser of average power 3 W/cm² during 17.5 seconds resulting in a temperature increase from 37° C. to 45° C., ii) non-application of the laser during 19.5 seconds resulting in a temperature decrease from 45° C. to 37° C.; eighteenth sequence: i) application of the laser of average power 3 W/cm² during 17.5 seconds resulting in a temperature increase from 37° C. to 45° C., ii) non-application of the laser during 20 seconds resulting in a temperature decrease from 45° C. to 37° C.; nineteenth sequence: i) application of the laser of average power 3 W/cm² during 19 seconds resulting in a temperature increase from 37° C. to 45° C., ii) non-application of the laser during 18.5 seconds resulting in a temperature decrease from 45° C. to 37° C. FIGS. 2(c) and 3(c) show that: i) in the presence of 1 mg/mL of magnetosomes, heating and cooling steps can be reached, and ii) in the absence of magnetosomes, the cells do not produce any heat, and heating and cooling steps cannot be reached.

FIGS. 2(a) and 3(a) show the percentage of living cells for U87-MG cells (FIG. 2(a)) and 3T3 cells (FIG. 3(a)) brought into contact with 1 mg/mL of magnetosomes (right column) or not brought into contact with the magnetosomes (left column) and either not exposed to the laser (control, W/O L), exposed continuously to the laser of an average power 3 W/cm² during 6 minutes (Continuous L), or sequentially exposed to the laser of an average power 3 W/cm² during ~13 minutes (Sequential L).

FIG. 2(a) shows that when the quantity of magnetosomes brought into contact with U87-MG cells is increased from 0 to 1 mg/mL, the percentage of living cells decreases: from 100% to 65% (no laser application), 95% to 25% (continuous laser application), 95% to 10% (sequential laser application).

FIG. 3(a) shows that when the quantity of magnetosomes brought into contact with 3T3 cells is increased from 0 to 1 mg/mL, the percentage of living cells decreases: from 100% to 85% (no laser application), 95% to 40% (continuous laser application), 95% to 15% (sequential laser application).

In conclusion, we have shown that:
i) It was possible to carry out regular or periodic sequences of temperature increase up to 45° C. of average duration 16 seconds by applying the laser of an average power 3 W/cm² followed by temperature decreases from 45° C. to 37° C. of average duration 22 seconds by not applying the laser.
ii) The sequential application of the laser enables destroying more cells than the continuous application of the laser for the two studied cell lines (U87-Luc and 3T3 cells).

The invention claimed is:
1. A method of medically, chemically, biologically or cosmetically treating a body part of an individual in need thereof by laser radiation, comprising:
administering an effective amount of magnetic nanoparticles to the body part of the individual in need thereof; and
subjecting the magnetic nanoparticles to laser radiation comprising:
i) performing a first step comprising irradiating the magnetic nanoparticles by laser radiation at a first power, and heating and dissociating at least one compound from at least one magnetic nanoparticle; and
ii) optionally repeating the first step,
wherein each magnetic nanoparticle comprises a central part and a coating,
wherein the at least one compound comprises at least one substance, atom, ion, or chemical function, which is included in the central part or the coating of the at least one magnetic nanoparticle before dissociation,
wherein the at least one compound is dissociated from the at least one magnetic nanoparticle when the at least one compound is located at a distance of more than 1 nm from the at least one magnetic nanoparticle,
wherein the at least one compound is dissociated from the at least one magnetic nanoparticle during or after the irradiation of the at least one magnetic nanoparticle, and
wherein the magnetic nanoparticles are one of:
(a) magnetosomes synthesized by a magnetotactic *bacterium*, or
(b) nanoparticles not synthesized by a magnetotactic *bacterium* and having in common with magnetosomes at least one property of being ferrimagnetic or ferromagnetic and having a chain arrangement.

2. The method according to claim 1, wherein the heating of the first step is performed by at least one of:
a heating temperature characterized by at least one property selected in the group consisting of:
an average heating temperature that is lower than 100° C.,
an average heating temperature that is lower than the maximum temperature reached during the medically, chemically, biologically or cosmetically treating,
a maximum heating temperature that is lower than 100° C.,
an average heating temperature reached by sequentially irradiating the magnetic nanoparticles with a laser after at least two steps comprising irradiation that is lower than an average heating temperature reached by continuously irradiating the magnetic nanoparticles with a laser, or
a number of heating gradients characterized by at least one property selected in the group consisting of:
a number of heating temperature gradients that is larger than 2, and
a number of heating temperature gradients reached by sequentially irradiating the magnetic nanoparticles with a laser after at least two steps comprising irradiation that is larger than a number of heating temperature gradients reached by continuously irradiating the magnetic nanoparticles with a laser,
wherein a heating temperature gradient is a temperature increase of the heating in the first step.

3. The method according to claim 1, wherein a second step is performed and comprises cooling and/or non-dissociation of at least one compound from the magnetic nanoparticles.

4. The method according to claim 3, wherein the cooling of the second step is performed by at least one of:
a cooling temperature characterized by an average cooling temperature that is larger than 0° C., or
a number of cooling temperature gradients that is larger than 2,
wherein a cooling temperature gradient is a temperature decrease of the cooling of the second step.

5. The method according to claim 3, wherein the second step is carried out in the presence of a substance or equipment that decreases the temperature of the body part or magnetic nanoparticles, wherein:
 i) the duration of the second step is shorter in the presence than in the absence of such substance or equipment,
 ii) the difference between a maximum and a minimum temperature of the second step is larger in the presence than in the absence of such substance or equipment,
 iii) the laser power that irradiates the magnetic nanoparticles during the first step is lower in the presence than in the absence of such substance or equipment,
 iv) a concentration of the magnetic nanoparticles, comprised in the body part, is smaller in the presence than in the absence of such substance or equipment,
 and/or
 v) a number of sequences that is carried out during at least one session is larger in the presence than in the absence of such substance or equipment.

6. The method according to claim 1, wherein the first step comprises heating and the second step comprises cooling, and a heating temperature of the first step and/or a cooling temperature of the second step is/are stable or varies by less than $10^3$, 10, 1 or $10^{-1}$° C., for less than 99.9% of the duration of the first step and/or second step, and/or for less than $10^5$ seconds.

7. The method according to claim 1, wherein the first step and/or second step(s) is/are characterized by at least one property selected in the group consisting of:
a duration of between $10^{-3}$ and $10^3$ minutes, and
an inter-step duration separating the first step from the second step that between $10^{-5}$ and $10^3$ minute(s), or ii) shorter than the duration of the first and/or second step(s).

8. The method according to claim 1, wherein at least one sequence comprising the first step and second step is characterized by at least one property selected in the group consisting of:
a duration of a sequence that is between $10^{-3}$ and $10^3$ minutes,
a duration between two successive sequences or inter-sequence duration that is between $10^{-5}$ and $10^3$ minutes,
a duration of at least one sequence that is longer than a duration of at least one step,
and
a duration of at least one inter-sequence that is shorter than a duration of at least one sequence or a duration of at least one step.

9. The method according to claim 1, wherein a succession of at least one sequence is a treatment session, wherein a treatment session is characterized by at least one property selected in the group consisting of:
each treatment session has a duration that is between $10^{-3}$ and $10^3$ minutes,
there is an inter-session duration between two treatment sessions which is between $10^{-5}$ and $10^5$ minute(s)
at least one session has a duration that is longer than a duration of at least one sequence, and
there is at least one inter-session between two treatment sessions that has a duration that is longer than a duration of at least one sequence.

10. The method according to claim 1, wherein the first step and/or the second step(s) is/are ended when a given percentage of dissociation of at least one compound from the magnetic nanoparticles is reached and/or when a given temperature of the first step, $GT_{FS}$, and/or a given temperature of the second step, $GT_{SS}$, is reached, wherein $GT_{SS}$ and $GT_{FS}$ are characterized by at least one property selected from the group consisting of:
$GT_{SS}$ is above $GT_{FS}$,
$(GT_{SS}-GT_{FS})$ is between $10^{-3}$ and $10^3$° C.,
$GT_{SS}$ and/or $GT_{FS}$ are comprised between $-273$ and $10^3$° C.,
$GT_{SS}$ is within a range of temperatures reached during a hyperthermia treatment,
$GT_{FS}$ is above: i) $-40$° C., ii) 0° C., or iii) 37° C.,
$GT_{SS}$ and $GT_{FS}$ are below: i) 100° C., or ii) 70° C., and
$GT_{SS}$ and $GT_{FS}$ are less than $10^3$, 10, 5, 2 or 1° C. above 37° C.

11. The method according to claim 1, wherein the subjecting the magnetic nanoparticles to laser radiation is associated with at least one property selected in the group consisting of: i) a decrease in magnetic nanoparticles diffusion outside of a portion of the body part comprising the magnetic nanoparticles, ii) an increase of a percentage of dissociation of at least one compound from the at least one magnetic nanoparticle, iii) an increase of a number of temperature gradients or variations, and iv) a decrease of an average temperature reached during medically, chemically, biologically or cosmetically treating.

12. The method according to claim 1, wherein the subjecting the magnetic nanoparticles to laser radiation is carried out in a sequential manner by following at least one of the following steps:
 i) determining a maximum temperature or maximum percentage of dissociation in the first step and a minimum temperature or minimum percentage of dissociation in the second step prior to treating,
 ii) setting or fixing a parameter of a laser providing the laser radiation at a first value to reach the maximum temperature and/or maximum percentage of dissociation in the first step and then setting or fixing a parameter of the laser at a second value to reach the minimum temperature and/or minimum percentage of dissociation in the second step,
 iii) optionally, measuring the duration(s) of the first and/or second step(s) required to reach these maximum or minimum temperatures and/or the maximum or minimum percentages of dissociation,
 and
 iv) optionally, repeating the first and/or second step(s) during the measured duration(s) of the first and/or second step(s).

13. The method according to claim 1, wherein the method is for medically treating a body part having a disease selected from a cancer, a tumor, and an infection.

14. The method according to claim 1, wherein the method is for treating cosmetically the body part by repairing, replacing, coloring, imaging, curing, healing and/or contrasting the body part.

15. An irradiated magnetic nanoparticle obtained by the method of claim 1, said irradiated magnetic nanoparticle having at least one property selected from the group consisting of:
  i) a size of the irradiated magnetic nanoparticle that is smaller than a size of a non-irradiated magnetic nanoparticle, by a percentage between $10^{-3}$% and 99.99%, where this percentage is $S_I/S_{NI}$ or $(S_{NI}-S_I)/S_{NI}$, where $S_{NI}$ and $S_I$ are sizes of the non-irradiated and irradiated magnetic nanoparticles, respectively,
  ii) a number of irradiated compounds bound to the irradiated magnetic nanoparticle, $n_I$, that is smaller than a number of compounds bound to a non-irradiated magnetic nanoparticle, $n_{NI}$, where $n_{NI}/n_I$ is between 1 and $10^5$,
  iii) a binding strength of least one bond between an irradiated compound and the irradiated magnetic nanoparticle, $S_I$, that is smaller than a binding strength of at least one bond between a non-irradiated compound and a non-irradiated magnetic nanoparticle, $S_{NI}$,
  iv) a breaking of at least one bond between an irradiated compound and the irradiated magnetic nanoparticle,
  v) a bond-dissociation energy between an irradiated compound and the irradiated magnetic nanoparticle, $E_{dI}$, that is smaller than a bond-dissociation energy between a non-irradiated compound and a non-irradiated magnetic nanoparticle, $E_{dNI}$,
  vi) a coating thickness of the irradiated magnetic nanoparticle, $CT_I$, that is smaller than a coating thickness of a non-irradiated magnetic nanoparticle, $CT_{NI}$,
  vii) a percentage in mass of organic material or carbon of the irradiated magnetic nanoparticle that is smaller than a percentage in mass of organic material or carbon of a non-irradiated magnetic nanoparticle,
  viii) a cluttering of an irradiated compound bound to the irradiated magnetic nanoparticle that is smaller than a cluttering of a non-irradiated compound bound to a non-irradiated magnetic nanoparticle,
  and
  ix) a number of irradiated compounds $N_{1I}$ that prevent a release of irradiated compounds $N_{2I}$ from the irradiated magnetic nanoparticle that is smaller than a number of non-irradiated compounds $N_{1NI}$ that prevent a release of non-irradiated compounds $N_{2NI}$ from a non-irradiated magnetic nanoparticle,
  wherein the non-irradiated magnetic nanoparticle is a magnetic nanoparticle that is either not subjected to laser irradiation at all or subjected to continuous laser irradiation.

16. The irradiated magnetic nanoparticles according to claim 1, wherein the irradiated magnetic nanoparticles are synthesized by a living organism.

17. A cosmetic or medical or diagnosis composition, comprising the irradiated magnetic nanoparticles of claim 1 and at least one color or contrasting agent or imaging agent or diagnosis agent or therapeutic agent, for modifying at least one property of the body part selected in the group consisting of:
  i) color of the body part,
  ii) contrast of the body part,
  iii) imaging capacity of the body part, and
  iv) healing or repair capacity of the body part.

18. The method according to claim 1, wherein a second step is performed, which comprises at least one of the following events:
  i) not irradiating the irradiated magnetic nanoparticles obtained from the first step,
  ii) irradiating the irradiated magnetic nanoparticles obtained from the first step by laser radiation at a second power lower than the first power.

19. The method according to claim 18, wherein the first and second steps comprises a sequence, which is repeated at least once.

* * * * *